(12) United States Patent
Deretic

(10) Patent No.: US 12,285,470 B2
(45) Date of Patent: Apr. 29, 2025

(54) TRIM PROTEINS AND GALECTINS COOPERATE AND CODIRECT AUTOPHAGY AND ARE USEFUL IN THE TREATMENT OF AUTOPHAGY RELATED DISEASES

(71) Applicant: UNM RAINFOREST INNOVATIONS, Albuquerque, NM (US)

(72) Inventor: Vojo Deretic, Placitas, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 170 days.

(21) Appl. No.: 16/321,699

(22) PCT Filed: Jul. 31, 2017

(86) PCT No.: PCT/US2017/044619
§ 371 (c)(1),
(2) Date: Jan. 29, 2019

(87) PCT Pub. No.: WO2018/023108
PCT Pub. Date: Feb. 1, 2018

(65) Prior Publication Data
US 2024/0261378 A1    Aug. 8, 2024

Related U.S. Application Data

(60) Provisional application No. 62/368,624, filed on Jul. 29, 2016.

(51) Int. Cl.
*A61K 38/53* (2006.01)
*A61K 31/05* (2006.01)
(Continued)

(52) U.S. Cl.
CPC ............... *A61K 38/53* (2013.01); *A61K 31/05* (2013.01); *A61K 31/137* (2013.01);
(Continued)

(58) Field of Classification Search
None
See application file for complete search history.

(56) References Cited

U.S. PATENT DOCUMENTS

2015/0250808 A1    9/2015   Deretic et al.
2016/0136123 A1*   5/2016   Deretic ............... A61K 31/201
                                                   436/71

FOREIGN PATENT DOCUMENTS

WO    WO 2014/062621    *    4/2014

OTHER PUBLICATIONS

Zuber et al., Biomedicines 11: 1668 (2023).*
(Continued)

*Primary Examiner* — Erin M. Bowers
(74) *Attorney, Agent, or Firm* — Henry D. Coleman; R. Neil Sudol

(57) ABSTRACT

The present invention relates to compositions and methods of influencing autophagy by modulating TRIM (tripartite motif containing) proteins, especially TRIM 8, TRIM: 10, TRIM 16, TRIM 19 and/or TRIM 51 (preferably TRIM 16} and galectins, especially galectins 3 m order to influence autophagy and treat a number of disease states and/or conditions which are mediated and/or influenced by autophagy, including inflammatory disease states and/or conditions, including a microbial infection such as a *Mycobacterium* infection, among numerous others, an inflammatory disorder, a lysosomal, storage disorder, an immune disorder, a neurodegenerative disorder and a cancer.

20 Claims, 55 Drawing Sheets
Specification includes a Sequence Listing.

(51) Int. Cl.
  *A61K 31/137* (2006.01)
  *A61K 31/155* (2006.01)
  *A61K 31/436* (2006.01)
  *A61K 31/4375* (2006.01)
  *A61K 31/616* (2006.01)
  *A61K 31/7016* (2006.01)
  *A61K 31/702* (2006.01)
  *A61K 38/17* (2006.01)
  *A61K 45/06* (2006.01)
  *A61P 31/04* (2006.01)

(52) U.S. Cl.
  CPC .......... *A61K 31/155* (2013.01); *A61K 31/436* (2013.01); *A61K 31/4375* (2013.01); *A61K 31/616* (2013.01); *A61K 31/7016* (2013.01); *A61K 31/702* (2013.01); *A61K 38/1732* (2013.01); *A61K 45/06* (2013.01); *A61P 31/04* (2018.01)

(56) References Cited

OTHER PUBLICATIONS

Din FV et al.; Aspirin inhibits mTor signaling, activates AMP-activated protein kinase, and induces autophagy in colorectal cancer cells. Gastroenterology Jun. 2012; vol. 142 nr. 7, pp. 1504-1515 e3. doi: 10:1053/j.gastro.2012.02.050. Epub Mar. 6, 2012.

Kimura T et al.; TRIM-mediated precision autophagy targets cytoplasmic regulators of innate immunity. J. Cell Biol. Sep. 14, 2015, vol. 210, nr 6, pp. 973-989. PMID; 26347139, doi: 10.1083/jcb.201503023.

Thurston TL et al.; Galectin 8 targets damaged vesicles for autophagy to defend cells against bacterial invasion. NATURE, Jan. 15, 2012; vol. 482, nr. 7385, pp. 414-418. PMID: 22246324, doi: 10.1038/nature 10744.

* cited by examiner

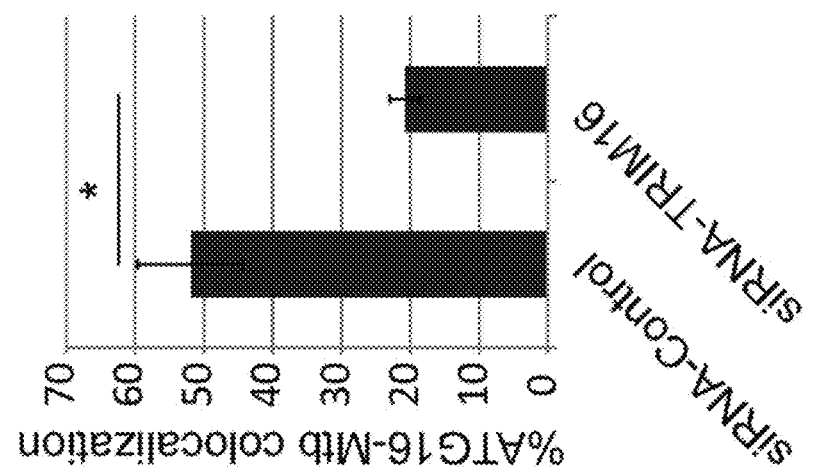
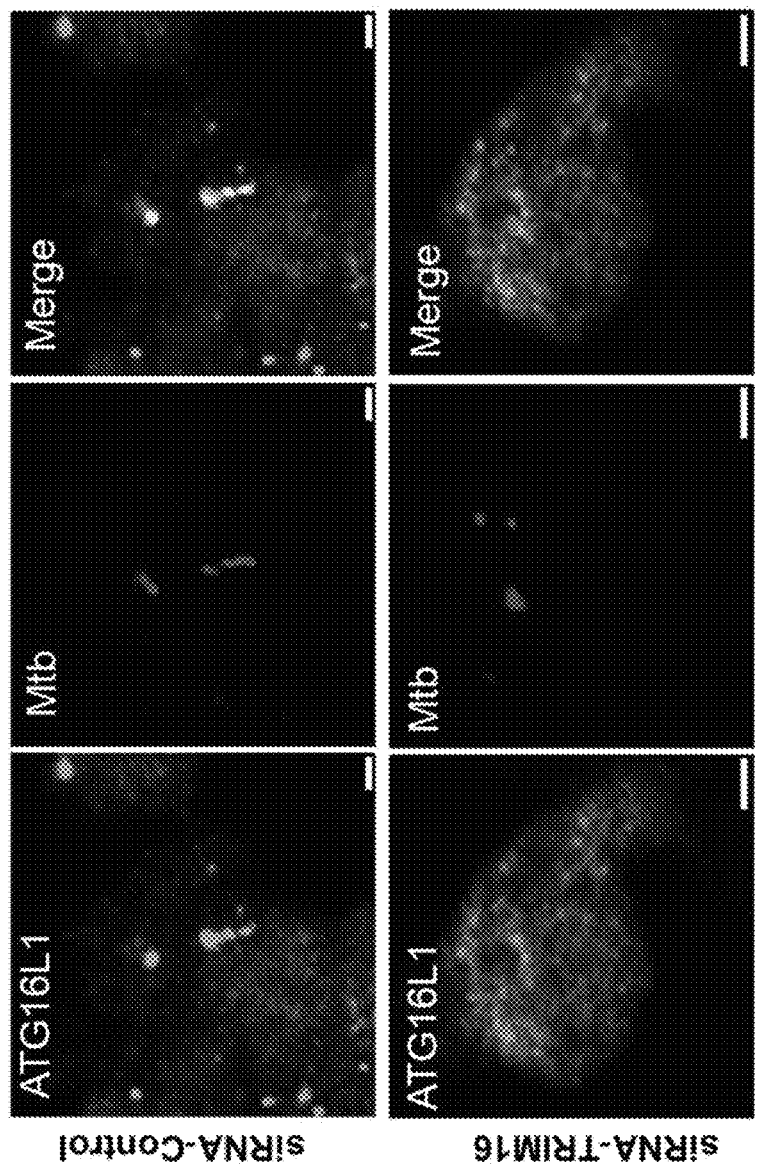
FIGURE 5 (cont.)

FIGURE 9 (cont.)

```
F   481 TCTCTTGTCTGACTTGGGCTGCAGATCCTGGGCCAAGGGACAGAAGAAAGAGACAGCCTA    540  SEQ ID NO: 44
     58 TCTCTTGTCTGACTTGGGCTGCAGATCCTGGGCCAAGGGACAGAAGAAAGAGACAGCCTA    117  SEQ ID NO: 44
        ************************************************************

541 GGAGCAGAGCCTCCCAGATGGCTGAGTTGGATCTAATGGCTCCAGGGGCCACTGCCCAGGG   600  SEQ ID NO: 45
    118 GGAGCAGAGCNNN-----------------------------------NNCCAGGG       138  SEQ ID NO: 46
        *************                                   **  *****

601 CCACTGCTCAGCCCCCAGCCCTCTCAGCCCAGACTCTGGGTCACCCAGCCCAGATTCTG    660  SEQ ID NO: 47
    139 CCACTGCTCAGCCCCCAGCCCTCTCAGCCCAGACTCTGGGTCACCCAGCCCAGATTCTG    198  SEQ ID NO: 47
        ************************************************************
```

FIGURE 11 (cont.)
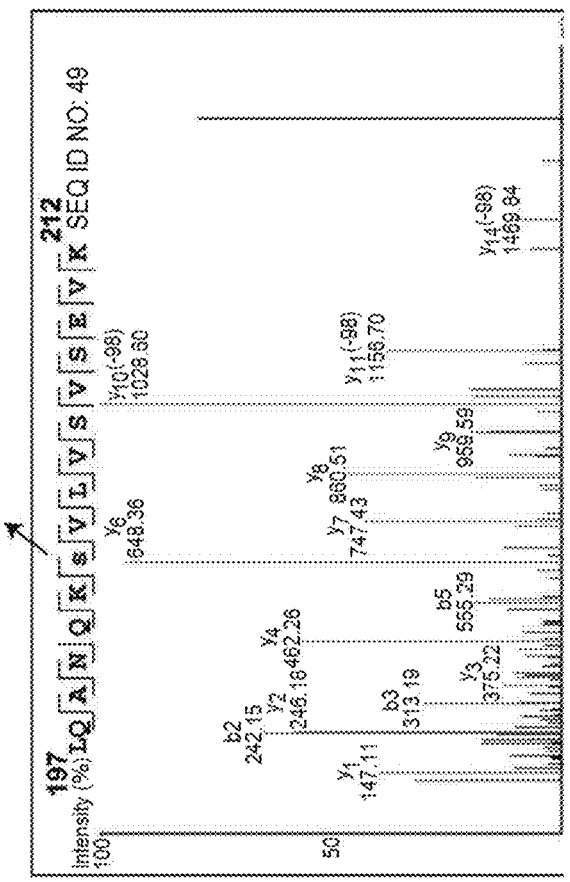
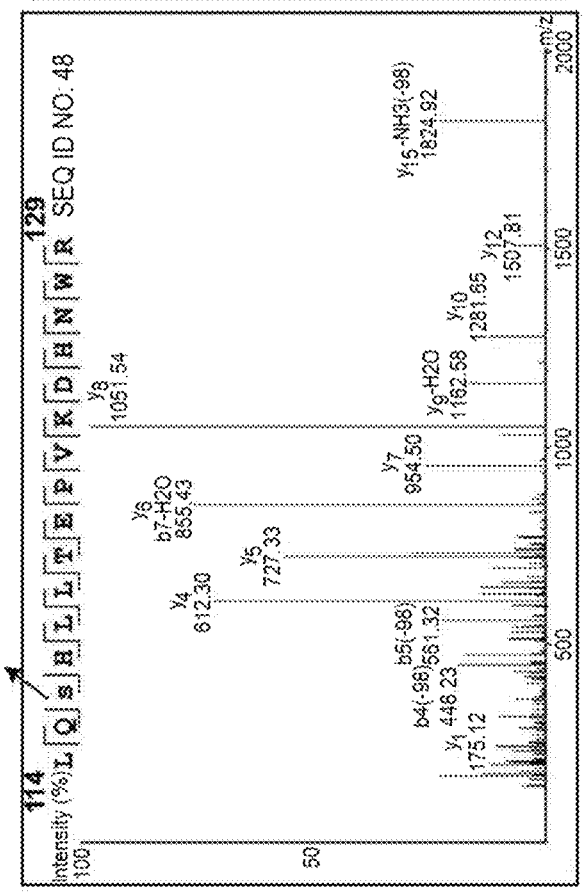

FIGURE 14 (cont.)
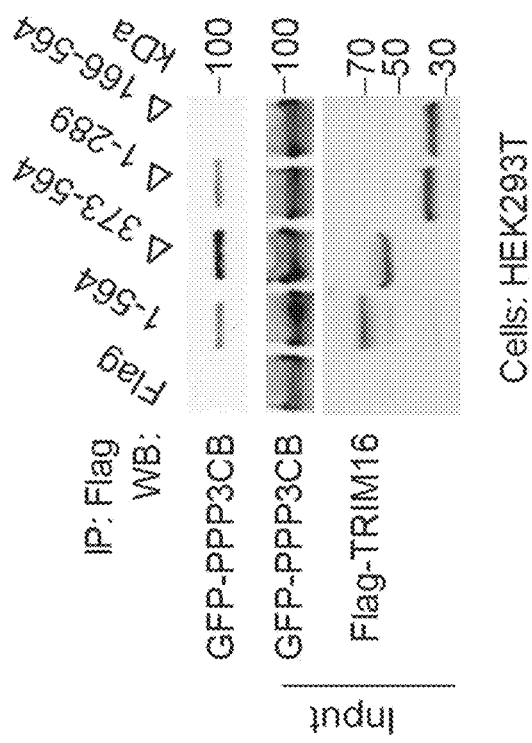
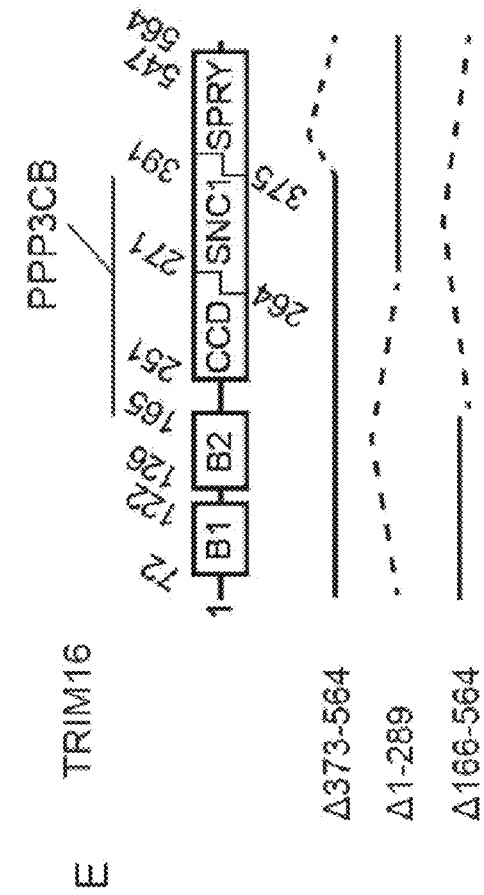

FIGURE 15 (cont.)
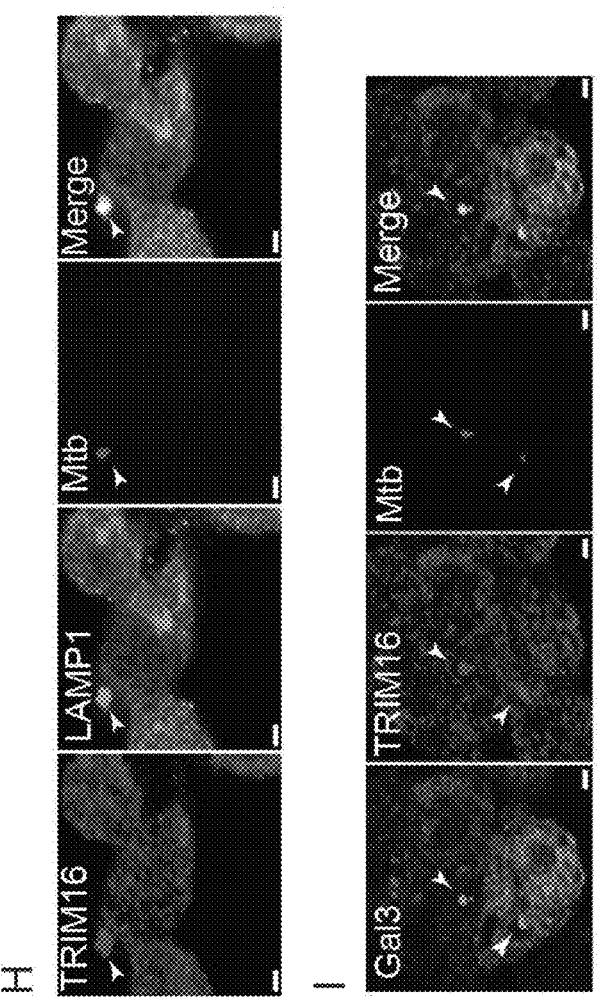
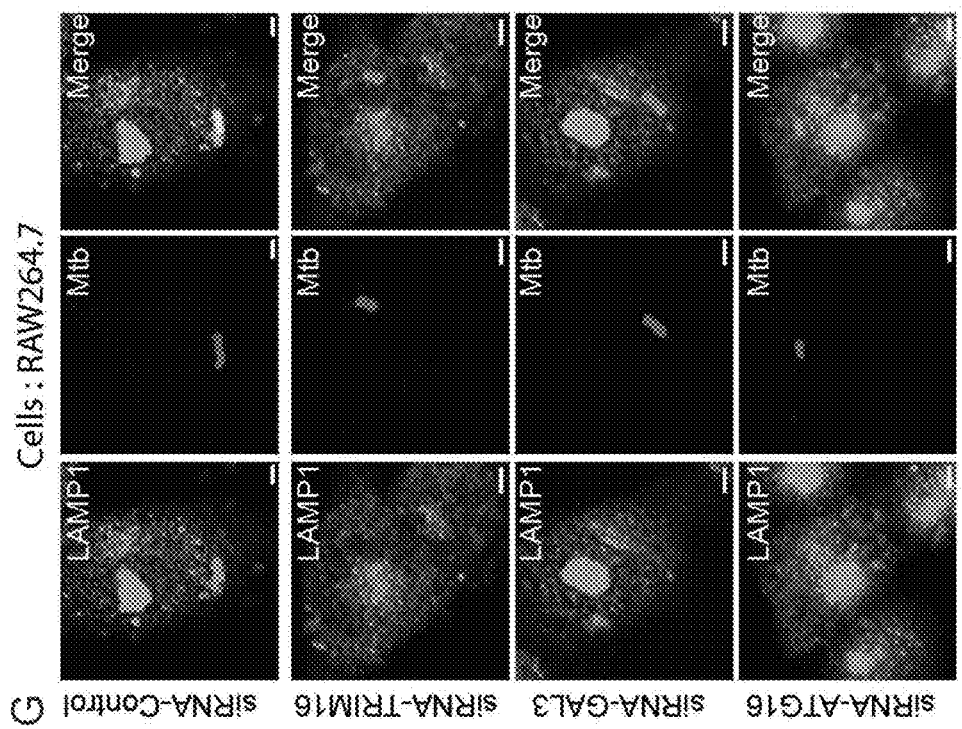

FIGURE 25

THE ReFRAME LIBRARY

Rationale for a High-Value Screening Set

- Initiating drug discovery campaigns from known drugs or compounds that have adequate clinical safety/PK significantly decreases the cost and time associated with finding new therapies
- ReFRAME is a consolidated, comprehensive set of such compounds (~12,000) that enables and accelerates new drug discovery efforts, allowing high-value assays to be deployed, especially in challenging therapeutic areas that have a paucity of leads
- This initiative was supported by a $20M grant from the Bill & Melinda Gates Foundation, allowing us to include compounds with challenging/costly syntheses and generate 20+ mg of pure material for each library compound
- Calibr now has a number of examples of direct repurposing (e.g., auranofin, clofazimine) programs derived from ReFRAME screens

Deployment of a Unique Resource

- ReFRAME is being made available under Global Access terms to investigators working on unmet global heath needs
- Intellectual property policy allows investigators to freely pursue and commercialize findings

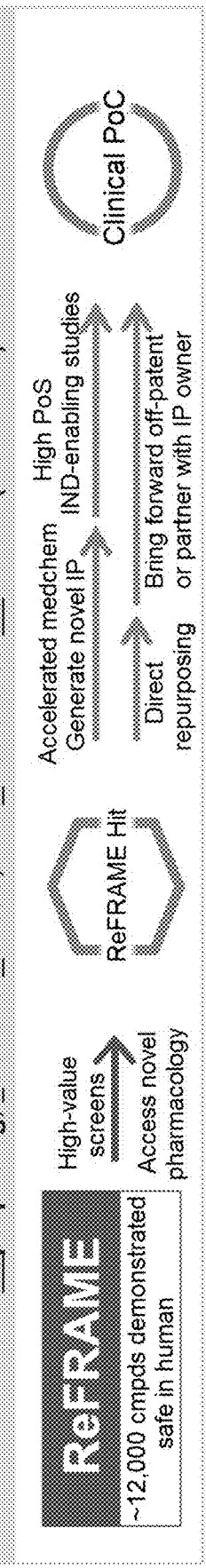

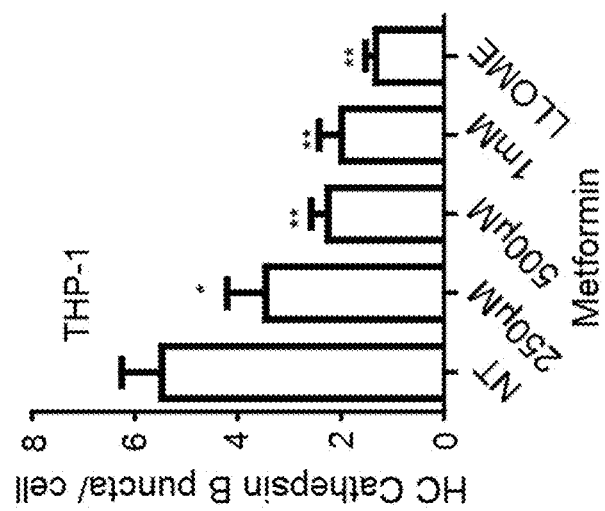
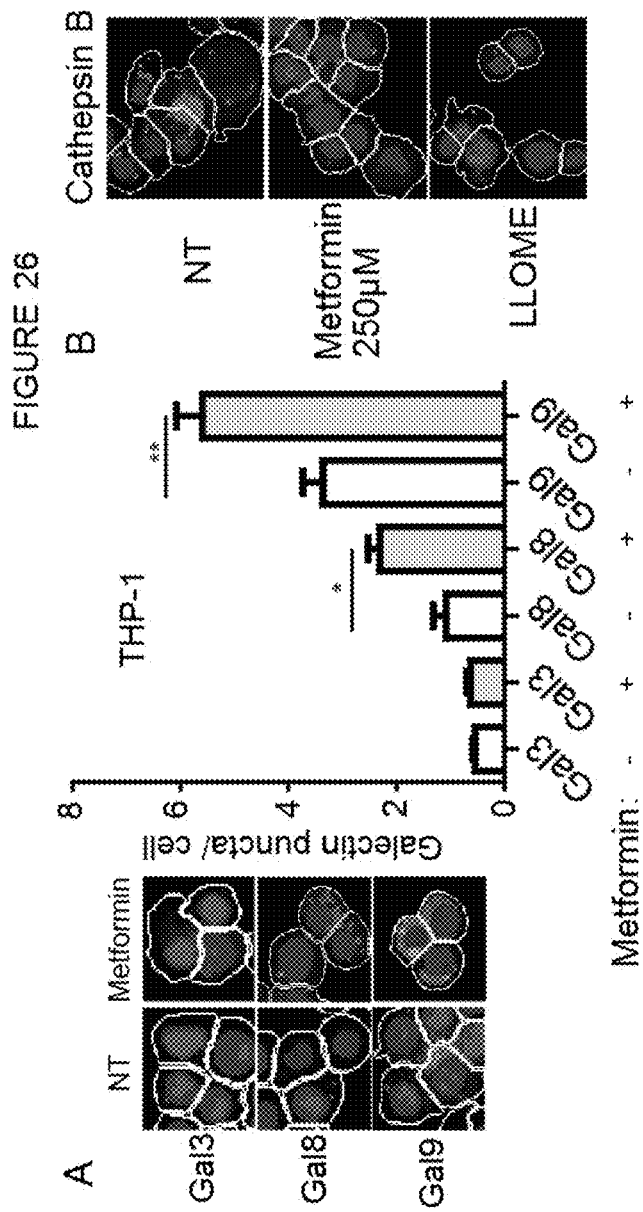
FIGURE 26

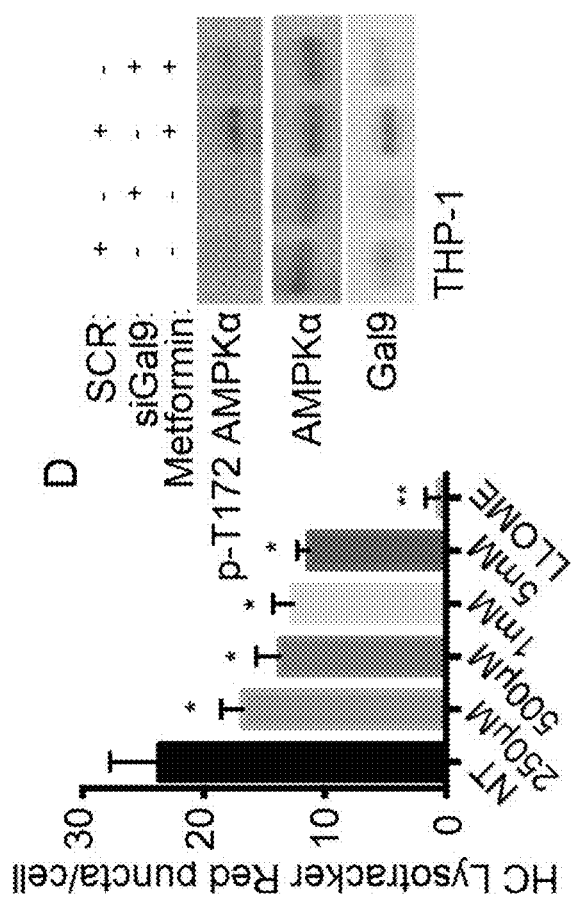
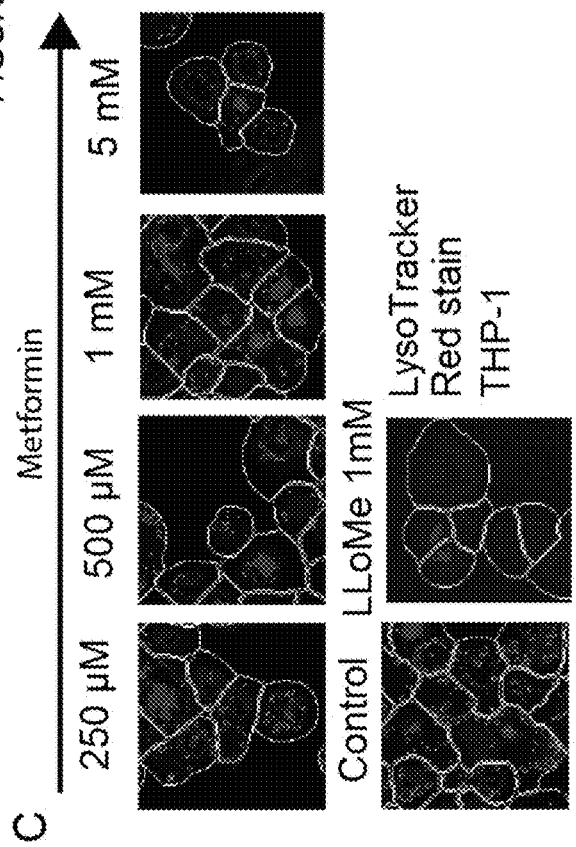
FIGURE 26 (cont.)

US 12,285,470 B2

TRIM PROTEINS AND GALECTINS COOPERATE AND CODIRECT AUTOPHAGY AND ARE USEFUL IN THE TREATMENT OF AUTOPHAGY RELATED DISEASES

This application is a United States national phase patent application which is based upon international patent application number PCT/US2017/044619 of international filing date 31 Jul. 2017, which claims the benefit of priority of United States provisional application number U.S. 62/368,624, entitled "TRIM Proteins and Galectins Cooperate and Codirect Autophagy In Endomembrane Homeostasis", filed Jul. 29, 2016, the entire contents of which said two applications is incorporated by reference herein.

RELATED APPLICATIONS

This application claims the benefit of priority of United States provisional application number U.S. 62/368,624, entitled "TRIM Proteins and Galectins Cooperate and Codirect Autophagy In Endomembrane Homeostasis", filed Jul. 29, 2016, the entire contents of which application is incorporated by reference herein.

This invention was made with government support under Grant Nos. AI042999 and AI111935 awarded by the National Institutes of Health (NIH). The government has certain rights in the invention.

FIELD OF THE INVENTION

The present invention relates to compositions and methods of influencing autophagy by modulating autophagy with TRIM (tripartite motif containing) proteins, especially TRIM 8, TRIM 10, TRIM 16, TRIM 19 and TRIM 51 (preferably TRIM 16) and galectins in combination, especially Galectin-3, Galectin-8, Galectin-9 and Galectin-12, preferably Galectin 3 in order to influence autophagy and treat a number of disease states and/or conditions which are mediated and/or influenced by autophagy, including inflammatory disease states and/or conditions including a microbial infection such as a *Mycobacterium* infection, including tuberculosis, among numerous others, an inflammatory disorder, a lysosomal storage disorder, an immune disorder, especially an autoimmune disorder, a neurodegenerative disorder, cardiovascular disease and cancer.

BACKGROUND AND OVERVIEW OF THE INVENTION

Autophagy maintains nutrient, energy and organellar homeostasis, participates in intracellular quality control and ensures functionality and sterility of the eukaryotic cell (Mizushima et al., 2011). The most commonly studied form of autophagy, referred to as macroautophagy, is a pathway dependent on highly conserved ATG factors whereby cytoplasmic cargo is captured into autophagosomes, endomembranous organelles decorated with Atg8 in yeast, or in mammalian cells with mammalian Atg8 homologs (mAtg8s) (Mizushima et al., 2011). Autophagy is co-regulated transcriptionally with lysosomal biogenesis via TFEB and other MiT/TEF factors (Napolitano and Ballabio, 2016).

The core autophagy machinery in mammals includes several interconnected components: (i) a phosphatidylinositol 3-kinase VPS34 complex containing ATG14L (Sun et al., 2008), and Beclin 1 (Liang et al., 1999), which upon activation initiates autophagy through production of phosphatidylinositol 3-phosphate (PI3P); (ii) a key upstream protein Ser/Thr kinase Atg1/ULK1 (Mizushima et al., 2011), which phosphorylates and activates Beclin 1 (Russell et al., 2013); (iii) the six mAtg8 homologs (LC3A, B and C, GABARAP, GABARAPL1, and GABARAPL2) undergoing ATG5-ATG12/ATG16L1 E3 ligase-sponsored C-terminal lipidation with phosphatidylethanolamine (PE), a modification engendering their membrane association (Kabeya et al., 2004), and playing distinct roles in autophagosome membrane biogenesis. (iv) A PIP-binding ATG factor known as WIPI2, connecting PI3P production, ULK1, and the PE conjugation system; WIPI2 recognizes PI3P-modified membranes and interacts with ATG16L1 (Dooley et al., 2014), whereas in turn ATG16L1 is both a localizer of the E3 ligase-like system leading to mAtg8 PE-lipidation (Fujita et al., 2008) and a binding partner for FIP200, a component of the ULK1 complex systems (Fujita et al., 2013). (v) The above systems are set in motion by various signals transduced by upstream signaling systems including Ser/Thr protein kinases mTOR, AMPK, and MK2/MK3 (Kim et al., 2011; Wei et al., 2015).

Less is known about how selective autophagy connects with the upstream regulatory systems, albeit the homing and fidelity of selective autophagy is an area of intense study. The best-understood processes underlying selective autophagy in mammalian systems involve a group of ubiquitin-binding receptors termed Sequestosome 1/p62-like receptors (SLRs) (Birgisdottir et al., 2013; Deretic et al., 2013). The unifying property for SLRs is their ability to bind ubiquitin and associate with LC3. Individual or distinct subsets of SLRs recognize ubiquitin or phosphorylated ubiquitin on targets, delivering them to autophagosomes (Khaminets et al., 2016). Other recognition tags, provided by cytosolic lectins termed Galectins have been implicated in selective autophagy (Thurston et al., 2012). Galectins bind to β-galactoside glycoconjugates (normally sequestered from the cytosol by being located within the lumen-oriented endofacial membrane leaflets) when they become exposed to the cytosol upon endomembrane damage, such as within phagosomes harboring bacteria with membrane penetrating properties (Thurston et al., 2012), or lysosomes (Maejima et al., 2013) and phagosomes (Fujita et al., 2013) perforated by damaging inanimate objects. While intriguing, Galectin-based selective autophagy has thus far been linked to only one of the SLRs, NDP52 (Thurston et al., 2012). Furthermore, how recognition of autophagic targets tagged by ubiquitin or Galectins is integrated with the localized activation of the core autophagic apparatus is not well understood.

The TRIM proteins (Reymond et al., 2001) play a dual role as receptors and regulators of autophagy (Kimura et al., 2015; Kimura et al., 2016; Mandell et al., 2014). TRIMs recognize targets and assemble autophagy regulators ULK1 and Beclin 1 in their activated forms (Kimura et al., 2015; Mandell et al., 2014). The majority of TRIMs contain E3 ligase domains (Kimura et al., 2016; Reymond et al., 2001). The inventors have discovered that TRIMs possess another surprising feature, i.e. that they broadly interact with Galectins. Using lysosomal and phagosomal damage models, the inventors have shown that one TRIM in particular, TRIM16, recognizes endomembrane damage through interactions with Galectin-3 in an ULK1-dependent manner, with ULK1 playing a structural role in enhancing TRIM16-Galectin-3 interactions. TRIM16 binds ATG16L1 and associates with key autophagy regulators ULK1 and Beclin 1. Furthermore, TRIM16 influences TFEB and mTOR activation states.

BRIEF DESCRIPTION OF THE INVENTION

The present invention is directed to the discovery that TRIM proteins such as TRIM 8, TRIM 10, TRIM 16 and/or TRIM 19 and/or TRIM 51 especially including TRIM 16 cooperate with galectins, especially including galectin 3, 8, 9 and 12 to modulate (i.e., to upregulate or downregulate autophagy) and act to inhibit and/or treat a number of disease states and/or conditions which are mediated through autophagy. In the present invention, it has been discovered that the TRIM proteins TRIM 8, TRIM 10, TRIM 16, TRIM 19 and TRIM 51 (also TRIM 1, TRIM 20, TRIM 21, TRIM 22, TRIM 56, TRIM 65), especially TRIM 16, administered directly or upregulated through the administration of an interferon compound as discussed herein, a biguanide such as metformin, buformin, proguanil and/or phenformin, a combination of a biguanide and a salicylate (preferably aspiring or salicylic acid), berberine, ambroxol or mixtures thereof, combined with an agonist of Galectin (1, 2, 3, 4, 7, 8, 9, 10, 12 and/or 13), especially Galectin-3, Galectin-8, Galectin-9, Galectin 12, especially Galectin-3 or a sugar agonist of a Galectin as described herein can be used to upregulate autophagy to provide therapy for a large number of disease states and/or conditions which are mediated through autophagy, including inflammatory disease states and/or conditions, infections, especially a microbial infection such as a *Mycobacterium* infection (especially tuberculosis), among numerous others, an inflammatory disorder, a lysosomal storage disorder, an immune/autoimmune disorder or a neurodegenerative disorder as otherwise disclosed herein. In addition, compositions may further include an additional autophagy modulator and/or an mTOR inhibitor such as Torin, pp242, rapamycin/serolimus (which also may function as an autophagy modulator), everolimus, temsirolomis, ridaforolimis, zotarolimis, 32-dexoy-rapamycin, among others including epigallocatechin gallate (EGCG), caffeine, curcumin or reseveratrol or mixtures thereof to enhance the effect of the autophagy modulator.

In embodiments, the present invention relates to the discovery that a TRIM protein inhibitor, especially including an SIRNA of a TRIM protein such as TRIM 8, TRIM 10, TRIM 16, TRIM 19 and TRIM 51 (also TRIM 1, TRIM 20, TRIM 21, TRIM 22, TRIM 56, TRIM 65), especially TRIM 16, (preferably TRIM 16 and/or TRIM $1), or an antibody, especially a monoclonal antibody that can bind/inhibit TRIM protein, especially TRIM 8, TRIM 10, TRIM 16, TRIM 19 and/or TRIM 51 in combination with a galectin inhibitor such as an inhibitor of Galectin (e.g. 1, 2, 3, 4, 7, 8, 9, 10, 12 and/or 13), often a Galectin-3, Galectin-8, Galectin-9 and/or a Galectin-12 inhibitor especially a galectin-3 inhibitor is an effective therapy for the treatment of cancer. These treatments may include inhibitors of autophagy (e.g. tetrachloroisophthalonitrile, phenylmercuric acetate and their pharmaceutically acceptable salts) and/or mTor inhibitors to enhance the impact of the autophagy agents in the treatment of cancer.

In embodiments, the present invention relates to pharmaceutical compositions comprising a combination of agents which comprise one or more TRIM proteins such as TRIM 8, TRIM 10, TRIM 16, TRIM 19 and/or TRIM 51 (also TRIM 1, TRIM 20, TRIM 21, TRIM 22, TRIM 56, TRIM 65), especially TRIM 16, and/or at least one compound/composition which upregulates TRIM proteins, such as an interferon (especially including alpha, beta or gamma interferon), in combination with a Galectin agonist, including a Galectin protein (e.g. 1, 2, 3, 4, 7, 8, 9, 10, 12 and/or 13), including Galectin 3, 8, 9 or 12 or a galactose containing sugar or other sugar compound which acts as an agonist of Galectin, in combination with a pharmaceutically acceptable carrier, additive and/or excipient. These compositions may also include an mTOR inhibitor to enhance the effect of the autophagy inhibitor.

In still other embodiments, the present invention relates to pharmaceutical compositions comprising a combination of agents comprising a TRIM protein inhibitor, preferably a SiRNA of a TRIM protein or an antibody which binds to a TRIM protein, especially TRIM 16 or TRIM 51 in combination with an inhibitor of Galectin, preferably an inhibitor of Galectin-3, Galectin-8, Galectin-9 and/or Galectin-12, especially Galectin 3, preferably a galactoside inhibitor or alternatively, a lactulose amine such as N-lactulose-octamethylenediamine (LDO); N,N-dilactulose-octamethylenediamine (D-LDO), and N,N-dilactulose-dodecamethylenediamine (D-LDD)), GR-MD-02, GM-CT-01, GCS-100, ipilimumab, a pectin, a taloside inhibitor or an antibody, preferably a human or humanized antibody raised against Galectin in combination with a pharmaceutically acceptable carrier, additive and/or excipient. These compositions are useful for the treatment of cancer. These compositions may also include an autophagy inhibitor such as tetrachloroisophthalonitrile, phenylmercuric acetate and their pharmaceutically acceptable salts, and/or a mTOR inhibitor to enhance the effect of the autophagy inhibitor. Additional anti-cancer agents may also be included in these compositions.

In another embodiment the present invention is directed to a method of treating an autophagy-mediated disease state or condition as otherwise described herein comprising administering effective amount of at least one TRIM protein, such as TRIM 8, TRIM 10, TRIM 16, TRIM 19 and TRIM $1 (also TRIM 1, TRIM 20, TRIM 21, TRIM 22, TRIM 56, TRIM 65) and/or at least one TRIM protein agonist (such as one or more interferons as described herein) in combination with a Galectin protein (Galectin 1, 2, 3, 4, 7, 8, 9, 10, 12 and 13), preferably Galectin-3, Galectin-8, Galectin-9 and/or Galectin-12 or a Galectin agonist such as a sugar agonist as otherwise described. The autophagy disease state and/or condition is an inflammatory disease states and/or conditions including an infection, especially a microbial infection such as a *Mycobacterium* infection (especially tuberculosis), among numerous others, an inflammatory disorder, a lysosomal storage disorder, an immune/autoimmune disorder or a neurodegenerative disorder or other disease or disorder as described herein.

In another embodiment, compositions which are described above as being useful in the treatment of cancer are used to treat cancer in a patient in need. In this method, an anti-cancer effective amount of a composition useful in the treatment of cancer as described above is administered to a patient with cancer in need, either alone or in combination with at least one additional anticancer agent for treating cancer.

In another embodiment, the present invention is directed to methods of treating mycobactium infections, especially *Mycobacterium tuberculosis* infections, the method comprising administering to a patient in need (which can include a patient with tuberculosis or who is at risk for tuberculosis) an effective amount of at least one Galectin selected from the group consisting of Galectin-3, Galectin-8, Galectin-9, Galectin-12 or mixtures thereof, optionally in combination with a TRIM protein, especially TRIM 8, TRIM 10, TRIM 16, TRIM 19 and/or TRIM 51 or a compound which upregulates TRIM protein such as an interferon, a biguanide, a biguanide in combination with a salicylate, berberine, ambroxol and mixtures thereof. In certain embodiments, Galectin-8 and/or Galectin-9, and/or an agonist of Galectin-8 and/or Galectin-9 (e.g., galactose, a galactoside or a sugar containing at least one galactose unit) or a pharmaceutically acceptable salt thereof are used to treat tuberculosis, optionally in combination with a TRIM protein, especially TRIM 8, TRIM 10, TRIM 16, TRIM 19 and/or TRIM 51, a compound which upregulates TRIM protein and/or at least one additional autophagy agent. In certain embodiments an mTOR inhibitor such as Torin, pp242, rapamycin/serolimus (which also may function as an autophagy modulator), everolimus, temsirolomis, ridaforolimis, zotarolimis, 32-dexoy-rapamycin and mixtures thereof among others including epigallocatechin gallate (EGCG), caffeine, curcumin or reseveratrol is used to enhance the effect of the autophagy modulator, especially including the Galectin protein and/or the compound which upregulates Galectin (galactose, galactoside or sugar containing at least one galactose unit). In certain embodiments, biguanides selected from the group consisting of buformin, proguanil, phenformin and mixtures thereof alone or in combination with a salicylate are used. In still other embodiments, a biguanide including metformin is combined with a salicylate (especially aspirin) for the treatment or prevention of a tuberculosis infection.

(D) Immunoblot analysis of siRNA knock down efficiency of TRIM16 in HeLa cells. (E) Immunoblot analysis of CRISPR-Cas9-mediated knock out of TRIM16 in HeLa cells, clone A9. (F) The clone A9 was subjected to next generation sequencing to characterize the mutation. Sequence alignment (top human TRIM16 genomic NCBI NM_006470 sequence; bottom, 62,593 bp next generation reads of a 259 bp contig, with 99.81% representation; a minor species with a 0.18% representation had additional changes in the region); The gap represents deletion introduced by Cas9, and it encompasses start codon at position 558 (NM_006470); the target sequence (red font) starts at position 551 (NM_006470). Bottom, a schematic showing TRIM16 exons and location of the Cas9-introduced deletion (orange); blue, TRIM16 coding sequence. (G) Independently obtained CRISPR TRIM16 knockout clone C2 in Hela cells. C2, knockout clone, F11, clone that is not a knockout. (H,I) Confocal images in H of HeLa cells transfected with control or TRIM16 siRNA treated with LLOMe, and processed for immunofluorescence with LC3B antibody. Graph in I represents average corrected total fluorescence intensity of cells±SD.>50 cells from 6 fields from three different experiments were measured using Image J. Student's unpaired t test was used to test for statistical significance: *, p<0.05. (J) Autophagic response (HC, LC3 puncta) to LLOMe (0.5 mM, 2 h) in Hela cells and their CRISPR TRIM16KO mutant derivative C2. (K) Dose-dependent increase in the abundance of ubiquitin puncta in Hela cells upon LLOMe treatment as determined by high content microscopy. (L,M) Confocal imaging analysis of HeLa cells transfected with control or TRIM16 siRNA treated with LLOMe and immunofluorescence performed with ubiquitin antibody (M). Graph represents average corrected total cell fluorescence of cells #standard deviation (SD) (N). >50 cells from 6 fields from three different experiments were measured using Image J. Student's unpaired t test was used to test for statistical significance: *, p<0.05. (N,O) Screen for the effects of TRIM family knockdowns (specific TRIM identified indicated by numbers) on ubiquitin response to lysosomal damage by LLOMe. Images of HeLa cells treated or not with 0.5 mM LLOMe, stained with anti-ubiquitin (red), and subjected to high content microscopic imaging and analysis (N). White masks, cell boundaries. Yellow masks, ubiquitin puncta. Expression of a subset of TRIMs was knocked down by siRNAs in HeLa cells (O). Following LLOMe treatment, the number of ubiquitin puncta per cell was determined by high content microscopy. (P) Ubiquitination response, revealed with FK2 mouse monoclonal antibody in HeLa vs. TRIM16$^{KO}$ HeLa mutant C2. HC data: means (n>3); t-test (1,0) or ANOVA (J) *, p<0.05.

Figure 2:
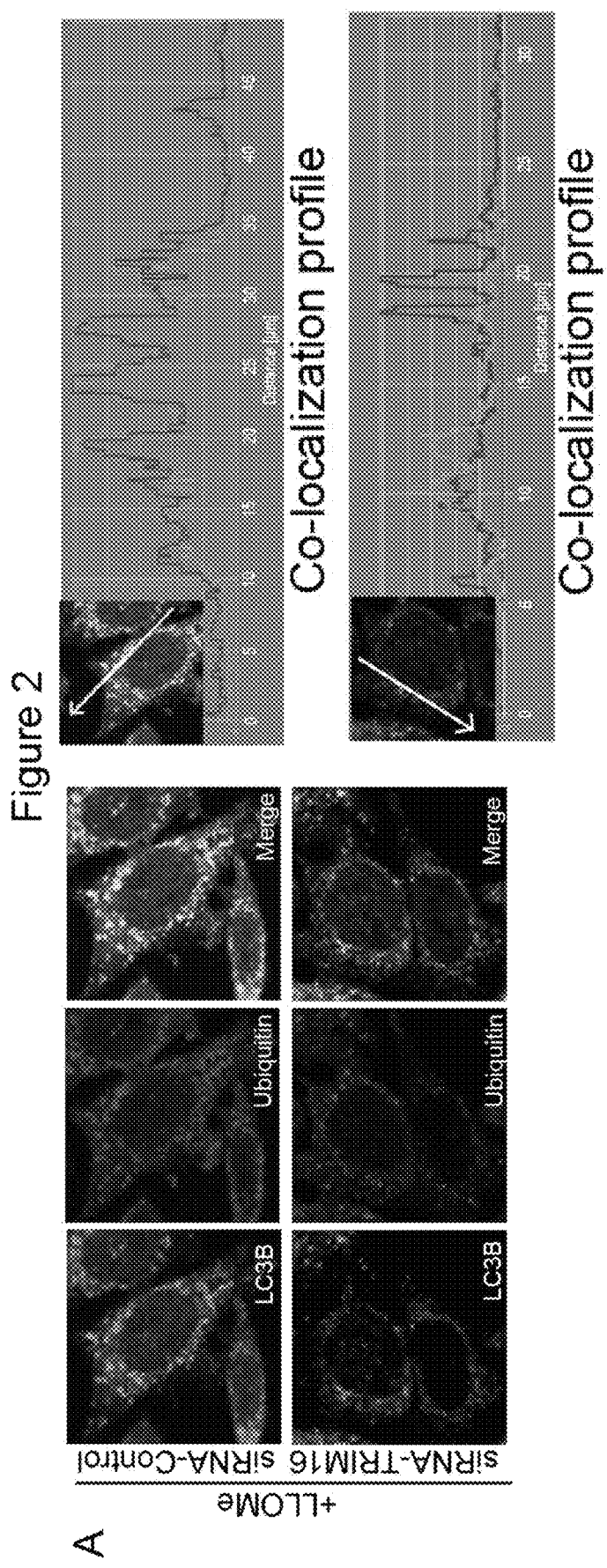
FIG. 2 shows the colocalization between TRIM16, ubiquitin and LC3B. (A) Confocal microscopy analysis of endogenous LC3B puncta and endogenous ubiquitin profiles localization in cells knocked down for TRIM16. Right, line tracers showing fluorescence peaks. (β-C) HC analysis of LC3B and ubiquitin profiles colocalization (%) in Hela cells and CRISPR TRIM16$^{KO}$ mutant (A9) exposed to 0.5 mM LLOMe for 2 h. Yellow mask, ubiquitin puncta. Scale bar, 10 μm. (D,E) Confocal image analysis of THP1 cells untreated or treated with 0.5 mM LLOMe and immunostained for endogenous TRIM16, ubiquitin or LC3B. Bottom panels, line tracings representing fluorescence peaks. Scale bar, 10 μm.
Figure 2:
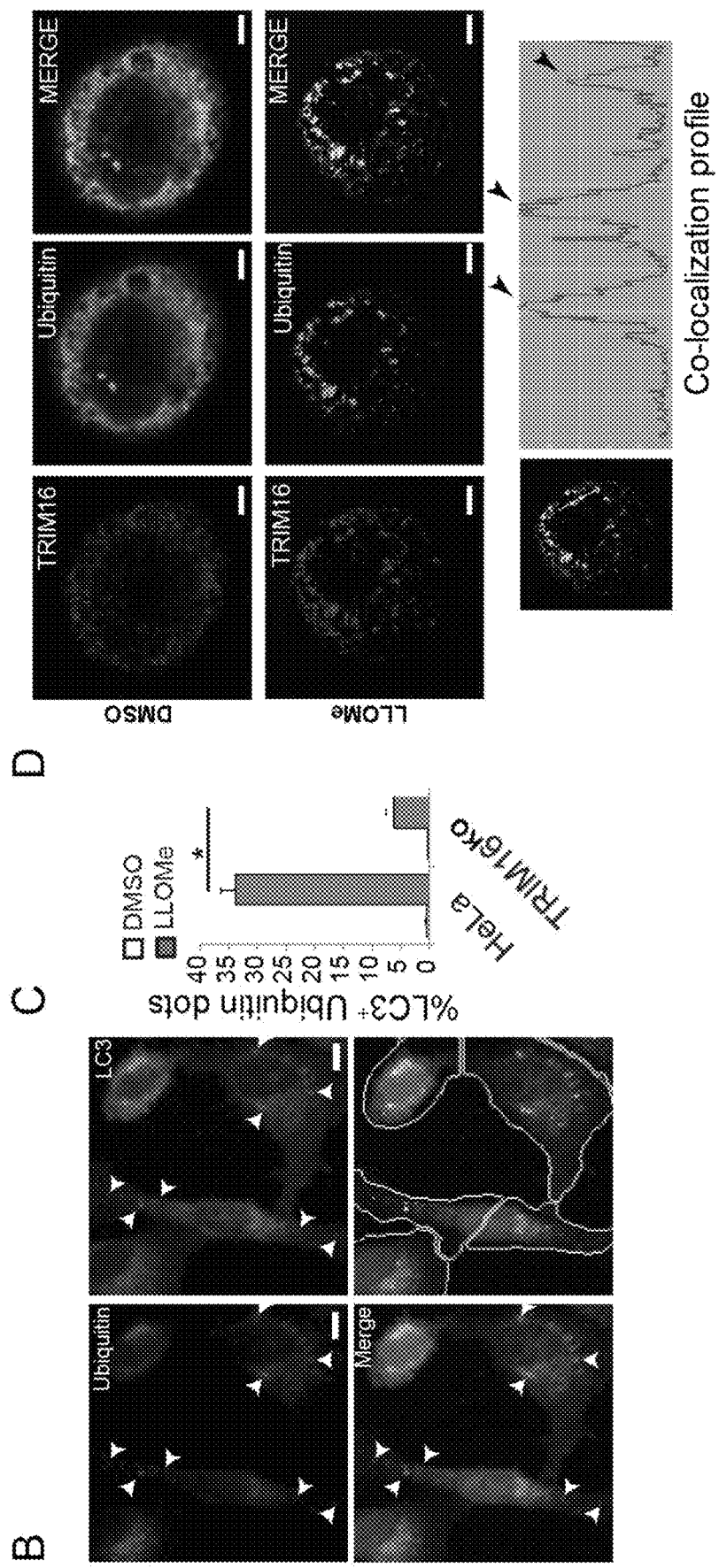
Figure 2:
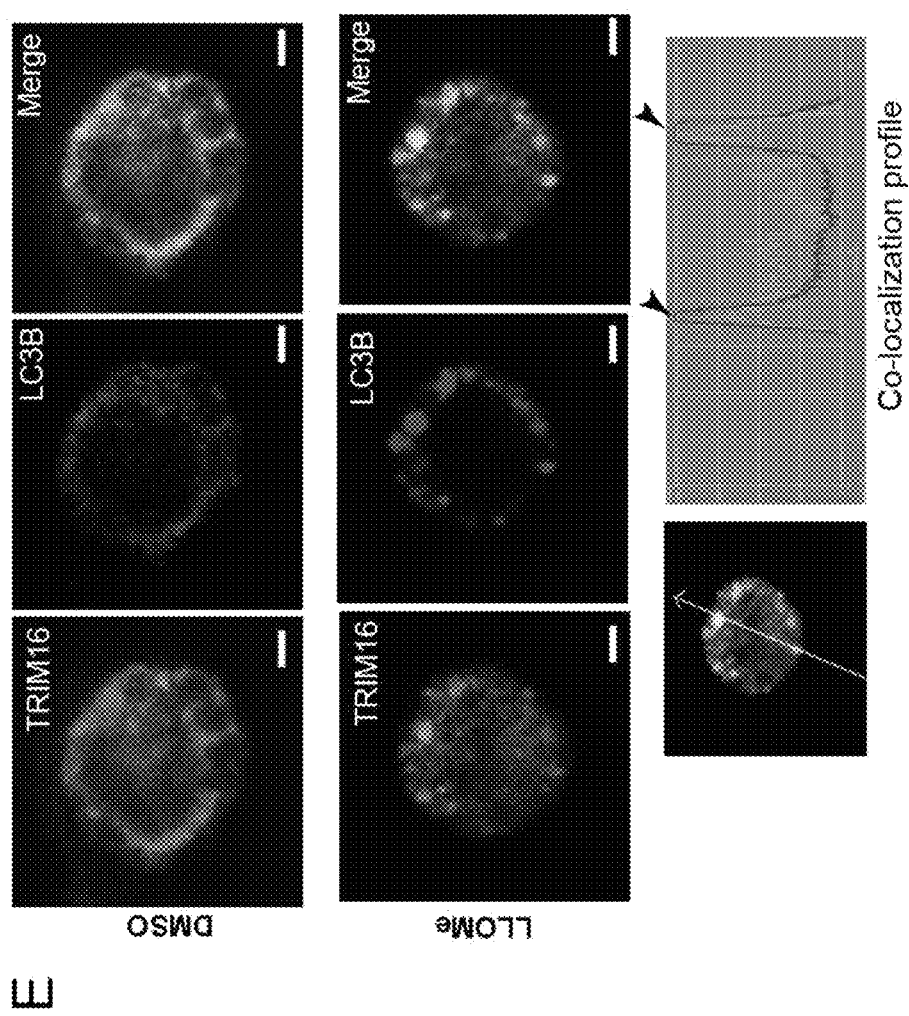
Figure 10:
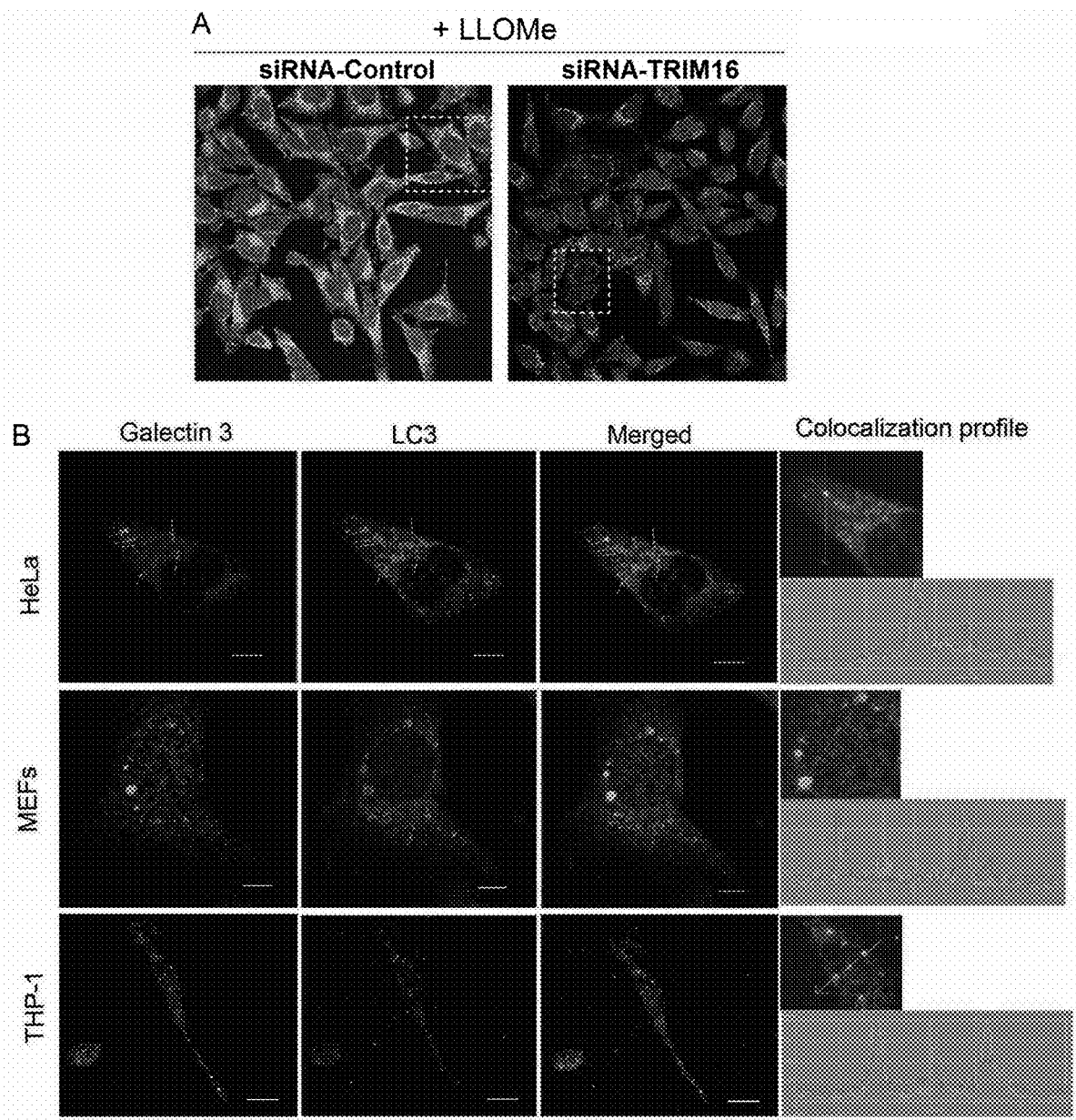

FIG. 10 (Related to FIG. 2) shows that TRIM16 is important for endomembrane damaged induced autophagy response. (A) Whole microscopic field of the images analyzed in FIG. 2A. (B) Galectin-3 puncta formation and colocalization analysis with the autophagosomal marker LC3 in THP-1, Mouse embryonic fibroblast, and HeLa cells. HeLa and MEFs were treated with 1 mM LLOMe for 2h, while MEFs were treated with 0.5 mM of LLOMe for 45 min.

Figure 11:
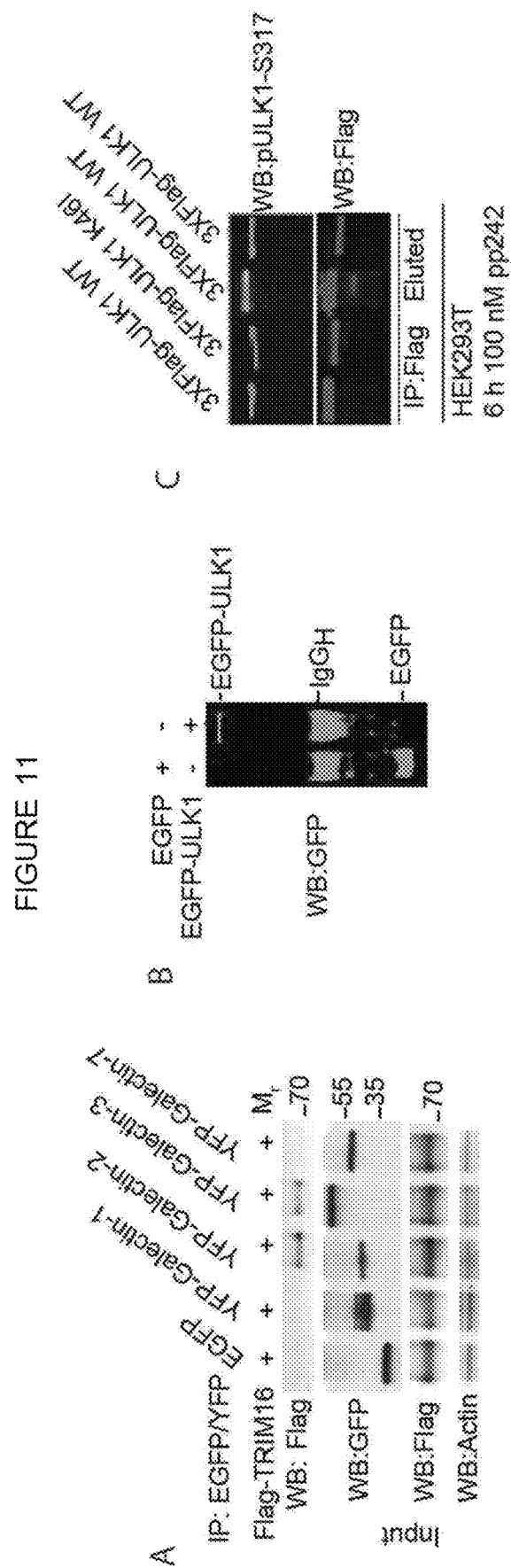
Figure 11:
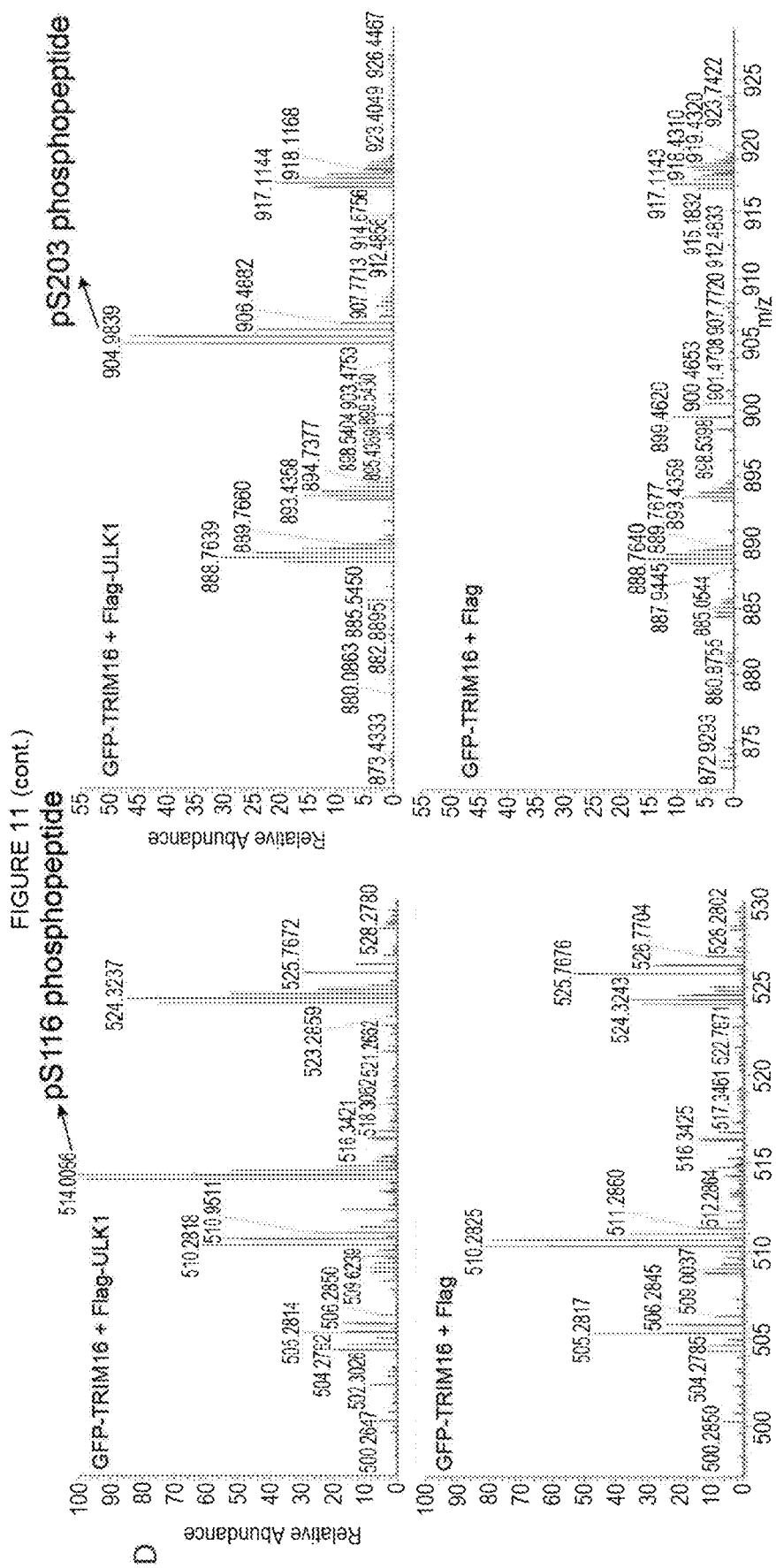
Figure 11:
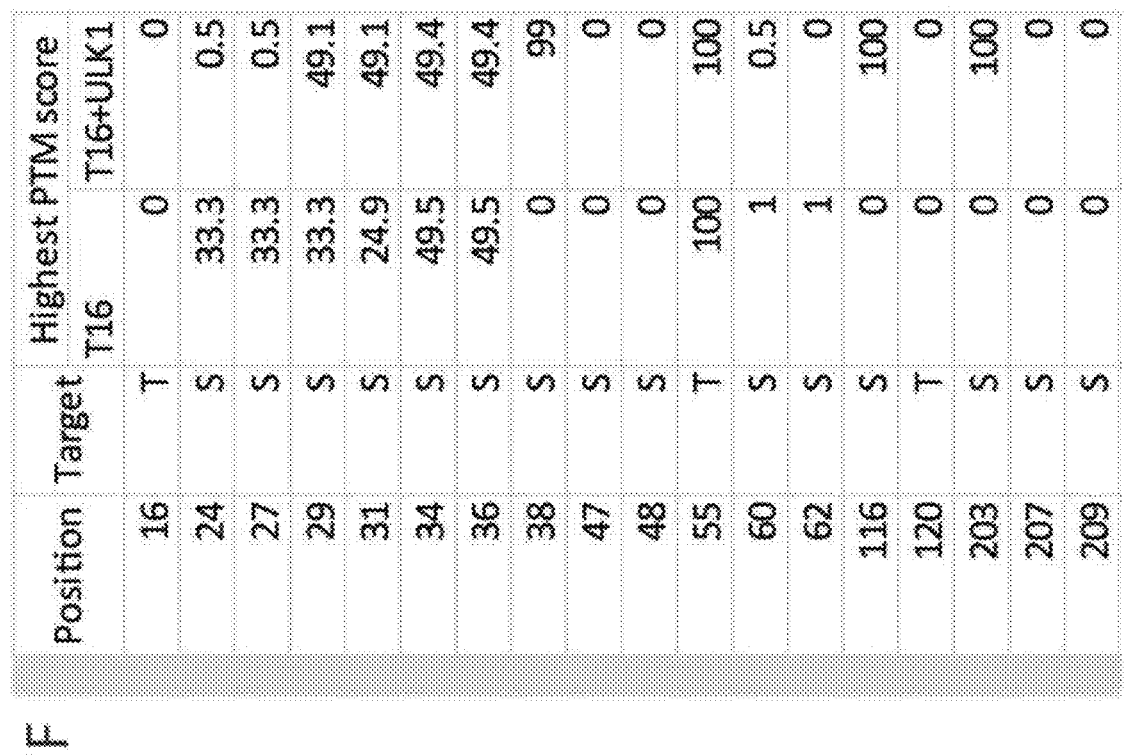

FIG. 11 (related to FIG. 3) shows co-immunoprecipitation analyses between TRIM16 and different Galectins and ULK1 preparations and identification of ULK1—dependent phospho-Ser residues on TRIM16. (A) Co-immunoprecipitation (Co-IP) analysis of interactions between TRIM16 and Galectins in HEK293T cell lysates expressing GFP or GFP-Galectin proteins (galectin-1, 2, 3 and 7) and fFlag-TRIM16. (B) EGFP-ULK1 preparation. (C) 3×flag-ULK1 preparation (wild type and enzymatically dead mutant K46I. (D) Mass spectra showing new peaks (514.009 and 904.982) appearing with GFP-TRIM16 in the presence of Flag-ULK1 fusion compared to Flag alone. (E) Annotated tandem mass spectra for fragmented precursor ions (514.009 and 904.982) from the scans shown in (D), demonstrating that the peptides are from phosphorylated TRIM16 (S116 and S203). (F) Table showing percentage probabilities of specific sites in TRIM16 being phosphorylated in an ULK1-dependent or ULK1-independent manner. (G,H) Ulk1/2 double knockout MEFs were treated with LLOMe and number of LC3 (G) or ubiquitin (H) puncta per cell determined by HC. HC data: means (n>3); t-test **, p<0.01.

Figure 4:
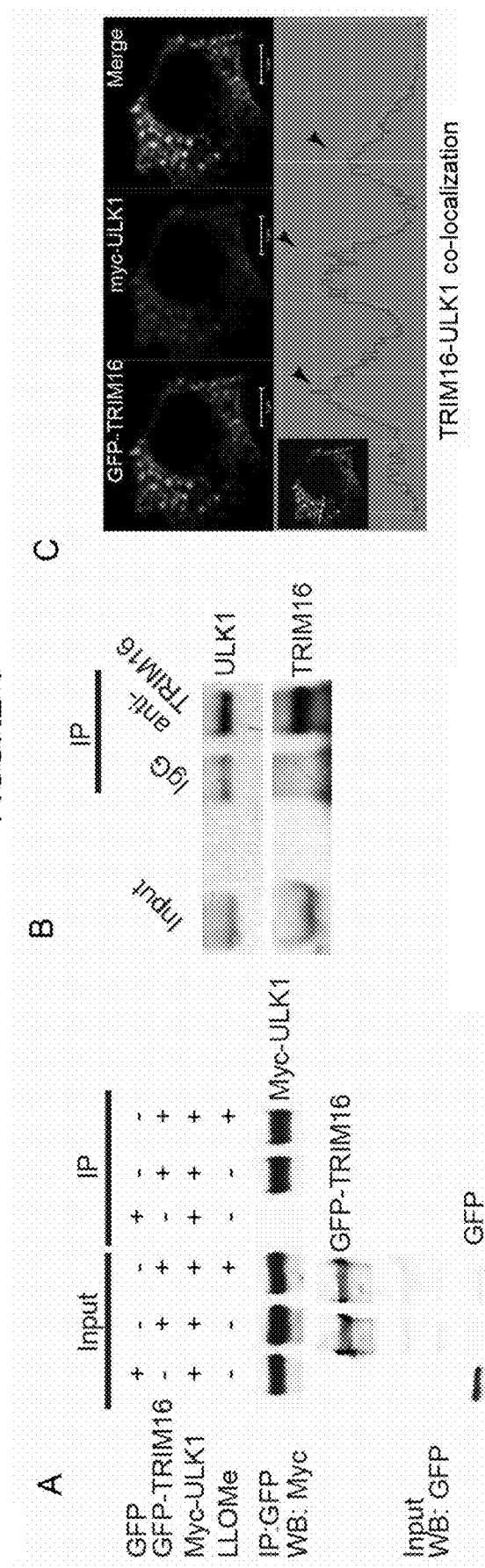
FIG. 4 shows that TRIM16 interacts, co-localizes with, and stabilizes ULK1 and Beclin 1. (A) Co-IP analysis of TRIM16 and ULK1 interactions in HEK293T lysates from cells expressing GFP or GFP-TRIM16 and Myc-ULK1. (B) Co-IP analysis of interactions between endogenous TRIM16 and endogenous ULK1 (HeLa lysates). (C) Confocal microscopy images of HEK293T cells transiently expressing GFP-TRIM16 and Myc-ULK1, and co-localization trace profiles. (D) HEK293T cell lysates co-expressing Myc-ULK1 and either GFP or GFP-TRIM16 were subjected to immunoblotting analysis. (E) Western blot analysis of relative abundance of endogenous ULK1 in wild type HeLa and CRISPR TRIM16KO HeLa derivative A9. (F) Analysis of ULK1 ubiquitination in cells co-expressing Myc-ULK1 and HA-tagged ubiquitin C mutated for all lysines except Lysine 63 (HA-K63) in the absence and presence of Flag-TRIM16. Immunoprecipitation was performed with K63 antibody followed by the Western blotting (WB) with indicated antibodies. (G) Confocal images of THP1 cells (treated with LLOMe); immunofluorescence with TRIM 16, ULK1 and ubiquitin antibodies. Right, co-localization tracer profile along the line indicated in the inset. (H) Co-IP analysis of interactions between TRIM16 and Beclin1 in HEK293T lysates of cells expressing GFP or GFP-TRIM16 and Flag-Beclin1. (I) Confocal images of HEK293T cells transiently expressing GFP-TRIM16 and Flag-Beclin 1. Co-localization profile tracer along line indicated in the enlarged region. (J) Analysis of Beclin 1 ubiquitination in cells co-expressing Flag-Beclin 1 and HA-tagged Ubiquitin C (HA-K63) and either GFP or GFP-TRIM16. IP, immunoprecipitation performed with Flag antibody, followed by WB (Western blotting) with indicated antibodies. (K) HEK293T cell lysates expressing Flag-Beclin 1 in absence and presence GFP-TRIM16 were subjected to immunoblotting with antibodies as indicated.
Figure 4:
Figure 4:
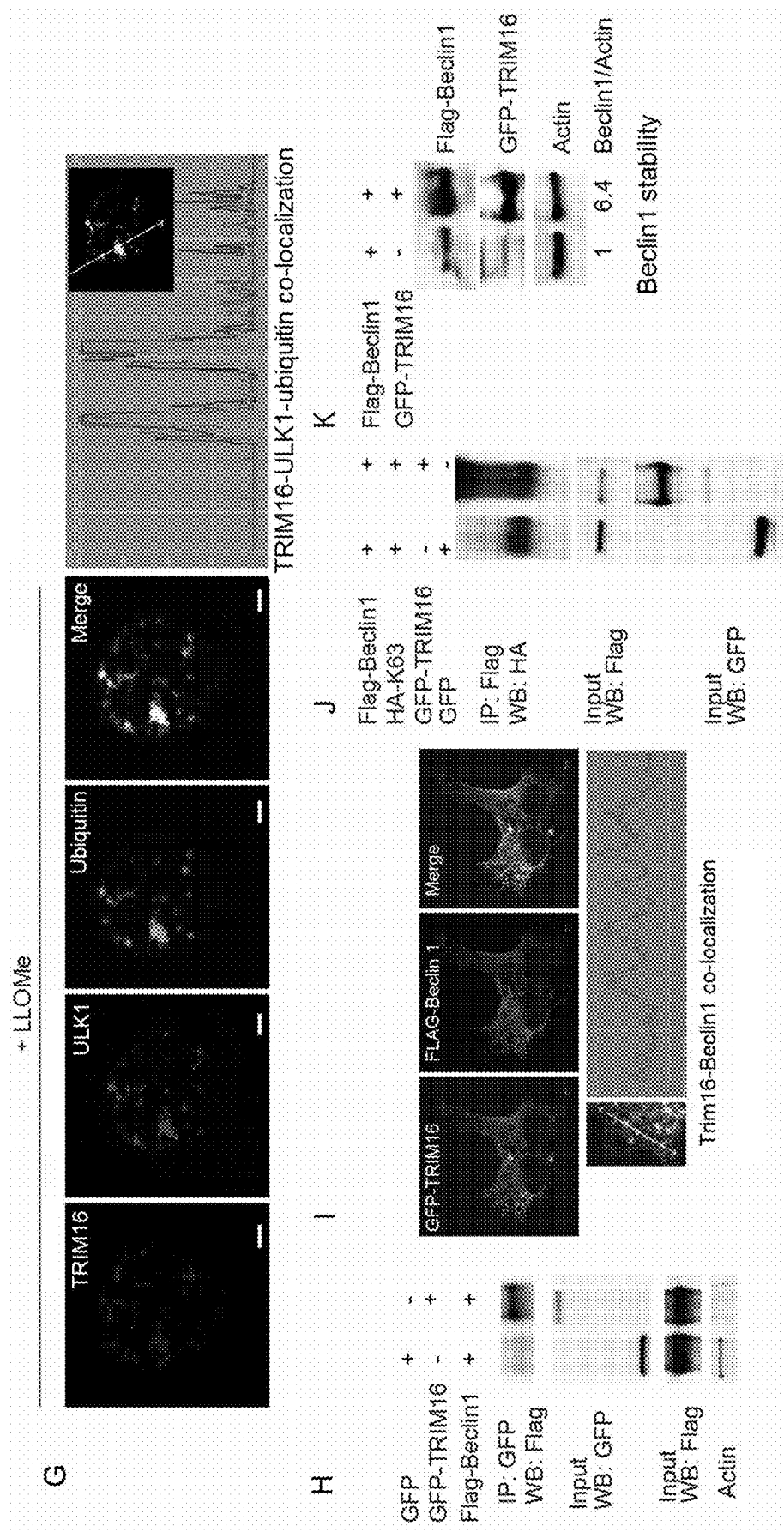
Figure 12:
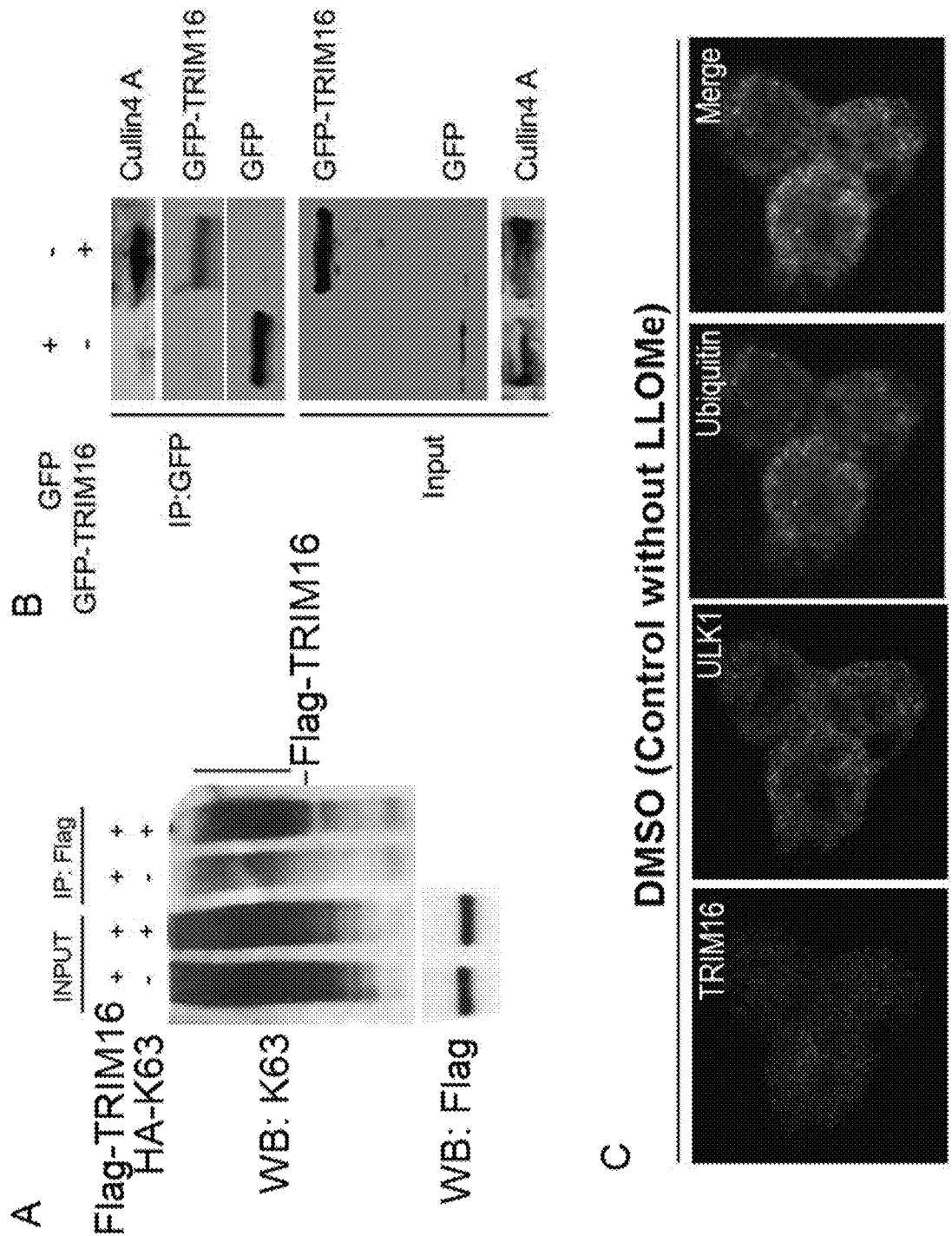

FIG. 12 (related to FIG. 4) shows an analysis of TRIM16 role in ubiquitination. (A) Analysis of TRIM16 ubiquitination in cells expressing flag-TRIM16 in absence and presence of HA-tagged ubiquitin C mutated for all lysine except Lysine 63 (HA-K63). Immunoprecipitation was performed with flag antibody followed by the Western blotting with indicated antibodies. (B) 293T cells transfected with GFP or GFP-TRIM16 were subjected to co-IP analysis as indicated. (C) Confocal images of DMSO treated THP-1 cells; immunofluorescence was performed with TRIM16, ULK1 and ubiquitin antibody.

Figure 5:
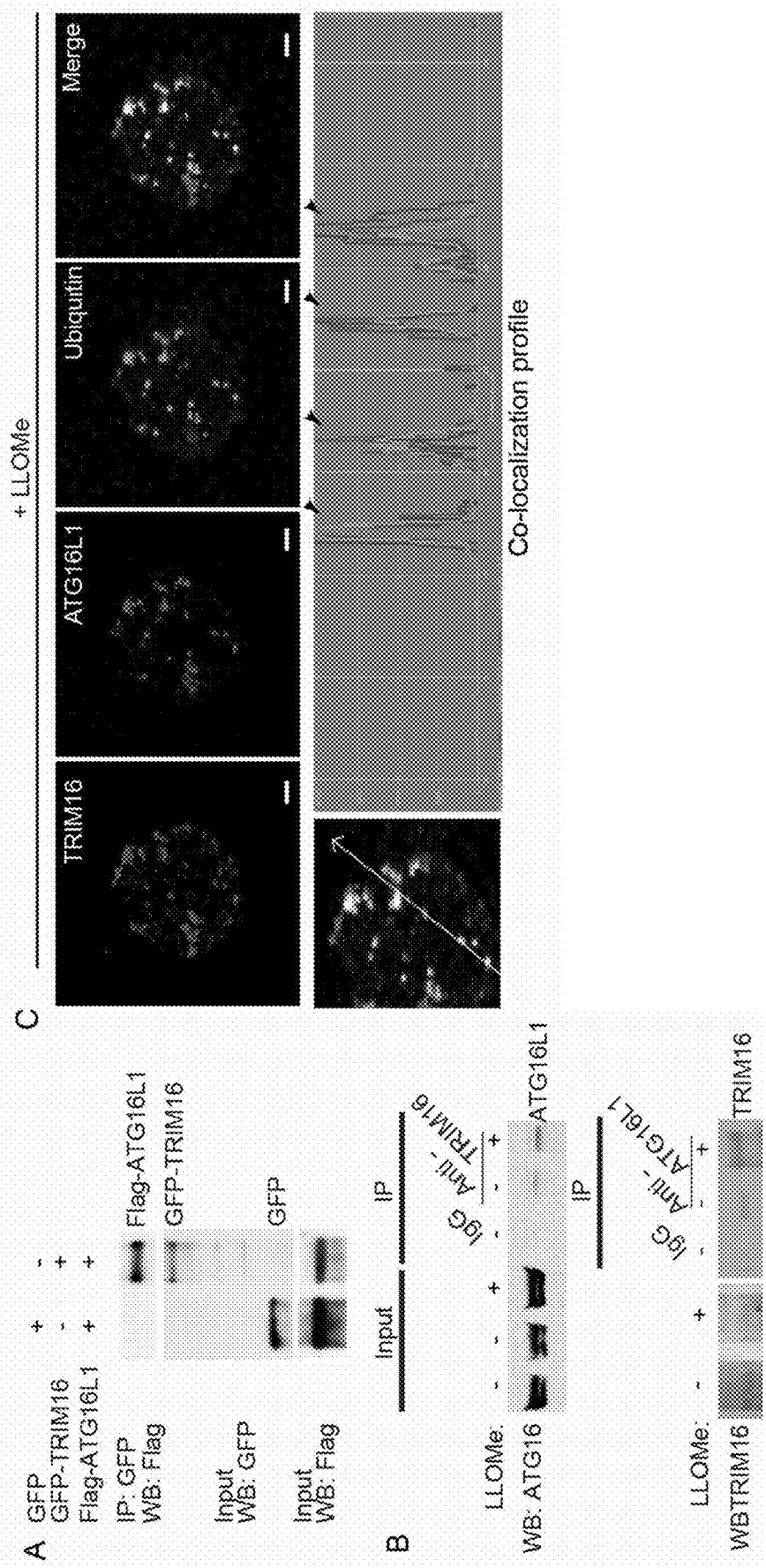
FIG. 5 shows that TRIM16 interacts with and recruits ATG16L1 in response to endomembrane damage. (A) Co-IP analysis of interaction between TRIM16 and ATG16L1 in HEK293T lysates from cells co-expressing GFP or GFP-TRIM16 with Flag-ATG16L1. (B) Co-IP and reverse Co-IP analyses of interaction between endogenous TRIM16 and endogenous ATG16L1 in resting and LLOMe-treated Hela cells. (C) Confocal images of THP1 cells treated with LLOMe and processed for immunofluorescence microscopy analysis with TRIM16, ATG16L1 and ubiquitin antibodies. Bottom, co-localization profile measurement along straight line using LSM510 software. (D) Co-IP analysis of interactions between TRIM16 and ATG16L1 from LLOMe treated and untreated HEK293T cell lysates co-expressing GFP or GFP-TRIM16 with Flag-ATG16L1. (E) Mapping of ATG16L1 regions interacting with TRIM16. Lysates of HEK293T cells co-expressing GFP-TRIM16 and Flag-ATG16L1 variants (see scheme, right panel) were subjected to immunoprecipitation with anti-GFP and blots were probed as indicated. (F) Confocal images of RAW264.7 macrophage cell line infected with Alexa-568-labeled *M. tuberculosis* Erdman and immunostained for ATG16L1 and TRIM16. (G) RAW264.7 cells were transfected with siRNAs against TRIM16 or control siRNAs for 48 h. Cells were then infected with Alexa-568-labeled *M. tuberculosis* Erdman for 4 h followed by immunofluorescence staining for ATG16L1. Data, means #SEM; n=3 (at least 100 phagosomes per condition); *, p<0.05 (t-test). Bar, 2 μm.
Figure 5:
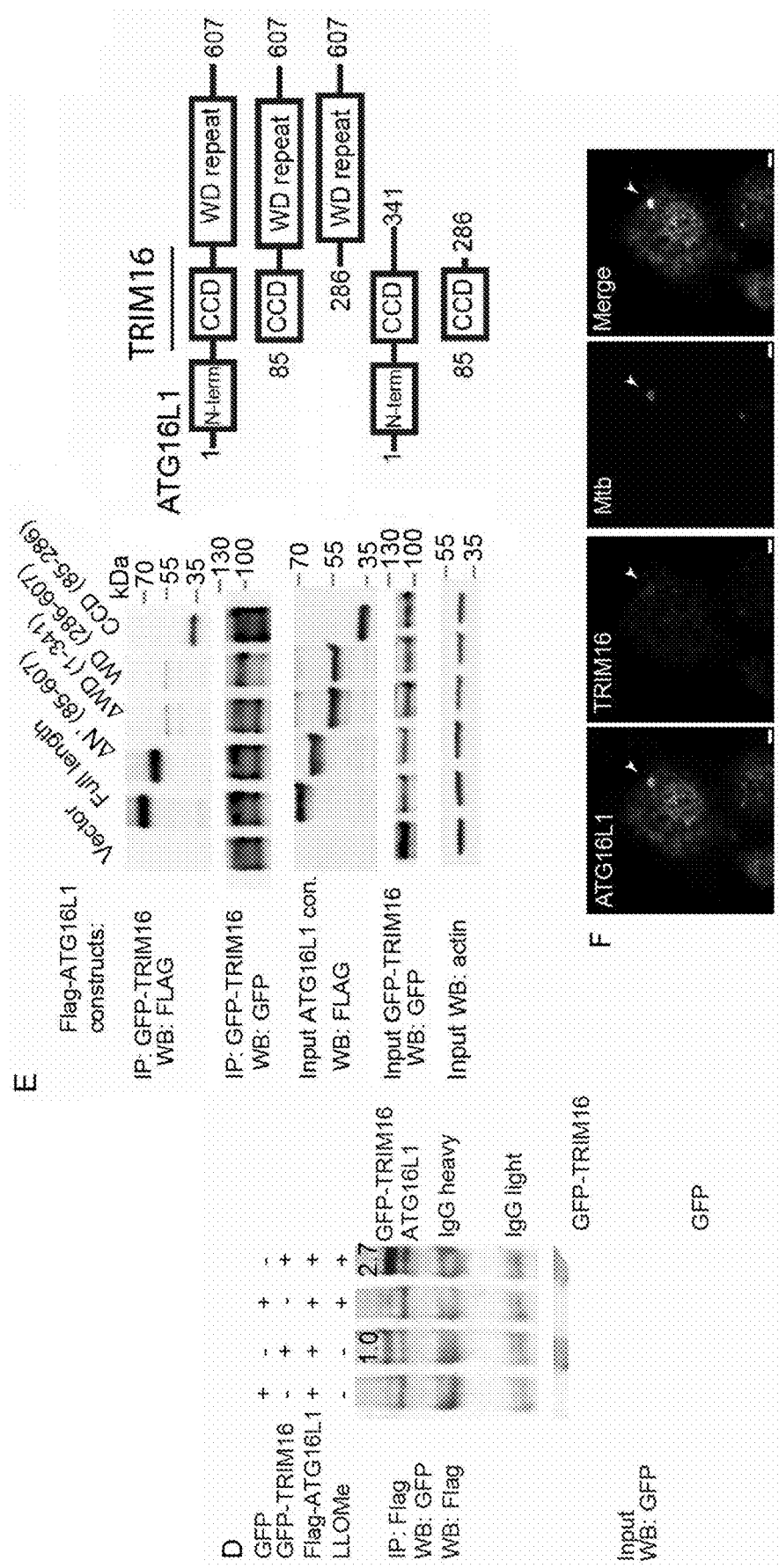
Figure 13:
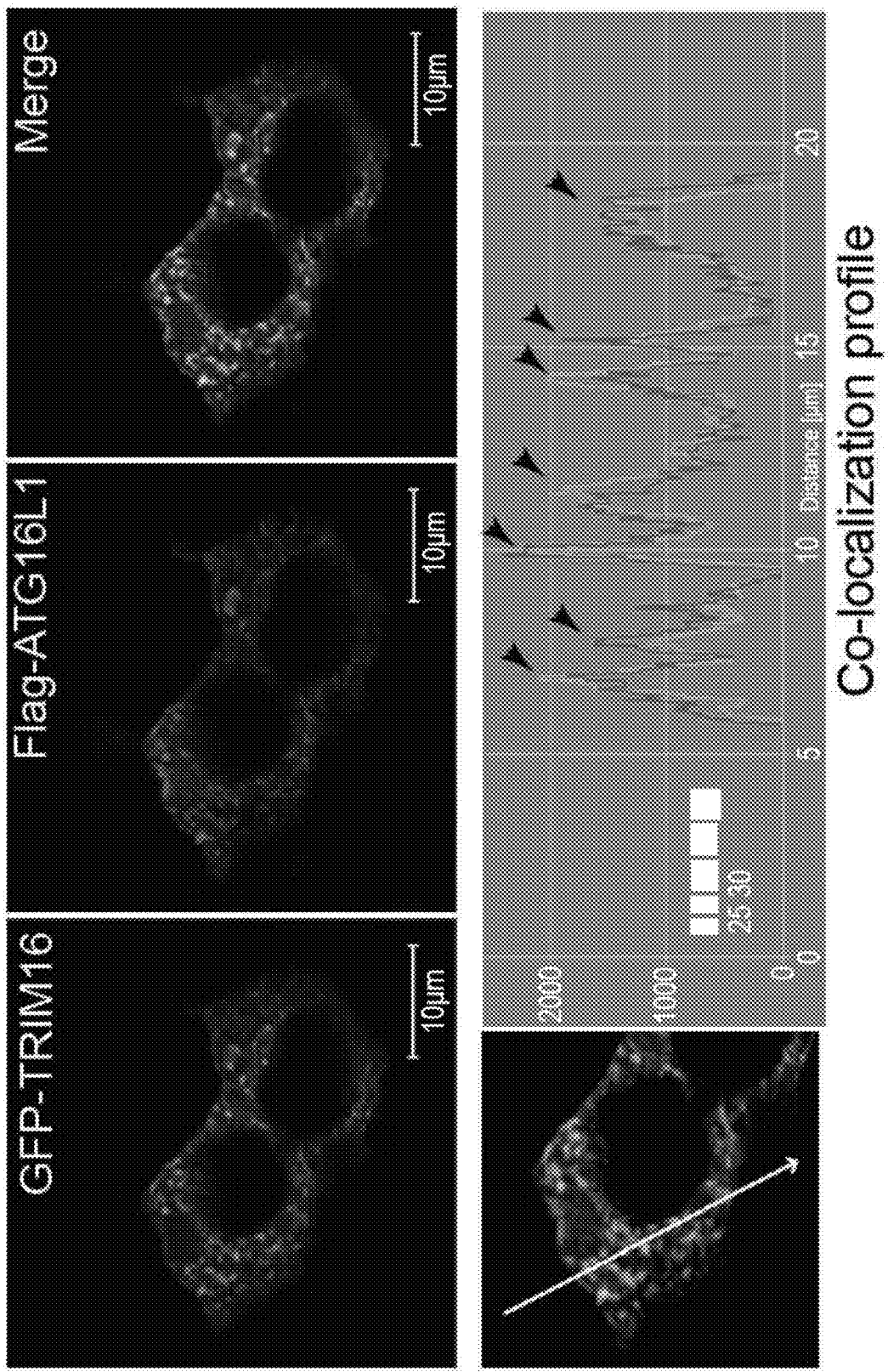
Figure 13:
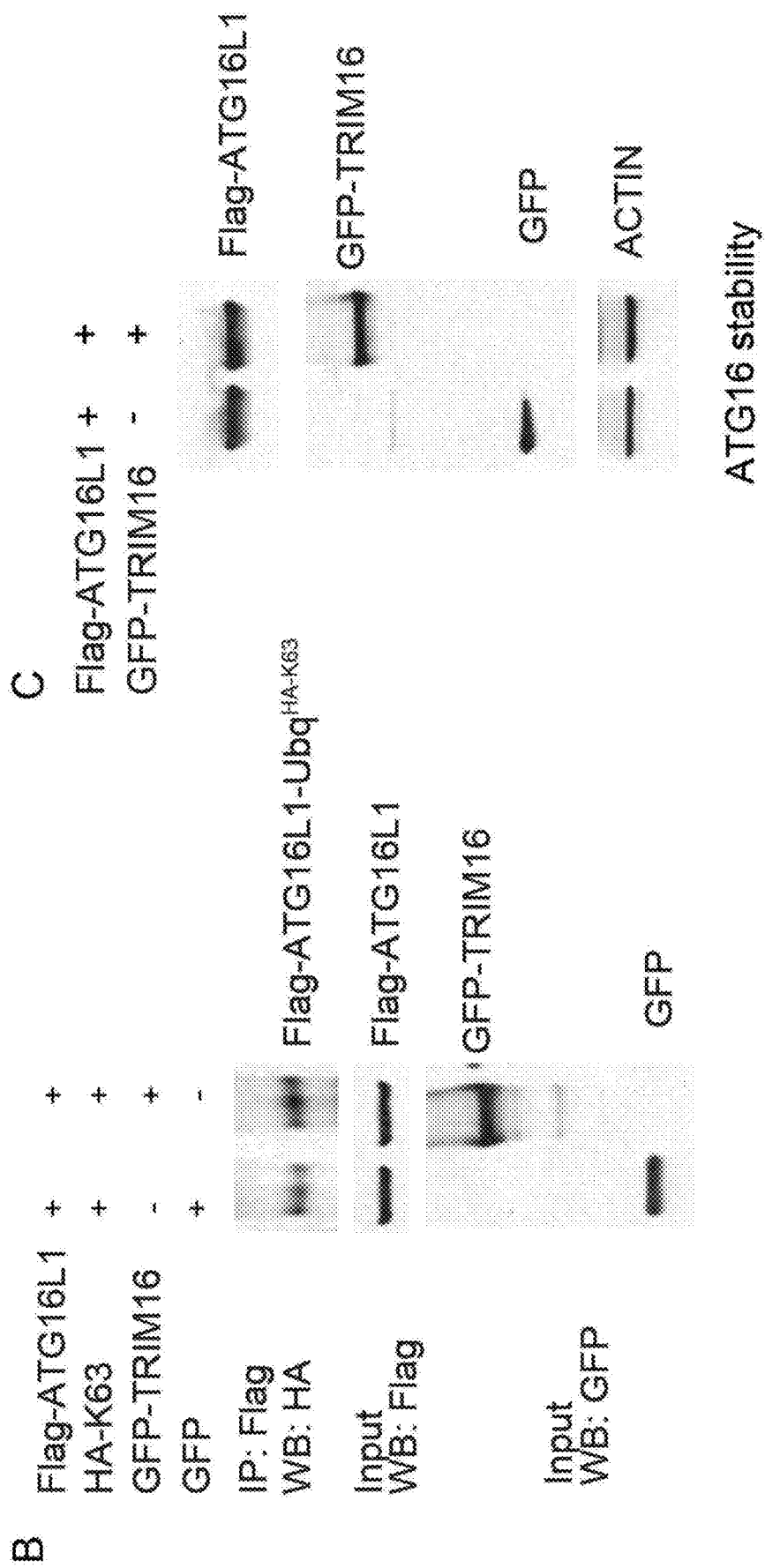
Figure 13:
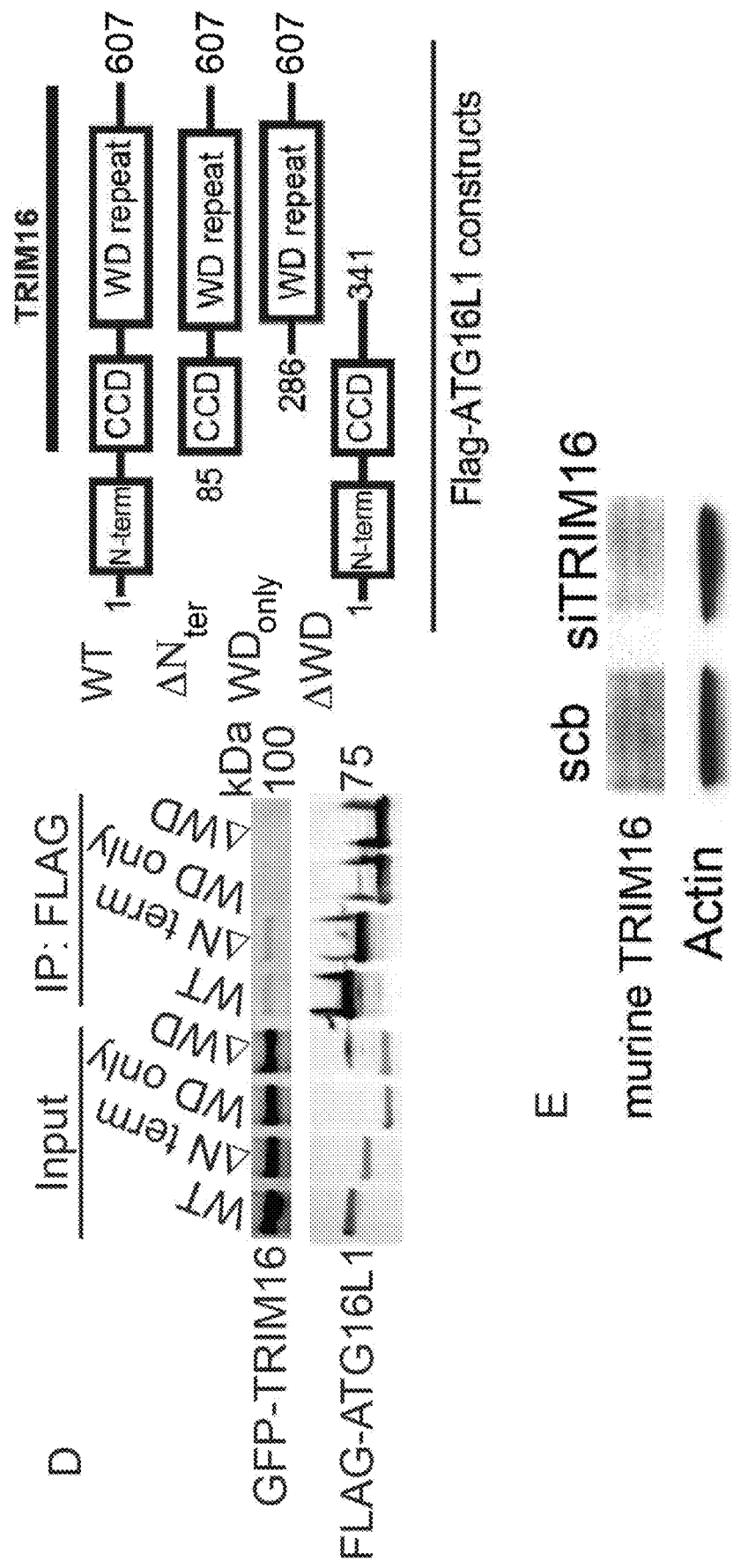

FIG. 13 (related to FIG. 5) shows that TRIM16 does not increase K63-linked ubiquitination and stability of ATG16L1 and domain mapping of TRIM16-ATG16L1 interactions.

(A) Top confocal microscopy images of HEK293T cells transiently expressing GFP-TRIM16 and flag-ATG16L1. Bottom, co-localization profile tracer along straight line generated using LSM510 software. (B) Analysis of ATG16L1 ubiquitination in cells co-expressing flag-ATG16L1, HA-K63 and GFP or GFP-TRIM16. Immunoprecipitation was performed with flag antibody followed by the Western blotting with indicated antibodies.

(C) Western blot analysis of total amount of ATG16L1 in presence and absence of TRIM16 in HEK293T cells transiently expressing Flag-ATG16L1 and GFP or GFP-TRIM16. (D) Left panel, lysates of HEK293T cells co-expressing GFP-TRIM16 and the indicated Flag-ATG16L1 variants (see right panel) were subjected to immunoprecipitation with anti-GFP and blots were probed as indicated. Right panel, schematic of ATG16L1 domain structure along with deletion constructs used in Co-IP analysis. (E) Western blot analysis of siRNA knock down efficiency of TRIM16 in RAW264.7 cells.

Figure 6:
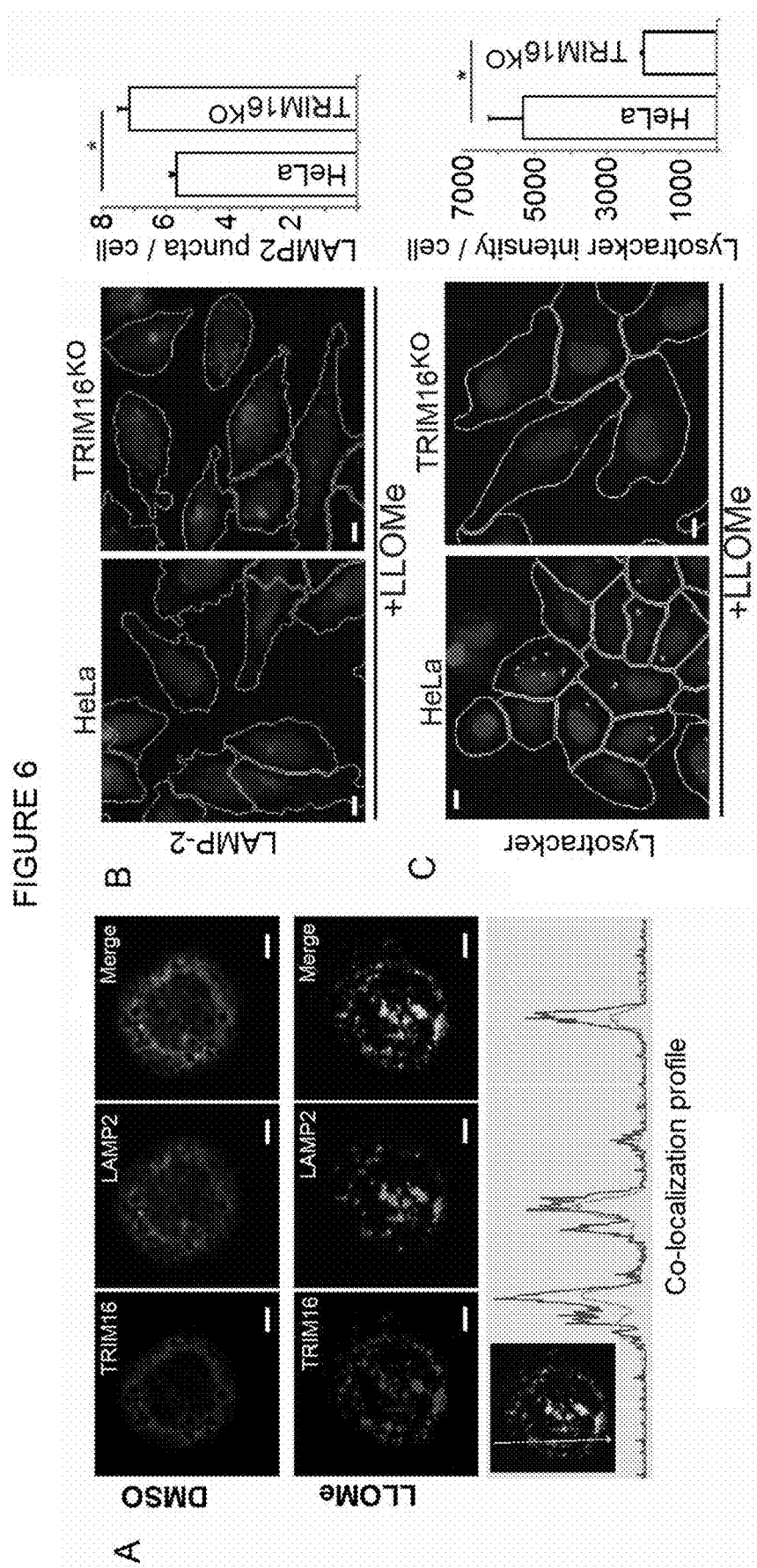
FIG. 6 shows that TRIM16 is required for lysosomal quality control and function. (A) Confocal immunofluorescence microscopy images of THP1 cells untreated or treated with 0.5 mM LLOMe and stained for endogenous TRIM16 and LAMP2. (B) HC analysis of lysosome abundance (green, anti-LAMP2 staining; blue, Hoeschst 3342 nuclear stain) in Hela cells or their CRISPR TRIM 1680 derivative A9 following 1 mM LLOMe treatment for 2 h. (C) HC analysis of lysosomal acidification (Lysotracker Red) in HeLa cells or their CRISPR TRIM16$^{KO}$ derivative A9 following 1 mM LLOMe treatment for 2 h. (D) HC analysis of nuclear partition of TFEB in resting HeLa cells vs. their CRISPR TRIM16KO derivative cells (A9), and translocation of TFEB to the nucleus upon LLOMe treatment. HC masks: pink, nuclei (blue, Hoechst stain), yellow, nuclear TFEB (green fluorescence, Alexa-488). Data: means (n>3); t-test *, p<0.05. All HC experiments were carried out in 96 well plates, with >12 wells/condition with >500 valid objects/well. (E) Co-IP analysis of interaction between GFP-TRIM16 and endogenous DEPTOR and Cullin-5 in HEK293T lysates from cells expressing GFP or GFP-TRIM16. (F) Levels of DEPTOR in extracts of HeLa cells subjected to LLOMe-induced lysosomal damage (1 mM LLOMe, 2_h) (G,H) Co-IP analysis of interactions between GFP-TRIM16 and endogenous RagB (G) or RagD (H) in HEK293T lysates from cells expressing GFP or GFP-TRIM16. (I) Co-IP analysis of interactions between GFP-TRIM16 and endogenous calcineurin catalytic subunit isoform β (PPP3CB) as in E. G and H. (J) Model of TRM16 action and consequences of its absence. Top, pictorial summary of relationships in wild type TRIM16 cells. Bottom, a depiction of what happens in the absence of TRIM16-dependent homeostatic repair of lysosomal membranes.
Figure 6:
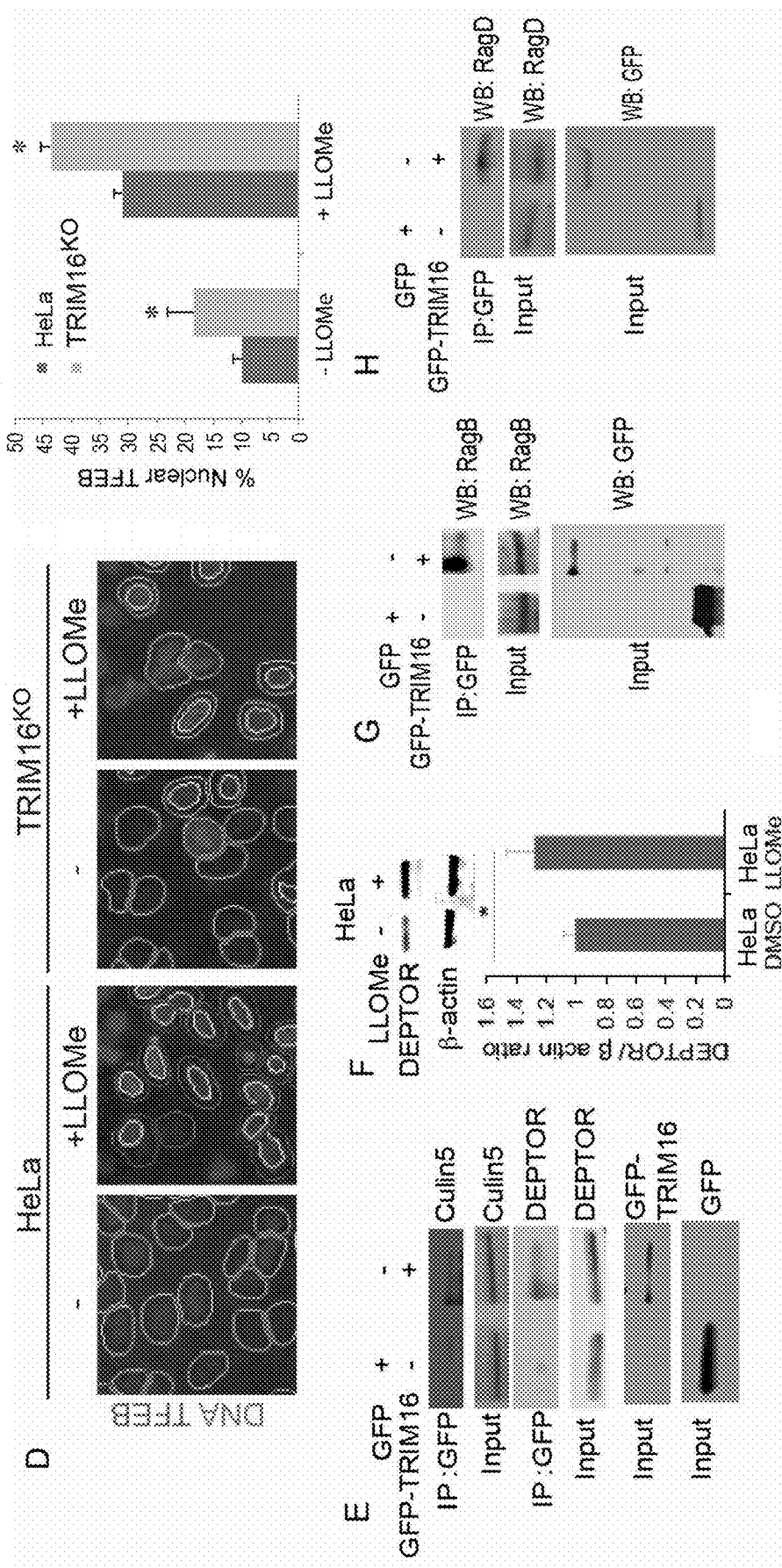
Figure 6:
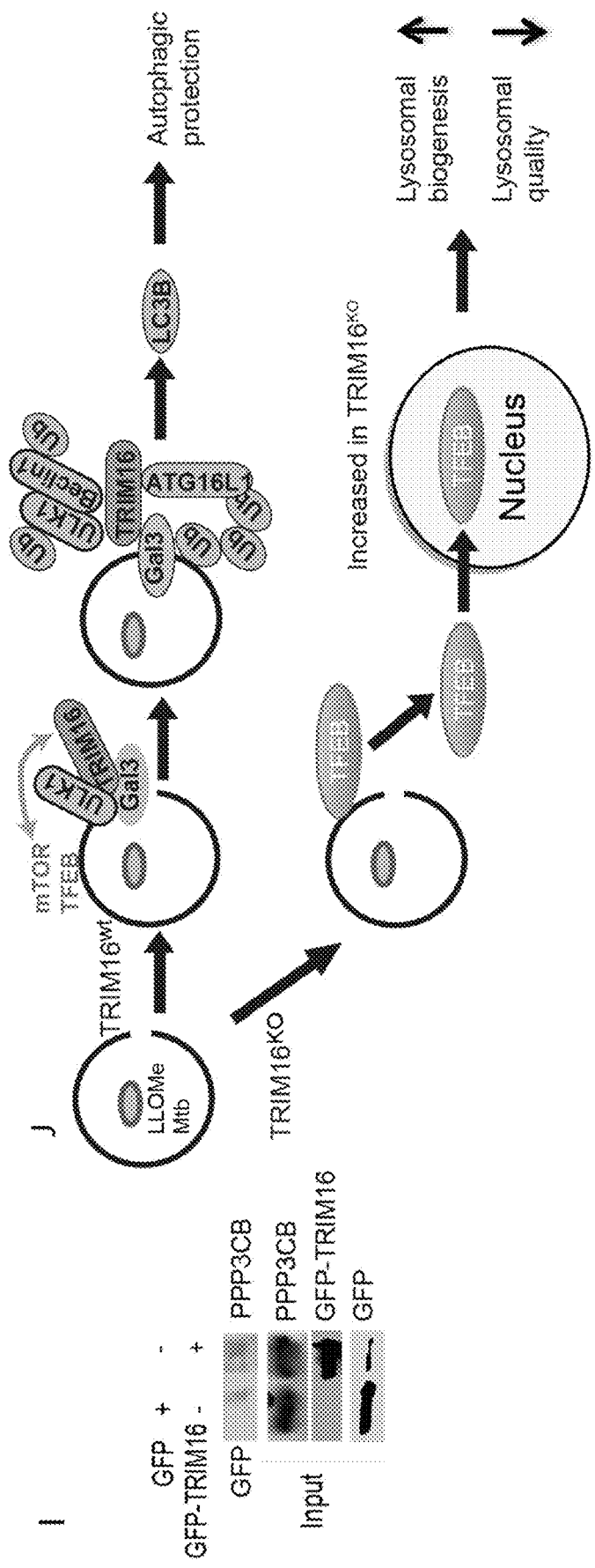
Figure 14:
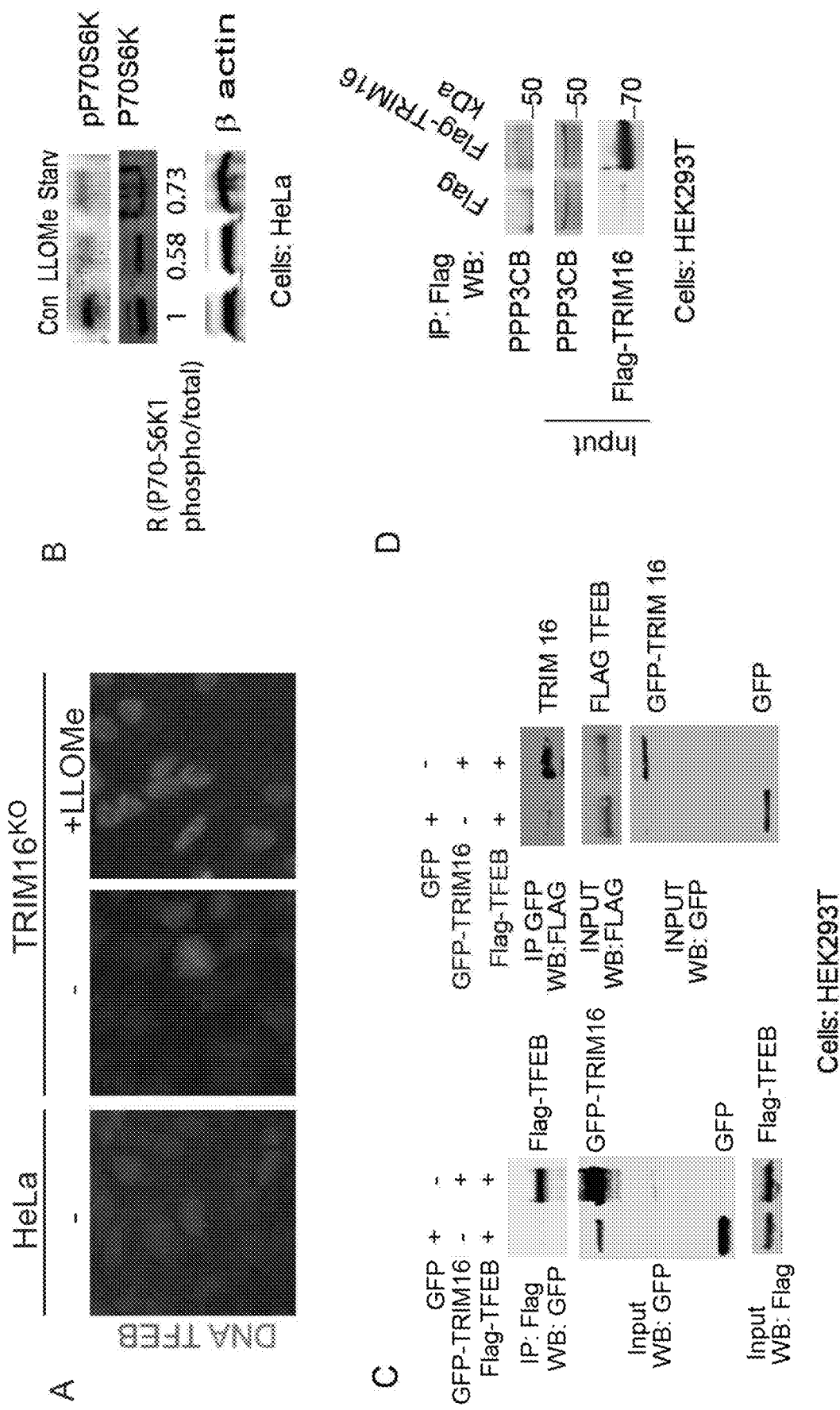

FIG. 14 related to FIG. 6. Comparison of nuclear TFEB partition in CRISPR TRIM16$^{KO}$ vs HeLa cells, detection and mapping of TRIM16 interactions with TFEB and calcineurin, and analysis of the role of Galecin-3, TRIM16 and ATG16L1 in acquisition of LAMP1 by M. tuberculosis phagosomes. (A) HC images with masks removed, corresponding to FIG. 6D. (B) Analysis of S6K1 phosphorylation (mTOR target) in Hela cells treated with LLOMe. Con, solvent DMSO control; LLOMe, 1 mM LLOMe, 2h incubation; Starv, starvation in EBSS for 2h. (C) Co-IP and reverse Co-IP analysis of interactions between GFP-TRIM16 and Flag-TFEB in HEK293T cells. (D) Co-IP analysis of interactions between Flag-TRIM16 and endogenous calcineurin catalytic subunit PPP3CB in HEK293T cells. (E,F) Mapping of the TRIM16 region required for it being in complexes with PPP3CB.

Figure 7:
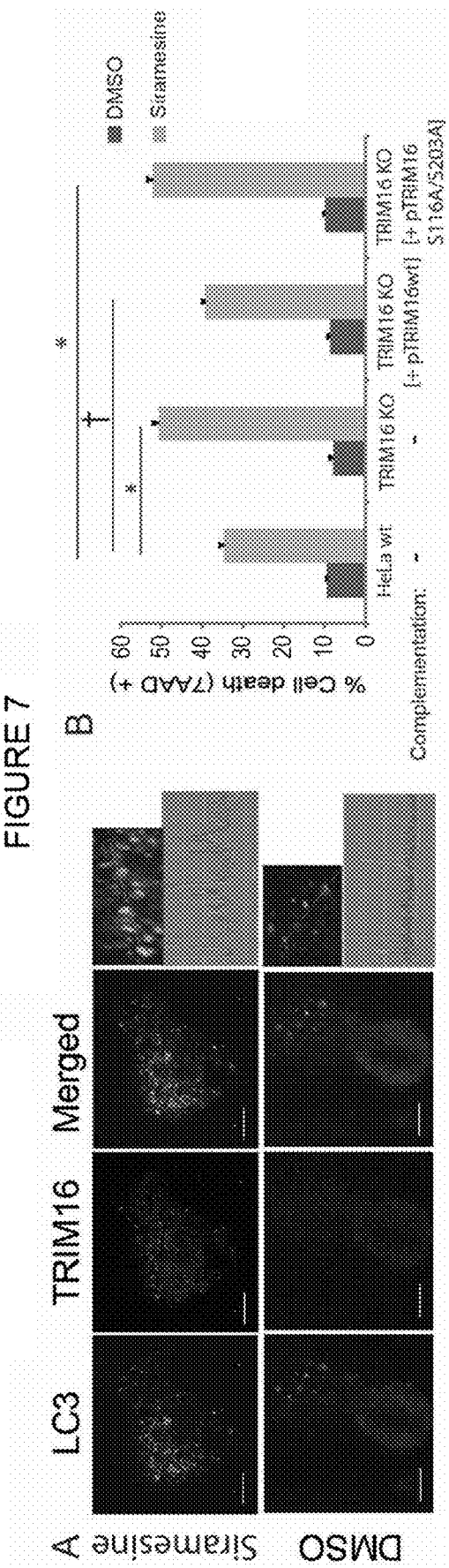
FIG. 7 shows that TRIM16-Galectin-3 system protects against endomembrane damage associated with lysosomal dysfunction and pathogen-mediated phagosomal perforation. (A) Confocal images of Hela cells treated with DMSO or siramesine; immunofluorescence, endogenous LC3B and TRIM16 revealed with corresponding antibodies. Graphs on the right, line tracing colocalization analyses. (B) HeLa, CRISPR TRIM16KO HeLa cells A9, or TRIM16$^{KO}$ HeLa cells A9 transfected with expression plasmids for wt TRIM16 or TRIM16$^{S116A/S203A}$ mutant were incubated with siramesine and cell death was measured using 7AAD nuclear staining. Data, means; n>3; †, p≥0.05*, p<0.05 (ANOVA). (C,D) RAW264.7 macrophages were infected with Alexa-568-labeled wild-type *M. tuberculosis* Erdman or its ESX-1 mutant at MOI=10 for 4 h and then processed for confocal microscopy analysis of *M. tuberculosis* (Mtb) colocalization with Galectin-3. Data, means±SEM (n>3; at least 100 Mtb phagosomes per condition were quantified); *, p<0.05 (t-test). Bar 2 μm. (E,F) RAW264.7 macrophages were infected with Alexa-568-labeled wild-type Mtb Erdman (WT) or its ESX-1 mutant at MOI=10 for 4 h and then processed for confocal microscopy analysis for the colocalization of Mtb with TRIM16. Data and statistics as in E. (G,H) RAW264.7 cells were infected with Alexa-568-labeled Mtb wild-type Erdman or its ESX-1 mutant for 4 h and then processed for immunofluorescence staining with anti-ubiquitin. Data and statistics as in D. (I) RAW264.7 macrophages were transfected with siRNAs against TRIM16 or control siRNAs for 48 h. Cells were then infected with Alexa-568-labeled wild-type Mtb Erdman for 4 h and processed for confocal microscopy analysis for the colocalization of Mtb with ubiquitin. Data and statistics as in D. (J) Time course of marker appearance on Mtb phagosomes; RAW264.7 macrophages were infected with Alexa-568-labeled wild-type *M. tuberculosis* Erdman at MOI=10 for 1 and 2 h and processed and data analyzed as in panels C-H. (K) Effectene-coated beads were phagocytosed by MEFs in 96 well plates, incubated for up to 24 h (>3h), stained with antibodies, and processed for HC microscopy (see images in FIG. 15D). Data: means (n>3); t-test *, p<0.05. Ninety six-well plates, with >12 wells/condition with >500 valid objects/well. (L) RAW264.7 cells were transfected with siRNAs against TRIM16, Galectin-3, or ATG16L1 or control siRNAs for 48 h. Cells were then infected with Alexa-568-labeled wild-type Mtb Erdman for 4 h followed by immunofluorescence staining for LAMP1 and % colocalization of Mtb phagosomes with LAMP1 determined (for representative images see FIG. 15G). Data, means±SEM (n=3; at least 100 Mtb phagosomes per condition were quantified). (M,N) RAW264.7 cells were transfected with siRNAs against Galectin-3 or control siRNAs for 48 h. Cells were then infected with Alexa-568-labeled wild-type Mtb Erdman for 4 h followed by immunofluorescence staining for ubiquitin. Data and statistics as in L. (O) Survival of wt C57BL and Galectin-3 C57BL knockout mice in a short-term acute infection model (high dose; 1-3×e$^3$ CFU) with *M. tuberculosis* Erdman aerosols. For data from a chronic model of infection with lower doses of *M. tuberculosis*, see FIG. 15J,K). (P) RAW264.7 cells were transfected with siRNAs against TRIM16, Galectin-3, or ATG16L1 or control siRNAs for 48 h. Cells were then infected with wild-type Mtb Erdman for 1 h (t=0) at MOI=10. Cells were then washed three times with complete medium to remove uninternalized mycobacteria and then continued to grow in complete medium for another 24 h (t=24). Cells were then harvested for CFU analysis of Mtb intracellular survival. Data, means #SEM of CFU at (=24 normalized to CFU at t=0 (n>3 independent experiments). *p<0.05 and **p<0.01, t-test relative to the scrambled (control) siRNA set at 100%.
Figure 7:
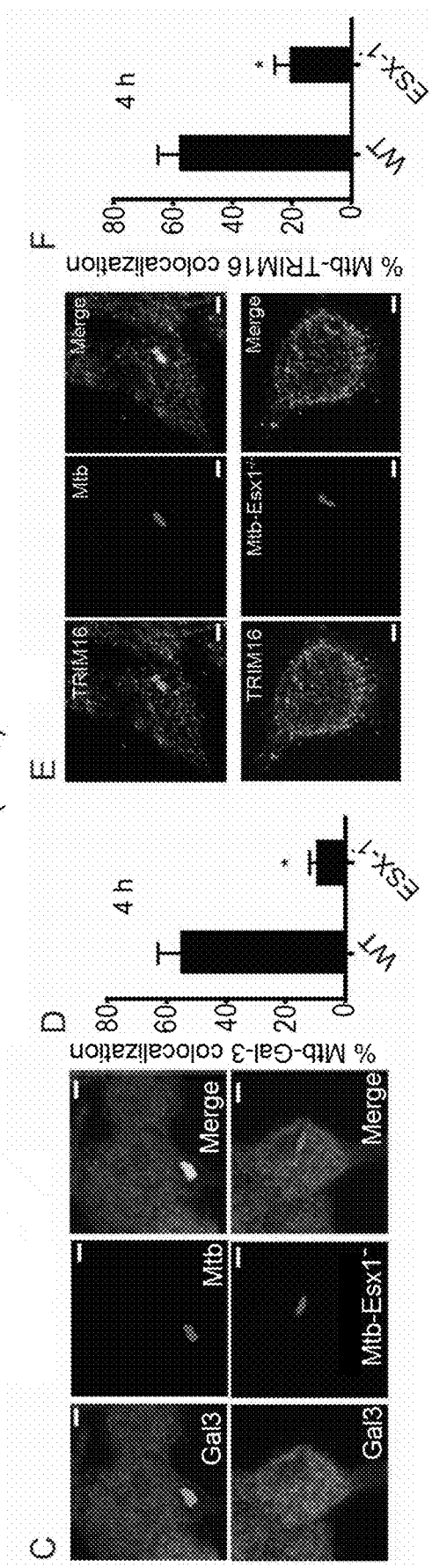
Figure 7:
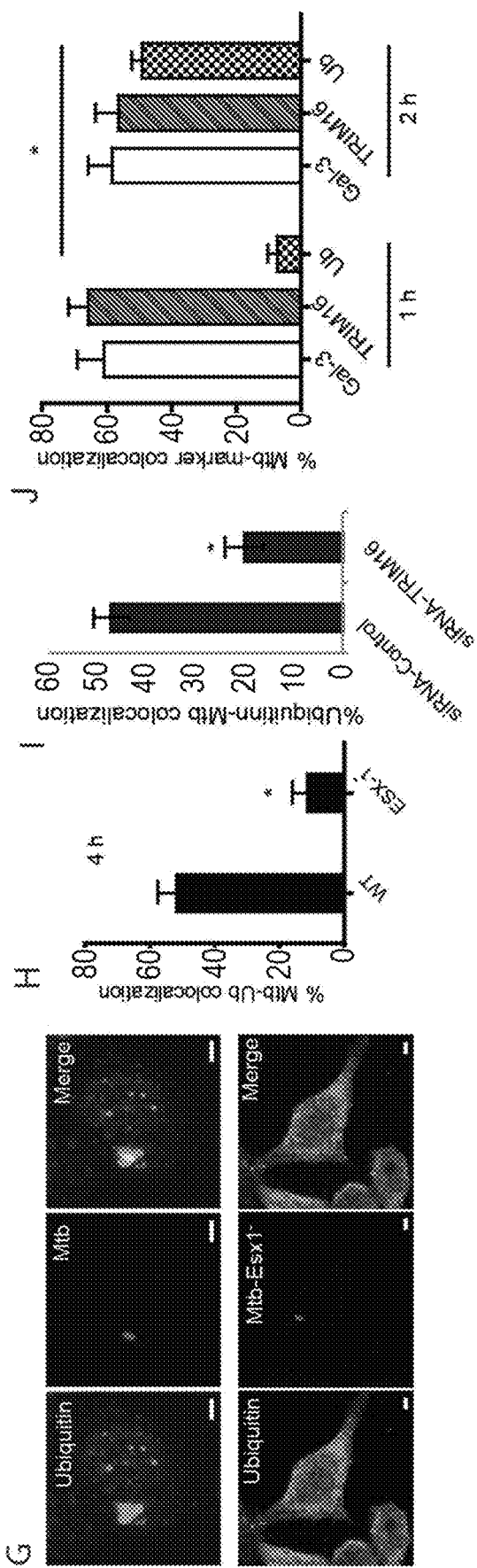
Figure 7:
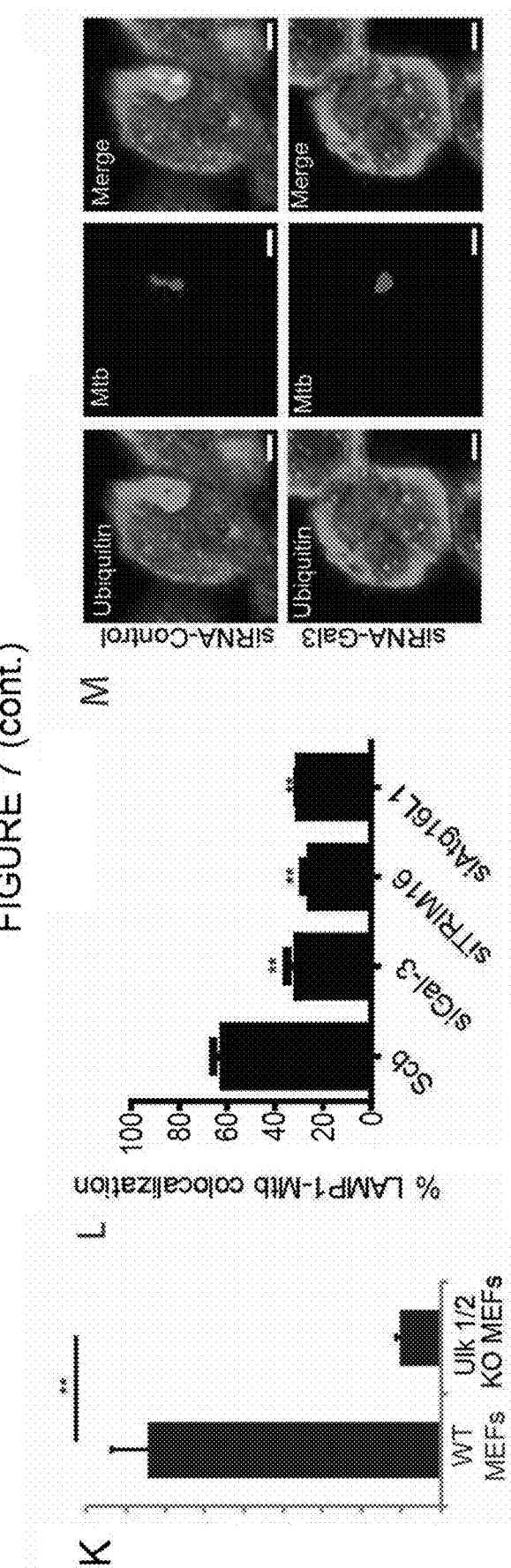
Figure 7:
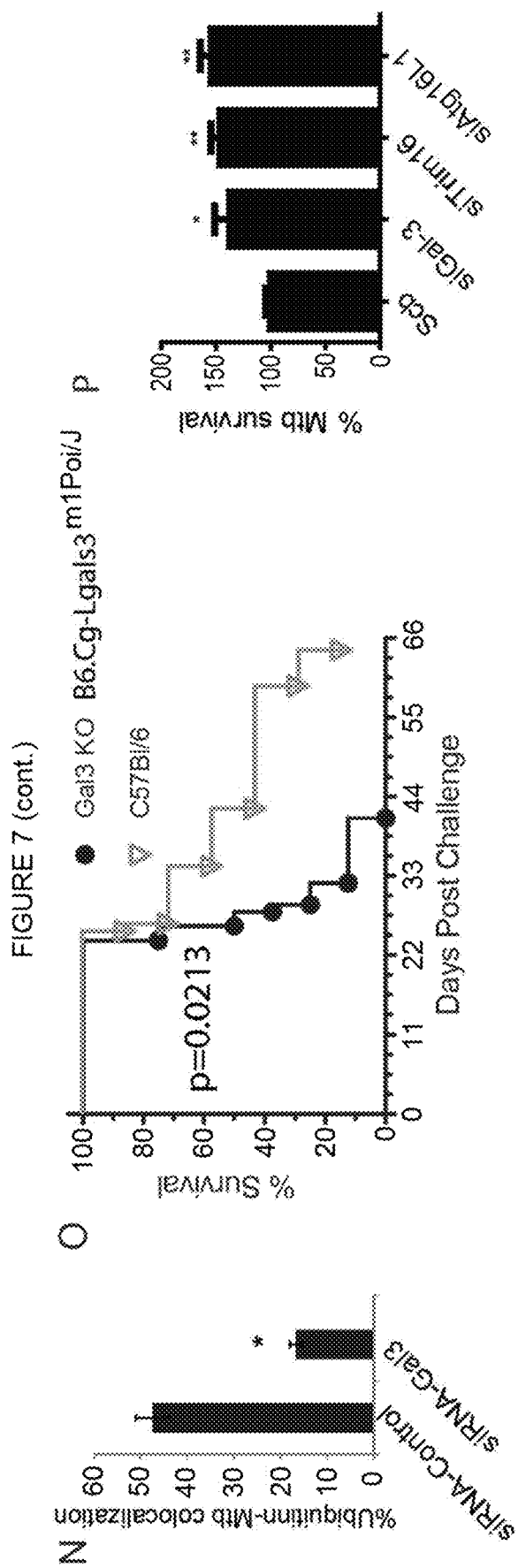
Figure 8:
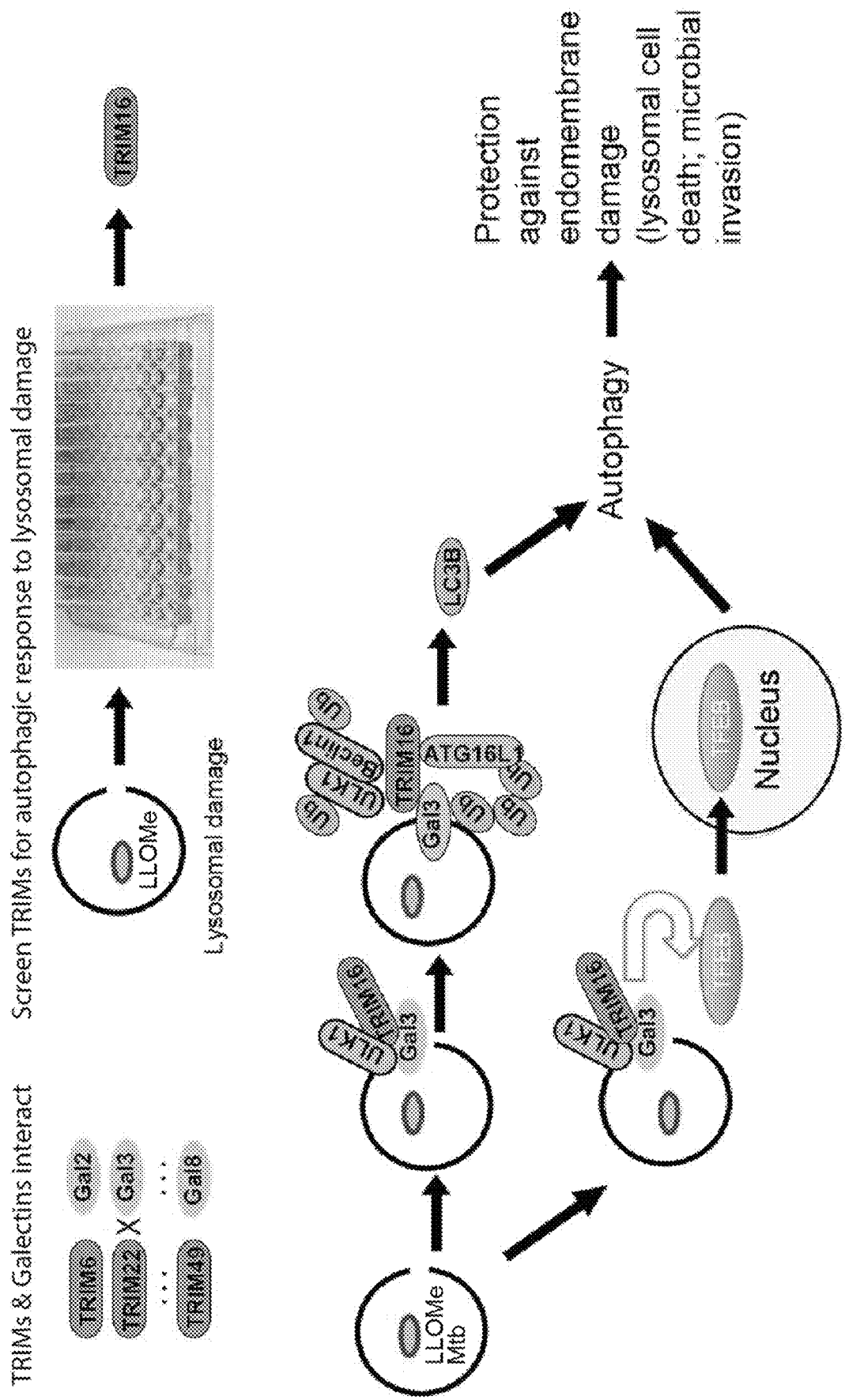
FIG. 8 shows the interation of TRIM proteins with Galectins and a proposed mechanism of action in autophagy.
Figure 15:
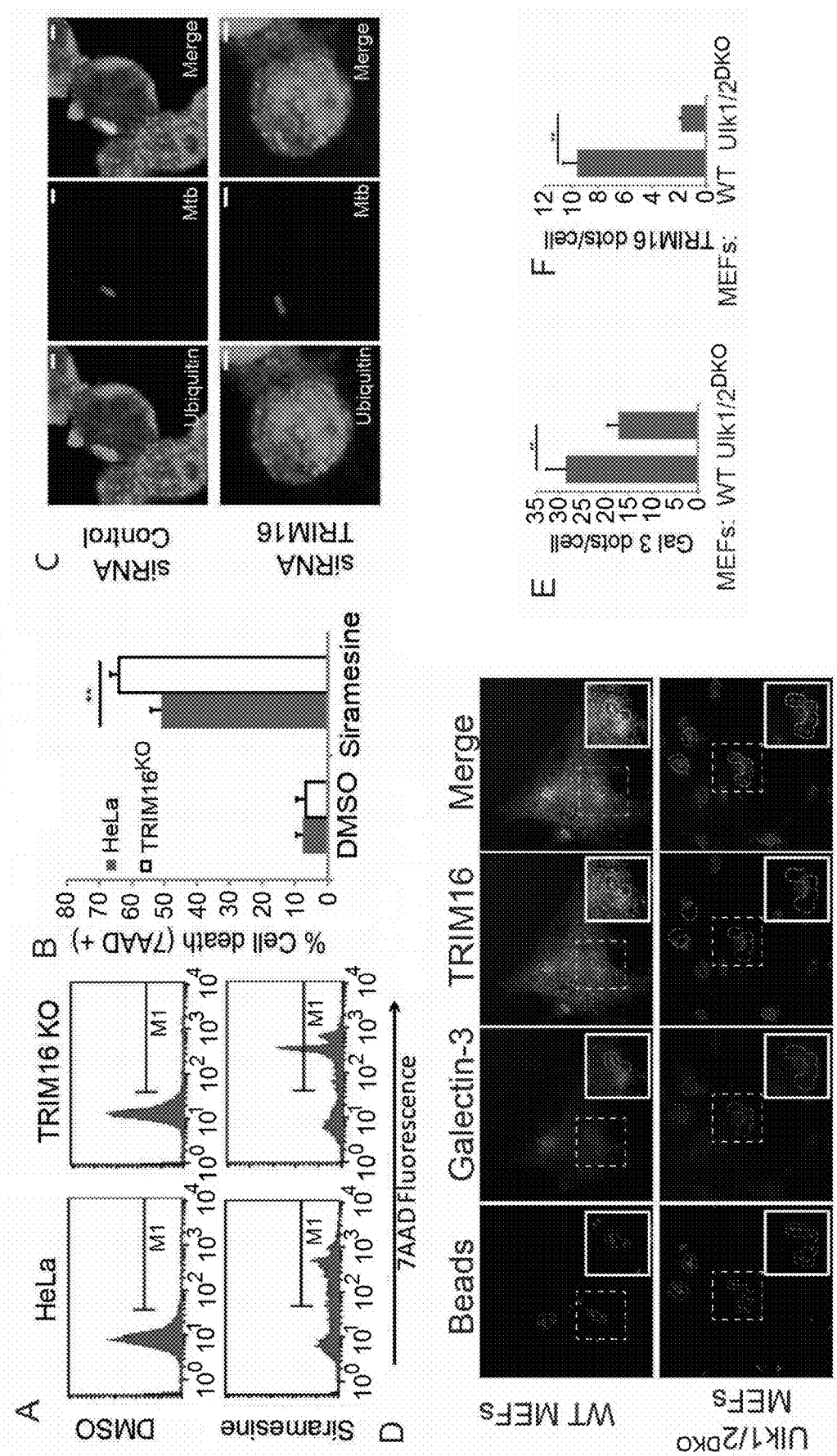
Figure 15:
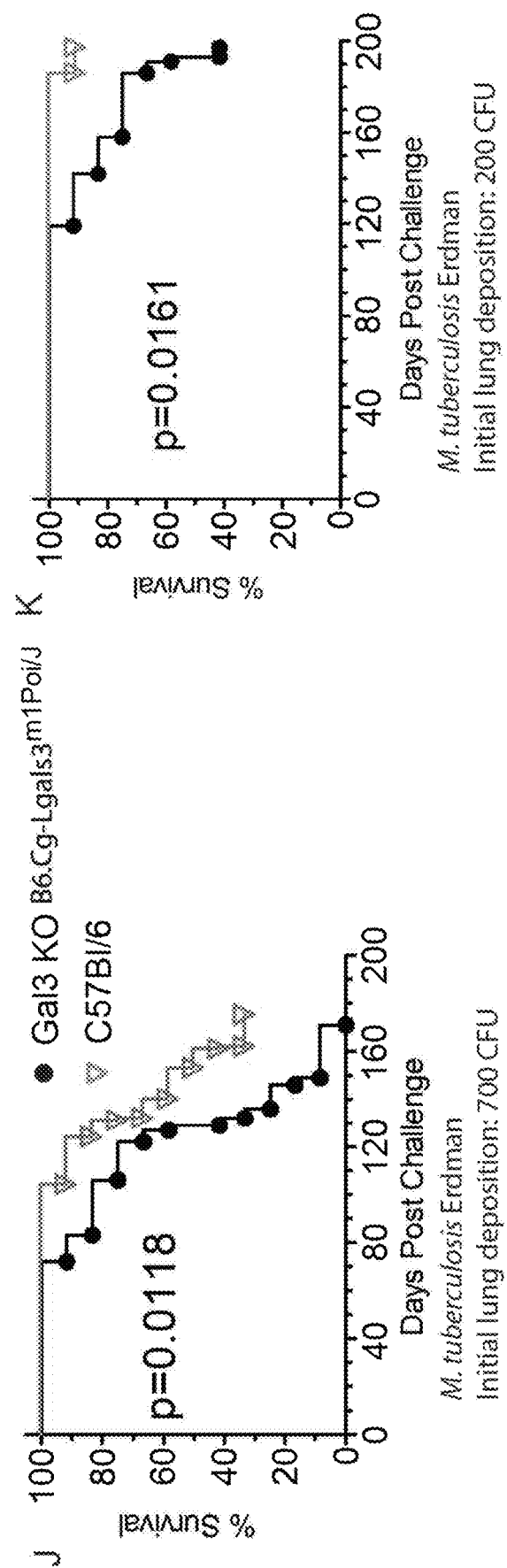

FIG. 15 related to FIG. 7. TRIM16, Galectin-3 and ATG16L1 colocalization on *M. tuberculosis* autophagolysosomes, and reduced survival of galectin-3 knockout mice infected with *M. tuberculosis* Erdman. (A, B) HeLa or CRISPR TRIM16KO Hela cells A9 were incubated with siramesine and cell death was measured using 7AAD nuclear staining. Data, means; n>3; **, p<0.01 (t-test). (C) RAW264.7 macrophages were transfected with siRNAs against TRIM16 or control siRNAs for 48 h. Cells were then infected with Alexa-568-labeled wild-type Mtb Erdman for 4 h and processed for confocal microscopy analysis for the colocalization of Mtb with ubiquitin. Images correspond to the graph in FIG. 7I. (D) Effectene-coated beads (fluorescence detected at 485 nm; rendered blue) were phagocytosed by wt or Ulk1/Ulk2 double KO MEFs in 96 well plates, incubated for 24 h, stained with antibodies (Galectin 3, fluorescence detected at 568 nm, rendered green; and TRIM16, far red fluorescence detected at 647 nm, rendered red), and imaging carried out and data processed by automated HC microscopy and analysis (graphs with data are shown in FIG. 7K. Arrows, Galectin-3 profiles colocalizing with TRIM16 on Effectene-beads. (E,F) Wild type and ULK1/2 KO MEFs were transfected with effectene coated beads for 24 h and incubated with Galectin 3 (E) or TRIM 16 (F) and imaging and data analysis carried out by automated HC microscopy and data analysis. (G) (Representative images for the data in FIG. 7L. Confocal images of RAW264.7 cells infected with Alexa-568-labeled wild-type Erdman and immunostained for LAMP1. Bar, 2 μm. (H,I) Confocal images of RAW264.7 cells infected with Alexa 568-labeled wild-type Erdman and immunostained for TRIM16, LAMP1, and Galectin-3, as indicated. Bar, 2 μm. (J,K) Survival curves of C57BL mice and their galectin-3 knockout derivative in a chronic model of respiratory infection with *M. tuberculosis*; medium dose, 600 CFU (J) and low dose, 200 CFU (K) of initial bacterial *M. tuberculosis* Erdman lung deposition following exposure to aerosols.

Figure 1:
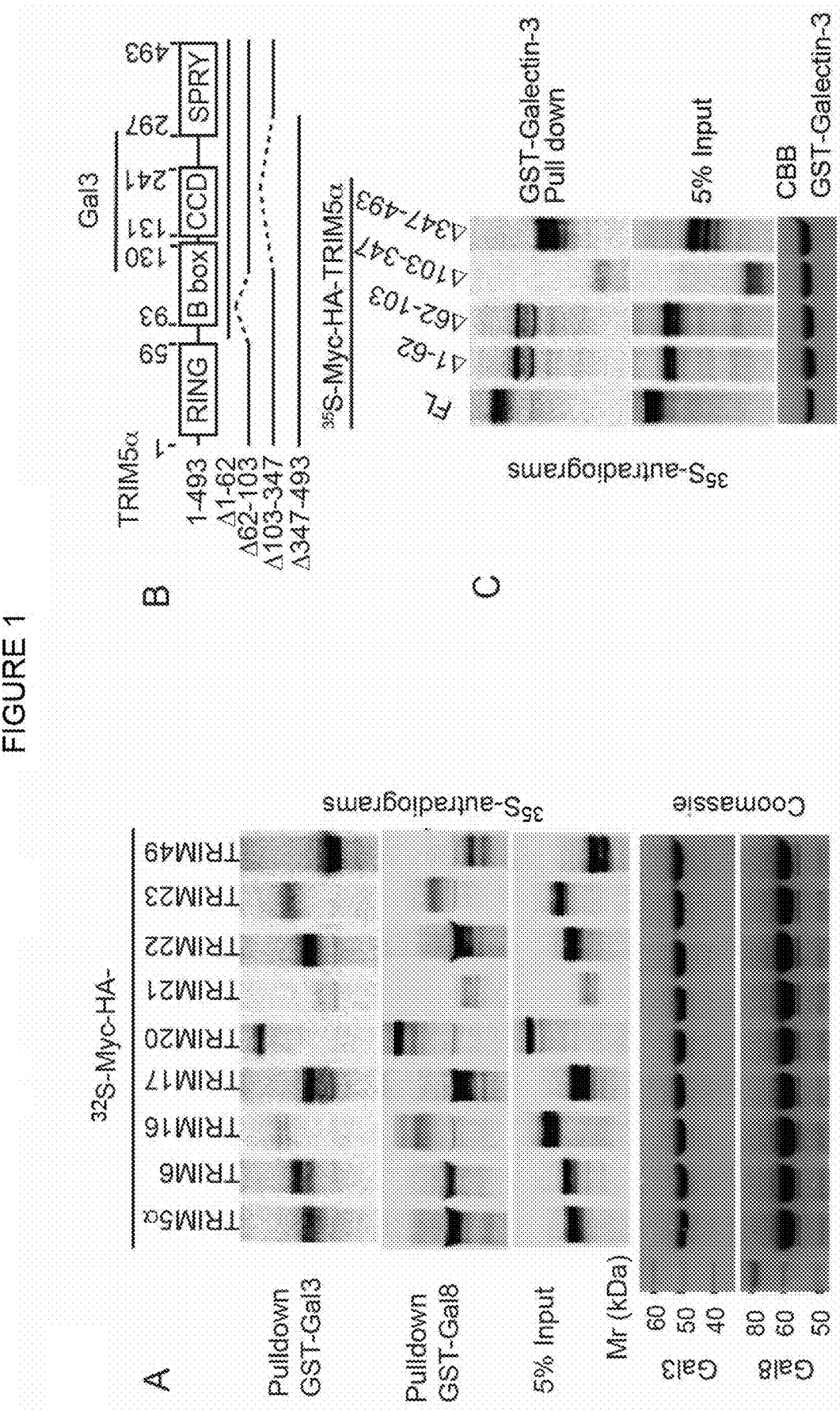
FIG. 1 shows that TRIMs and Galectins interact. (A) GST pulldowns of in vitro translated and radiolabeled $^{35}$S-Myc-HA-TRIMs (as indicted) with GST-Galectin-3 and GST-Galectin-8. (B) Mapping of Galectin-3 interaction domain within TRIM5α. Deletion constructs of TRIM5a used in C. (C) TRIM5α constructs depicted in B were radiolabeled as in A and subjected to GST-pulldowns, with GST-Galectin-3. (D-E) siRNA screen of human TRIMs (identified by TRIM numbers) for effects on LLOMe-induced autophagosome formation by high content microscopy and automated image acquisition and quantification (HC). Panels in D, program-assigned masks superimposed on epifluorescent images of HeLa cells treated with LLOMe or DMSO vehicle. Pink mask, automatically defined cell boundaries (primary objects). Blue, nuclei stained with Hoechst 3342 (10 ng/ml). Red mask, machine identified endogenous LC3 puncta (target objects). Scale bar, 10 μm. Graph in E, Autophagosome abundance (total area of endogenous LC3 puncta/cell; staining with 1:500 antibody against LC3B; PM036 from MBL) in cells subjected to TRIM knockdowns in 96 well plates and treated with 0.5 mM LLOMe for 2 h (E). Dashed line, 2 SD below the mean (cumulative, LC3 puncta area/cell) for all TRIMs tested. N≥500 cells imaged per well. (F-H) Autophagic response (HC, LC3 puncta) to LLOMe (0.5 mM, 2 h) in HeLa cells and their CRISPR TRIM16$^{KO}$ mutant derivative A9. (I-K) Ubiquitination response, revealed with FK2 mouse monoclonal antibody (1:500 dilution; MBL D058-3) and quantified by HC (ubiquitin puncta, yellow mask) in HeLa vs. TRIM16$^{KO}$ HeLa mutant A9. Same conditions as in F-H. Data: means (n>3); t-test *, p<0.05.
Figure 1:
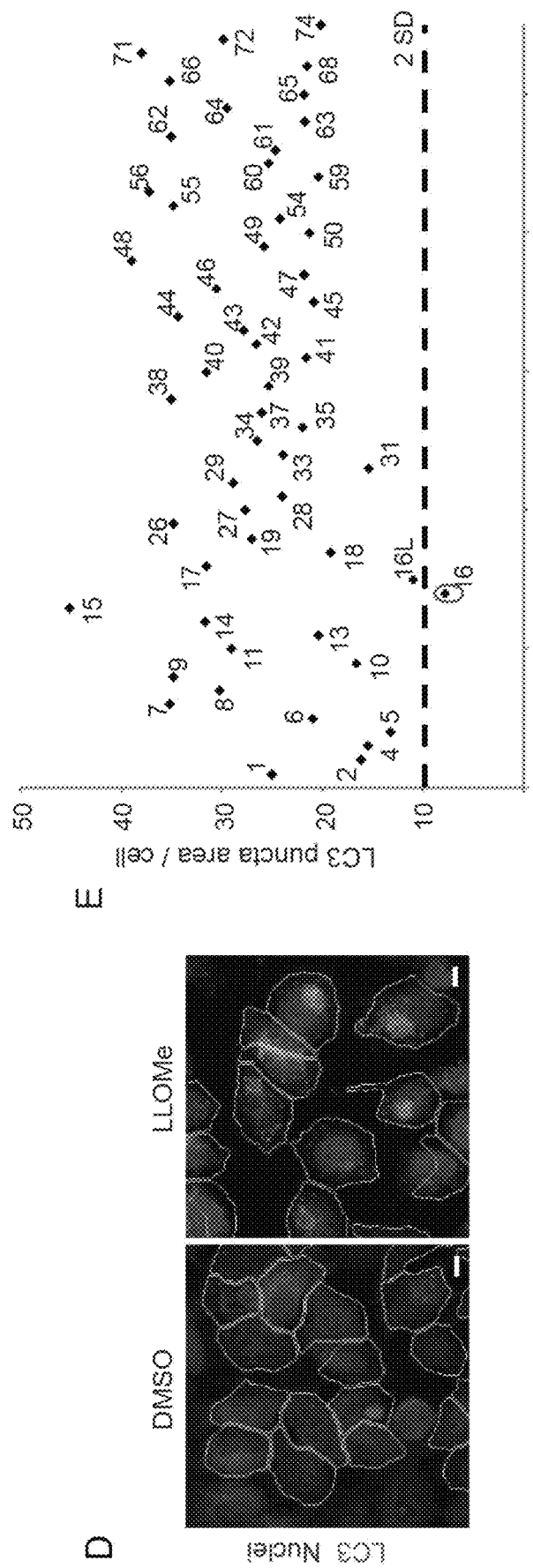
Figure 1:
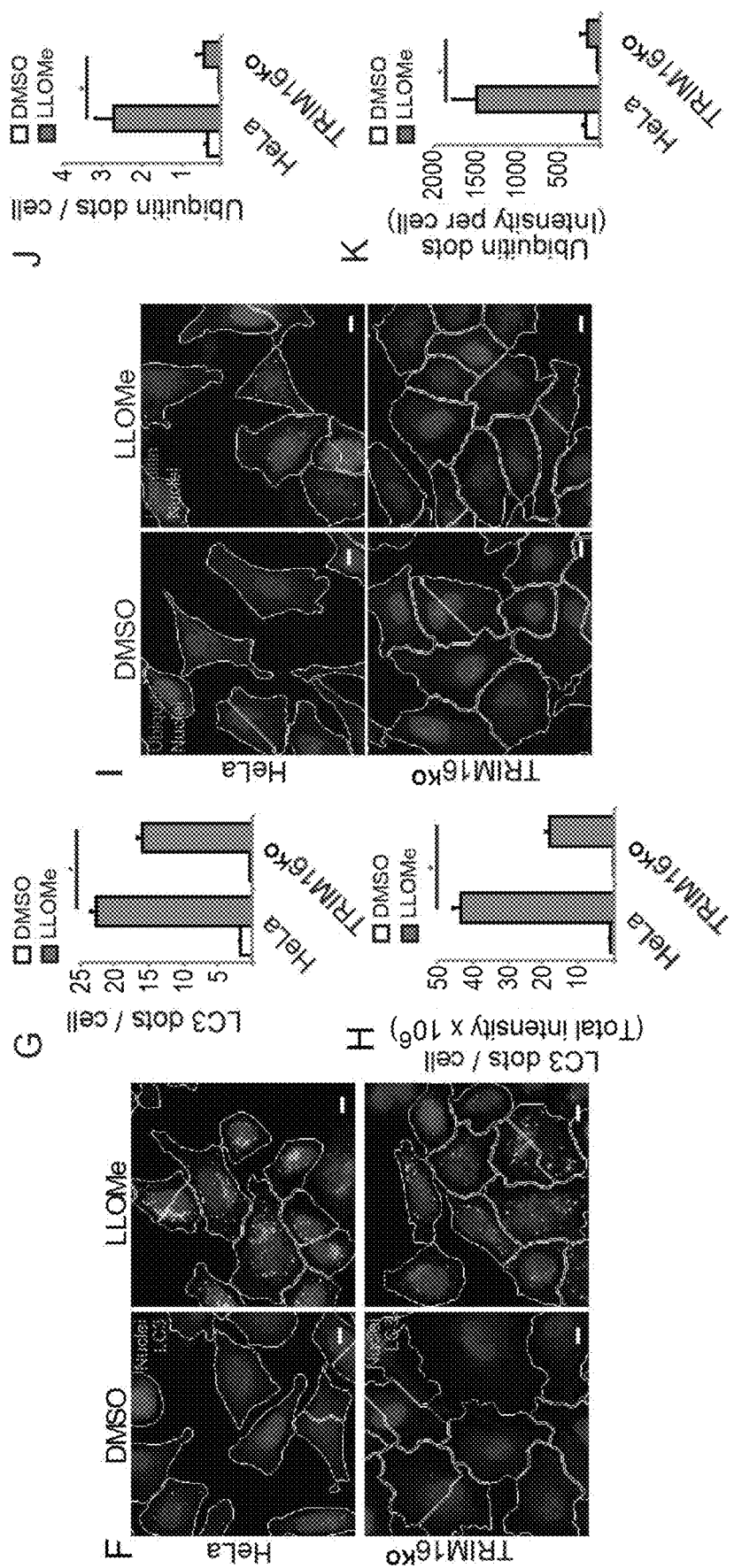
Figure 16:
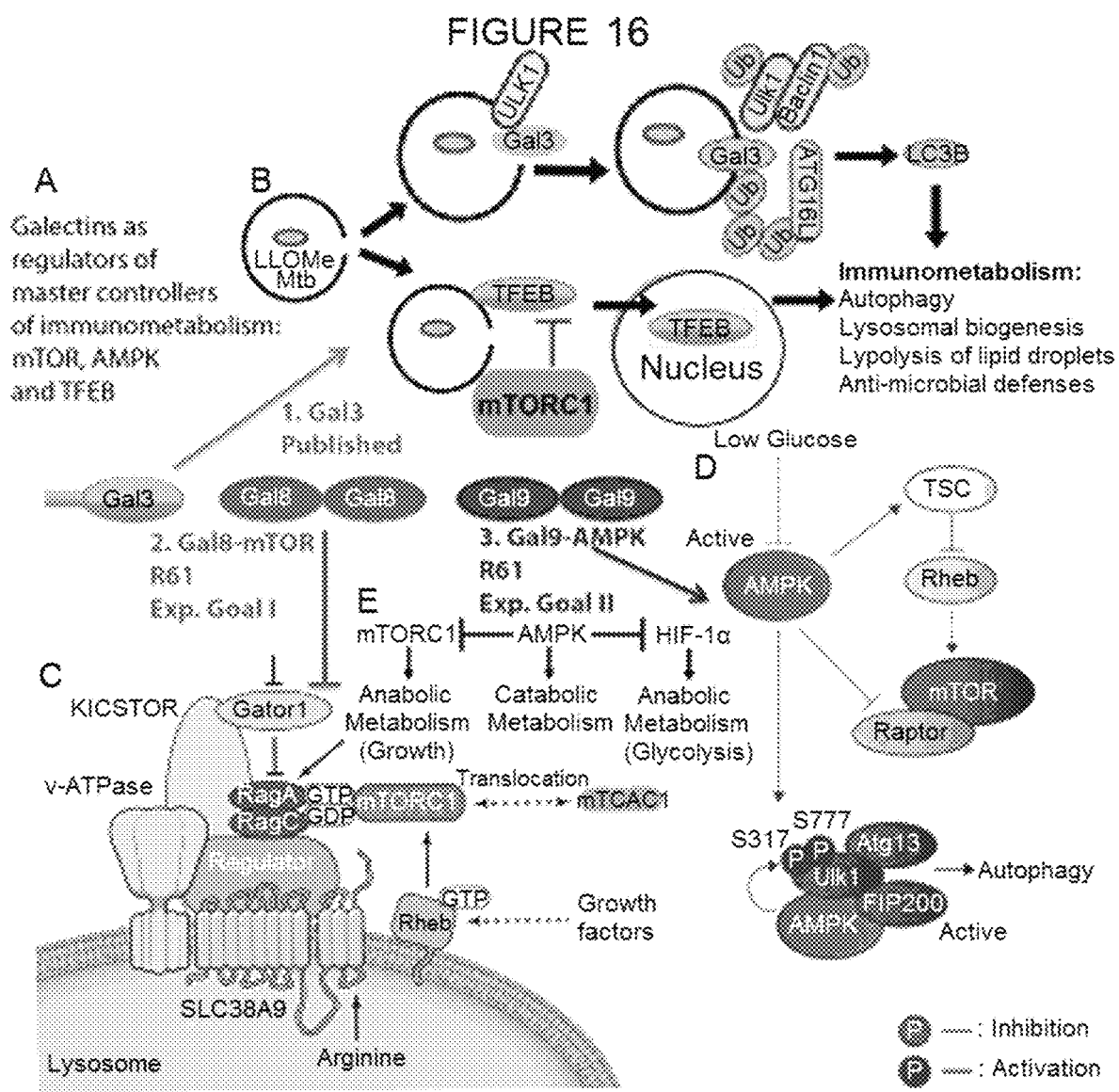

FIG. 16 shows the various proposed mechanisms of action of the Galectins. FIG. 1. A. Galectins and their proposed new roles (1-3) in immunometabolism following endomembrane damage. B. Detection (Gal3) of endomembrane damage, e.g. phagosomal damage by Mtb or lysosomal damage by LLOMe) leads to lysosomal/autophagosomal homeostasis, including lysophagy and elimination of Mtb. C. Recognition of damage by Gal8 leads to its direct role in mTOR inhibition. D. Recognition of damage by Gal9 results in Gal9 activating AMPK. E. Main switches in metabolism.

Figure 17:
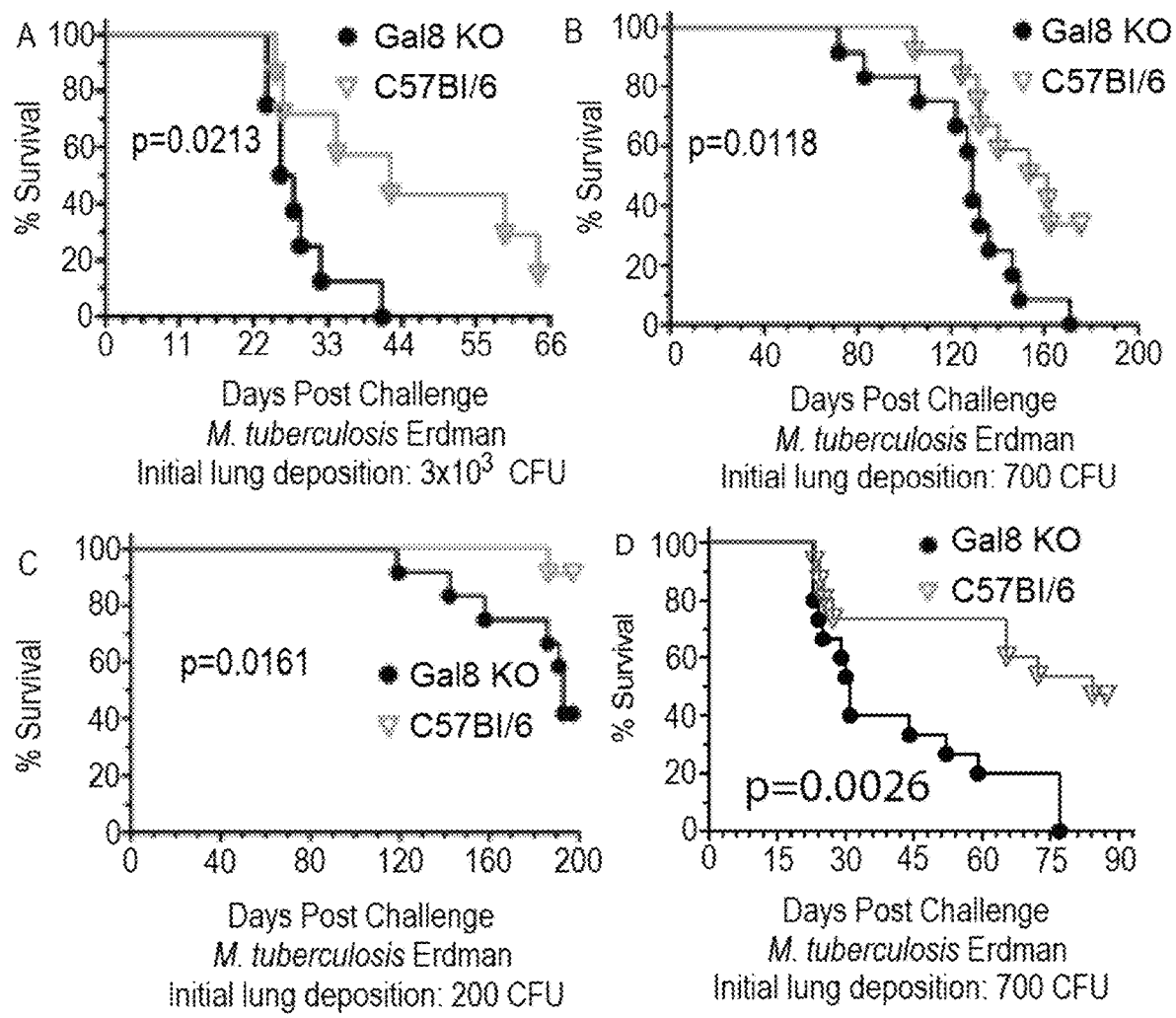

FIG. 17 A-C show the susceptibility of Gal3 KO mice to acute and chronic Mtb infection (from Chauhan et al, 2016). D. Gal8 KO mice (preliminary data). Statistics: Mantel-Cox (log-rank).

Figure 18:
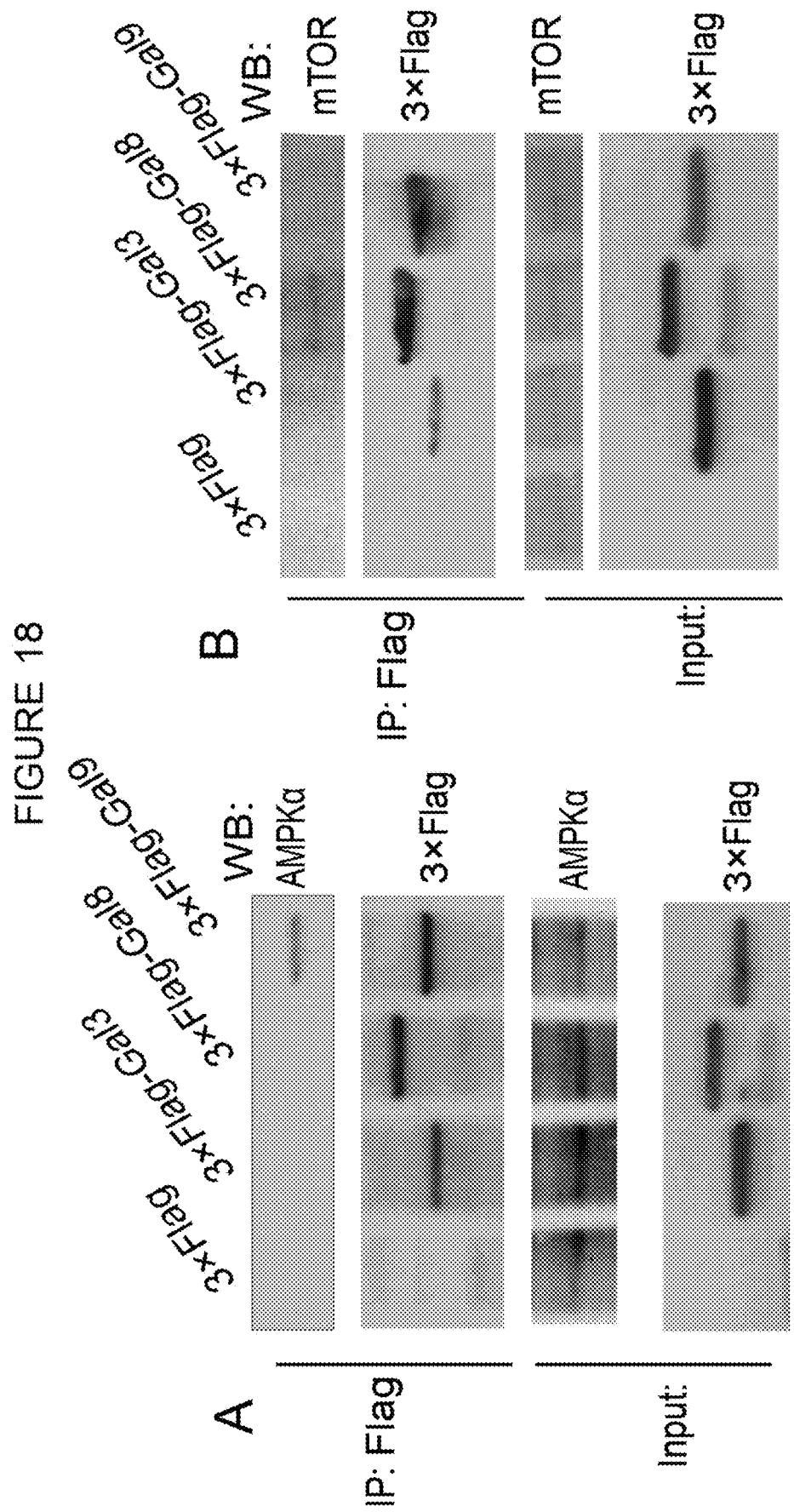
Figure 19:
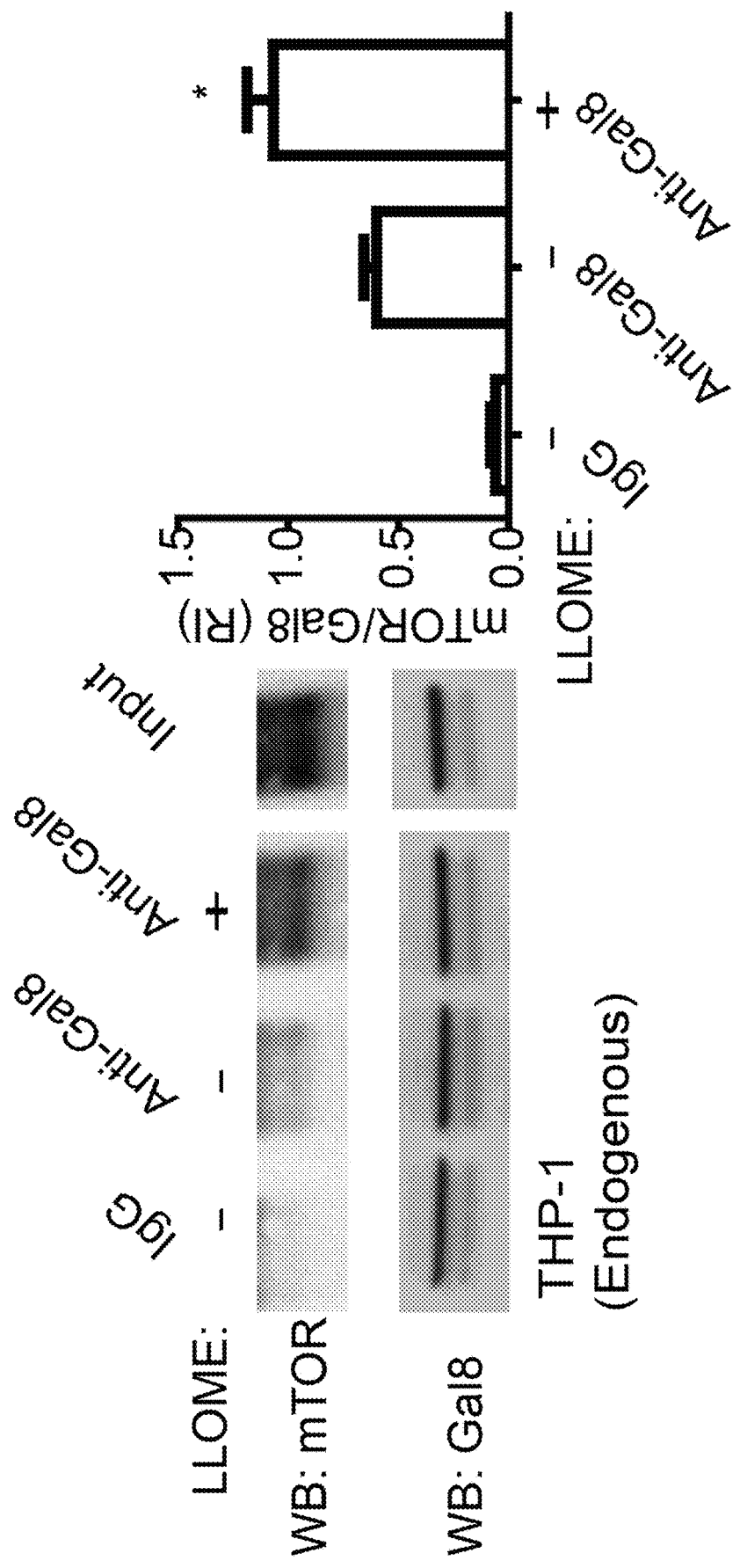

FIG. 18 shows that Gal9 is specifically in protein complexes with AMPK whereas Gal8 is found specifically in protein complexes with mTOR. Preliminary results, FIG. 19 shows that Lysosomal damage increases Gal8-mTORInteractions. ANOVA, Fisher LSD.

Figure 20:
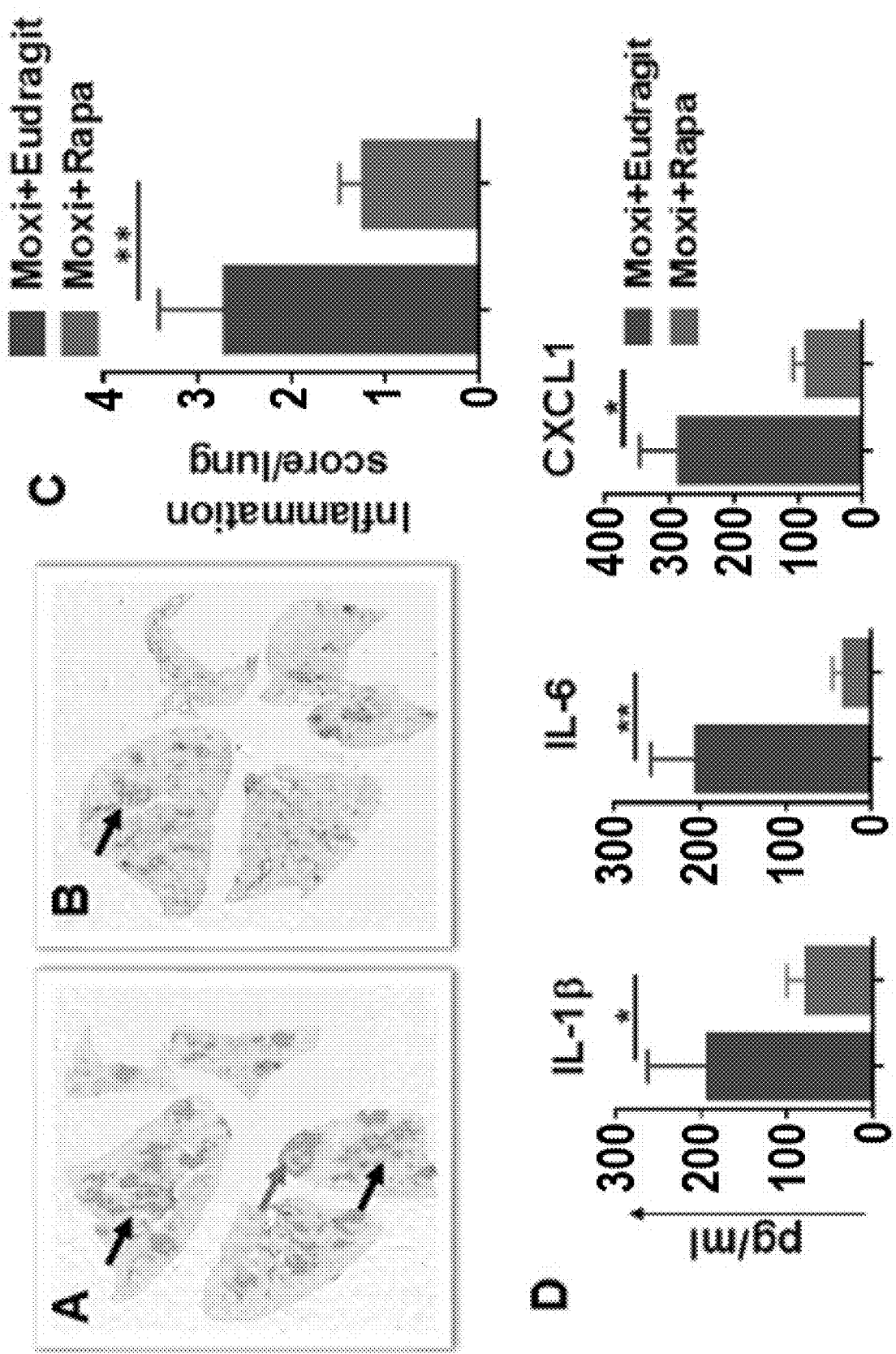

FIG. 20 A and B show that that H&E lung sections from C3HeB/FeJ mice treated at 7 weeks (following 200 cfu Mtb Erdman aerosol infection) with moxifloxacin (moxi)+eudragit (A; control) or moxi+rapamycin. C. shows inflammation scores: 1 (least inflamed) to 5 for all lung lobes. **, p=0.007 Mann Whitney test. D. Cytokines in lung lysates were measured by the multiplexed Mesoscale Discovery (MSD) platform. ANOVA, nonparametric & parametric post-hoc tests.

Figure 21:
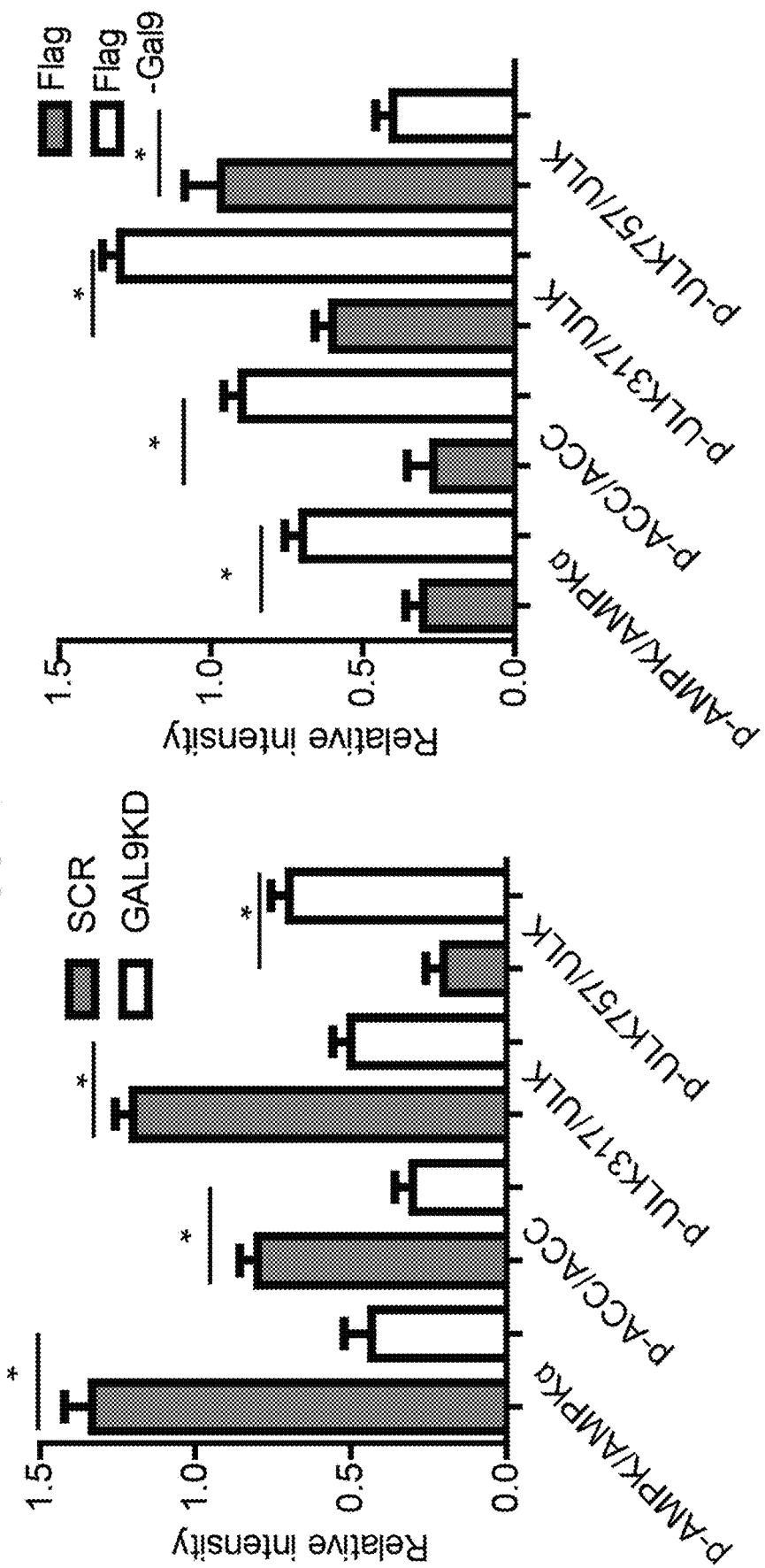

FIG. 21 shows Left, that Gal9 knockdown decreases AMPK activity, measured by decreased levels of pAMPK, pACC, and pULK317. Right, shows that over-expression of Gal9 increases AMPK phosphorylation of these targets. Converse is true for mTOR activity (pULK757 levels). n=3, ANOVA, Fisher's LSD posthoc test.

Figure 22:
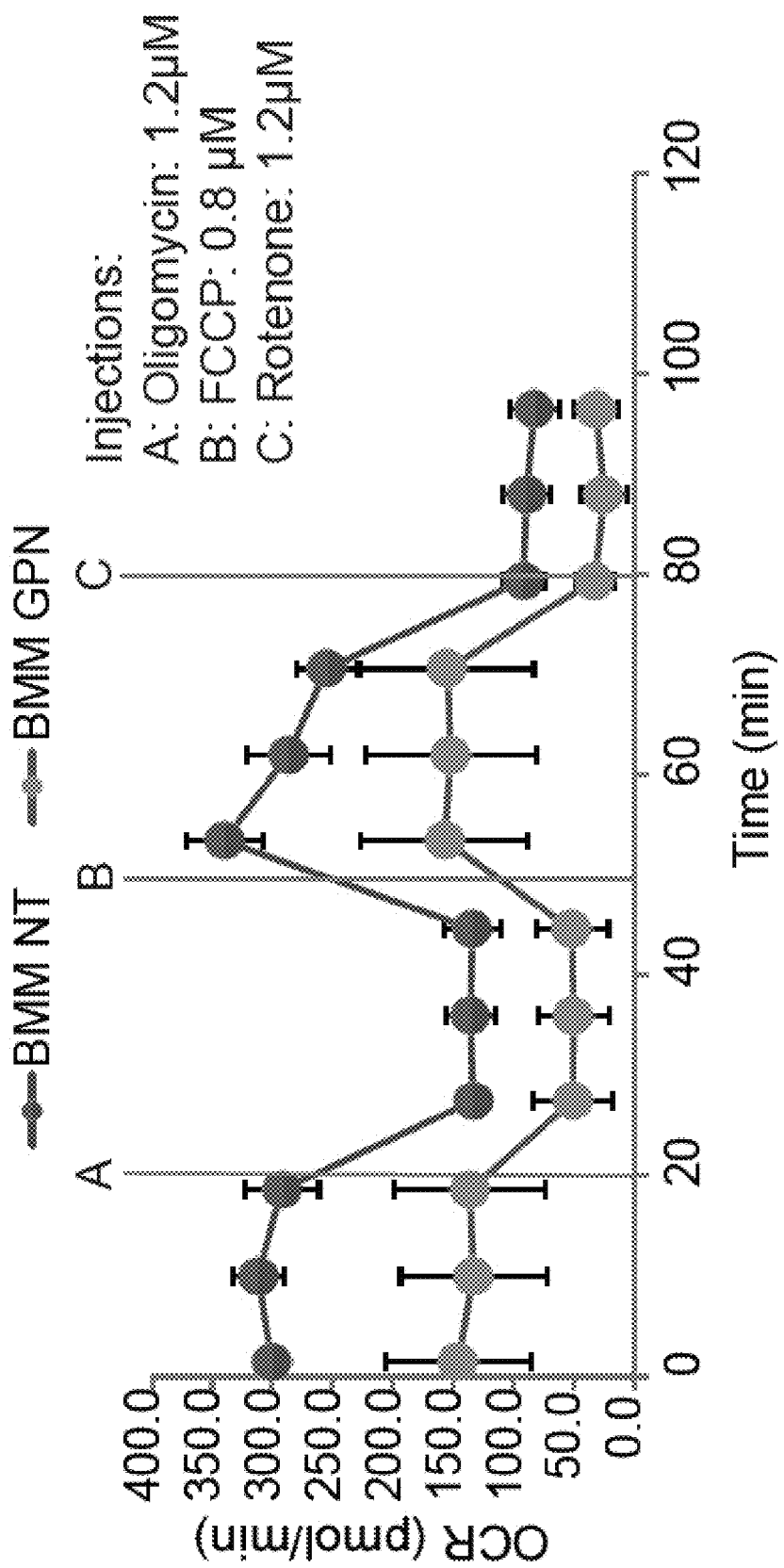

FIG. 22 shows that Lysosomal damaging agent GPN alters oxygen consumption rate (OCR) in primary murine bone marrow-derived macrophages (BMMs).

Figure 23:
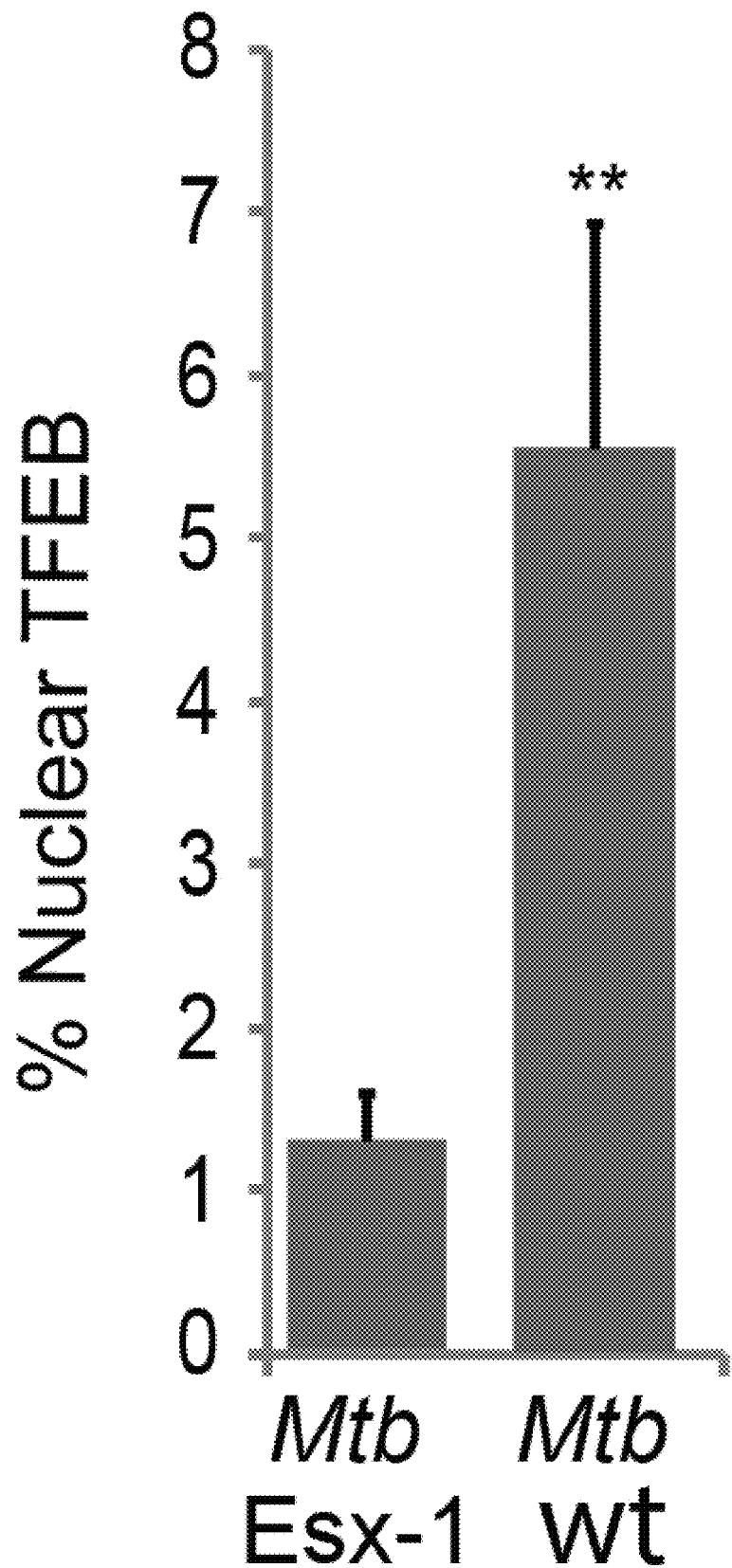

FIG. 23 shows that Mtb induces only a modest TFEB translocation to the nucleus. THP-1 cels; HC microscopy. **<0.01, t-test.

Figure 24:
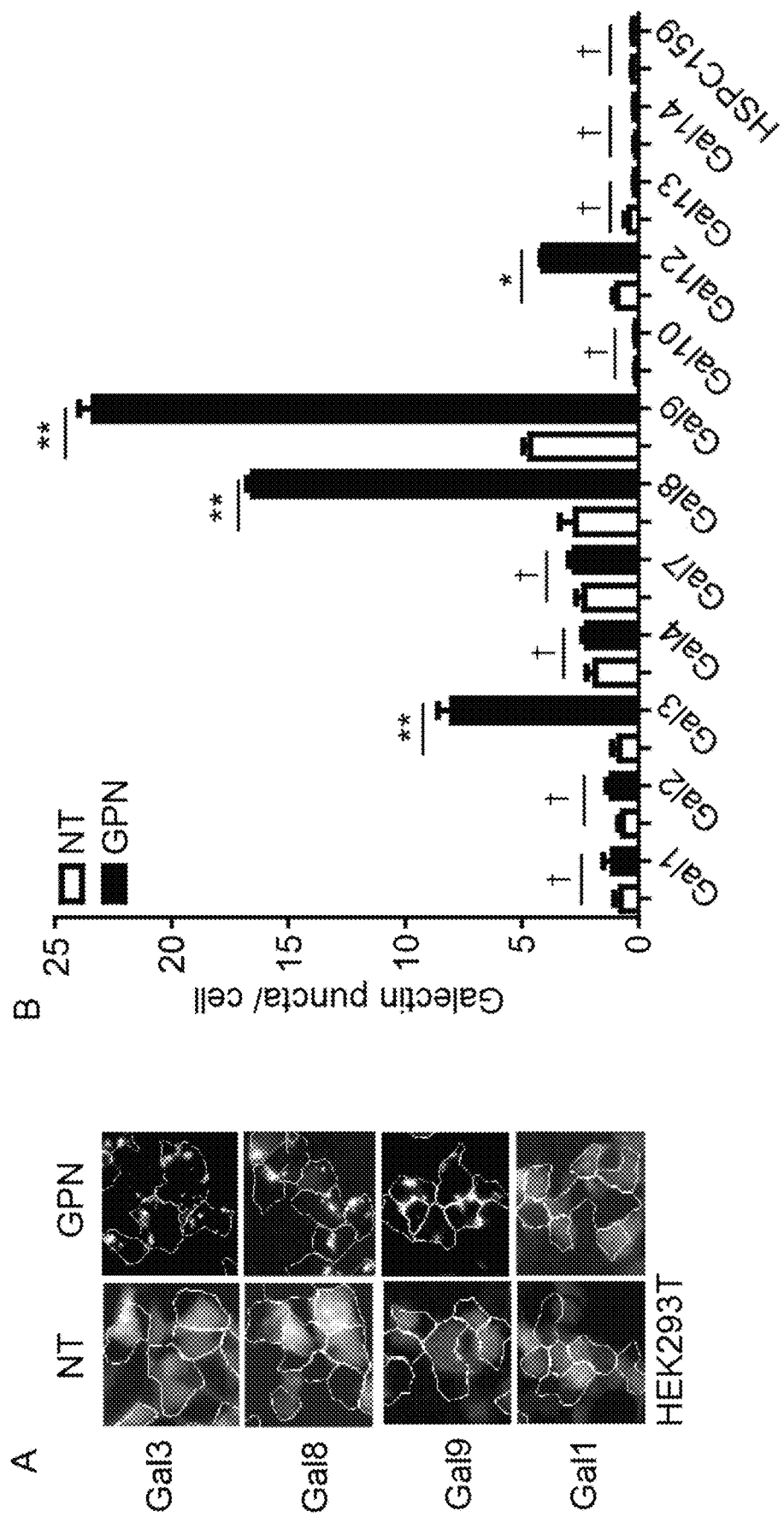

FIG. 24 shows that HEK293 cells with YFP-Gal fusion were treated with 100 μM GPN for 1h and analyzed by high-content (HC) microscopy. Data, means±SD; n=1000 cells per condition; n>3; ANOVA, Tukey's t test vs. control, *p<0.05.**p<0.01.

FIG. 25 shows an illustration of the ReFRAME library.

FIG. 26 shows that Metformin causes Gal3, Gal8, and Gal9 puncta formation, lysosomal damage, and Gal9-dependent AMPK activation in THP-1 macrophages. A. shows Gal puncta formation, 250 μM metformin (2h). B. shows lysosomal cathepsin B loss of activity. C. Reduction of LysoTracker Red stain. D. AMPK activation response to metformin in cells KD for Gal9.

Figure 27:
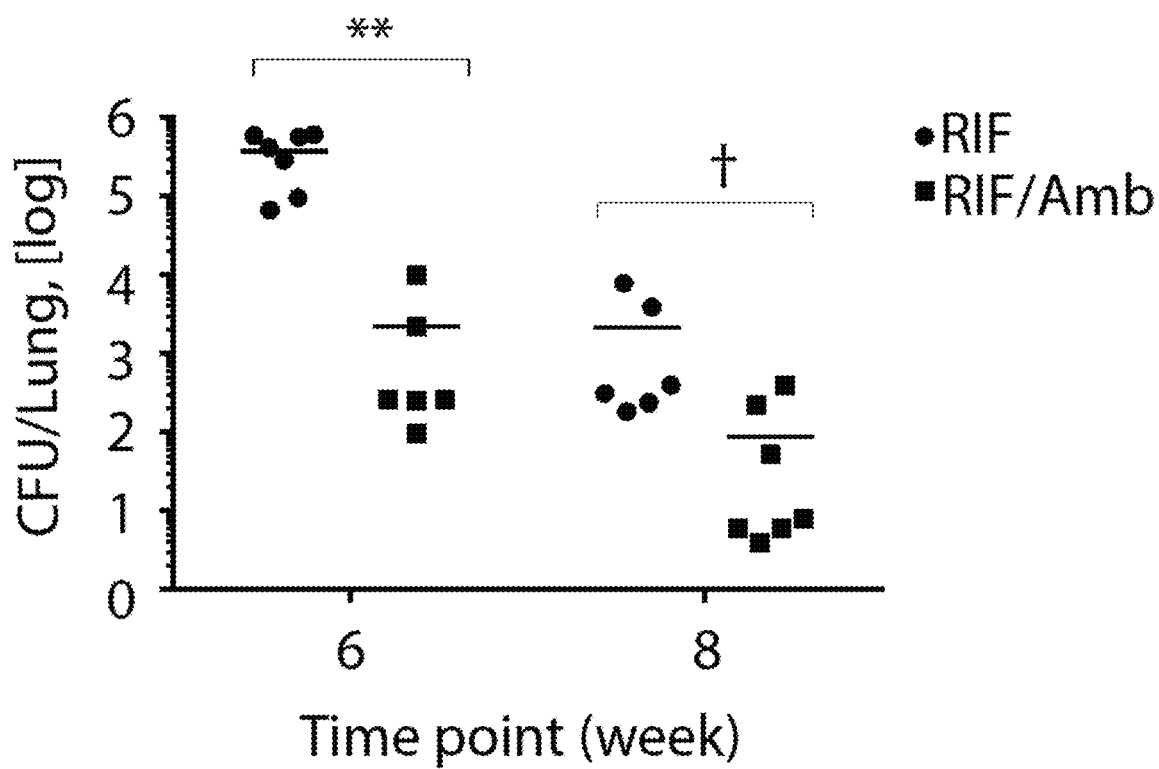

FIG. 27 shows the effect of Ambroxol on Mtb survival during Rifampicin treatment in C57BL/6J mice. Mice were aerosol infected (Glas Col apparatus) with Mtb Erdman (175 CFU of initial deposition per lung), left untreated for 2 weeks, then initiated on a chemotherapeutic regimen with rifampicin (RIF) with/without Ambroxol (Amb) for 4 or 6 weeks: RIF, 10 mg/kg b.w. (in drinking water); Amb, 12 mg/kg b.w (in transgenic paste). Mice were sacrificed and Mtb CFU quantified in lung tissues. Data, means of CFU (each dot representing a different mouse); n=6-7 mice per group. Statistics, Bonferroni multiple comparison test.

DETAILED DESCRIPTION OF THE INVENTION

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "compound" or "agent", as used herein, unless otherwise indicated, refers to any specific chemical compound or composition (such as a TRIM or Galectin protein) disclosed herein and includes tautomers, regioisomers, geometric isomers as applicable, and also where applicable, stereoisomers, including diastereomers, optical isomers (e.g. enantiomers) thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal, including a domesticated mammal including a farm animal (dog, cat, horse, cow, pig, sheep, goat, etc.) and preferably a human, to whom treatment, including prophylactic treatment (prophylaxis), with the methods and compositions according to the present invention is provided. For treatment of those conditions or disease states which are specific for a specific animal such as a human patient, the term patient refers to that specific animal, often a human.

The terms "effective" or "pharmaceutically effective" are used herein, unless otherwise indicated, to describe an amount of a compound or composition which, in context, is used to produce or affect an intended result, usually the modulation of autophagy within the context of a particular treatment or alternatively, the effect of a bioactive agent which is coadministered with the autophagy modulator (autotoxin) in the treatment of disease.

The terms "treat", "treating", and "treatment", etc., as used herein, refer to any action providing a benefit to a patient at risk for or afflicted by an autophagy mediated disease state or condition as otherwise described herein, especiallyi where excessive inflammation results from the disease state and/or condition. The benefit may be in curing the disease state or condition, inhibiting its progression, or ameliorating, lessening or suppressing one or more symptom of an autophagy mediated disease state or condition, especially including excessive inflammation caused by the disease state and/or condition. Treatment, as used herein, encompasses therapeutic treatment and in certain instances, prophylactic treatment, depending on context.

As used herein, the term "autophagy mediated disease state or condition" refers to a disease state or condition that results from disruption in autophagy or cellular self-digestion and in particular, causes or is a risk for causing excessive inflammation. Autophagy is a cellular pathway involved in protein and organelle degradation, and has a large number of connections to human disease. Autophagic dysfunction which causes inflammation is associated with inflammatory diseases, including neurodegeneration, autoimmune diseases, microbial infections, cardiovascular diseases and metabolic diseases including diabetes mellitus, among numerous other disease states and/or conditions. Although autophagy plays a principal role as a protective process for the cell, it also plays a role in cell death. Disease states and/or conditions which are mediated through autophagy (which refers to the fact that the disease state or condition may manifest itself as a function of the increase or decrease in autophagy in the patient or subject to be treated and treatment requires administration of an inhibitor or agonist of autophagy in the patient or subject) include, for example, lysosomal storage diseases (discussed hereinbelow), neurodegeneration (including, for example, Alzheimer's disease, Parkinson's disease, Huntington's disease; other ataxias), immune response (T cell maturation, B cell and T cell homeostasis, counters damaging inflammation), autoimmune diseases and chronic inflammatory diseases resulting in excessive inflammation (these disease states may promote excessive cytokines when autophagy is defective), including, for example, inflammatory bowel disease, including Crohn's disease, rheumatoid arthritis, lupus, multiple sclerosis, chronic obstructive pulmony disease/COPD, pulmonary fibrosis, cystic fibrosis, Sjogren's disease; hyperglycemic disorders, diabetes (I and II), affecting lipid metabolism islet function and/or structure, excessive autophpagy may lead to pancreatic β-cell death and related hyperglycemic disorders, including severe insulin resistance, hyperinsulinemia, insulin-resistant diabetes (e.g. Mendenhall's Syndrome, Werner Syndrome, leprechaunism, and lipoatrophic diabetes) and dyslipidemia (e.g. hyperlipidemia as expressed by obese subjects, elevated low-density lipoprotein (LDL), depressed high-density lipoprotein (HDL), and elevated triglycerides) and metabolic syndrome, liver disease (excessive autophagie removal of cellular entities—endoplasmic reticulum), renal disease (apoptosis in plaques, glomerular disease), cardiovascular disease (especially including infarction, ischemia, stroke, pressure overload and complications during reperfusion), muscle degeneration and atrophy, symptoms of aging (including amelioration or the delay in onset or severity or frequency of aging-related symptoms and chronic conditions including muscle atrophy, frailty, metabolic disorders, low grade inflammation, gout, silicosis, atherosclerosis and associated conditions such as cardiac and neurological both central and peripheral manifestations including stroke, age-associated dementia and sporadic form of Alzheimer's disease, and psychiatric conditions including depression), stroke and spinal cord injury, arteriosclerosis, infectious diseases (microbial infections, removes microbes, provides a protective inflammatory response to microbial products, limits adapation of autophagy of host by microbe for enhancement of microbial growth, regulation of innate immunity) including bacterial, fungal, cellular and viral (including secondary disease states or conditions associated with infectious diseases especially including Mycobacterial infections such as *M. tuberculosis*, and viral infections such as hepatitis B and C and HIV I and II), including AIDS, among others.

In addition, an autophagy disease state or condition includes autoimmune diseases such as myocarditis, Antiglomercular Base Membrane Nephritis, lupus erythematosus, lupus nephritis, autoimmune hepatitis, primary biliary cirrhosis, alopecia areata, autoimmune urticaria, bullous pemphagoid, dermatitis herpetiformis, epidermolysis bullosa acquisita, linear IgA disease (LAD), pemphigus vulgaris, psoriasis, Addison's disease, autoimmune polyendocrine syndrome I, II and III (APS I, APS II, APS III), autoimmune pancreatitis, type I diabetes, autoimmune thyroiditis, Ord's thyroiditis, Grave's disease, autoimmune oophoritis, Sjogren's syndrome, autoimmune enteropathy, Coeliac disease, Crohn's disease, autoimmune hemolytic anemia, autoimmune lymphoproliferative syndrome, autoimmune neutropenia, autoimmune thrombocytopenia purpura, Cold agglutinin disease, Evans syndrome, pernicious anemia, Adult-onset Still's disease, Felty syndrome, juvenile arthritis, psoriatic arthritis, relapsing polychondritis, rheumatic fever, rheumatoid arthritis, myasthenia gravis, acute disseminated encephalomyelitis (ADEM), balo concentric sclerosis, Guillain-Barré syndrome, Hashimoto's encephalopathy, chronic inflammatory demvelinating polyneuropathy, Lambert-Eaton myasthenic syndrome, multiple sclerosis, autoimmune uveitis, Graves opthalmopathy, Granulomatosis with polyangitis (GPA), Kawasaki's disease, vasculitis and chronic fatigue syndrome, among others.

The term "TRIM protein" or "tripartite motif protein" is used to describe a family of proteins which which are involved in pathogen-recognition and regulation of transcriptional pathways in host defence. They are often induced by interferons. There are approximately 76 TRIM family members, which regulate autophagy and can target While any number of TRIM proteins may be used in the present invention, most notably TRIM 8, TRIM 10, TRIM 16, TRIM 19 and TRIM 51 (also TRIM 1, TRIM 20, TRIM 21, TRIM 22, TRIM 56, TRIM 65). The use of TRIM 16 and/or TRIM 51 may be preferred and human TRIM proteins and their pharmaceutically acceptable salts also are preferred. As used herein, the term TRIM protein describes the following TRIM proteins or variants thereof having at least 80%, 85%, 90% or 95% sequence identity as described herein. The following sequences are representative of the TRIM proteins which are of preferred use herein.

Additional TRIM proteins which may be used are described in international patent application number PCT/US16/19599, filed 25 Feb. 2016, published as WO2016/138286 1 Sep. 2016, relevant portions of which are incorporated by reference herein. The following TRIM proteins (human) and their pharmaceutically acceptable salts are used in preferred embodiments of the present invention.

TRIM 8 Accession No. NM_030912 SEQ ID NO: 1
TRIM 10 Accession No. NM_052828 SEQ ID NO: 2
TRIM 16 Accession No. NM_006470 SEQ ID NO: 3
TRIM 19 Accession No. NM_033247 SEQ ID NO: 4
TRIM 51 Accession No. NM_032681 SEQ ID NO: 5
TRIM 1 Accession No. NM_012216 SEQ ID NO: 6
SEQ ID NO: 7 TRIM 20 Accession No. NM_000243
TRIM 21 Accession No. NM_003141 SEQ ID NO: 8
TRIM 22 Accession No. NM_006074 SEQ ID NO: 9
TRIM 56 Accession No. NM_030961 SEQ ID NO: 10
TRIM 65 Accession No. NM_173547 SEQ ID NO: 11

The term "Galectin" or "Galectin protein" is used to describe family of proteins defined by their binding specificity for β-galactoside sugars, such as N-acetyllactosamine (Galβ1-3GlcNAc or Galβ1-4GlcNAc), which can be bound to proteins by either N-linked or O-linked glycosylation. They are also termed S-type lectins due to their dependency on disulphide bonds for stability and carbohydrate binding. Galectins are a large family with relatively broad specificity. Thus, they have a broad variety of functions including mediation of cell-cell interactions, cell-matrix adhesion and transmembrane signaling. Their expression and secretion is well regulated and there is substantial overlap for essential functions. The list of functions for galectins is extensive and include regulating cell death (apoptosis), suppression of T-cell receptor activation, adhesion, pre-mRNA splicing. The galectins are implicated in a wide range of disease states as indicated by the present invention.

There have been 15 galectins identified in mammals; these include Galectin-1, -2, -3, -4, -7, -8, -9, -10, -12 and -13 have been identified in humans. In preferred aspects of the invention, human galectins are used, more preferably Galectin-3, Galectin-8, Galectin-9 and Galectin-10. As used herein, the term Galectin protein describes Galectin-1, -2, -3, -4, -7-, 8, -9, -10, -12 and -13 and includes variants thereof having at least 80%, 85%, 90% or 95% sequence identity to the most common form of the protein, which is preferably the human protein. Preferred Galectin proteins include the following Galectin proteins or variants thereof having at least 80%, 85%, 90% or 95% sequence identity. The following sequences are representative of the human Galectin proteins which are of preferred use herein.

Galectin-3 Accession No. NP_002297.2 SEQ ID NO: 12
Galectin-8 Accession No. NP_006490.3 SEQ ID NO: 13
Galectin-9 Accession No. NP_001036150.1 SEQ ID NO: 14
Galectin-12 Accession No. NP 001136007.1 SEQ ID NO: 15

The term "lysosomal storage disorder" refers to a disease state or condition that results from a defect in lysosomomal storage. These disease states or conditions generally occur when the lysosome malfunctions. Lysosomal storage disorders are caused by lysosomal dysfunction usually as a consequence of deficiency of a single enzyme required for the metabolism of lipids, glycoproteins or mucopolysaccharides. The incidence of lysosomal storage disorder (collectively) occurs at an incidence of about about 1:5,000-1:10,000. The lysosome is commonly referred to as the cell's recycling center because it processes unwanted material into substances that the cell can utilize. Lysosomes break down this unwanted matter via high specialized enzymes. Lysosomal disorders generally are triggered when a particular enzyme exists in too small an amount or is missing altogether. When this happens, substances accumulate in the cell. In other words, when the lysosome doesn't function normally, excess products destined for breakdown and recycling are stored in the cell. Lysosomal storage disorders are genetic diseases, but these may be treated using autophagy modulators according to the present invention, especially where the disease state or condition produces excessive inflammation as otherwise described herein. All of these diseases share a common biochemical characteristic, i.e., that all lysosomal disorders originate from an abnormal accumulation of substances inside the lysosome. Lysosomal storage diseases mostly affect children who often die as a consequence at an early stage of life, many within a few months or years of birth. Many other children die of this disease following years of suffering from various symptoms of their particular disorder.

Examples of lysosomal storage diseases include, for example, activator deficiency/GM2 gangliosidosis, alpha-mannosidosis, aspartylglucoaminuria, cholesteryl ester storage disease, chronic hexosaminidase A deficiency, cystinosis, Danon disease, Fabry disease, Farber disease, fucosidosis, galactosialidosis, Gaucher Disease (Types I, II and III), GM! Ganliosidosis, including infantile, late infantile/juvenile and adult/chronic), Hunter syndrome (MPS II), I-Cell disease/Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency, Niemann-Pick disease, Neuronal ceroid lipofuscinoses, CLN6 disease, Jansky-Bielschowsky disease, Pompe disease, pycnodysostosis, Sandhoff disease, Schindler disease, Tay-Sachs and Wolman disease, among others.

The term "modulator of autophagy", "regulator of autophagy" or "autostatin" is used to refer to a compound which functions as an agonist (inducer or up-regulator) or antagonist (inhibitor or down-regulator) of autophagy. Depending upon the disease state or condition, autophagy may be upregulated (and require inhibition of autophagy for therapeutic intervention) or down-regulated (and require upregulation of autophagy for therapeutic intervention). In most instances, in the case of cancer treatment with a modulator of autophagy as otherwise described herein, the autophagy modulator is often an antagonist (down-regulator or inhibitor) of autophagy. In the case of cancer, the antagonist (inhibitor) of autophagy may be used alone or combined with an agonist of autophagy. In other instances, the modulator is an upregulator of autophagy.

The following compounds have been identified as autophagy modulators according to the present invention and can be used in the treatment of an autophagy mediated disease state or condition as otherwise described herein. These include interferon types I and II, especially interferon-alpha, interferon-beta, interferon interferon-gamma (IFN-gamma), pegylated interferon (PEG-IFN) type 1 or type 2 (especially including interferon alpha 2a and/or 2b), mixtures thereof, other cytokines and related compounds and certain TRIM proteins (especially human TRIM proteins and their pharmaceutically acceptable salts), in particular, TRIM 8, TRIM 10, TRIM 16, TRIM 19 and TRIM 51 (also TRIM 1, TRIM 20, TRIM 21, TRIM 22, TRIM 56, TRIM 65) and mixtures thereof. In addition, Galectin proteins (1, 2, 3, 4, 7, 8, 9, 10, 12 and 13), preferably human Galectin proteins may also be included as autophagy modulators, especially Galectin-3, with Galectin-3, Galectin-8, Galectin-9 and Galectin-12, with Galectin-3 being preferred. Agonists and/or inhibitors of the Galectin proteins, including a galactose containing sugar or other sugar compound (especially lactose, including N-linked and O-linked lactose such as N-acetyl lactosamine which acts as an agonist or an inhibitor such as a galactoside inhibitor or alternatively, a lactulose amine such as N-lactulose-octamethylenediamine (LDO)); N,N-dilactulose-octamethylenediamine (D-LDO), and N,N-dilactulose-dodecamethylenediamine (D-LDD)), GR-MD-02, GM-CT-01, GCS-100, ipilimumab, a pectin, or a taloside inhibitor may also be used.

In addition, the following sugars may also be used as inhibitors and/or agonists of the Galectins, especially Galectin-3, Galectin-8, Galectin-9 and/or Galectin 12. These sugars include, for example, monosaccharides, including β-galactoside sugars, such as galactose, including N- or O-linked (e.g., acetylated) galactosides and disaccharides, oligosaccharides and polysaccharides which contain at least one galactose sugar moiety. These include lactose, mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinulose and xylobiose, among others, and trehalose, all of which can be N and O)-linked. Oligosaccharides for use in the present invention as can include any sugar of three or more (up to about 100) individual sugar (saccharide) units as described above (i.e., any one or more saccharide units described above, in any order, especially including galactose units such as galactooligosaccharides and mannan-oligosaccharides ranging from three to about ten-fifteen sugar units in size. Sugars which are galactosides or contain galactose (galactose derivatives) are preferred for use in the present invention. These sugars may function as inhibitors or agonists of galectins, especially galectin 3. One or more of these above sugars may be combined with a TRIM protein (preferably a human TRIM protein), especially TRIM 8, TRIM 10, TRIM 16, TRIM 19 and TRIM 51 (also TRIM 1, TRIM 20, TRIM 21, TRIM 22, TRIM 56, TRIM 65), preferably TRIM 16 and/or TRIM 51 and most often TRIM 16 and/or an agent which induces TRIM proteins, such as an interferon, a biguanide, a salicylate and a biguanide, berberine, ambroxol or a mixture thereof in order to upregulate autophagy and treat the autophagy diseases where upregulation is beneficial (e.g., inflammatory disease states and/or conditions including a microbial infection such as a *Mycobacterium* infection, among numerous others, an inflammatory disorder, a lysosomal storage disorder, an immune disorder, a neurodegenerative disorder, an autoimmune disease).

Alternatively, one or more sugars described above may function as an inhibitor of Galectin to be used in combination with an inhibitor of a TRIM protein for the treatment of certain cancers. Useful galectin inhibitors include galactoside inhibitors or alternatively, a lactulose amine such as N-lactulose-octamethylenediamine (LDO); N,N-dilactulose-octamethylenediamine (D-LDO), and N,N-dilactulose-dodecamethylenediamine (D-LDD)), GR-MD-02, ipilimumab, a pectin, or a taloside inhibitor, among others may be used as an inhibitor of a galectin as described herein, especially galectin 3. These agents are particularly effective as anticancer agents with certain cancers especially when combined with an inhibitor of a TRIM protein, including a SIRNA (especially of TRIM 8, TRIM 16, TRIM 19 and TRIM 51, especially TRIM 16 and/or TRIM 51 such as the following SiRNAs).

```
TRIM 8 SIRNAs:
                              SEQ ID NO: 16
GCAAGAUUCUCGUCUGUUC

SEQ ID NO: 17
GGAAUGAAAUCCGGAAGAU

SEQ ID NO: 18
GGACAACUGUUACUGUUCU

SEQ ID NO: 19
GAACACCAAGUCUGUGAAA

TRIM10 SIRNAs:
                              SEQ ID NO: 20
GAGAGGAGAUUCAAGAAAU

SEQ ID NO: 21
CAGAAGCACUCUAAUAAGA

SEQ ID NO: 22
GGGAACAAAUCCAUAAGUG

SEQ ID NO: 23
GCUUUGAGUUGGACUAUGA

TRIM 16 SIRNAS:
                              SEQ ID NO: 24
GACCACAACUGGCGAUACU;

SEQ ID NO: 25
GCAGUGAAGUCCUGUCUAA;

SEQ ID NO: 26
GGAACAGGACAGCGACUCU;

SEQ ID NO: 27
CCGCAUCAGGUGAACAUCA;

SEQ ID NO: 28
GAGGAGUACUGCAAGUUUA;

SEQ ID NO: 29
GCAAAGGCAUCGACCAGAA;

SEQ ID NO: 30
GCAAAGUUAUCACGGAAUC;

SEQ ID NO: 31
AGGAUAAACUCUCGGGCAU.

TRIM 19 SIRNAs:
                              SEQ ID NO: 32
GGGGAAAGAUGCAGCUGUA

SEQ ID NO: 33
GCAAAGAGUCGGCCGACUU

SEQ ID NO: 34
GCGCUGGUGCAGAGGAUGA

SEQ ID NO: 35
CCGAUGGCUUCGACGAGUU
```

-continued

```
TRIM 51 SIRNAS:
                                       SEQ ID NO: 36
GGAAGGAUUAUGUGAGUUU;

SEQ ID NO: 37
ACUUGGAAAGGCUGCGAAA;

SEQ ID NO: 38
AAGCAGAUGUGGAGCUACU;

SEQ ID NO: 39
GGACAGCCUCAGUGGAUUC.
```

The term "biguanide" is used to describe an active compound for use herein which is based on the general formula $HN(C(NH)NH_2)_2$. These compounds are shown to be upregulators of autophagy through TRIM protein upregulation, inhibition of mTOR and upregulation of AMP Kinase. Biguanide compounds include metformin, buformin, proguanil and phenformin, with buformin, proguanil and/or phenformin being preferred alone (i.e., in the absence of a salicylate) whereas any one or more of the biguanides may be used in concert with a salicylate (preferably aspirin) to upregulate the TRIM proteins and autophagy.

The term "salicylate" is used to describe compounds

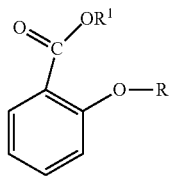

Where R is H or a $C_2$-$C_{10}$ acyl group (preferably, H or an acetyl other straight-chained alkyl group) and R' is a $C_1$-$C_{10}$ alkyl group or a pharmaceutically acceptable salt thereof. In preferred aspects of the invention, the salicylate compound is acetylsalicylic acid (aspirin, R=$C_2$ acyl or acetyl group and $R^1$ is H or salicylic acid, R is H and $R^1$ is H) or a pharmaceutically acceptable salt thereof.

The following compounds have been identified as autophagy modulators which may be used in combination with the above-identified autophagy agents. These agents include, for example flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon and nortriptyline, tetrachlorisophthalonitrile, phenylmercuric acetate and pharmaceutically acceptable salts thereof. It is noted that flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline, benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, betaescin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, Methimazole, Trimeprazine, Ethoxyquin, Clocortolone, Doxycycline, Pirlindole mesylate, Doxazosin, Deptropine, Nocodazole, Scopolamine, Oxybenzone, Halcinonide, Oxybutynin, Miconazole, Clomipramine, Cyproheptadine, Doxepin, Dyclonine, Salbutamol, Flavoxate, Amoxapine, Fenofibrate, Pimethixene, and mixtures thereof, alternative TRIM proteins (especially human TRIM proteins), including, but not limited to, TRIM5α, TRIM6, TRIM10, TRIM17, TRIM41, TRIM55, TRIM72, TRIM76, TRIM2, TRIM23, TRIM26, TRIM28, TRIM31, TRIM 32, TRIM33, TRIM38, TRIM42, TRIM44, TRIM45, TRIM49, TRIM50, TRIM51, TRIM58, TRIM59, TRIM68, TRIM73, TRIM74 and TRIM76 and mixtures thereof.

The term "co-administration" or "combination therapy" is used to describe a therapy in which at least two active compounds in effective amounts are used to treat an autophagy mediated disease state or condition as otherwise described herein, either at the same time or within dosing or administration schedules defined further herein or ascertainable by those of ordinary skill in the art. Although the term co-administration preferably includes the administration of two active compounds to the patient at the same time, it is not necessary that the compounds be administered to the patient at the same time, although effective amounts of the individual compounds will be present in the patient at the same time. In addition, in certain embodiments, co-administration will refer to the fact that two compounds are administered at significantly different times, but the effects of the two compounds are present at the same time. Thus, the term co-administration includes an administration in which one active agent (especially an autophagy modulator) is administered at approximately the same time (contemporaneously), or from about one to several minutes to about 24 hours or more than the other bioactive agent coadministered with the autophagy modulator.

The additional bioactive agent may be any bioactive agent, but is generally selected from an additional autophagy mediated compound or another agent such as a mTOR inhibitor such as Torin, pp242, rapamycin/serolimus (which also may function as an autophagy modulator), everolimus, temsirolomis, ridaforolimis, zotarolimis, 32-dexoy-rapamycin, among others including epigallocatechin gallate (EGCG), caffeine, curcumin or reseveratrol (which mTOR inhibitors find particular use as enhancers of autophagy using the compounds disclosed herein. In certain embodiments, an mTOR inhibitor selected from the group consisting of Torin, pp242, rapamycin/serolimus, everolimus, temsirolomis, ridaforolimis, zotarolimis, 32-dexoy-rapamycin, epigallocatechin gallate (EGCG), caffeine, curcumin or reseveratrol and mixtures thereof may be combined with at least one agent selected from the group consisting of digoxin, xylazine, hexetidine and sertindole, the combination of such agents being effective as autophagy modulators in combination.

The terms "cancer" and "neoplasia" are used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated.

As used herein, the terms malignant neoplasia and cancer are used synonymously to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, non-melanoma skin cancer (especially basal cell carcinoma or squamous cell carcinoma), acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. In certain aspects, the cancer which is treated is lung cancer, breast cancer, ovarian cancer and/or prostate cancer.

Neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms (cancer) are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, stomach and thyroid; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medalloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991). All of these neoplasms may be treated using compounds according to the present invention.

Representative common cancers to be treated with compounds according to the present invention include, for example, prostate cancer, metastatic prostate cancer, stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. Because of the activity of the present compounds, the present invention has general applicability treating virtually any cancer in any tissue, thus the compounds, compositions and methods of the present invention are generally applicable to the treatment of cancer and in reducing the likelihood of development of cancer and/or the metastasis of an existing cancer.

In certain particular aspects of the present invention, the cancer which is treated is metastatic cancer, a recurrent cancer or a drug resistant cancer, especially including a drug resistant cancer. Separately, metastatic cancer may be found in virtually all tissues of a cancer patient in late stages of the disease, typically metastatic cancer is found in lymph system/nodes (lymphoma), in bones, in lungs, in bladder tissue, in kidney tissue, liver tissue and in virtually any tissue, including brain (brain cancer/tumor). Thus, the present invention is generally applicable and may be used to treat any cancer in any tissue, regardless of etiology.

The term "tumor" is used to describe a malignant or benign growth or tumefacent.

The term "additional anti-cancer compound", "additional anti-cancer drug" or "additional anti-cancer agent" is used to describe any compound (including its derivatives) which may be used to treat cancer. The "additional anti-cancer compound", "additional anti-cancer drug" or "additional anti-cancer agent" can be an anticancer agent which is distinguishable from a CIAE-inducing anticancer ingredient such as a taxane, *vinca* alkaloid and/or radiation sensitizing agent otherwise used as chemotherapy/cancer therapy agents herein. In many instances, the co-administration of another anti-cancer compound according to the present invention results in a synergistic anti-cancer effect. Exemplary anti-cancer compounds for co-administration with formulations according to the present invention include anti-metabolites agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and tyrosine kinase inhibitors or ABL kinase inhibitors (e.g. imatinib).

Anti-cancer compounds for co-administration include, for example, agent(s) which may be co-administered with compounds according to the present invention in the treatment of cancer. These agents include chemotherapeutic agents and include one or more members selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGER-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-eru, nolatrexed, azd2171, batabolin, ofatumumab, zanolimumab, edotecarin, tetrandrine, rubitecan, tesmilifene, oblimersen, ticilimumab, ipilimumab, gossypol, Bio 111, 131-1-TM-601, ALT-110, BIO 140, CC 8490, cilengitide, gimatecan, IL13-PE38QQR, INO 1001, IPdR; KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorobicin, liposomal doxorubicin, 5'-deoxy-5-fluorouridine, vincristine, temozolomide, ZK-304709, seliciclib: PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(But) 6, Azgly 10] (pyro-Glu-His-Trp-Ser-Tyr-D-Ser(Bu t)-Leu-Arg-Pro-Azgly-$NH_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-S72016, Ionafarnib, BMS-214662, tipifamib; amifostine, NVP-LAQ824, suberoyl analide hydroxamic acid, valproic acid, trichostatin A, FK-228, SU11248, sorafenib, KRN951, aminoglutethimide, arusacrine, anagrelide, L-asparaginase, Bacillus Calmette-Guerin (BCC) vaccine, bleomycin, buserelin, busulfan, carboplatin, carmustine, chlorambocil, cisplatin, cladribine, clodronate, cyproterone, cytarabine, dacarbazine, dactinomycin, daunorubicin, diethylstilbestrol, epirubicin, fludarabine, fludrocortisone. fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SUS416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O)-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, ipilimumab, nivolomuab, pembrolizumab, dabrafenib, trametinib and vemurafenib among others.

Co-administration of one of the formulations of the invention with another anticancer agent will often result in a synergistic enhancement of the anticancer activity of the other anticancer agent, an unexpected result. One or more of the present formulations comprising an IRGM modulator optionally in combination with an autophagy modulator (autostatin) as described herein may also be co-administered with another bioactive agent (e.g., antiviral agent, antihyperproliferative disease agent, agents which treat chronic inflammatory disease, among others as otherwise described herein).

The term "antiviral agent" refers to an agent which may be used in combination with autophagy modulators (autostatins) as otherwise described herein to treat viral infections, especially including HIV infections, HBV infections and/or HCV infections. Exemplary anti-HIV agents include, for example, nucleoside reverse transcriptase inhibitors (NRTI), non-nucleoside reverse transcriptase inhibitors (NNRTI), protease inhibitors, fusion inhibitors, among others, exemplary compounds of which may include, for example, 3TC (Lamivudine), AZT (Zidovudine), (-)-FTC, ddI (Didanosine), ddC (zalcitabine), abacavir (ABC), tenofovir (PMPA), D-D4FC (Reverset), DAT (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development. Exemplary anti-HBV agents include, for example, hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof. Anti-HCV agents include, for example, interferon, pegylated intergeron, ribavirin, NM 283, VX-950 (telaprevir), SCH 50304, TMC435, VX-500, BX-813, SCHS03034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9 Agonist, PHX1766, SP-30 and mixtures thereof.

An "inflammation-associated metabolic disorder" includes, but is not limited to, lung diseases, hyperglycemic disorders including diabetes and disorders resulting from insulin resistance, such as Type I and Type II diabetes, as well as severe insulin resistance, hyperinsulinemia, and dyslipidemia or a lipid-related metabolic disorder (e.g. hyperlipidemia (e.g., as expressed by obese subjects), elevated low-density lipoprotein (LDL), depressed high-density lipoprotein (HDL), and elevated triglycerides) and insulin-resistant diabetes, such as Mendenhall's Syndrome, Werner Syndrome, leprechaunism, and lipoatrophic diabetes, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-deficiency, GH resistance, Turner's syndrome, Laron's syndrome, short stature, increased fat mass-to-lean ratios, immunodeficiencies including decreased $CD4^+$ T cell counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., diseases of the central nervous system including Alzheimer's disease, or Parkinson's disease or multiple sclerosis, and diseases of the peripheral nervous system and musculature including peripheral neuropathy, muscular dystrophy, or myotonic dystrophy, and catabolic states, including those associated with wasting caused by any condition, including, e.g., mental health condition (e.g., anorexia nervosa), trauma or wounding or infection such as with a bacterium or human virus such as HIV, wounds, skin disorders, gut structure and function that need restoration, and so forth.

An "inflammation-associated metabolic disorder" also includes a cancer and an "infectious disease" as defined herein, as well as disorders of bone or cartilage growth in children, including short stature, and in children and adults disorders of cartilage and bone in children and adults, including arthritis and osteoporosis. An "inflammation-associated metabolic disorder" includes a combination of two or more of the above disorders (e.g., osteoporosis that is a sequela of a catabolic state). Specific disorders of particular interest targeted for treatment herein are diabetes and obesity, heart dysfunctions, kidney disorders, neurological disorders, bone disorders, whole body growth disorders, and immunological disorders.

In one embodiment, "inflammation-associated metabolic disorder" includes: central obesity, dyslipidemia including particularly hypertriglyceridemia, low HDL cholesterol, small dense LDL particles and postpranial lipemia; glucose intolerance such as impaired fasting glucose; insulin resistance and hypertension, and diabetes. The term "diabetes" is used to describe diabetes mellitus type I or type II. The present invention relates to a method for improving renal function and symptoms, conditions and disease states which occur secondary to impaired renal function in patients or subjects with diabetes as otherwise described herein. It is noted that in diabetes mellitus type I and II, renal function is impaired from collagen deposits, and not from cysts in the other disease states treated by the present invention.

Mycobacterial infections often manifest as diseases such as tuberculosis. Human infections caused by mycobacteria have been widespread since ancient times, and tuberculosis remains a leading cause of death today. Although the incidence of the disease declined, in parallel with advancing standards of living, since the mid-nineteenth century, mycobacterial diseases still constitute a leading cause of morbidity and mortality in countries with limited medical resources. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent. Nearly one third of the world's population is infected with *Mycobacterium tuberculosis* complex, commonly referred to as tuberculosis (TB), with approximately 8 million new cases, and two to three million deaths attributable to TB yearly. Tuberculosis (TB) is the cause of the largest number of human deaths attributable to a single etiologic agent (see Dye et al., J. Am. Med. Association, 282, 677-686, (1999); and 2000 WHO/OMS Press Release).

Mycobacteria other than *M. tuberculosis* are increasingly found in opportunistic infections that plague the AIDS patient. Organisms from the *M. avium-intracellulare* complex (MAC), especially serotypes four and eight, account for 68% of the mycobacterial isolates from AIDS patients. Enormous numbers of MAC are found (up to $10^{10}$ acid-fast bacilli per gram of tissue), and consequently, the prognosis for the infected AIDS patient is poor.

In many countries the only measure for TB control has been vaccination with *M. bovis* bacille Calmette-Guerin (BCG). The overall vaccine efficacy of BCG against TB, however, is about 50% with extreme variations ranging from 0% to 80% between different field trials. The widespread emergence of multiple drug-resistant *M. tuberculosis* strains is also a concern.

*M. tuberculosis* belongs to the group of intracellular bacteria that replicate within the phagosomal vacuoles of resting macrophages, thus protection against TB depends on T cell-mediated immunity. Several studies in mice and humans, however, have shown that Mycobacteria stimulate antigen-specific, major histocompatibility complex (MHC) class II- or class I-restricted CD4 and CD8 T cells, respectively. The important role of MHC class I-restricted CD8 T cells was convincingly demonstrated by the failure of β2-microglobulin) deficient mice to control experimental *M. tuberculosis* infection.

As used herein, the term "tuberculosis" comprises disease states usually associated with infections caused by mycobacteria species comprising *M. tuberculosis* complex. The term "tuberculosis" is also associated with mycobacterial infections caused by mycobacteria other than *M. tuberculosis*. Other mycobacterial species include *M. avium-intracellulare, M. kansarii, M. fortuitum, M. chelonae, M. leprae, M. africanum*, and *M. microti, M. avium paratuberculosis, M. intracellulare, M. scrofulaceum, M. xenopi, M. marinum, M. ulcerans.*

An "infectious disease" includes but is limited to those caused by bacterial, mycological, parasitic, and viral agents. Examples of such infectious agents include the following: staphylococcus, streptococcaceae, neisseriaaceae, cocci, enterobacteriaceae, pseudomonadaceae, vibrionaceae, campylobacter, pasteurellaceae, bordetella, francisella, brucella, legionellaceae, bacteroidaceae, gram-negative hacilli, clostridium, corynebacterium, propionibacterium, gram-positive bacilli, anthrax, actinomyces, nocardia, mycobacterium, treponema, borrelia, leptospira, mycoplasma, ureaplasma, rickettsia, chlamydiae, systemic mycoses, opportunistic mycoses, protozoa, nematodes, trematodes, cestodes, adenoviruses, herpesviruses, poxviruses, papovaviruses, hepatitis viruses, orthomyxoviruses, paramyxoviruses, coronaviruses, picornaviruses, reoviruses, togaviruses, flaviviruses, bunyaviridae, rhabdoviruses, human immunodeficiency virus and retroviruses.

In certain embodiments, an "infectious disease" is selected from the group consisting of tuberculosis, leprosy, Crohn's Disease, acquired immunodeficiency syndrome, Lyme disease, cat-scratch disease, Rocky Mountain spotted fever and influenza or a viral infection selected from HIV (I and/or II), hepatitis B virus (HBV) or hepatitis C virus (HCV).

According to various embodiments, the combination of compositions and/or compounds according to the present invention may be used for treatment or prevention purposes in the form of a pharmaceutical composition. This pharmaceutical composition may comprise one or more of an active ingredient as described herein.

As indicated, the pharmaceutical composition may also comprise a pharmaceutically acceptable excipient, additive or inert carrier. The pharmaceutically acceptable excipient, additive or inert carrier may be in a form chosen from a solid, semi-solid, and liquid. The pharmaceutically acceptable excipient or additive may be chosen from a starch, crystalline cellulose, sodium starch glycolate, polyvinylpyrolidone, polyvinylpolypyrolidone, sodium acetate, magnesium stearate, sodium laurylsulfate, sucrose, gelatin, silicic acid, polyethylene glycol, water, alcohol, propylene glycol, vegetable oil, corn oil, peanut oil, olive oil, surfactants, lubricants, disintegrating agents, preservative agents, flavoring agents, pigments, and other conventional additives. The pharmaceutical composition may be formulated by admixing the active with a pharmaceutically acceptable excipient or additive.

The pharmaceutical composition may be in a form chosen from sterile isotonic aqueous solutions, pills, drops, pastes, cream, spray (including aerosols), capsules, tablets, sugar coating tablets, granules, suppositories, liquid, lotion, suspension, emulsion, ointment, gel, and the like. Administration route may be chosen from subcutaneous, intravenous, intestinal, parenteral, oral, buccal, nasal, intramuscular, transcutaneous, transdermal, intranasal, intraperitoneal, and topical. The pharmaceutical compostions may be immediate release, sustained/controlled release, or a combination of immediate release and sustained/controlled release depending upon the compound(s) to be delivered, the compound(s), if any, to be coadministered, as well as the disease state and/or condition to be treated with the pharmaceutical composition. A pharmaceutical composition may be formulated with differing compartments or layers in order to facilitate effective administration of any variety consistent with good pharmaceutical practice.

The subject or patient may be chosen from, for example, a human, a mammal such as domesticated animal, or other animal. The subject may have one or more of the disease states, conditions or symptoms associated with autophagy as otherwise described herein.

The compounds according to the present invention may be administered in an effective amount to treat or reduce the likelihood of an autophagy-mediated disease and/or condition as well one or more symptoms associated with the disease state or condition. One of ordinary skill in the art would be readily able to determine an effective amount of active ingredient by taking into consideration several variables including, but not limited to, the animal subject, age, sex, weight, site of the disease state or condition in the patient, previous medical history, other medications, etc.

For example, the dose of an active ingredient which is useful in the treatment of an autophagy mediated disease state, condition and/or symptom for a human patient is that which is an effective amount and may range from as little as 100 µg or even less to at least about 500 mg or more, which may be administered in a manner consistent with the delivery of the drug and the disease state or condition to be treated. In the case of oral administration, active is generally administered from one to four times or more daily. Transdermal patches or other topical administration may administer drugs continuously, one or more times a day or less frequently than daily, depending upon the absorptivity of the active and delivery to the patient's skin. Of course, in certain instances where parenteral administration represents a favorable treatment option, intramuscular administration or slow IV drip may be used to administer active. The amount of active ingredient which is administered to a human patient is an effective amount and preferably ranges from about 0.05 mg/kg to about 20 mg/kg, about 0.1 mg/kg to about 7.5 mg/kg, about 0.25 mg/kg to about 6 mg/kg., about 1.25 to about 5.7 mg/kg.

The dose of a compound according to the present invention may be administered at the first signs of the onset of an autophagy mediated disease state, condition or symptom. For example, the dose may be administered for the purpose of lung or heart function and/or treating or reducing the likelihood of any one or more of the disease states or conditions which become manifest during an inflammation-associated metabolic disorder or tuberculosis or associated disease states or conditions, including pain, high blood pressure, renal failure, or lung failure. The dose of active ingredient may be administered at the first sign of relevant symptoms prior to diagnosis, but in anticipation of the disease or disorder or in anticipation of decreased bodily function or any one or more of the other symptoms or secondary disease states or conditions associated with an autophagy mediated disorder to condition.

These and other aspects of the invention are described further in the following illustrative examples which are provided for illustration of the present invention and are not to be taken to limit the present invention in any way.

EXAMPLES

Experimental Procedures

Cells and Cell Lines

RAW264.7, 293T, THP-1 and HeLa cells were obtained directly from ATCC and maintained in ATCC recommended media. Ulk1/2 double knockout MEFs and matching wild type MEFs were from Sharon Tooze, The Francis Crick Institute.

Cell Culture and Biochemical Methods

Cells and cell lines, GST pull-downs, ULK1 phosphorylation assay, mass spectrometry, antibodies source and dilutions, immunoblotting, coimmunoprecipitation, plasmids, siRNA, and transfection are described in Supplementary Experimental Procedures.

CRISPR Knockout Cell Lines and their Complementation

Figure 9:
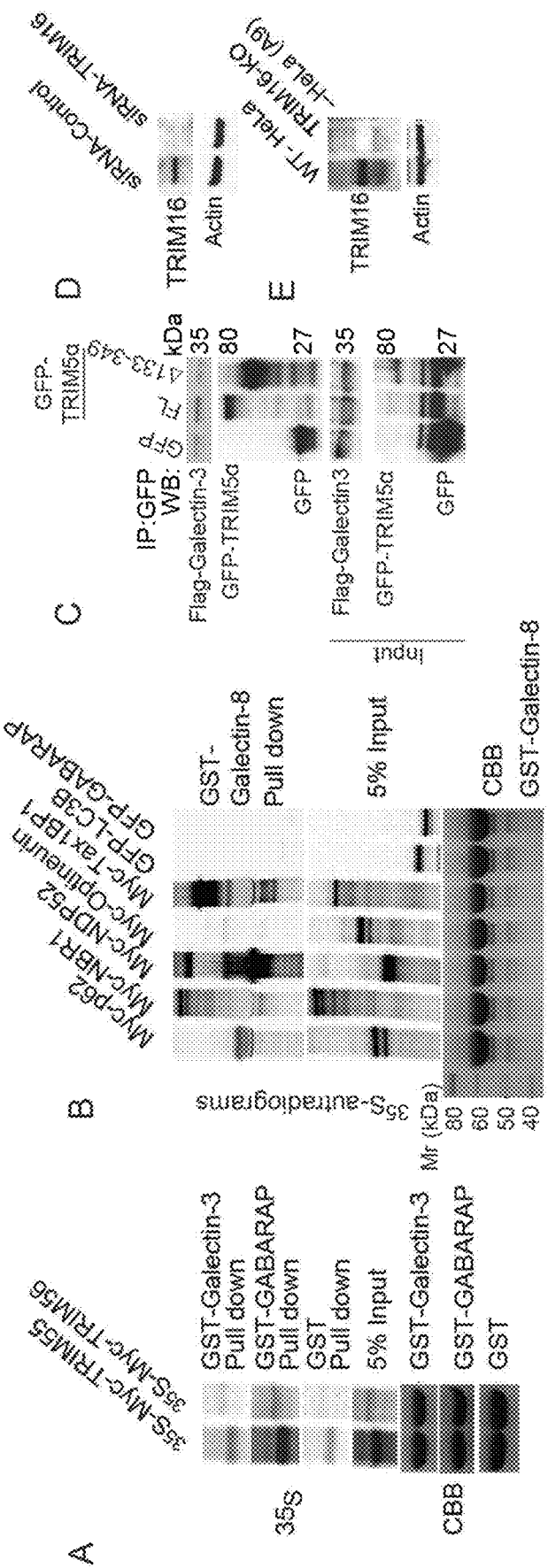
FIG. 9 (Related to FIG. 1) shows an analysis of interactions with Galectins, knockdown and knockout of TRIM16, and screen of TRIM family for effects on ubiquitination response to lysosomal damage. (A) GST-galectin-3 pull-downs of TRIM55 and TRIM56. (B) GST-galectin-8 pull-downs with Sequestosome 1-like receptors. (C) Co-IP analysis of GFP-TRIM5α (full-length vs CCD deletion Ä133-349) and Flag-Galectin-3
Figure 9:
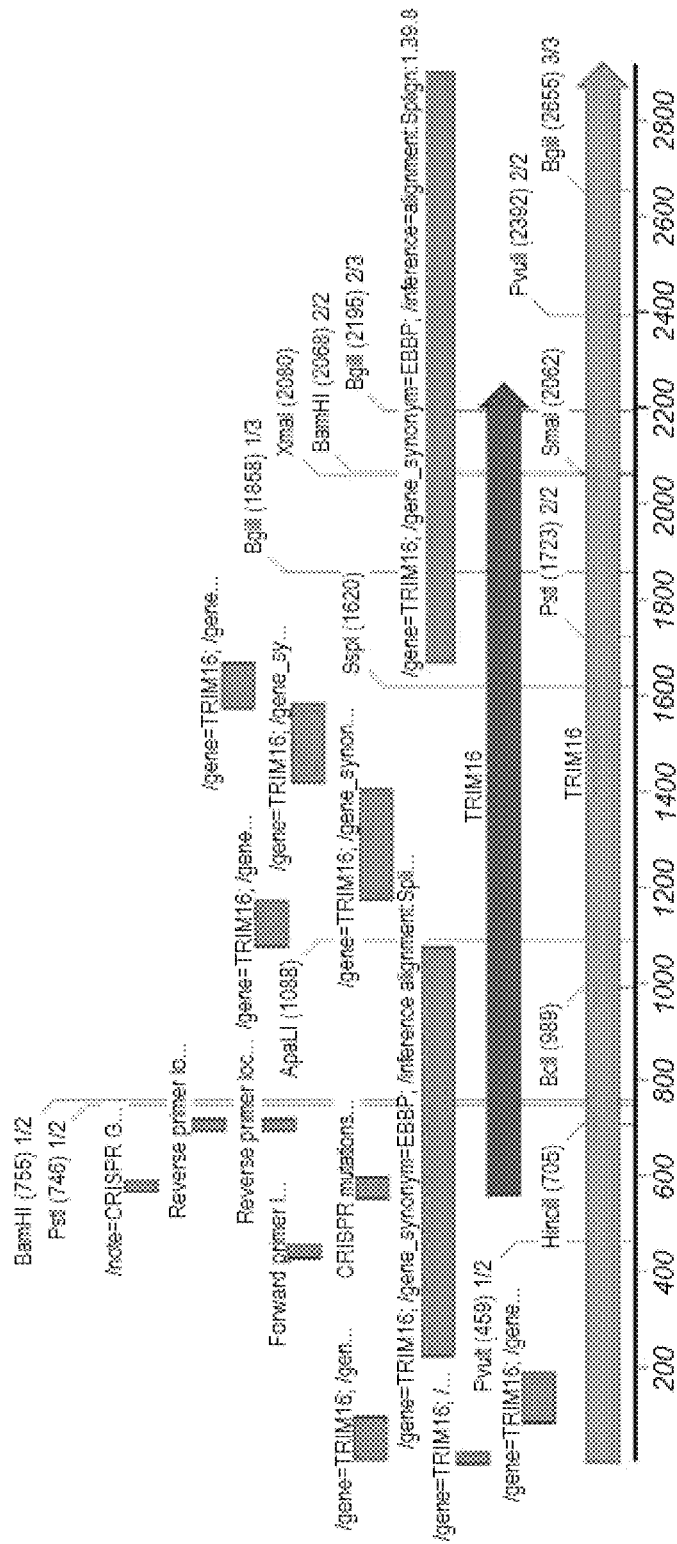
Figure 9:
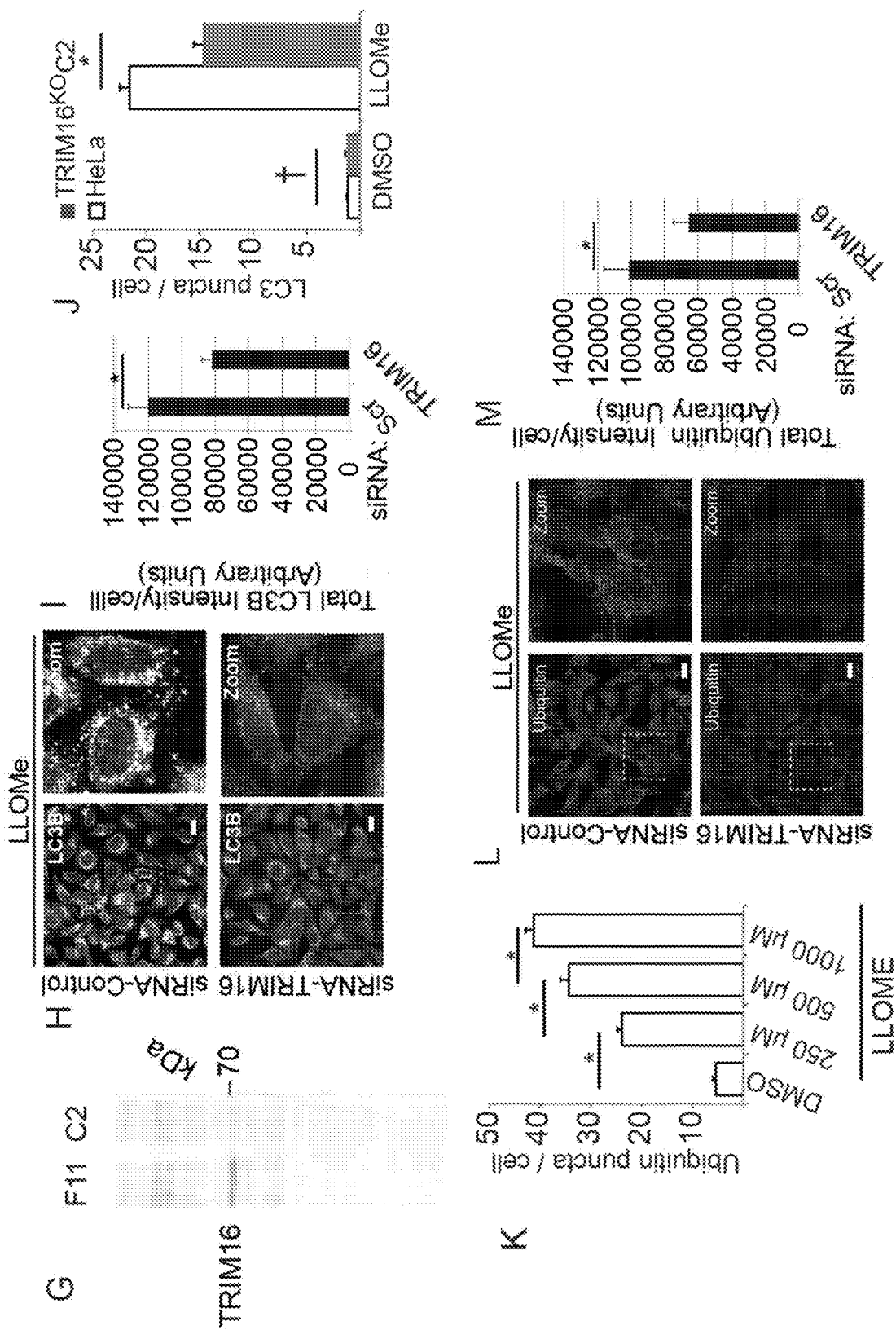

To generate CRISPR knock out cell lines, Hela cells were transfected with a PX458 (Addgene plasmid #48138) (Ran et al., 2013) encoding the U6 promoter, human TRIM16 target sequence located within the first exon (AGTTG-GATCTAATGGCTCCA, with the 5' nucleotide A changed into a G; this sequence is followed on the chromosome by a protospacer adjacent motif GGG and was selected using crispr.mit.edu/guides site) fused to a chimeric guide RNA, *S. pyogenes* Cas9, and GFP. Transfected cells (green fluorescence) were sorted by flow cytometry and single cell clones analyzed by immunoblotting for a loss of TRIM16 band. Positive clones were subjected to next generation sequencing (Illumina; Massachusetts General Hospital core) to characterize the mutation (FIG. 9F). For complementation, TRIM16KO HeLa cells were transfected with empty vector, WT TRIM 16 or phosphorylation mutated TRIM16 with >60% transfection efficiency. After 24 h of transfection cells were subjected to response assays.

Bacterial Strains and Procedures

*M. tuberculosis* wild-type Erdman and ESX-I mutant (Manzanillo et al., 2012) were cultured in Middlebrook 7H9 broth supplemented with 0.05% Tween 80, 0.2% glycerol, and 10% oleic acid, albumin, dextrose, and catalase (OADC; BD Biosciences) at 37° C. and homogenized to generate single-cell suspension for macrophage infection studies. For acute (short-term) aerosol infection, C57BL mice or their Galectin-3 knockout derivative B6.Cg-Lgals3$^{tm1Poi}$/J (Jackson Laboratory) were exposed to high dose *M. tuberculosis* Erdman aerosols (1-4×e$^3$ CFU deposition) as previously described (Castillo et al., 2012), with a modification of using a GlasCol apparatus for aerosol delivery, and survival monitored for 2.5 months post-infection. For chronic (long-term) infection with lower doses of *M. tuberculosis*, mice were exposed in a GlasCol apparatus to medium dose (6×e$^2$ CFU initial lung deposition) and low dose (2×e$^2$ CFU initial lung deposition) of *M. tuberculosis* Erdman aerosols as previously described (Manzanillo et al., 2012), (Castillo et al., 2012)(Castillo et al., 2012) and survival monitored for up to 200 days post-infection. For intracellular mycobacterial survival assays and fluorescence microscopy see Supplementary Experimental Procedures.

High Content Microscopy, Confocal Microscopy, Flow Cytometry, Cell Survival

High content microscopy with automated image acquisition and quantification was carried out using a Cellomics HCS scanner and iDEV software (Thermo) in 96-well plates (Mandell et al., 2014). Immunofluorescence confocal microscopy was performed using an LSM510 confocal microscope and Zeiss software package. For quantification of puncta or total cell fluorescence, image J was used as described previously (Chauhan et al., 2015). For quantifying cell death, HeLa and derivative cells treated with 15 μM siramesine for 12 h were incubated with 7AAD (BD Pharmingen™; cat #559925) for 30 min and fluorescence of 7AAD bound to nuclear DNA measured in a flow cytometer.

Supplementary Experimental Procedures

GST Pull Downs and ULK1 Phosphorylation Assay

GST-fusion proteins were expressed in *Escherichia coli* SoluBL21 (Amsbio). GST fusion proteins were purified and immobilized on glutathione-coupled sepharose beads (Amersham Bioscience, Glutathione-sepharose 4 Fast Flow) and pull-down assays with in vitro translated [$^{35}$S]-labeled proteins were done as described previously (Pankiv et al., 2007). The [$^{35}$S] labeled proteins were produced using the TNT T7 Quick Coupled Transcription/Translation System (Promega) in the presence of [$^{35}$S] L-methionine. The proteins were eluted from washed beads by boiling in SDS-PAGE gel loading buffer. separated by SDS-PAGE, and radiolabeled proteins were detected in a Fujifilm bioimaging analyzer BAS-5000 (Fuji).

In vitro phosphorylation assays were performed by incubating the recombinant proteins with FLAG-ULK1 kinase immunoprecipitated from the transfected HEK293 cells in a standard kinase buffer containing 50 μM of cold ATP and 2.5 μCi [g-$^{32}$P]-ATP per reaction at 30° C. for 30 min. The reaction was stopped by adding SDS sample buffer and boiling, and then subjected to SDS-PAGE gel and autoradiography. For pull-downs assays without 32p radiolabeling (i.e. cold-phosphorylation), cold ATP was used in a mixture with TRIM16 and then the standard in-vitro pull-downs were performed.

In vivo phosphorylation and Liquid Chromatography—Mass Spectrometry

For in vivo phosphorylation analyses, subconfluent HEK293 cells in 10 cm dishes were transfected with total 5 μg plasmids (i.e. pDest-eGFP-TRIM16, plus pDest-3× FLAG or pDest-3×FLAG-ULK1) using Metafectene Pro (Biontex) following the supplier's instructions. Twenty-four hours after transfection cells were rinsed with ice-cold PBS prior to lysis in RIPA buffer (50 mm Tris-HCl, pH 7.5, 150 mm NaCl, 1 mm EDTA, 1% Nonidet P-40 (v/v), 0.25% Triton X-100) supplemented with Complete Mini EDTA-free protease inhibitor mixture tablets (1 tablet per 10 ml) (Roche Applied Science) and phosphatase inhibitor mixture set II (Calbiochem). Lysates were cleared by centrifugation and the cleared lysates were then incubated with the Anti-GFP MicroBeads (Miltenyi Biotec Norden AB) for 30 min at 4° C. The GFP-precipitated immunocomplexes were washed five times with RIPA lysis buffer and eluted following the supplier's instructions. The eluted samples were subjected to SDS-PAGE and gel bands containing TRIM16 were excised and subjected to in-gel reduction, alkylation, and tryptic digestion with 6 ng/μl trypsin (Promega). OMIX C18 tips (Varian, Inc.) was used for sample cleanup and concentration. Peptide mixtures containing 0.1% formic acid were loaded onto a Thermo Fisher Scientific EASY-nLC1000 system and EASY-Spray column (C18, 2 μm, 100 Å, 50 μm, 50 cm). Peptides were fractionated using a 2-100% acetonitrile gradient in 0.1% formic acid over 50 min at a flow rate of 200 nl/min. The separated peptides were analyzed using a Thermo Scientific Q-Exactive mass spectrometer. Data was collected in data dependent mode using a Top10 method. The raw data were processed using the Proteome Discoverer 1.4 software (Thermo Scientific) and the PEAKS Studio 7 software (v. 7.0, Bioinformatics Solutions). The fragmentation spectra from Proteome Discoverer was searched against the Swissprot database using an in-house Mascot server (Matrix Sciences). The phosphoRS 3.0 tool in the Proteome Discoverer software was used to validate potential phosphosites in the samples. A human Swissprot database was used for the de novo peptide sequencing assisted search engine database searching by the PEAKS software. Peptide mass tolerances used in the searches were 10 ppm, and fragment mass tolerance was 0.02 Da. Both software's identified the $203 and S116 phosphosites in TRIM16 in the samples with ULK1, but not in the FLAG control. The presence of these phosphorylations in the ULK1 samples but not in the FLAG control was manually verified by inspecting the LC-MS spectra in the Excalibur 2.2 software (Thermo Scientific).

Antibodies

The following antibodies and dilutions were used: TRIM16 (goat polyclonal antibody, Santa Cruz; sc-79770; 1:50-1:100 for immunofluorescence (IF) and 1:200-1:1,000 for Western blots (WB)); Galectin-3 (rabbit polyclonal Abcam; cat #ab53082; 1:100, IF; or mouse monoclonal Santa Cruz sc-32790 1:100 (IF) and 1:250 (WB)); ubiquitin (mouse monoclonal FK2, MBL; cat #D058-3; 1:100-1:500, IF); LAMP1 (mouse monoclonal Abcam; cat #ab25630; 1:100; IF); LAMP2 (mouse monoclonal Hybridoma Bank, University of Iowa; 1:500 (IF)); ULK1 (rabbit polyclonal Santa Cruz, sc33182; 1:100 (IF); 1:500 (WB)); ATG16L1 (rabbit polyclonal MBL (PM040); 1:2,000 (WB)) K63 ubiquitin (rabbit monoclonal Millipore 05-1308; 1:100 (IF); 1:500 (WB); TFEB (rabbit polyclonal anti-human; Cell Signaling CST 4240, 1:200 (IF)); phospho p70s6K (rabbit polyclonal Cell Signaling CST 9205; 1:750 (WB)) p70s6k (rabbit polyclonal Cell Signaling CST 9202; 1:1,000 (WB)); RagB (rabbit polyclonal Cell Signaling CST 8150; 1:500); Rag D (rabbit polyclonal Cell Signaling CST 4470; 1:500);

DEPTOR (Rabbit monoclonal Cell Signaling CST 11816; 1:1000); Callin4A (rabbit monoclonal antibody Abcam #ab92554 1:500 (WB)); Cullin5 (rabbit polyclonal antibody #ab34840; 1:500). GFP (rabbit polyclonal Abcam; cat #ab290; 0.5 µg/ml IP and 1:5,000 (WB)); PPP3CB (rabbit polyclonal antibody Abcam, ab96573 1:500 (WB)) Flag (mouse monoclonal Sigma; cat #F1804, used at 1:1,000); Myc (mouse monoclonal Santa Cruz, sc-40; 1:200 (IF); 1:500 (WB)); HA (mouse monoclonal Millipore 05-904; 1:1,000 (WB)); and actin (mouse monoclonal Abcam; cat #ab8226, used at 1:4,000).

Immunoblots and Co-Immunoprecipitation Assays

Immunoblots and co-IPs assays for endogenous or exogenously expressed proteins were carried out as described previously (Chauhan et al., 2015). For immunoprecipitation experiments with exogenously expressed proteins, 293T cells were transfected with 5 µg of expression constructs by calcium phosphate for 24 h and lysed on ice using NP-40 buffer (Invitrogen) containing protease inhibitor cocktail (Roche, cat #11697498001) and PMS (Sigma, cat #93482). Lysates were mixed with antibody (2-3 µg) incubated at 4° C. for 2 h followed by incubation with protein G Dynabeads (Life technologies) for 2 h at 4° C. Beads were washed four times with PBS and then boiled with SDS-PAGE buffer for analysis of interacting protein by Immunoblotting. Input lanes contained 10% of material unless otherwise indicated.

Analysis of Effectene-Bead Phagosomes

Wild type (WT) and Ulk1/Ulk2 double KO mouse embryonic fibroblasts (McAlpine et al., 2013) in 96-well plates were incubated with Fluoresbrite bead (3 µm; Polysciences Inc. cat #21637-1; fluorescence detected at 485 nm) treated with effectene transfection reagent as described previously (Fujita et al., 2013). The beads were not spun onto the cells but were allowed to spontaneously uptake the beads, which required times >3h. After up to 24 h of incubation, cells were processed for immunofluorescence microscopy with Galectin-3 and TRIM16 antibodies for 2 h followed by treatment with secondary antibodies (goat anti-mouse Alexa Flour 568 and goat anti-rabbit Alexa Flour 647). High content microscopy was carried out in a Cellomics HCS scanner and images analyzed and objects quantified using iDEV software (Thermo) (Mandell et al., 2014).

For intracellular mycobacterial survival assays see Supplementary experimental procedures. RAW264.7 cells were infected with mycobacteria and quantification of mycobacterial survival carried out as previously described (Ponpuak et al., 2009). In brief, $3 \times 10^5$ cells of RAW264.7 macrophages were plated onto each well of 12-well plates 12 h before infections. Cells were then infected with single cell suspension of mycobacteria in complete media at MOI of 10 for 1 h. Cells were then washed three times with PBS to remove un-internalized mycobacteria. Infected cells were then lysed to determine the number of intracellular mycobacteria at t=0 by plating onto Middlebrook 7H11 agar supplemented with 0.05% Tween 80, 0.2% glycerol, and 10% OADC (BD Biosciences) and grown at 37° C. or infected cells were continued to grow until harvesting at t=24 for CFU analysis. Percent mycobacteria survival was calculated by dividing the number of intracellular mycobacteria at t=24 over that of t=0 multiply by 100 and relative to control cells set to 100%.

Bacterial Phagosomes, Intracellular Mycobacterial Survival, and Fluorescence Microscopy of Infected Macrophages For immunofluorescence microscopy with mycobacteria-infected macrophages, $3 \times 10^5$ cells of RAW264.7 macrophages were plated onto coverslips in 12-well plates 12 h before infections. Cells were then infected with $3 \times 10^6$ Alexa-568-labeled mycobacteria per well in complete media at 37° C. for 15 min, washed three times in PBS, and chased for 1 h in complete media as previously described (Ponpuak et al., 2009). Cells were then washed three times with PBS and incubated in complete media for the indicated times. Cells were then fixed with 4% paraformaldehyde/PBS for 15 min followed by permeabilization with 0.1% Triton X-100/PBS for 5 min. Coverslips were then blocked in PBS containing 3% BSA and then stained with primary antibodies according to manufacturer's recommendation. Cells were washed three times with PBS and then incubated with appropriate secondary antibodies (Invitrogen) for 2 h at room temperature. Coverslips were then mounted using ProLong Gold Antifade Mountant (Invitrogen) and analyzed by confocal microscopy using the Zeiss LSM510 Laser Scanning Microscope. At least 50 phagosomes per experimental condition in three independent experiments were quantified. For quantification, % mycobacteria-marker colocalization was fraction of total mycobacterial phagosomes examined counted as positive when one or more puncta were observed on or in contact with the RAW264.7 cells were infected with mycobacteria and quantification of mycobacterial survival carried out as previously described (Ponpuak et al., 2009). In brief, $3 \times 10^5$ cells of RAW264.7 macrophages were plated onto each well of 12-well plates 12 h before infections. Cells were then infected with single cell suspension of mycobacteria in complete media at MOI of 10 for 1 h. Cells were then washed three times with PBS to remove un-internalized mycobacteria. Infected cells were then lysed to determine the number of intracellular mycobacteria at t=0 by plating onto Middlebrook 7H11 agar supplemented with 0.05% Tween 80, 0.2% glycerol, and 10% OADC (BD Biosciences) and grown at 37° C. or infected cells were continued to grow until harvesting at t=24 for CFU analysis. Percent mycobacteria survival was calculated by dividing the number of intracellular mycobacteria at t=24 over that of t=0 multiply by 100 and relative to control cells set to 100%.

For immunofluorescence microscopy with mycobacteria-infected macrophages, $3 \times 10^5$ cells of RAW264.7 macrophages were plated onto coverslips in 12-well plates 12 h before infections. Cells were then infected with $3 \times 10^6$ Alexa-568-labeled mycobacteria per well in complete media at 37° C. for 15 min, washed three times in PBS, and chased for 1 h in complete media as previously described (Ponpuak et al., 2009). Cells were then washed three times with PBS and incubated in complete media for the indicated times. Cells were then fixed with 4% paraformaldehyde/PBS for 15 min followed by permeabilization with 0.1% Triton X-100/PBS for 5 min. Coverslips were then blocked in PBS containing 3% BSA and then stained with primary antibodies according to manufacturer's recommendation. Cells were washed three times with PBS and then incubated with appropriate secondary antibodies (Invitrogen) for 2 h at room temperature. Coverslips were then mounted using ProLong Gold Antifade Mountant (Invitrogen) and analyzed by confocal microscopy using the Zeiss LSM510 Laser Scanning Microscope. At least 50 phagosomes per experimental condition in three independent experiments were quantified. For quantification, % mycobacteria-marker colocalization was fraction of total mycobacterial phagosomes examined counted as positive when one or more puncta were observed on or in contact with the Plasmids, siRNAs, cell transfections TRIMs, SLRs, Galectins, and GABARAP cDNA were first cloned into pENTR or pDONR221 vectors from Invitrogen, and then (Gateway) cloned into either pDestMye or pDest53 (GFP) using LR-II enzyme from Invitrogen. (GST-Galectin-3, GST-Galectin-8 and GST-GABARAP are described in Figure-1). pENTR clones of different TRIM5α deletion constructs (ÄRING, ÄB.Box, ÄCCD and ÄSPRY) including the full-length TRIM5α were generated using Phusion DNA Polymerase (from NEB) and T4-DNA ligase (from NEB), and then (Gateway) cloned into pDestMyc using LR-II enzyme from Invitrogen. Constructs containing cDNAs encoding Flag-ATG16L1 and its deletions and Flag-Galectin-3 were cloned by amplifying with primer pairs 5'caccatggcccaactgaggattaag3' (forward) and 5'teagcgtctcc-caaagatattagtgataga3' (reverse) and S'caccategcagacaat-ttttegetccat3' (forward) and 5'ttatatcatggtatatgaagcact3' (reverse), respectively, followed by subcloning into pENTRY (Invitrogen) and recombined into pDEST 3xFlag. pTRIM16 wt and pTRIM16S116A/S203A were generated as Gateway clones in _pDEST_ vector encoding Flag-TRIM16 fusions.

All siRNAs were from Dharmacon. TRIM screens were carried out as previously described (Mandell et al., 2014). TRIM RAW264.7 cells were transfected with 1.5 μg of siRNAs as previously described (Ponpuak et al., 2009); 10' cells were resuspended in 100 μl of Nucleofector solution kit V (Amaxa), siRNAs were then added to the cell suspension and cells were nucleoporated using Amaxa Nucleofector apparatus with program D-032. Cells were re-transfected with a second dose of siRNAs 24 h after the first transfection, and assayed after 48 h.

Results

TRIMs and Galectins Interact

During the screens uncovering a broad role of TRIMs in autophagy (Kimura et al., 2015; Mandell et al., 2014), we observed an unanticipated propensity of TRIMs to bind Galectins. Of the TRIMs tested, TRIM5α, TRIM6, TRIM 17, TRIM20, TRIM22, TRIM23 and TRIM49 bound both Galectin-3 and Galectin-8, whereas TRIM16, TRIM21, TRIM55 and TRIM56 did not (FIGS. 1A and 9A). Galectin-8 bound NDP52 as expected (Thurston et al., 2012) and its close homolog TAX1BP1 but not Optineurin and other controls (FIG. 9B). For specificity, we mapped the Galectin-3-binding region in TRIM5α and found that a region spanning TRIM5α's CCD, but not its β-Box or SPRY domains, was required for Galectin-3 (FIG. 1B and FIG. 9C). Thus, TRIMs, through specific regions as delimited within TRIM5α, have a propensity to associate with Galectins.

Screen for TRIMs Involved in Autophagic Response to Lysosomal Damage

Galectins participate in autophagic response to endomembrane perforations caused by lysosomal damaging agents and by bacteria (Fujita et al., 2013; Maejima et al., 2013; Thurston et al., 2012). Based on interactions between Galectins and TRIMs detected above, we hypothesized that TRIMs might play a role in autophagic response to endomembrane damage. The lysosomal damaging agent Leu-Leu-O-Me (LLOMe), which is condensed into a membranolytic polymer via the transpeptidase action of cathepsin C within lysosomes (Fujita et al., 2013; Maejima et al., 2013), elicited a consistent LC3 dose response with dynamic range suitable for a screen. We employed high content microscopy with automated image acquisition and quantification (HC) (Kimura et al., 2015; Mandell et al., 2014) of endogenous LC3B puncta (FIG. 1D) and screened the human TRIM family by siRNA knockdowns in HeLa cells for effects on LC3 response to LLOMe treatment (FIG. 1E). TRIM16 showed the strongest effect (FIG. 1E).

TRIM16 is Necessary for Autophagic Response and Ubiquitination Upon Lysosomal Damage The screening data were confirmed by follow-up siRNA knockdowns (FIG. 9C) and by generating a TRIM16 CRISPR knockout in Hela cells (TRIM1680). Two independent CRISPR mutants, HeLa TRIM16KO A9 (FIG. 9D,E) and C2 (FIG. 9F) were generated. TRIM16 knockdowns diminished LC3B response (FIG. 9G,H). HC imaging analysis in TRIM16 knockout cell line A9 demonstrated that TRIM16 was required for a full autophagic response to lysosomal injury caused by LLOMe (FIGS. 1F-H). This was confirmed in a different TRIM16 CRISPR clone, C2 (FIG. 9I).

In addition to LC3' autophagosomes (Maejima et al., 2013), LLOMe-induced lysosomal damage elicits ubiquitin puncta formation on lysosomes (Maejima et al., 2013), in a dose response fashion (FIG. 9J). HC screen using ubiquitin puncta as a lysosomal-damage response readout (Maejima et al., 2013) again indicated a requirement for TRIM16 (FIG. 9K,L). TRIM16 was needed for optimal ubiquitin response to LLOMe when tested by siRNA knockdowns (FIG. 9M,N), and was absolutely required for ubiquitin dots formation when tested in TRIM16 CRISPR knockout HeLa A9 cells (FIGS. 1I-K). This was confirmed in the TRIM16 CRISPR knockout clone C2 (FIG. 9O).

TRIM16 was required for colocalization between LC3B and ubiquitin puncta in response to LLOMe (FIGS. 2A and 10A) as quantified by HC imaging (FIG. 2B,C). TRIM16 puncta were morphologically prominent in response to LLOMe in leukocytes (FIG. 2D,E) but not in Hela cells, most likely due to differential cathepsin C levels. TRIM16 puncta and ubiquitin profiles (FIG. 2D)) and TRIM16 puncta and LC3B puncta (FIG. 2E) colocalized in THP-1 cells exposed to LLOMe. Thus, TRIM16 is required for optimal ubiqutination and autophagic response in response to lysosomal damage.

TRIM16 is in Protein Complexes with Galectin-3 in Cells

Galectin-3 is a marker for damaged lysosomes (Aits et al., 2015). Consistent with the prior reports using GFP-Galectin-3 (Maejima et al., 2013) we found endogenous Galectin-3 colocalizing with or juxtaposed to a number of LC3 profiles induced in response to LLOMe in different cell types (FIG. 10B). Although the initial GST-Galectin pull-downs (FIG. 1A) indicated that TRIM16 did not bind Galectin-3 in vitro, the finding that TRIM16 was a stand-out in our screens, and the acknowledged pivotal role of Galectins, and specifically that of Galectin-3, in recognition of lysosomal damage (Aits et al., 2015; Maejima et al., 2013), prompted us to re-asses the apparent absence of TRIM 16-Galectin-3 interactions. TRIM16 was found in co-IPs with Galectin-2 and Galectin-3 in cellular extracts (FIG. 11A). We focused on Galectin-3 as an accepted marker for damaged lysosomes (Aits et al., 2015). A reverse tag co-IP (FIG. 3A) confirmed TRIM 16-Galectin-3 association. TRIM55 and TRIM56 were not found in co-IPs with Galectin-3 (FIG. 3A) indicating selectivity of Galectin-3-TRIM16 associations. Endogenous protein co-IPs detected TRIM16 and Galectin-3 in common complexes (FIG. 3B). The association between endogenous TRIM16 and Galectin-3 increased in cells exposed to LLOMe (FIG. 3B).

TRIM16 Interacts with Galectin-3 in an ULK1-Dependent Manner

Figure 3:
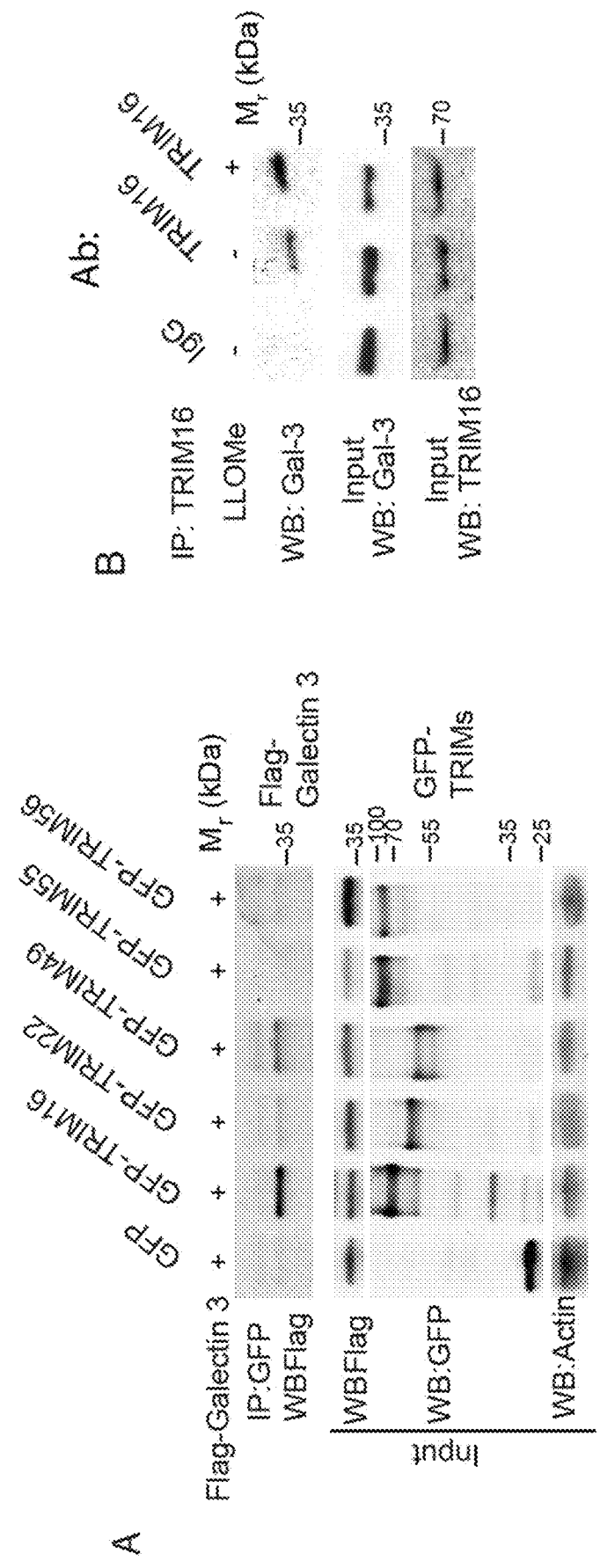
FIG. 3 shows that TRIM16 is phosphorylated by ULK1 and interacts with Galectin-3 in the presence of ULK1 as a platform. (A) Co-immunoprecipitation (Co-IP) analysis of interaction between Galectin-3 and a panel of TRIMs in HEK293T cell lysates expressing GFP or GFP-TRIM fusions and Flag-Galectin-3. (B) Co-IP analysis of endogenous TRIM16 and endogenous Galectin-3 in the absence and presence of LLOMe. (C) Indicated GST-fusion proteins were incubated in a phosphorylation reaction (with $\gamma^{32}$P ATP) with EGFP-ULK1 enriched from HEK293T cells and products separated by PAGE. Left, autoradiogram; right, coommassie brilliant blue (CBB). Dots, position of GST-fusion protein bands on the CBB gel. (D) Flag-ULK1 wt or K46I catalytic ULK1 mutant were incubated with GST fusion protein substrates and processed as in C. (E) In vitro translated and radiolabeled [$^{35}$S] myc-HA-TRIM16 wild type incubated with potential interactors in the presence (+) or absence (−) of Flag-ULK1 and cold ATP, GST pulldowns performed and amount of [$^{35}$S] radiolabeled Myc-HA-TRIM16 determined by PAGE and autoradiography. Amounts of GST fusion proteins are shown in coommassie brilliant blue (CBB)-stained gels (F) Co-IP analysis of interactions between endogenous TRIM16 and Gal3 proteins in Hela cells knocked down for ULK1 by siRNA. (G) GST pulldown analysis as in E, using [$^{35}$S] myc-HA-TRIM16-S116A/S203A mutant instead of wild type TRIM16. Note that both wt (in E) and the ULK1-non-phosphorylatable TRIM16-S116A/S203A (in G) mutant promote association between TRIM16 and Galectin-3.
Figure 3:
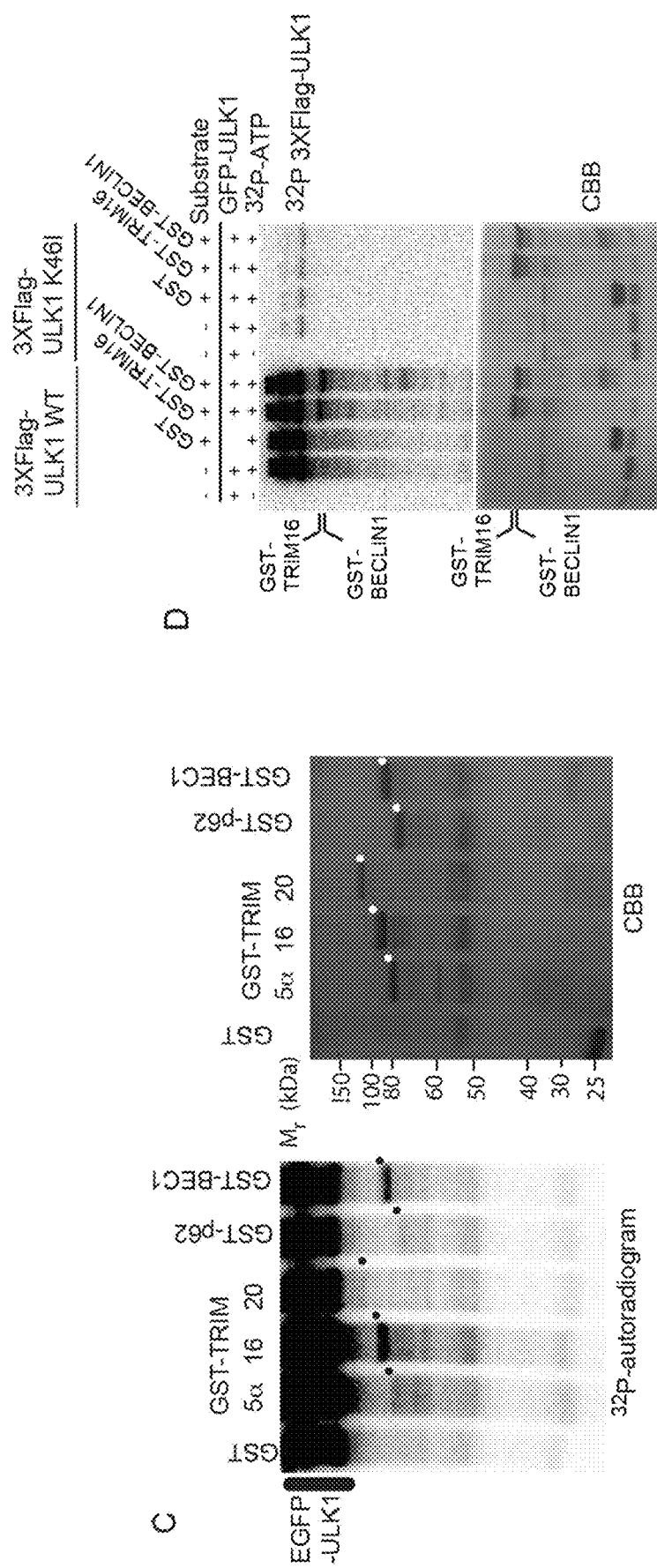
Figure 3:
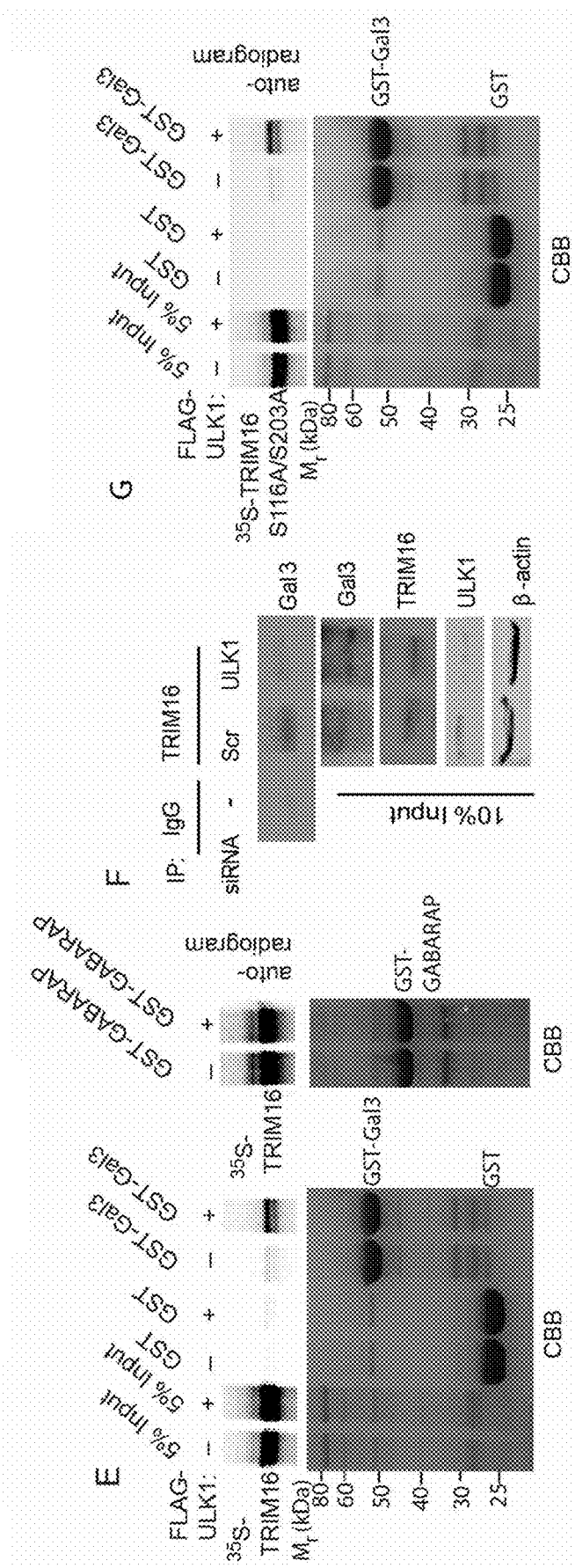

We investigated the basis for the association between Galectin-3 and TRIM16 detected in cells. TRIM 16 turned out to be a substrate for phosphorylation (FIG. 3) by ULK1 (Figure 11B) similarly to the known ULK1 substrate Beclin 1 (Russell et al., 2013) (FIG. 3C). Using a different preparations of ULK1 (FIG. 11C), and comparing active vs. kinase dead ULK1 we established that TRIM16 was a substrate for ULK1 phosphorylation (FIG. 3D). We next tested whether ULK1 modulated TRIM16 and Galectin-3 association observed in cells. GST pull-downs (initially negative for TRIM16-Galectin-3 interactions; FIG. 1A), were repeated in the presence of ULK1. We observed enhancement of interactions between GST-Galectin-3 and TRIM16 (in vitro translated and radiolabeled) when ULK1 was added (FIG. 3E), contrasting with no effect on the binding (Mandell et al., 2014) between TRIM16 and GABARAP (FIG. 3E). In keeping with the above, a knockdown of ULK1 reduced the levels of Galectin-3 found in complexes with TRIM 16 (FIG. 3F).

TRIM16 was phosphorylated at S116 and S203 in an ULK1-dependent manner as determined by mass spectrometry (FIG. 11D,F). When these TRIM16 residues were doubly mutated into a non-phosphorylatable form (S116A and S203A), TRIM16 nevertheless retained its capacity to promote TRIM 16-Galectin-3 interactions (FIG. 3G). Thus, ULK1 serves primarily as a platform for formation of TRIM16-Galectin-3 complexes. This played a function in response to LLOMe, as determined by using ULK1/2 knockout MEFs. Wild type MEEs showed LC3 (FIG. S3G) and ubiquitin (FIG. S3H) response to LLOMe, whereas ULK1/2 MEFs could not mount that response. Since as shown previously (Fujita et al., 2013), ubiquitin dots precede LC3 membrane formation, these findings also indicate that ULKs are required for ubiquitination events preceding LC3 response.

TRIM16 Interacts with Key Autophagy Regulators ULK1 and Beclin 1

TRIM16 showed a capacity to associate with ULK1 (FIG. 4A,B) and colocalized (FIG. 4C) in cells. Co-expression of GFP-TRIM16 increased levels of myc-ULK1 (FIG. 4D), whereas a TRIM16 knockdown diminished endogenous ULK1 (FIG. 4E). TRIM16 promoted ULK1 K63-linked ubiquitination (FIG. 4F), a modification stabilizing autophagy regulators (Nazio et al., 2013). This action of TRIM16 could be either direct, since it has an E3 ubiquitin ligase activity (Bell et al., 2012) (confirmed in FIG. 12A), or indirect by recruiting/activating other E3 ligases controlling activity of ULK1 (Nazio et al., 2013). The latter possibility was underscored by the co-immunoprecipitation of TRIM16 with cullin ubiquitin ligase components (Cullin 4A; FIG. 12B) implicated in regulation of autophagy (Antonioli et al., 2014). LLOMe-elicited TRIM16 puncta colocalized with ubiquitin and ULK1 (FIGS. 4G and 12C). GFP-TRIM16 co-IPed (FIG. 4H) and co-localized (FIG. 4I) with Flag-Beclin 1. Co-expression of GFP-TRIM16 with Flag-Beclin 1 stimulated K63-linked ubiquitination of Beclin 1 (FIG. 4J), which could be direct or through other E3 ligases described previously (Shi and Kehrl, 2010; Xia et al., 2013), and increased cellular levels of Flag-Beclin 1 (FIG. 4K).

ATG16L1 Associates with TRIM16 Upon Endomembrane Damage

ATG16L1 is a core autophagy factor implicated in response to lysosomal damage (Fujita et al., 2013), through a convergence of at least three different association events: FIP200, binding to upstream residues within ATG16L1, ubiquitin recognized by ATG16L1's C-terminal WD domain, and an unidentified factor that required the middle section of ATG16L1 (Fujita et al., 2013). Thus, we tested whether TRIM16 interacted with ATG16L1. GFP-TRIM16 and Flag-ATG16L1 co-IP-ed (FIG. 5A) and colocalized in cells (FIG. 13A). Endogenous ATG16L1 and TRIM16 coimmunoprecipitated (FIG. 5B) and colocalized in THP1 cells treated with LLOMe (FIG. 5C), Endogenous TRIM 16 and ATG16L1 colocalized with ubiquitin puncta in THP1 macrophages exposed to LLOMe (FIG. 5C).

LLOMe treatment increased TRIM 16 and ATG16L1 association (FIG. 5D). ATG16L1 K63 ubiquitination was enhanced by TRIM16 (FIG. 13B) but TRIM 16 had no effect on levels of ATG16L1 (FIG. 13C). TRIM16 association was delimited to ATG16L1 residues 85-286 (FIGS. 5E and 13D) encompassing residues in ATG16L1 implicated in binding of an unknown factor initiating autophagic response to lysosomal damage (Fujita et al., 2013).

We next employed another model of endomembrane damage, based on phagosome damage caused by *M. tuberculosis*, which permeabilizes phagosomal membranes eliciting autophagic response including LC3B and ubiquitin (Watson et al., 2012). For these experiments we used murine RAW264.7 macrophages, and detected colocalization between ATG16L1, TRIM16 and *M. tuberculosis* (FIG. 5F). ATG16L1 and *M. tuberculosis* colocalization was reduced upon knocking down TRIM16 in RAW264.7 cells (FIG. 5G and 13E). Thus, TRIM16 and ATG16L1 cooperate in autophagic responses to different types of endomembrane damage.

TRIM16 Affects Lysosomal Quality and Quantity

Following LLOMe exposure, TRIM16 translocated to LAMP2-positive lysosomal profiles in THP1 cells (FIG. 6A), a cell type highly susceptible to LLOMe-caused lysosomal damage. We next used TRIM16 50 Hela cells to assess the status of lysosomes upon LLOMe treatment (FIG. 6B,C). Although the number of lysosomes increased (FIG. 6B), the quality of these lysosomes was compromised, as evidenced by lessened acidification quantified by Lyso Tracker Red (FIG. 6C).

Lysosomal and autophagosomal systems are co-activated by the transcriptional factor TFEB (Settembre et al., 2011). TFEB is phosphorylated by Ser/Thr protein kinases, notably by mTOR, whereupon it resides in inactive cytoplasmic complexes, but translocates to the nucleus upon starvation to activate transcription (Martina et al., 2012; Roczniak-Ferguson et al., 2012; Settembre et al., 2012). TRIM16KO HeLa had increased TFEB presence in the nucleus under basal conditions cells (FIG. 6D). TFEB translocated to the nucleus in response to lysosomal damage caused by LLOMe (FIGS. 6D and 14A), and mTOR activity was inhibited upon LLOMe treatment (FIG. 14B). The LLOMe-induced levels of nuclear TFEB were higher in TRIM16$^{KO}$ cells relative to wt HeLa (FIG. 6D). Thus, TRIM16 controls quantity and quality of lysosomes and affects localization of TFEB.

TRIM16 is in Complexes with Regulators of mTOR, and with Calcineurin and TFEB

The increased TFEB in the nucleus of TRIM16$^{KO}$ may be secondary to defective lysosomes in cells lacking TRIM16 quality control. Nevertheless, we found TRIM16 in protein complexes regulating mTOR and TFEB (Napolitano and Ballabio, 2016). TRIM16 immunoprecipitates from cells expressing GFP-TRIM16 contained endogenous DEPTOR (FIG. 6E), an mTOR inhibitor (Peterson et al., 2009) whose stability is regulated by Cullin-5 (Antonioli et al., 2014). Cellular DEPTOR increased upon LLOMe treatment (FIG. 6F) and TRIM16-DEPTOR complexes contained Cullin-5 (FIG. 6E). GFP-TRIM16 protein immunoprecipitates contained endogenous RagB and RagD (FIG. 6G,H) factors recruiting mTOR to lysosomes where it is activated (Bar-Peled and Sabatini, 2014). GFP-TRIM16 coimmunoprecipitated with Flag-TFEB (FIG. 14C). GFP-TRIM16 coimmunoprecipitated with endogenous calcineurin catalytic subunit isoform @ (PPP3CB) (FIG. 6I) known to dephosphorylate TFEB and facilitate its translocation to the nucleus (Medina et al., 2015). Flag-TRIM16 coimmunoprecipitated with endogenous PPP3CB (FIG. 14D). The TRIM16 region required for PPP3CB association was delimited to the 166-373 segment of TRIM16 (FIG. 14E,F). Thus, under homeostatic conditions when all components are present, TRIM16 coordinates its activities with mTOR, calcineurin and TFEB. When TRIM 16 is absent, as in TRIM1680 cells, basal levels of nuclear TFEB increase due to perturbed interactions and/or indirectly due to compromised lysosomal quality (FIG. 6J).

TRIM16 Protects Cells Against Consequences of Endomembrane Damage

Although LLOMe can cause limited lysosomal damage in HeLa, it cannot cause significant lysosomal cell death in these cells. However, other lysosome damaging agents can (Petersen et al., 2013). We thus used lysosome-destabilizing experimental anticancer lysosomotropic agent siramesine (Ostenfeld et al., 2008), because it can promote cell death in Hela cells (Petersen et al., 2013). Siramesine, unlike LLOMe, caused in HeLa cells the formation of TRIM16 puncta that colocalized with LC3B (FIG. 7A). Absence of TRIM16 in TRIM16KO Hela cells increased sensitivity to cell death caused by siramesine (FIG. 15A,B). Wild type TRIM16 but not mutant TRIM16$^{S116A/S203A}$ rescued this phenotype (FIG. 7B). This indicates that whereas S116 and S203 (the residues phosphorylated by ULK1) are not critical for Galectin-3-TRIM16 interactions they are required for protection against lysosomal damage-induced cell death.

Galectin-3, TRIM16, and ATG16L1 Protect Against *M. tuberculosis* Infection

*M. tuberculosis* ESX-I secretion substrates cause phagosomal damage (Manzanillo et al., 2013; Watson et al., 2012). We examined whether TRIM16 and its interactors contribute to autophagic control of *M. tuberculosis*. Galectin-3 and TRIM16 localized to phagosomes when macrophages were infected with *M. tuberculosis* wild type strain Erdman and not when its ESX-1 mutant was used (FIG. 7C-F). Ubiquitin dots were present on wild type phagosomes but not on phagosomes with the ESX-1 mutant (FIG. 7G,H). TRIM16 was needed for ubiquitin colocalization on *M. tuberculosis* phagosomes (FIGS. 7I and 15C), and ubiquitin appeared after the recruitment of Galectin-3 and TRIM16 (FIG. 7J).

A question arose whether ULK1 affected colocalization of Galectin 3 and TRIM16 on phagosomes. We used MEFs and phagosomes with membrane-damaging beads coated with Effectene (Fujita et al., 2013). The Ulk1$^{KO}$/Ulk2$^{KO}$ MEFs had diminished numbers of and reduced colocalization between TRIM16 and Galectin-3 puncta on phagosomes relative to wt MEFs (FIGS. 7K and 15D-F).

TRIM16 was required for translocation of *M. tuberculosis* to LAMP1$^+$ compartments (FIG. 7L and FIG. 15G) and TRIM16 localized on LAMP1' autophagolysosomes (FIG. 15H). Like TRIM16, Galectin-3 was required for translocation of *M. tuberculosis* to LAMP1$^+$ compartments (FIG. 7L and FIG. 15G). Galectin-3 was required for ubiquitin deposits on *M. tuberculosis* phagosomes (FIG. 7M,N). Galectin-3 and TRIM16 colocalized on *M. tuberculosis* phagosomes (FIG. 15I). Finally, Galectin-3 protected mice in models of acute (FIG. 7O) and chronic (FIG. 15J,K) infection following aerosol exposure to *M. tuberculosis*. ATG16L1 was required for translocation of *M. tuberculosis* to autophagolysosomal compartments (FIG. 7L and FIG. 15G). Finally, all three components, Galectin-3, TRIM16, and ATG16L1 were required for control of intracellular *M. tuberculosis* (FIG. 7P). Thus, TRIM 16 along with Galectin-3 and ATG16L1, protects cells from the invading mycobacteria. In summary, the Galectin-3-TRIM16-ATG16L1 axis affords autophagic protection against lysosomal and phagosomal damage in diverse physiological contexts.

Discussion

This work shows that TRIMs (Reymond et al., 2001) and Galectins (Arthur et al., 2015; Blidner et al., 2015; de Waard et al., 1976; Nabi et al., 2015) interact and that the TRIM16-Galectin-3 system organizes autophagic response to endomembrane damage. TRIM16 controls ubiquitination of damaged compartments, and regulates the core autophagy regulators ULK1, Beclin 1, and ATG16L1, which confer localized autophagic sequestration of damaged lysosomes (Maejima et al., 2013). TRIM 16 also affects TFEB activation and nuclear translocation. Thus, TRIM16, in cooperation with Galectin-3, organizes core autophagy factors and orchestrates sequential stages of autophagic responses to lysosomal and phagosomal damage. These relationships are depicted in FIG. 6J.

Our understanding of the role of TRIMs (Kimura et al., 2015; Kimura et al., 2016; Mandell et al., 2014) and Galectins (Aits et al., 2015; Chen et al., 2014; Fujita et al., 2013; Hung et al., 2013; Maejima et al., 2013; Thurston et al., 2012) in autophagy is growing. The present study underscores the significance of both of these families of proteins and reports the key new finding that these two systems interact. This work furthermore expands the number of autophagic receptors and regulators of autophagy that utilize Galectins as cofactors in recognition of autophagic targets (e.g. damaged membranes).

The interaction of TRIM16 with ATG16L1 is of particular interest. ATG16L1, occupies a unique place among core autophagy factors by acting as a hub that brings together the principal parts of the autophagic apparatus: (i) ATG16L1 is a component of the LC3-PE conjugation system (Mizushima et al., 2011); (ii) ATG16L1 interacts with the WIP12 (Dooley et al., 2014), which in turn binds to PI3P produced by Beclin1-VPS34; and (iii) ATG16L1 associates with FIP200, a component of the ULK1 complex systems (Dooley et al., 2014; Fujita et al., 2013). Although ATG16L1 has intrinsic affinity for ubiquitin it requires an additional (hitherto unidentified) factor in order to be recruited to the correct membranes (Fujita et al., 2013). TRIM16 fits the properties of this missing link as it binds to the region of ATG16L1 spanning the critical residues in ATG16L1 postulated (Fujita et al., 2013) to interact with the putative factor that homes ATG16L1 to damaged lysosomal membranes. Thus, TRIM16, by interacting with ATG16L1 and Galectin-3, guides the placement of ATG16L1 on damaged membranes.

TRIM 16 and its interacting partner Galectin-3 protect cells from lysosomal cell death or microbial invasion. Galectin-3 has been previously observed on mycobacterial phagosomes and implicated in control of mycobacteria in a short term infection of Galectin-3 knockout mice (Beatty et al., 2002). These studies are congruent with the results of murine survival studies in the aerosol *M. tuberculosis* infection model reported here. Given the connections to autophagic machinery via TRIM16, the role of Galectin-3 in control of bacteria or pathology associated with mycobacterial infection can now be mechanistically linked to the TRIM-driven process of precision autophagy (Kimura et al., 2016), which differs from bulk autophagy. TRIM16 is also known as estrogen-responsive B box protein, and its role in cancer (a general property of TRIMs (Hatakeyama, 2011)) has been linked to specific effects on immune signaling (Sutton et al., 2014), cell survival (Kim et al., 2013), cell migration and metastasis (Marshall et al., 2010; Sutton et al., 2014) through various mechanisms, including measures of membrane repair (Cheung et al., 2012; Marshall et al., 2010), with the latter potentially overlapping with the processes described in this work.

TRIM 16 absence elevates TFEB's partitioning to the nucleus. Both of these proteins can localize to lysosomes as their station for exerting regulatory and effector functions. TFEB is coupled to the mTOR system, with mTOR phosphorylating TFEB to keep it locked in the cytosol, which can be reversed upon starvation that inactivates mTOR, further coupled with $Ca^{2+}$ efflux from the lysosomes thus activating calcineurin to dephosphorylate TFEB and allow its nuclear translocation (Medina et al., 2015; Settembre et al., 2011; Settembre et al., 2012). These processes are modulated by TRIM16 action as suggested through interactions of TRIM16 shown here for DEPTOR, Rag GTPases, calcineurin, and TFEB itself. Absence of these interactions may lead to elevated TFEB in the nucleus. In summary, the relationships demonstrated here show convergence of the previously known and the newly uncovered precision autophagy systems in control of autophagic responses to endomembrane damage of significance in cancer and infectious diseases.

Experimental Procedures

Cells and Cell Lines

RAW264.7, 293T, THP-1 and HeLa cells were obtained directly from ATCC and maintained in ATCC recommended media. Ulk1/2 double knockout MEFs and matching wild type MEFs were from Sharon Tooze, The Francis Crick Institute.

Cell Culture and Biochemical Methods

Cells and cell lines, GST pull-downs, ULK1 phosphorylation assay, mass spectrometry, antibodies source and dilutions, immunoblotting, coimmunoprecipitation, plasmids, siRNA, and transfection are described in Supplementary Experimental Procedures.

CRISPR Knockout Cell Lines and their Complementation

To generate CRISPR knock out cell lines, Hela cells were transfected with a PX458 (Addgene plasmid #48138) (Ran et al., 2013) encoding the U6 promoter, human TRIM16 target sequence located within the first exon (AGTTG-GATCTAATGGCTCCA, with the 5' nucleotide A changed into a G; this sequence is followed on the chromosome by a protospacer adjacent motif GGG and was selected using crispr.mit.edu/guides site) fused to a chimeric guide RNA, S. pyogenes Cas9, and GFP. Transfected cells (green fluorescence) were sorted by flow cytometry and single cell clones analyzed by immunoblotting for a loss of TRIM16 band. Positive clones were subjected to next generation sequencing (Illumina; Massachusetts General Hospital core) to characterize the mutation (FIG. 9F). For complementation, TRIM16KO HeLa cells were transfected with empty vector, WT TRIM 16 or phosphorylation mutated TRIM 16 with >60% transfection efficiency. After 24 h of transfection cells were subjected to response assays.

Bacterial Strains and Procedures

*M. tuberculosis* wild-type Erdman and ESX-1 mutant (Manzanillo et al., 2012) were cultured in Middlebrook 7H9 broth supplemented with 0.05% Tween 80, 0.2% glycerol, and 10% oleic acid, albumin, dextrose, and catalase (OADC; BD Biosciences) at 37° C. and homogenized to generate single-cell suspension for macrophage infection studies. For acute (short-term) aerosol infection, C57BL mice or their Galectin-3 knockout derivative B6.Cg-Lgals3$^{m1Pol}$/J (Jackson Laboratory) were exposed to high dose *M. tuberculosis* Erdman aerosols ($1-4 \times e^3$ CFU deposition) as previously described (Castillo et al., 2012), with a modification of using a GlasCol apparatus for aerosol delivery, and survival monitored for 2.5 months post-infection. For chronic (long-term) infection with lower doses of *M. tuberculosis*, mice were exposed in a GlasCol apparatus to medium dose ($6 \times e^2$ CFU initial lung deposition) and low dose ($2 \times e^2$ CFU initial lung deposition) of *M. tuberculosis* Erdman aerosols as previously described (Manzanillo et al., 2012), (Castillo et al., 2012)(Castillo et al., 2012) and survival monitored for up to 200 days post-infection. For intracellular mycobacterial survival assays and fluorescence microscopy see Supplementary Experimental Procedures.

High Content Microscopy, Confocal Microscopy, Flow Cytometry, Cell Survival

High content microscopy with automated image acquisition and quantification was carried out using a Cellomics HCS scanner and iDEV software (Thermo) in 96-well plates (Mandell et al., 2014). Immunofluorescence confocal microscopy was performed using an LSM510 confocal microscope and Zeiss software package. For quantification of puncta or total cell fluorescence, image J was used as described previously (Chauhan et al., 2015). For quantifying cell death, HeLa and derivative cells treated with 15 μM siramesine for 12 h were incubated with 7AAD (BD Pharmingen™; cat #559925) for 30 min and fluorescence of 7AAD bound to nuclear DNA measured in a flow cytometer.

Supplementary Experimental Procedures

GST Pull Downs and ULK1 Phosphorylation Assay

GST-fusion proteins were expressed in *Escherichia coli* SoluBL21 (Amsbio). GST fusion proteins were purified and immobilized on glutathione-coupled sepharose beads (Amersham Bioscience, Glutathione-sepharose 4 Fast Flow) and pull-down assays with in vitro translated [$^{35}$S]-labeled proteins were done as described previously (Pankiv et al., 2007). The [$^{35}$S] labeled proteins were produced using the TNT T7 Quick Coupled Transcription/Translation System (Promega) in the presence of [$^{35}$S] L-methionine. The proteins were eluted from washed beads by boiling in SDS-PAGE gel loading buffer, separated by SDS-PAGE, and radiolabeled proteins were detected in a Fujifilm bioimaging analyzer BAS-5000 (Fuji).

In vitro phosphorylation assays were performed by incubating the recombinant proteins with FLAG-ULK1 kinase immunoprecipitated from the transfected HEK293 cells in a standard kinase buffer containing 50 μM of cold ATP and 2.5 μCi [g-$^{32}$P]-ATP per reaction at 30° C. for 30 min. The reaction was stopped by adding SDS sample buffer and boiling, and then subjected to SDS-PAGE gel and autoradiography. For pull-downs assays without $^{32}$P radiolabeling (i.e. cold-phosphorylation), cold ATP was used in a mixture with TRIM 16 and then the standard in-vitro pull-downs were performed.

In Vivo Phosphorylation and Liquid Chromatography—Mass Spectrometry

For in vivo phosphorylation analyses, subconfluent HEK293 cells in 10 cm dishes were transfected with total 5 g plasmids (i.e. pDest-eGFP-TRIM16, plus pDest-3×FLAG or pDest-3×FLAG-ULK1) using Metafectene Pro (Biontex) following the supplier's instructions. Twenty-four hours after transfection cells were rinsed with ice-cold PBS prior to lysis in RIPA buffer (50 mm Tris-HCl, pH 7.5, 150 mm NaCl, 1 mm EDTA, 1% Nonidet P-40 (v/v), 0.25% Triton X-100) supplemented with Complete Mini EDTA-free protease inhibitor mixture tablets (1 tablet per 10 ml) (Roche Applied Science) and phosphatase inhibitor mixture set II (Calbiochem). Lysates were cleared by centrifugation and the cleared lysates were then incubated with the Anti-GFP MicroBeads (Miltenyi Biotec Norden AB) for 30 min at 4° C. The GFP-precipitated immunocomplexes were washed five times with RIPA lysis buffer and eluted following the supplier's instructions. The eluted samples were subjected to SDS-PAGE and gel bands containing TRIM16 were excised and subjected to in-gel reduction, alkylation, and tryptic digestion with 6 ng/µl trypsin (Promega). OMIX C18 tips (Varian, Inc.) was used for sample cleanup and concentration. Peptide mixtures containing 0.1% formic acid were loaded onto a Thermo Fisher Scientific EASY-nLC1000 system and EASY-Spray column (C18, 2 µm, 100 Å, 50 µm, 50 cm). Peptides were fractionated using a 2-100% acetonitrile gradient in 0.1% formic acid over 50 min at a flow rate of 200 nl/min. The separated peptides were analyzed using a Thermo Scientific Q-Exactive mass spectrometer. Data was collected in data dependent mode using a Top10 method. The raw data were processed using the Proteome Discoverer 1.4 software (Thermo Scientific) and the PEAKS Studio 7 software (v. 7.0, Bioinformatics Solutions). The fragmentation spectra from Proteome Discoverer was searched against the Swissprot database using an in-house Mascot server (Matrix Sciences). The phosphoRS 3.0 tool in the Proteome Discoverer software was used to validate potential phosphosites in the samples. A human Swissprot database was used for the de novo peptide sequencing assisted search engine database searching by the PEAKS software. Peptide mass tolerances used in the searches were 10 ppm, and fragment mass tolerance was 0.02 Da. Both software's identified the S203 and S116 phosphosites in TRIM16 in the samples with ULK1, but not in the FLAG control. The presence of these phosphorylations in the ULK1 samples but not in the FLAG control was manually verified by inspecting the LC-MS spectra in the Excalibur 2.2 software (Thermo Scientific).

Antibodies

The following antibodies and dilutions were used: TRIM16 (goat polyclonal antibody, Santa Cruz; sc-79770; 1:50-1:100 for immunofluorescence (IF) and 1:200-1:1,000 for Western blots (WB)); Galectin-3 (rabbit polyclonal Abcam; cat #ab53082; 1:100, IF; or mouse monoclonal Santa Cruz sc-32790 1:100 (IF) and 1:250 (WB)); ubiquitin (mouse monoclonal FK2, MBL; cat #D058-3; 1:100-1:500, IF); LAMP1 (mouse monoclonal Abcam; cat #ab25630; 1:100; IF); LAMP2 (mouse monoclonal Hybridoma Bank, University of Iowa; 1:500 (IF)); ULK1 (rabbit polyclonal Santa Cruz, sc33182; 1:100 (IF); 1:500 (WB)); ATG16L1 (rabbit polyclonal MBL (PM040); 1:2,000 (WB)) K63 ubiquitin (rabbit monoclonal Millipore 05-1308; 1:100 (IF); 1:500 (WB); TFEB (rabbit polyclonal anti-human; Cell Signaling CST 4240, 1:200 (IF)); phospho p70s6K (rabbit polyclonal Cell Signaling CST 9205; 1:750 (WB)) p70s6k (rabbit polyclonal Cell Signaling CST 9202; 1:1,000 (WB)); RagB (rabbit monoclonal Cell Signaling CST 8150; 1:500); Rag D (rabbit polyclonal Cell Signaling CST 4470; 1:500); DEPTOR (Rabbit monoclonal Cell Signaling CST 11816; 1:1000); Cullin4A (rabbit monoclonal antibody Abcam #ab92554 1:500 (WB)); Cullin5 (rabbit polyclonal antibody #ab34840; 1:500). GFP (rabbit polyclonal Abcam; cat #ab290; 0.5 µg/ml IP and 1:5,000 (WB)); PPP3CB (rabbit polyclonal antibody Abcam, ab96573 1:500 (WB)) Flag (mouse monoclonal Sigma; cat #F1804, used at 1:1,000); Myc (mouse monoclonal Santa Cruz, sc-40; 1:200 (IF); 1:500 (WB)); HA (mouse monoclonal Millipore 05-904; 1:1,000 (WB)); and actin (mouse monoclonal Abcam; cat #ab8226, used at 1:4,000).

Immunoblots and Co-Immunoprecipitation Assays

Immunoblots and co-IPs assays for endogenous or exogenously expressed proteins were carried out as described previously (Chauhan et al., 2015). For immunoprecipitation experiments with exogenously expressed proteins, 293T cells were transfected with 5 µg of expression constructs by calcium phosphate for 24 h and lysed on ice using NP-40 buffer (Invitrogen) containing protease inhibitor cocktail (Roche, cat #11697498001) and PMS (Sigma, cat #93482). Lysates were mixed with antibody (2-3 ng) incubated at 4° C. for 2 h followed by incubation with protein G Dynabeads (Life technologies) for 2 h at 4° C. Beads were washed four times with PBS and then boiled with SDS-PAGE buffer for analysis of interacting protein by Immunoblotting. Input lanes contained 10% of material unless otherwise indicated.

Analysis of Effectene-Bead Phagosomes

Wild type (WT) and Ulk1/Ulk2 double KO mouse embryonic fibroblasts (McAlpine et al., 2013) in 96-well plates were incubated with Fluoresbrite bead (3 µm; Polysciences Inc. cat #21637-1; fluorescence detected at 485 nm) treated with effectene transfection reagent as described previously (Fujita et al., 2013). The beads were not spun onto the cells but were allowed to spontaneously uptake the beads, which required times >3h. After up to 24 h of incubation, cells were processed for immunofluorescence microscopy with Galectin-3 and TRIM16 antibodies for 2 h followed by treatment with secondary antibodies (goat anti-mouse Alexa Flour 568 and goat anti-rabbit Alexa Flour 647). High content microscopy was carried out in a Cellomics HCS scanner and images analyzed and objects quantified using iDEV software (Thermo) (Mandell et al., 2014).

For intracellular mycobacterial survival assays see Supplementary experimental procedures. RAW264.7 cells were infected with mycobacteria and quantification of mycobacterial survival carried out as previously described (Ponpuak et al., 2009). In brief, $3 \times 10^5$ cells of RAW264.7 macrophages were plated onto each well of 12-well plates 12 h before infections. Cells were then infected with single cell suspension of mycobacteria in complete media at MOI of 10 for 1 h. Cells were then washed three times with PBS to remove un-internalized mycobacteria. Infected cells were then lysed to determine the number of intracellular mycobacteria at t=0 by plating onto Middlebrook 7H11 agar supplemented with 0.05% Tween 80, 0.2% glycerol, and 10% OADC (BD Biosciences) and grown at 37° C. or infected cells were continued to grow until harvesting at t=24 for CFU analysis. Percent mycobacteria survival was calculated by dividing the number of intracellular mycobacteria at t=24 over that of t=0 multiply by 100 and relative to control cells set to 100%.

Bacterial Phagosomes, Intracellular Mycobacterial Survival, and Fluorescence Microscopy of Infected Macrophages For immunofluorescence microscopy with mycobacteria-infected macrophages, $3 \times 10^5$ cells of RAW264.7 macrophages were plated onto coverslips in 12-well plates 12 h before infections. Cells were then infected with $3 \times 10^6$ Alexa-568-labeled mycobacteria per well in complete media at 37° C. for 15 min, washed three times in PBS, and chased for 1 h in complete media as previously described (Ponpuak et al., 2009). Cells were then washed three times with PBS and incubated in complete media for the indicated times. Cells were then fixed with 4% paraformaldehyde/PBS for 15 min followed by permeabilization with 0.1% Triton X-100/PBS for 5 min. Coverslips were then blocked in PBS containing 3% BSA and then stained with primary antibodies according to manufacturer's recommendation. Cells were washed three times with PBS and then incubated with appropriate secondary antibodies (Invitrogen) for 2 h at room temperature. Coverslips were then mounted using ProLong Gold Antifade Mountant (Invitrogen) and analyzed by confocal microscopy using the Zeiss LSM510 Laser Scanning Microscope. At least 50 phagosomes per experimental condition in three independent experiments were quantified. For quantification, % mycobacteria-marker colocalization was fraction of total mycobacterial phagosomes examined counted as positive when one or more puncta were observed on or in contact with the mycobacterial phagosomes.

RAW264.7 cells were infected with mycobacteria and quantification of mycobacterial survival carried out as previously described (Ponpuak et al., 2009). In brief, $3 \times 10"$ cells of RAW264.7 macrophages were plated onto each well of 12-well plates 12 h before infections. Cells were then infected with single cell suspension of mycobacteria in complete media at MOI of 10 for 1 h. Cells were then washed three times with PBS to remove un-internalized mycobacteria. Infected cells were then lysed to determine the number of intracellular mycobacteria at t=0 by plating onto Middlebrook 7H11 agar supplemented with 0.05% Tween 80, 0.2% glycerol, and 10% OADC (BD Biosciences) and grown at 37° C. or infected cells were continued to grow until harvesting at t=24 for CFU analysis. Percent mycobacteria survival was calculated by dividing the number of intracellular mycobacteria at t=24 over that of t=0 multiply by 100 and relative to control cells set to 100%.

For immunofluorescence microscopy with mycobacteria-infected macrophages, $3 \times 10^5$ cells of RAW264.7 macrophages were plated onto coverslips in 12-well plates 12 h before infections. Cells were then infected with $3 \times 10^6$ Alexa-568-labeled mycobacteria per well in complete media at 37° C. for 15 min, washed three times in PBS, and chased for 1 h in complete media as previously described (Ponpuak et al., 2009). Cells were then washed three times with PBS and incubated in complete media for the indicated times. Cells were then fixed with 4% paraformaldehyde/PBS for 15 min followed by permeabilization with 0.1% Triton X-100/PBS for 5 min. Coverslips were then blocked in PBS containing 3% BSA and then stained with primary antibodies according to manufacturer's recommendation. Cells were washed three times with PBS and then incubated with appropriate secondary antibodies (Invitrogen) for 2 h at room temperature. Coverslips were then mounted using ProLong Gold Antifade Mountant (Invitrogen) and analyzed by confocal microscopy using the Zeiss LSM510 Laser Scanning Microscope. At least 50 phagosomes per experimental condition in three independent experiments were quantified. For quantification, % mycobacteria-marker colocalization was fraction of total mycobacterial phagosomes examined counted as positive when one or more puncta were observed on or in contact with the mycobacterial phagosomes.

Plasmids, siRNAs, Cell Transfections

TRIMs, SLRs, Galectins, and GABARAP cDNA were first cloned into pENTR or pDONR221 vectors from Invitrogen, and then (Gateway) cloned into either pDestMyc or pDest53 (GFP) using LR-II enzyme from Invitrogen. (GST-Galectin-3, GST-Galectin-8 and GST-GABARAP are described in Figure-1). pENTR clones of different TRIM5α deletion constructs (ÄRING, ÄB.Box, ÄCCD and ÄSPRY) including the full-length TRIM5α were generated using Phusion DNA Polymerase (from NEB) and T4-DNA ligase (from NEB), and then (Gateway) cloned into pDestMyc using LR-II enzyme from Invitrogen. Constructs containing cDNAs encoding Flag-ATG16L1 and its deletions and Flag-Galectin-3 were cloned by amplifying with primer pairs 5'caccatggeccaactgaggattaag3' (forward) SEQ ID NO: 40 and 5'tcagcgtctcccaaagatattagtgataga3' (reverse) SEQ ID NO: 41 and S'caccatggcagacaattittegctccat3' (forward) SEQ ID NO: 42 and S'ttatatcatggtatatgaagcact3' (reverse) SEQ ID NO: 43, respectively, followed by subcloning into pENTRY (Invitrogen) and recombined into pDEST 3×Flag. pTRIM16 wt and pTRIM16S116A/S203A were generated as Gateway clones in _pDEST_ vector encoding Flag-TRIM16 fusions.

All siRNAs were from Dharmacon. TRIM screens were carried out as previously described (Mandell et al., 2014). TRIM RAW264.7 cells were transfected with 1.5 µg of siRNAs as previously described (Ponpuak et al., 2009); $10^7$ cells were resuspended in 100 µl of Nucleofector solution kit V (Amaxa), siRNAs were then added to the cell suspension and cells were nucleoporated using Amaxa Nucleofector apparatus with program D-032. Cells were re-transfected with a second dose of siRNAs 24 h after the first transfection, and assayed after 48 h.

Results

TRIMs and Galectins Interact

During the screens uncovering a broad role of TRIMs in autophagy (Kimura et al., 2015; Mandell et al., 2014), we observed an unanticipated propensity of TRIMs to bind Galectins. Of the TRIMs tested, TRIM5α, TRIM6, TRIM 17, TRIM20, TRIM22, TRIM23 and TRIM49 bound both Galectin-3 and Galectin-8, whereas TRIM16, TRIM21, TRIM55 and TRIM56 did not (FIGS. 1A and 9A). Galectin-8 bound NDPS2 as expected (Thurston et al., 2012) and its close homolog TAX1BP1 but not Optineurin and other controls (FIG. 9B). For specificity, we mapped the Galectin-3-binding region in TRIM5α and found that a region spanning TRIM5α's CCD, but not its β-Box or SPRY domains, was required for Galectin-3 (FIG. 1B and FIG. 9C). Thus, TRIMs, through specific regions as delimited within TRIM5α, have a propensity to associate with Galectins.

Screen for TRIMs Involved in Autophagie Response to Lysosomal Damage

Galectins participate in autophagic response to endomembrane perforations caused by lysosomal damaging agents and by bacteria (Fujita et al., 2013; Maejima et al., 2013; Thurston et al., 2012). Based on interactions between Galectins and TRIMs detected above, we hypothesized that TRIMs might play a role in autophagic response to endomembrane damage. The lysosomal damaging agent Leu-Leu-O-Me (LLOMe), which is condensed into a membranolytic polymer via the transpeptidase action of cathepsin C within lysosomes (Fujita et al., 2013; Maejima et al., 2013), elicited a consistent LC3 dose response with dynamic range suitable for a screen. We employed high content microscopy with automated image acquisition and quantification (HC) (Kimura et al., 2015; Mandell et al., 2014) of endogenous LC3B puncta (FIG. 1D) and screened the human TRIM family by siRNA knockdowns in Hela cells for effects on LC3 response to LLOMe treatment (FIG. 1E). TRIM16 showed the strongest effect (FIG. 1E).

TRIM16 is Necessary for Autophagic Response and Ubiquitination Upon Lysosomal Damage The screening data were confirmed by follow-up siRNA knockdowns (FIG. 9C) and by generating a TRIM16 CRISPR knockout in Hela cells (TRIM16KO). Two independent CRISPR mutants, HeLa TRIM16$^{KO}$ A9 (FIG. 9D,E)

and C2 (FIG. 9F) were generated. TRIM16 knockdowns diminished LC3B response (FIG. 9G,H). HC imaging analysis in TRIM16 knockout cell line A9 demonstrated that TRIM16 was required for a full autophagic response to lysosomal injury caused by LLOMe (FIG. 1F-H). This was confirmed in a different TRIM 16 CRISPR clone, C2 (FIG. 9I).

In addition to LC3$^+$ autophagosomes (Maejima et al., 2013), LLOMe-induced lysosomal damage elicits ubiquitin puncta formation on lysosomes (Maejima et al., 2013), in a dose response fashion (FIG. 9J). HC screen using ubiquitin puncta as a lysosomal-damage response readout (Maejima et al., 2013) again indicated a requirement for TRIM16 (FIG. 9K,L). TRIM16 was needed for optimal ubiquitin response to LLOMe when tested by siRNA knockdowns (FIG. 9M,N), and was absolutely required for ubiquitin dots formation when tested in TRIM16 CRISPR knockout HeLa A9 cells (FIG. 1I-K). This was confirmed in the TRIM16 CRISPR knockout clone C2 (FIG. 9O).

TRIM16 was required for colocalization between LC3B and ubiquitin puncta in response to LLOMe (FIGS. 2A and 10A) as quantified by HC imaging (FIG. 2B,C). TRIM16 puncta were morphologically prominent in response to LLOMe in leukocytes (FIG. 2D),E) but not in HeLa cells, most likely due to differential cathepsin C levels. TRIM16 puncta and ubiquitin profiles (FIG. 2D) and TRIM16 puncta and LC3B puncta (FIG. 2E) colocalized in THP-1 cells exposed to LLOMe. Thus, TRIM16 is required for optimal ubiqutination and autophagic response in response to lysosomal damage.

TRIM16 is in Protein Complexes with Galectin-3 in Cells

Galectin-3 is a marker for damaged lysosomes (Aits et al., 2015). Consistent with the prior reports using GFP-Galectin-3 (Maejima et al., 2013) we found endogenous Galectin-3 colocalizing with or juxtaposed to a number of LC3 profiles induced in response to LLOMe in different cell types (FIG. 10B). Although the initial GST-Galectin pull-downs (FIG. 1A) indicated that TRIM16 did not bind Galectin-3 in vitro, the finding that TRIM16 was a stand-out in our screens, and the acknowledged pivotal role of Galectins, and specifically that of Galectin-3, in recognition of lysosomal damage (Aits et al., 2015; Maejima et al., 2013), prompted us to re-asses the apparent absence of TRIM 16-Galectin-3 interactions. TRIM16 was found in co-IPs with Galectin-2 and Galectin-3 in cellular extracts (FIG. 11A). We focused on Galectin-3 as an accepted marker for damaged lysosomes (Aits et al., 2015). A reverse tag co-IP (FIG. 3A) confirmed TRIM16-Galectin-3 association. TRIM55 and TRIM56 were not found in co-IPs with Galectin-3 (FIG. 3A) indicating selectivity of Galectin-3-TRIM16 associations. Endogenous protein co-IPs detected TRIM16 and Galectin-3 in common complexes (FIG. 3B). The association between endogenous TRIM16 and Galectin-3 increased in cells exposed to LLOMe (FIG. 3B).

TRIM16 Interacts with Galectin-3 in an ULK1-Dependent Manner

We investigated the basis for the association between Galectin-3 and TRIM16 detected in cells. TRIM 16 turned out to be a substrate for phosphorylation (FIG. 3) by ULK1 (Figure 11B) similarly to the known ULK1 substrate Beclin 1 (Russell et al., 2013) (FIG. 3C). Using a different preparations of ULK1 (FIG. 11C), and comparing active vs. kinase dead ULK1 we established that TRIM16 was a substrate for ULK1 phosphorylation (FIG. 3D). We next tested whether ULK1 modulated TRIM16 and Galectin-3 association observed in cells. GST pull-downs (initially negative for TRIM 16-Galectin-3 interactions; FIG. 1A), were repeated in the presence of ULK1. We observed enhancement of interactions between GST-Galectin-3 and TRIM16 (in vitro translated and radiolabeled) when ULK1 was added (FIG. 3E), contrasting with no effect on the binding (Mandell et al., 2014) between TRIM16 and GABARAP (FIG. 3E). In keeping with the above, a knockdown of ULK1 reduced the levels of Galectin-3 found in complexes with TRIM16 (FIG. 3F).

TRIM 16 was phosphorylated at S116 and S203 in an ULK1-dependent manner as determined by mass spectrometry (FIG. 11D,F). When these TRIM16 residues were doubly mutated into a non-phosphorylatable form (S116A and S203A), TRIM16 nevertheless retained its capacity to promote TRIM16-Galectin-3 interactions (FIG. 3G). Thus, ULK1 serves primarily as a platform for formation of TRIM16-Galectin-3 complexes. This played a function in response to LLOMe, as determined by using ULK1/2 knockout MEFs. Wild type MEFs showed LC3 (FIG. 11G) and ubiquitin (FIG. 11H) response to LLOMe, whereas ULK1/2 MEFs could not mount that response. Since as shown previously (Fujita et al., 2013), ubiquitin dots precede LC3 membrane formation, these findings also indicate that ULKs are required for ubiquitination events preceding LC3 response.

TRIM16 Interacts with Key Autophagy Regulators ULK1 and Beclin 1

TRIM16 showed a capacity to associate with ULK1 (FIG. 4A,B) and colocalized (FIG. 4C) in cells. Co-expression of GFP-TRIM16 increased levels of myc-ULK1 (FIG. 4D), whereas a TRIM16 knockdown diminished endogenous ULK1 (FIG. 4E). TRIM16 promoted ULK1 K63-linked ubiquitination (FIG. 4F), a modification stabilizing autophagy regulators (Nazio et al., 2013). This action of TRIM16 could be either direct, since it has an E3 ubiquitin ligase activity (Bell et al., 2012) (confirmed in FIG. 12A), or indirect by recruiting/activating other E3 ligases controlling activity of ULK1 (Nazio et al., 2013). The latter possibility was underscored by the co-immunoprecipitation of TRIM16 with cullin ubiquitin ligase components (Cullin 4A; FIG. 12B) implicated in regulation of autophagy (Antonioli et al., 2014). LLOMe-elicited TRIM16 puncta colocalized with ubiquitin and ULK1 (FIGS. 4G and 12C). GFP-TRIM16 co-IPed (FIG. 4H) and co-localized (FIG. 4I) with Flag-Beclin 1. Co-expression of GFP-TRIM16 with Flag-Beclin 1 stimulated K63-linked ubiquitination of Beclin 1 (FIG. 4J), which could be direct or through other E3 ligases described previously (Shi and Kehrl, 2010; Xia et al., 2013), and increased cellular levels of Flag-Beclin 1 (FIG. 4K).

ATG16L1 Associates with TRIM16 Upon Endomembrane Damage

ATG16L1 is a core autophagy factor implicated in response to lysosomal damage (Fujita et al., 2013), through a convergence of at least three different association events: FIP200, binding to upstream residues within ATG16L1, ubiquitin recognized by ATG16L1's C-terminal WD domain, and an unidentified factor that required the middle section of ATG16L1 (Fujita et al., 2013). Thus, we tested whether TRIM16 interacted with ATG16L1. GFP-TRIM16 and Flag-ATG16L1 co-IP-ed (FIG. 5A) and colocalized in cells (FIG. 13A). Endogenous ATG16L1 and TRIM 16 coimmunoprecipitated (FIG. 5B) and colocalized in THP1 cells treated with LLOMe (FIG. 5C). Endogenous TRIM16 and ATG16L1 colocalized with ubiquitin puncta in THP1 macrophages exposed to LLOMe (FIG. 5C).

LLOMe treatment increased TRIM16 and ATG16L1 association (FIG. 5D). ATG16L1 K63 ubiquitination was enhanced by TRIM 16 (FIG. 13B) but TRIM16 had no effect on levels of ATG16L1 (FIG. 13C). TRIM16 association was delimited to ATG16L1 residues 85-286 (FIGS. 5E and 13D) encompassing residues in ATG16L1 implicated in binding of an unknown factor initiating autophagic response to lysosomal damage (Fujita et al., 2013).

We next employed another model of endomembrane damage, based on phagosome damage caused by *M. tuberculosis*, which permeabilizes phagosomal membranes eliciting autophagic response including LC3B and ubiquitin (Watson et al., 2012). For these experiments we used murine RAW264.7 macrophages, and detected colocalization between ATG16L1, TRIM16 and *M. tuberculosis* (FIG. 5F). ATG16L1 and *M. tuberculosis* colocalization was reduced upon knocking down TRIM16 in RAW264.7 cells (FIGS. 5G and 13E). Thus, TRIM16 and ATG16L1 cooperate in autophagic responses to different types of endomembrane damage.

TRIM16 Affects Lysosomal Quality and Quantity

Following LLOMe exposure, TRIM16 translocated to LAMP2-positive lysosomal profiles in THP1 cells (FIG. 6A), a cell type highly susceptible to LLOMe-caused lysosomal damage. We next used TRIM16$^{KO}$ HeLa cells to assess the status of lysosomes upon LLOMe treatment (FIG. 6B,C). Although the number of lysosomes increased (FIG. 6B), the quality of these lysosomes was compromised, as evidenced by lessened acidification quantified by LysoTracker Red (FIG. 6C).

Lysosomal and autophagosomal systems are co-activated by the transcriptional factor TFEB (Settembre et al., 2011). TFEB is phosphorylated by Ser/Thr protein kinases, notably by mTOR, whereupon it resides in inactive cytoplasmic complexes, but translocates to the nucleus upon starvation to activate transcription (Martina et al., 2012; Roczniak-Ferguson et al., 2012; Settembre et al., 2012). TRIM16KO HeLa had increased TFEB presence in the nucleus under basal conditions cells (FIG. 6D). TFEB translocated to the nucleus in response to lysosomal damage caused by LLOMe (FIGS. 6D and 14A), and mTOR activity was inhibited upon LLOMe treatment (FIG. 14B). The LLOMe-induced levels of nuclear TFEB were higher in TRIM16KO cells relative to wt HeLa (FIG. 6D). Thus, TRIM16 controls quantity and quality of lysosomes and affects localization of TFEB.

TRIM16 is in Complexes with Regulators of mTOR, and with Calcineurin and TFEB

The increased TFEB in the nucleus of TRIM16 80 may be secondary to defective lysosomes in cells lacking TRIM16 quality control. Nevertheless, we found TRIM16 in protein complexes regulating mTOR and TFEB (Napolitano and Ballabio, 2016). TRIM16 immunoprecipitates from cells expressing GFP-TRIM16 contained endogenous DEPTOR (FIG. 6E), an mTOR inhibitor (Peterson et al., 2009) whose stability is regulated by Cullin-5 (Antonioli et al., 2014). Cellular DEPTOR increased upon LLOMe treatment (FIG. 6F) and TRIM 16-DEPTOR complexes contained Cullin-5 (FIG. 6E). GFP-TRIM 16 protein immunoprecipitates contained endogenous RagB and RagD (FIG. 6G,H) factors recruiting mTOR to lysosomes where it is activated (Bar-Peled and Sabatini, 2014). GFP-TRIM16 coimmunoprecipitated with Flag-TFEB (FIG. 14C). GFP-TRIM16 coimmunoprecipitated with endogenous calcineurin catalytic subunit isoform β (PPP3CB) (FIG. 6I) known to dephosphorylate TFEB and facilitate its translocation to the nucleus (Medina et al., 2015). Flag-TRIM 16 coimmunoprecipitated with endogenous PPP3CB (FIG. 14D). The TRIM16 region required for PPP3CB association was delimited to the 166-373 segment of TRIM16 (FIG. 14E,F). Thus, under homeostatic conditions when all components are present, TRIM16 coordinates its activities with mTOR, calcineurin and TFEB. When TRIM16 is absent, as in TRIM16KO cells, basal levels of nuclear TFEB increase due to perturbed interactions and/or indirectly due to compromised lysosomal quality (FIG. 6J).

TRIM16 Protects Cells Against Consequences of Endomembrane Damage

Although LLOMe can cause limited lysosomal damage in HeLa, it cannot cause significant lysosomal cell death in these cells. However, other lysosome damaging agents can (Petersen et al., 2013). We thus used lysosome-destabilizing experimental anticancer lysosomotropic agent siramesine (Ostenfeld et al., 2008), because it can promote cell death in Hela cells (Petersen et al., 2013). Siramesine, unlike LLOMe, caused in Hela cells the formation of TRIM16 puncta that colocalized with LC3B (FIG. 7A). Absence of TRIM16 in TRIM16KO HeLa cells increased sensitivity to cell death caused by siramesine (FIG. 15A,B). Wild type TRIM16 but not mutant TRIM16$^{S16A/S203A}$ rescued this phenotype (FIG. 7B). This indicates that whereas S116 and S203 (the residues phosphorylated by ULK1) are not critical for Galectin-3-TRIM16 interactions they are required for protection against lysosomal damage-induced cell death.

Galectin-3, TRIM16, and ATG16L1 Protect Against *M. tuberculosis* Infection

*M. tuberculosis* ESX-1 secretion substrates cause phagosomal damage (Manzanillo et al., 2013; Watson et al., 2012). We examined whether TRIM16 and its interactors contribute to autophagic control of *M. tuberculosis*. Galectin-3 and TRIM16 localized to phagosomes when macrophages were infected with *M. tuberculosis* wild type strain Erdman and not when its ESX-I mutant was used (FIG. 7C-F). Ubiquitin dots were present on wild type phagosomes but not on phagosomes with the ESX-1 mutant (FIG. 7G,H). TRIM16 was needed for ubiquitin colocalization on *M. tuberculosis* phagosomes (FIGS. 7I and 15C), and ubiquitin appeared after the recruitment of Galectin-3 and TRIM16 (FIG. 7J).

A question arose whether ULK1 affected colocalization of Galectin 3 and TRIM 16 on phagosomes. We used MEFs and phagosomes with membrane-damaging beads coated with Effectene (Fujita et al., 2013). The Ulk1$^{KO}$/Ulk2$^{KO}$ MEFs had diminished numbers of and reduced colocalization between TRIM16 and Galectin-3 puncta on phagosomes relative to wt MEFs (FIGS. 7K and 15D-F).

TRIM16 was required for translocation of *M. tuberculosis* to LAMP1$^+$ compartments (FIG. 7L and FIG. 15G) and TRIM16 localized on LAMP1$^+$ autophagolysosomes (FIG. 15H). Like TRIM16, Galectin-3 was required for translocation of *M. tuberculosis* to LAMP1 compartments (FIG. 7L and FIG. 15G). Galectin-3 was required for ubiquitin deposits on *M. tuberculosis* phagosomes (FIG. 7M,N). Galectin-3 and TRIM16 colocalized on *M. tuberculosis* phagosomes (FIG. 15I). Finally, Galectin-3 protected mice in models of acute (FIG. 7O) and chronic (FIG. 15J,K) infection following aerosol exposure to *M. tuberculosis*. ATG16L1 was required for translocation of *M. tuberculosis* to autophagolysosomal compartments (FIG. 7L, and FIG. 15G). Finally, all three components, Galectin-3, TRIM16, and ATG16L1 were required for control of intracellular *M. tuberculosis* (FIG. 7P). Thus, TRIM16 along with Galectin-3 and ATG16L1, protects cells from the invading mycobacteria. In summary, the Galectin-3-TRIM16-ATG16L1 axis affords autophagic protection against lysosomal and phagosomal damage in diverse physiological contexts.

Discussion

This work shows that TRIMs (Reymond et al., 2001) and Galectins (Arthur et al., 2015; Blidner et al., 2015; de Waard et al., 1976; Nabi et al., 2015) interact and that the TRIM16-Galectin-3 system organizes autophagic response to endomembrane damage. TRIM16 controls ubiquitination of damaged compartments, and regulates the core autophagy regulators ULK1, Beclin 1, and ATG16L1, which confer localized autophagic sequestration of damaged lysosomes (Maejima et al., 2013). TRIM16 also affects TFEB activation and nuclear translocation. Thus, TRIM16, in cooperation with Galectin-3, organizes core autophagy factors and orchestrates sequential stages of antophagic responses to lysosomal and phagosomal damage. These relationships are depicted in FIG. 6J.

Our understanding of the role of TRIMs (Kimura et al., 2015; Kimura et al., 2016; Mandell et al., 2014) and Galectins (Aits et al., 2015; Chen et al., 2014; Fujita et al., 2013; Hung et al., 2013; Maejima et al., 2013; Thurston et al., 2012) in autophagy is growing. The present study underscores the significance of both of these families of proteins and reports the key new finding that these two systems interact. This work furthermore expands the number of autophagic receptors and regulators of autophagy that utilize Galectins as cofactors in recognition of autophagic targets (e.g. damaged membranes).

The interaction of TRIM16 with ATG16L1 is of particular interest. ATG16L1, occupies a unique place among core autophagy factors by acting as a hub that brings together the principal parts of the autophagic apparatus: (i) ATG16L1 is a component of the LC3-PE conjugation system (Mizushima et al., 2011); (ii) ATG16L1 interacts with the WIPI2 (Dooley et al., 2014), which in turn binds to PI3P produced by Beclin1-VPS34; and (iii) ATG16L1 associates with FIP200, a component of the ULK1 complex systems (Dooley et al., 2014; Fujita et al., 2013). Although ATG16L1 has intrinsic affinity for ubiquitin it requires an additional (hitherto unidentified) factor in order to be recruited to the correct membranes (Fujita et al., 2013). TRIM16 fits the properties of this missing link as it binds to the region of ATG16L1 spanning the critical residues in ATG16L1 postulated (Fujita et al., 2013) to interact with the putative factor that homes ATG16L1 to damaged lysosomal membranes. Thus, TRIM16, by interacting with ATG16L1 and Galectin-3, guides the placement of ATG16L1 on damaged membranes.

TRIM16 and its interacting partner Galectin-3 protect cells from lysosomal cell death or microbial invasion. Galectin-3 has been previously observed on mycobacterial phagosomes and implicated in control of mycobacteria in a short term infection of Galectin-3 knockout mice (Beatty et al., 2002). These studies are congruent with the results of murine survival studies in the aerosol *M. tuberculosis* infection model reported here. Given the connections to autophagic machinery via TRIM16, the role of Galectin-3 in control of bacteria or pathology associated with mycobacterial infection can now be mechanistically linked to the TRIM-driven process of precision autophagy (Kimura et al., 2016), which differs from bulk autophagy. TRIM16 is also known as estrogen-responsive B box protein, and its role in cancer (a general property of TRIMs (Hatakeyama, 2011)) has been linked to specific effects on immune signaling (Sutton et al., 2014), cell survival (Kim et al., 2013), cell migration and metastasis (Marshall et al., 2010; Sutton et al., 2014) through various mechanisms, including measures of membrane repair (Cheung et al., 2012; Marshall et al., 2010), with the latter potentially overlapping with the processes described in this work.

TRIM 16 absence elevates TFEB's partitioning to the nucleus. Both of these proteins can localize to lysosomes as their station for exerting regulatory and effector functions. TFEB is coupled to the mTOR system, with mTOR phosphorylating TFEB to keep it locked in the cytosol, which can be reversed upon starvation that inactivates mTOR, further coupled with $Ca^{2+}$ efflux from the lysosomes thus activating calcineurin to dephosphorylate TFEB and allow its nuclear translocation (Medina et al., 2015; Settembre et al., 2011; Settembre et al., 2012). These processes are modulated by TRIM16 action as suggested through interactions of TRIM16 shown here for DEPTOR, Rag GTPases, calcineurin, and TFEB itself. Absence of these interactions may lead to elevated TFEB in the nucleus. In summary, the relationships demonstrated here show convergence of the previously known and the newly uncovered precision autophagy systems in control of autophagic responses to endomembrane damage of significance in cancer and infectious diseases.

Treatment of *Mycobacterium tuberculosis* (Mtb)—Figures Labeled as #EXTB *Mycobacterium tuberculosis* (Mtb) is a pathogen of global significance[1]. Despite domestic and international[1,2,3] importance of Mtb, understanding tuberculosis (TB) pathogenesis remains elusive[4-20]. Fundamental and preclinical studies are proposed to identify causes and consequences of immunometabolic changes in Mtb-infected macrophages. Identification of mechanisms and their genetic and pharmacological validation (the R61 phase) will lead to identification of repurposing drugs against Mtb-induced pathogenesis (the R33 phase). Pharmacological interventions directed at modulating host immunometabolic pathways that Mtb evades will preserve lung function and improve outcomes of anti-mycobacterial/anti-retroviral treatments.

A multitude of converging reports highlight changes in Mtb infected macrophages, including inhibition of the host's protective metabolic response termed autophagy[21,22]. There are related findings showing that Mtb down-regulates AMP-activated protein kinase (AMPK)[21], inactivates the transcriptional factor EB (TFEB)[21] which is under control by the mechanistic target of rapamycin (mTOR)[23-26], and reprograms lipid and oxidative vs. glycolytic metabolism of host cells[27,28], collectively referred to as "immunometabolism" changes[29,30]. Peroxisome proliferator-activated receptor a is important in mice to resist Mtb[31]; it increases lipid catabolism, in part due to autophagic mobilization of neutral lipid stores (lipid droplets)[32,33], through a TFEB-controlled[34-36] autophagy-associated lipolysis[37-39]. All of the above metabolic aspects are directly hardwired into the process of autophagy in mammalian cells[40-44], and act as a concerted immunometabolic host defense response. The above targets to be studied in this project are individually listed in the RFA priorities stating a need "to evaluate the effects of these pathogens on core cell regulatory signaling molecules, including mTOR and AMPK".

The purpose of these experiments is to characterize the known and discover new intervention nodes in the above immunometabolic pathways affected by Mtb. We have recently uncovered novel aspects linking endomembrane (e.g. lysosomal and phagosomal) damage[45] with the signaling pathways controlling mTOR, AMPK, and TFEB (FIG. 1A-E). This is of direct relevance for Mtb, as Mtb minimizes endomembrane damage to evade recognition and activation of protective immunometabilic responses of the host. In the R61 phase, we will delineate key factors governing recognition of lysosomal damage and their links with immunometabolic responses (via mTOR, AMPK and TFEB). In the R33 phase, we target these pathways for drug repurposing in preclinical investigations.

A first aim of these experiments is to delineate the molecular cascade that detects and transduces endomembrane damage signals to the core immunometabolism regulators, mTOR, AMPK, and TFEB, and elicits protective effector responses against Mtb. Specific Aim 2 (R33). Identify drugs that can protect against Mtb and associated pathogenesis using immunometabolic targets characterized in Aim 1, test the candidate drugs in murine models of TB, and validate them in human cells from Mtb and HIV infected patients.

Experimental Strategy (A) Significance. *Mycobacterium tuberculosis* (Mtb) is a global human pathogen of domestic and worldwide[1,2,3] importance. Despite progress, understanding tuberculosis (TB) pathogenesis[46] remains an elusive target[4-20]. Fundamental studies of the known and new signaling pathways (FIG. 1A,B) governing immunometabolism[47] (FIG. 16 C-E) and autophagy as its components[48-50] followed by preclinical studies, as proposed here, will enable us to incite protective mechanisms in infected macrophages. This pertains to Mtb alone or in HIV co-infection. Improved antibacterial regimens, e.g. Nix-TB (pretomanid, bedaquiline, and linezolid) have addressed multi-drug resistance concerns (MDR)[51]. However, a completed chemotherapy can belie persistent patterns of active disease in "disease-free" TB patients[52]. Excessive lung damage leads to diverse long-term disability even after cure[53-56]. This calls[52] for discovering tissue protective host responses and how to stimulate them[29,57-60] to promote active-disease-free state, counter emergence of MDR Mtb, and prevent excessive lung damage leading to long-term post-treatment disability and morbidity.

Much of the initial Mtb infection, early and subsequent immunity control, disease progression, and lung pathology, occurs in or involves macrophages[61]. Macrophage function is profoundly influenced by immunometabolic changes[47,62]. For example, M1 macrophages utilize glycolysis and preserve/channel carbon into membrane and protein synthesis, whereas M2 macrophages burn carbon through oxidative phosphorylation (oxphos)[47,62]. Biogenesis oriented metabolic profile (anabolism, glycolysis) is promoted by mTOR and HIF1α (FIG. 16 center panel E) and curiously, resembles needs of rapidly growing cancer cells. Oxphos is a direct client of AMPK (FIG. 16 D) and is compatible with no or low cell proliferation. Similar dichotomy is reflected in effector T cells (glycolysis) vs. memory or regulatory T cells (oxphos)[47,62,63]. An important immunometabolic process, autophagy, known to act as an anti-Mtb defense mechanism, is co-regulated by mTOR[50] (negatively[64-68]) and AMPK[49] (positively[64-66]). A further key cellular client of mTOR is the master regulator of lysosomal biogenesis, TFEB[23-26]. TFEB is negatively regulated by mTOR[40-44] (FIG. 16 B). Among other functions, TFEB controls lipolysis and is a mobilizer of fatty acids from neutral lipid stores[26,34,69]. Thus, control of mTOR and AMPK is key to immunometabolism and a variety of immunometabolic effector mechanisms, with many already implicated in protection against Mtb. It follows, then, that their perturbations can lead to immunopathogenesis. The hypothesis of this proposal is based on the above relationships and consists of two parts: (a) Endomembrane damage activates protective immunometabolic responses against Mtb via Galectins, mTOR, AMPK and TFEB. (b) Pharmacological intervention, by targeting core immunometabolic regulators, can induce protective immunometabolism and counter the evasion strategies by Mtb, thus preventing excessive inflammation and bacterial loads.

As introduced above, immunometabolism regulators influence immune cell states and affect a multitude of effector mechanisms including autophagy as one of the key immunometabolic processes. Autophagy has numerous immunological roles[56,91-98]. Control of Mtb infection by autophagy[70-72], or by specific autophagy genes rather than the process as a whole[73], is a potential immunometabolic therapeutic target. Whereas there are many independent reports on autophagic protection against Mtb[15,27,72,74-78,31,71,79-90], it is evident that Mtb counters autophagy and inhibits host's ability to induce autophagy through a collection of mechanisms[21,27,91-97], including reported activation of mTOR. Among all of these, one recent analysis[21] is particularly telling: Mtb induces miR33/33* in host macrophages[21,98] to inhibit several autophagy (Atg) factors, counter AMPK and suppress TFEB. AMPK, mTOR and TFEB activities will be studied in Aim 1. In Aim 2 we will identify small molecules fit for repurposing, that can bypass Mtb interferences with and escape from protective mechanisms. These experiments, enhanced by work with both Mtb and HIV[100-104], identify processes and druggable targets converging on mTOR, AMPK, and TFEB in infected macrophages[105,106]. The targets are tested in macrophages and in vivo in mice for bacterial loads and sensitivity (CS7BL/6J background), and for inflammation and lung tissue pathology (C3HeB/Fe) mice)[46,107-111]. Finally, potential drugs will be tested in human macrophages from HIV-Mtb co-infected patients.

(B) Innovation. These experiments propose a new paradigm, supported by published[45] and preliminary data (described below), for how host cell may be able to recognize intracellular Mtb and induce appropriate immunometabolic responses, including autophagy and robust lysosomal biogenesis. However, this pathway needs pharmacological boost because Mtb evades recognition and induction of immunometabolic defenses. Recent reports[45] evidence that both lysosomal damage and Mtb phagosome damage are recognized by the same system. This system is based on Galectins that bind to lysosomal or phagosomal lumenal glycoconjugates exposed after organellar membrane damage[45]. Curiously, only <10% of virulent Mtb phagosomes are damaged in macrophages and marked by ubiquitin and the autophagy marker LC3[71,72]. Why? This intriguing question has remained unanswered. We now show (summarized in FIG. 1 A,B) that Galectins recognize membrane damage and transduce this signal to inactivate mTOR and activate AMPK. This reprograms immunometabolism: it shuts down protein and lipid biosynthesis (due to inhibition of mTOR) and activates fatty acid oxidation and oxphos (due to AMPK activation). It also results in upregulation of lysosomal biogenesis due to activation of TFEB, i.e. promotes its nuclear translocation[45], partially due to mTOR inactivation. These changes can be monitored by mTOR target phosphorylation (e.g. pS6K, pULK1Ser757) and AMPK targets phosphorylation (pACC, pULK1Ser777), induction of autophagy (LC3), and by monitoring TFEB nuclear translocation.

Only 10% of Mtb bacilli at a time penetrate the phagosomal membrane making Mtb stealthy. These experiments test whether existing drugs can be repurposed to activate the protective immunometabolic response despite Mtb's insidious capacity to evade detection by minimizing host endomembrane damage.

Experiments perform a novel drug discovery tool by high content microscopy (HC) using formation of endogenous Galectin puncta, as an easily visualized reporter of lysosomal damage and a pivotal event triggering downstream immunometabolic activation (i.e. concerted suppression of mTOR activity, increase in AMPK activity, and nuclear translocation of TFEB; see preliminary data). The use of HC microscopy enables robust and unbiased data collection and analysis, is based on single cell data collection at subcellular level, and has various capabilities in data mining. This approach offers both innovation and scientific rigor and reproducibility.

(C) Approach

Specific Aim 1 (R61). Delineate the molecular cascade that detects and transduces endomembrane damage signals to the core immunometabolism regulators, mTOR and AMPK, and elicits protective effector responses against Mtb.

Experimental Goal 1: Delineate how Intracellular Galectin 8 (Gal8) Controls mTOR in Response to Lysosomal Damage and its Role in Protection Against Mtb.

Experiments:

i) Gal8-mTOR. Test mTOR Control by Gal8 in Immunometabolic Responses to Endomembrane Damage.

*Background and purpose: Galectins recognize damaged lysosomes or permeabilized phagosomes alike[45]. Galectins, e.g. Gal3, can detect the permeabilized phagosomes containing intracellular Esx1+ Mtb and initiate autophagic response[45]. Gal3 KO mice are more sensitive to Mtb[45] (FIG. 17). But do Galectins (FIG. 18 A) act just as membrane damage tags for autophagy receptors as reported for several bacteria and viruses[45,112-119] or do they play a more active function? We will address this question and test the hypothesis that Galectins control mTOR activity. mTOR, a master coordinator of cell growth and metabolism, integrates inputs from nutrients via Rag GTPases (which recruit mTOR to lysosomes) and growth factors via Rheb GTPase (which is also on the lysosome and activates mTOR) (FIG. 16C). mTOR is ON only when both Rags and Rheb are activated, and this reflects mTOR's need for both nutrients and growth factors in order to be activated. Rags (acting as obligate heterodimers/pairs of RagA,B and RagC,D) respond to an abundance of amino acids[50], interact via another component termed Ragulator and are linked to the function of vacuolar $H^+$ ATPase (v-ATPase), and as shown very recently, to the abundance of cholesterol[120]. Interestingly, when active, mTOR is positioned on lysosomes and integrates these inputs while being at this locale. When amino acids (especially Arg and Leu) are not available, mTOR is inactive; mTOR is recruited to lysosomes via Rags, when RagA and B are loaded with GTP, through the action of the nucleotide exchange factor (GEF; the pentameric Ragulator complex of p14, p18, etc.). The Ragulator-Rag complex in turn interacts with vacuolar $H^+$ ATPase (v-ATPase)[121] and this megacomplex interacts with a particularly important lysosomal amino acid transporter SLC38A9[122-124]. SLC38A9 interacts with and activates Ragulator in response to lysosomal arginine[50] or cholesterol delivered via NPC1, which also interacts with the entire complex on the lysosome[120]. Relationships between different components change in response to inputs, e.g. presence of cholesterol reduces the interactions between p14 and RagA and RagC[120], and this can be used as a proxy measure in co-IPs as evidence of Rag and mTOR activation, with the latter's activity also being followed by phosphorylation of its targets S6K, 4EBP and ULK1.

*Experimental plan and methods: Our preliminary results show that Gal8 is found specifically in protein complexes with mTOR whereas Gal9 is in protein complexes with AMPK (FIG. 18). Gal3 is not found in co-immunoprecipitates (co-IPs) with either mTOR or AMPK. Our preliminary results also indicate that lysosomal damage increases Gal8-mTOR (FIG. 19) and Gal9-AMPK associations (not shown). The experiments test whether the mTOR sensory system (Ragulator and Rags, and potentially SLC38A9) responds to lysosomal damage to inactivate mTOR, at least in part through Gal8-mTOR complex interactions. The experiments follow the most recent study where a new signal (cholesterol) and a new sensory component (NPC1) interacting with the above complex were characterized. This includes: 1) Expected drop in mTOR substrate activity (p-T389 S6K, p-S65 4EBP, p-S757 ULK1, all by WB, nuclear TFEB translocation by HC analysis[45]) in response to LLOMe (Leu-Leu-OMe) and GPN (Gly-Phe-naphthylamide) lysosomal damage. Lysosomal damage will be monitored by dissipation of LysoTracker Red from lysosomes[125], delayed processing of cathepsins, and reduced proteolytic de-quenching of DQ Red BSA. 2) Expected endogenous mTOR dissociation from lysosomes (monitored by HC) and insensitivity of mTOR translocation in cells stably expressing Flag-RagB$^{Q99L}$, increased association between p14 (Ragulator component LAMTOR2) and RagA in co-IPs from cells treated with LLOMe or GPN. 3) Expected insensitivity of the published SLC38A9 CRISPR mutant to LLOMe/GPN effects on inhibition of mTOR. 4) Expected loss of effects of mutant β-galactoside binding sites in Gal8 (R69H, R232H). These experiments will establish how Gal8 transduces membrane damage information to mTOR.

ii) Test Significance of Gal8 in Control of Mtb.

*Background and purpose. Studies with Mtb infection of Gal8 KO mice (FIG. 2 EXTB) will be completed.

*Experimental plan and methods. The experiment uses a 200 cfu, standard low dose aerosol model[45] of Mtb infection in the C57BL/6J mouse background. The experiment monitors mouse survival, lung CFU, and histopathology[45] using Gal8 knockout (KO). Littermate controls, metagenome considerations, sex, and statistics: The experiment follows recommendations[126] to breed mice for infection experiments by starting with heterozygous parents and use littermate controls[126]. We will use both sexes (male and female). Group size (n=16) has been determined by our statistician—see letter of support (LOS) from Dr. Qeadan. Number of mice per group, was calculated based on published data[45].

iii) Test Effects of mTOR Inhibition in Control of Mtb.

*Background and purpose: To determine the potential of Galectin-based control of mTOR as a target for treatment in TB, aimed at reducing inflammation and lung damage.

*Experimental plan and methods. We will test this genetically and pharmacologically.

(a) Genetic experiments. For genetics we will utilize a critical mTOR effector—Raptor[50]. We have Raptor$^{F1/F1}$ mice (see LOS from Meilian Liu, PhD) and will breed them with: (a) LysM-Cre mice (for constitutive deletion in myeloid lineage including macrophages); and (b) with UBC-Cre-ERT2 mice with tamoxifen-inducible Cre (B6.Cg-Tg (UBC-cre/ERT2)1Ejb/2J), as we and others[127] have done with Atg7$^{F1/F1}$ UBC-Cre-ERT2. Tamoxifen dosage (intraperitoneal injection) is 200 mg/kg per day for 5 days for whole body deletion of Raptor (verified by genotyping and immunoblotting) at 3-4 weeks post-infection (aerosol, 200 cfu Mtb Erdman). Mouse survival and lung CFUs will be determined. We will use both sexes (male and female). Group size (n=16)[45].

(b) Pharmacological experiments. The timing of mTOR inhibition via administration of rapamycin (C3HeB/FeJ mice) (tamoxifen (Raptor$^{F1/F1}$ UBC-Cre-ERT2 mice) following Mtb infection is critical and will be determined by monitoring CFU, histopathology and inflammation. In our preliminary studies, we found that if rapamycin is given too early (e.g. 2 weeks following exposure to Mtb), this results in mice being more susceptible to Mtb. However, initiation of rapamycin at 4-7 weeks after infection is beneficial and prevents excessive pathology in the C3HeB/FeJ mouse model of Mtb infection and inflammation[46,107-111] (FIG. 20) whereas it does not increase Mtb loads in the lungs. Experimental Goal II: Delineate how Intracellular Galectin 9 Controls AMPK and its Role in Protection Against Mtb. Experiments:
i) Gal9-AMPK. Test AMPK Control by Gal9 in Response to Endomembrane Damage.

*Background and purpose: Gal9 plays a role in control of Mtb by macrophages through a yet not fully understood set of mechanisms[128]. We will test here the hypothesis that Gal9's roles include a novel effect on AMPK another key metabolism regulator[49] (see FIG. 16D). AMPK responds to cellular energy levels (AMP increase) and directs adaptive changes in growth, differentiation and metabolism under conditions of low energy. It also controls mTOR: AMPK activates TSC2, a GAP/negative regulator of mTOR, and phosphorylates negative regulatory sites on the key mTOR effector Raptor[129]. Thus, AMPK is a multipronged negative regulator of mTOR. These two kinases, mTOR and AMPK, together comprise the control center of cellular metabolism in general and reciprocally regulate autophagy (i.e. mTOR is a negative regulator of autophagy by phosphorylating inhibitory sites on ULK1[64] and on additional positive regulators of autophagy (AMBRA, UVRAG, etc.[67,68]), whereas AMPK phosphorylates activating sites on ULK1[64,65] and Beclin 1[66]. AMPK phosphorylates Beclin 1 and inhibitory-phosphorylates non-autophagic VPS34 complexes, whereas ATG14L "protects" autophagy-specific VPS34 from AMPK-inactivation thus favoring ATG14L-Beclin 1-VPS34 complexes at the expense of other[66].

*Experimental plan and methods: For AMPK-Gal9 interactions and their effects we will build our model on the recent findings that AMPK localizes on lysosomes and interacts with mTOR regulators. Our preliminary data indicate that Gal9 also plays a role in autophagic response to lysosomal damage. Moreover Gal9 knockdown decreases AMPK activation and activity (measured by decreased levels of pAMPK, pACC, PULK317; FIG. 21), Overexpression of Gal9 does the reverse—increases phosphorylation of these targets (FIG. 21). We will test a model in which Gal9 recruits upstream activators of AMPK, and will distinguish between LKB1, CaMKK2, and TAK1, as upstream activator kinases for AMPK[49]. Our preliminary results indicate that the Gal9 overexpression affects AMPK via TAK1. In keeping with this, we find in co-IPs of endogenous proteins TAK1 but neither LKB nor CaMKK2 in complexes with Gal9. We will establish that TAK1 is a close interactor of Gal9. We will use proximity ligation method based on modified ascorbate peroxidase probe (APEX2)[132,133]. Our preliminary results indicate that TAK1 is biotinylated by APEX2-Gal9, but this needs to be examined for a full panel of candidates that are expected or not expected (e.g. CaMKK2) to be in Gal9's proximity. Of importance is to examine whether proximity of Gal8-mTOR and Gal9-AMPK complexes on damaged lysosomes/endomembranes results in a coordinated regulation (inhibition of mTOR and activation of AMPK) in response to membrane damage to reprogram immunometabolic responses and activate autophagy. Our preliminary results show that whereas AMPK activity is reduced with Gal9 KD, mTOR is activated (increased pSer-757 on ULK1; FIG. 21, Left), and conversely inhibited when Gal9 is overexpressed (FIG. 21, Right). These studies will determine how Gal8 and 9 coordinately regulate mTOR and AMPK on damaged lysosomes. We will test how this affects autophagy in macrophages infected with Esx1+ (phagosome permeabilization-competent) and Esx1+ (phagosome permeabilization-deficient) Mtb[45]. We will also test (genetically and pharmacologically) how lysosomal damage, Gal8-mTOR, and Gal9-AMPK affect glycolysis (extracellular acidification rate/ECAR) and oxphos (oxygen consumption rate/OCR) using Seahorse measurements (FIG. 22; mTOR may be needed for OCR, depending on conditions[134-136]). We will dissect these relationships using bone marrow derived macrophages (BMMs) from Gal8 KO, Gal9 KO, and Raptor$^{F1/F1}$ LysM-Cre mice.
ii) Test Role of Gal9 and AMPK in Control of Mtb.

*Background and purpose: We will determine significance of Gal9 using Gal9 KO mice. We will test the significance of AMPK in control of Mtb pharmacologically, using metformin to activate AMPK and test in C3HeB/FeJ mouse model of TB its effects on inflammation and lung pathology.

*Experimental plan and methods: (a) Genetic experiments. We will carry out mouse survival, lung CFU and histopathology studies in the aerosol infection model of Mtb[45] using Gal9 knockout (KO) (Galectin9-KO, B6(FVB)-Lgals9$^{m1.1C/g}$/Mmcd) mice. (b) Pharmacological experiments. We will test metformin (pharmacological activator of AMPK) at 500 mg/kg/day[137], which allometrically scaled is equivalent to the maximum human dose of 2400 mg/day (associated with adverse GI events in humans). We will also test 375 mg/kg/day, which approximates levels seen in humans treated with 1750 mg/day (with fewer adverse events). Dosing and PK/PD matters will be under the purview of Dr. Timmins. Effects on CFUs (Mtb Erdman) will be tested in C57BL/6J mice when metformin is given alone, and for effects on histopathology (and CFUs) in C3HeB/FeJ mice when given (for 4 weeks starting at 4 weeks following infection) in combination with 100 mg/kg moxifloxacin, a second-line anti-TB drug. The C3HeB/FeJ mouse model of necrotizing responses similar to those observed in the human lung[46,107-111] is established in Dr. Salgame's laboratory. We will quantify necrotizing lesions and other parameters of inflammation (cytokines: IL-1, IL-6 and CXCL1, as detected with mTOR inhibitors in the C3HeB/FeJ mouse; FIG. 20D). Littermate controls, metagenome considerations, sex, and statistics: We follow recommendations[126] to breed mice for infection experiments by starting with heterozygous parents and use littermate controls[126]. We will use both sexes (male and female). Group size (n=16) has been determined by our statistician. Number of mice per group, was calculated based on published data[45]. In murine models of TB, female mice are generally used because of male mice being more aggressive presenting a husbandry issue and excessive loss of animals during experiments. However, we will repeat any major findings with male mice. Experimental goal III: Test the role of TFEB in control of Mtb in cellular and murine infection models.
Experiments
i) TFEB and Mtb in Infected Macrophages.

*Background and purpose: We have shown that damage to endomembranes (lysosome, phagosome) induces massive nuclear translocation of TFEB[45]. TFEB is negatively regulated by mTOR and by Rag GTPases on lysosomes[40-44]. Active Rags[44] recruit both mTOR and TFEB[44] to lysosomes, where mTOR phosphorylates TFEB[40-44] thus locking TFEB in the cytoplasm and preventing its activation/translocation to the nucleus. Understanding TFEB regulation in Mtb-infected cells will give us additional immunometabolic targets for drugs whereas TFEB nuclear translocation is a proxy assay for monitoring immunometabolic activation.

*Experimental plan and methods: We will test if Mtb infection activates TFEB in macrophages. Our preliminary studies indicate that TFEB translocates to the nucleus in Mtb infected cells, and that this translocation depends on a functional Esx1 locus (FIG. 23). However, Mtb infection induces only a very modest 6% nuclear translocation of TFEB (FIG. 23), in keeping with the mere 10% of intracellular Mtb being recognized by host systems detecting endomembrane damage. This is consistent with our model of Mtb evasion of endomembrane damage recognition by host cell systems.

We will test using BMMs from KO mice, whether Gal8 (as a negative regulator of mTOR) and Gal9 (as a positive regulator of AMPK which in turn negatively controls mTOR) are required for nuclear translocation of TFEB in response to lysosomal damage with escalating concentrations of GPN or LLOMe. We will determine how endomembrane damage affects lipid droplet levels and TFEB-directed lipolysis[138] using our published methods[37,39]. We will test whether Gal8 and Gal9 affect cellular lipid droplet content. Lipolysis antagonizes Mtb and its needs for lipid droplets/lipid body formation[21,27,139,140]. We will also measure autophagy, autophagy flux, translocation of Mtb to autolysosomes and lysosomal biogenesis. Finally, we will determine whether TFEB is required for killing of Mtb in murine macrophages from KO animals.

ii) TFEB in Control of Mtb In Vivo

*Background and purpose: TFEB is often referred to as a "master regulator of autophagosomal-lysosomal system", and is important for other aspects of immunometabolism, i.e. mobilization of fatty acids from neutral lipid stores[26,34-69]. TFEB is reportedly a target for downregulation by miR-33 in Mtb infected cells[21] and yet TFEB has surprisingly never been tested in vivo for its potential role in control of Mtb. TFEB full body KO is embryonically lethal[141]. Conditional TFEB knockout mice have been described[40,142], but have been studied only in the context of liver function. We will test them for susceptibility to Mtb infection.

*Experimental plan and methods: We have obtained the published TFEB$^{F1/F1}$ LysM-Cre mice[40] from Andrea Ballabio, and are expanding a breeding colony. Using murine models of TB (acute and chronic)[45], we will determine susceptibility (survival; CFU, histopathology) of TFEB$^{F1/F1}$ LysM-Cre mice to Mtb Erdman. Littermate controls metagenome considerations sex, and statistics: We follow recommendations[126] to breed mice for infection experiments by starting with heterozygous parents and use littermate controls[126]. We will use both sexes (male and female). Group size (n=16) has been determined by our statistician. The number of mice per group, was calculated based on published data[45].

Experimental Goal IV: Set Up the Testing System and Carry Out a Pilot Search for Drugs.

Experiments i) Drug Mini-Screen System Set Up

Background and Purpose:

For transition from R61 to R33 we plan on setting up the HC mini-screen based on Galectin puncta formation as a reporter of endomembrane damage and a proxy for induction of protective immunometabolic pathways to be delineated in experimental goals I-III.

Experimental Plan and Methods:

a) Screen set up. We have screened nearly all Galectins for cytoplasmic puncta formation in response to GPN, and found that Gal3, Gal8 and Gal9 give the most robust response (FIG. 24). Because Gal3 does not interact with mTOR or AMPK, whereas Gal8 interacts with and controls mTOR and Gal9 interacts with and control AMPK (FIG. 18) we will use Gal8 and Gal9 puncta formation as HC proxy for initiation of immunometabolic responses. Given that the endomembrane damage protection is a highly conserved process, we will use stable (Flp-In) YFP-Gal8 and YFP-Gal9 293A cells. For secondary tests, we will use THP-1 cells, a human macrophage-like cell line that shows relatively good behavior on tester plates, to confirm or narrow down 293A candidate drugs (once in a high throughput mode in the R33 phase). In THP-1 cells, we will use endogenous Gal8 and Gal9 responses to lysosomal damage control. Multiple 96 well plates with 7,500-10,000/well adherent cells will be prepared and chemicals (1 mM in DMSO, 1 h) robotically dispensed (in Dr. Sklar's facility), plates incubated, fixed and scored by HC microscopy for endogenous Gal8 and Gal9 puncta numbers and total area (simultaneously revealed with compatible antibodies: Gal8, Goat primary antibody; Gal9, Rabbit primary antibody; secondary antibodies: Donkey anti-Goat Alexa-568 and Donkey anti-Rabbit Alexa-488; robotic plate-washing is feasible and planned). Quantification of target 1 (Gal8) and target II (Gal9) intracellular objects (Gal8 puncta) will be done by automated HC microscopy on our Cellomics Array Scanner system and processed, as we have recently published[99]. We will use in primary tests parameters of 20 fields per well and >500 valid primary objects per well, corresponding to parameters that follow Z values of >0.5[155] in positive controls (100 μM GPN; 2 mM LLOMe) vs. negative controls (DMSO). For secondary tests of positive hits, 49 field/plate will be examined.

ii) Pilot-Screen of Small Library of Compounds

Background and Purpose:

To test the HC drug testing set up with a limited library.

Experimental Plan and Methods:

We will carry out a limited testing of compounds in the R61 phase, as this is meant just to set up the systems for the R33 phase. Among the many compound libraries available at UNM Center for Molecular Discovery (UNMCMD) for this "pilot" stage we use: the NCI Oncology collections (119 approved oncology drugs); the Oncology Collection of the Finnish Institute of Molecular Medicine (69 conventional chemotherapeutics, 236 kinase inhibitors (including all approved agents), 22 hormone therapy drugs, 51 epigenetic/differentiating drugs, 17 metabolic modifiers, 13 apoptotic modulators and 13 immunomodulators); The NIH Clinical Collection containing 446 small molecules used in human clinical trials. The clinically tested compounds in the NCC are drug-like with known safety profiles. These compounds provide excellent starting points for medicinal chemistry optimization and may be appropriate for human use in new disease areas. A number of individual drugs will be selected to add to this panel, guided by clinical leaders within this project. This includes metformin and several biguanides, which will be added to the lists when absent in libraries (see EG II—experiment ii for rationale).

Anticipated Results, Potential Problems, and Alternative Approaches a) Experimental goals I-IV. The deliverables are listed in Milestones. If experimental results prove that our hypothesis is correct, we will have demonstrated how Gal8 and Gal9 control immunometabolic responses via mTOR (inhibition), AMPK (activation), and TFEB (activation) in response to lysosomal-phagosomal damage. The Gal8 and Gal9 signaling cascade may not be sufficiently induced to control Mtb, and pharmacological interventions to augment this pathway may be needed, which will be tested as a proof of principle.

Anticipated outputs of the protective immunometabolic signaling are suppression of excessive inflammation and tissue damage during Mtb infection[70], induction of autophagy in macrophages[71,72,143,144], and host lipid catabolism of relevance for Mtb[27,106,140]. We will address lipid droplet metabolism to assess the latter, following our published methods in this area[39,145]. Behar and colleagues have already reported an in vivo role for Gal9 in Mtb pathogenesis[128]. They have proposed that Gal9 acts extracellularly as a ligand for an unidentified receptor on macrophages to stimulate an unidentified, but IL-1β-dependent cell-autonomous Mtb elimination process[128]. It is possible that this IL-1β-dependent mechanism is or includes autophagy, as we have described that IL-1β induces autophagy[146]. This can be tested both in vitro and in vivo if necessary. Gal9 and other Galectins have multiple roles and Gal9 may be involved in curbing the extent of T cell responses[147]. TFEB affects neutral lipid stores (lipid droplets), autophagy and entire lysosomal system, all of which affect intracellular Mtb. We expect that TFEB$^{F1/F1}$ LysM-Cre mice will be more susceptible to Mtb. Because Mtb infection of macrophages inhibits TFEB through activation of miR-33[21], we may need to take that into account. Lipid droplets are not to be confused with foamy macrophages laden with oxidized LDL[106]. We are cognizant of other members of the TFEB family (termed MIT/TFE: TFEB, TFE3, MITF), and have published on their use by knockdown analyses[99]. We do not intend to study additional MIT/TFE factors and are focused on TFEB as a dominant factor[45,99], as Tfe3 mice have no apparent general phenotype[148]. We anticipate no major issues with drug testing by HC and do not think that the limited libraries will provide a major hit, but keep our minds open for an early success. Alternative assays include monitoring lysosome status with LysoTracker Red (see R33).

***Animal studies and assay statistics: Numbers of mice (both sexes) per group are determined using power analysis and our published data with statistical parameters. An LOS from our statistician (Dr. Qeadan) is attached. Number of mice per group, n=16, is calculated based on our published data[45]). Quantitative microscopy carried out using HC imaging analyses (Cellomics) and iDev morphometric analysis and statistical package, are based on known statistical parameters[37,45,149-151] and variable effect size (from 0.3-0.8) with number of repeats >16, each reporting >500 primary objects (individual cells) per biological repeat for their intracellular targets (e.g. LC3 puncta). Confocal microscopy colocalization will be quantified using Pearson's correlation or Manders' two-component colocalization coefficient.

Specific Aim 2 (R33). Identify drugs that can protect against Mtb and associated pathogenesis using immunometabolic targets characterized in Aim 1, test the candidate drugs in murine models of TB, and validate them in human cells from Mtb and HIV infected patients.
Experimental Goal 1: Identify Drugs Targeting Endomembrane Damage Using Galectin Puncta HC Assay
Experiments:
i) Carry Out (a) High Content Testing of Compound Libraries Fit for Repurposing Using Galectin Puncta Formation as a Readout and (b) Compare Pilot Hits and Biguanides with Metformin as a Standard.
Background and Purpose:
Galectins can react to membrane damage and form intracellular puncta in response to lysosomal damaging agents such as polymers of LLOMe or GPN that poke membrane holes[152,153], or upon robust phagosome permeabilization by bacteria. Galectins have been implicated in recognition of intracellular *Legionella*[114,119] *Shigella*[112], *Listeria*[113], *Yersinia*[119], *Salmonella*[113,115,116], and inanimate objects such as latex beads[116,154] coated with transfection reagents[116]. An in vitro (in cells) protective role for Gal8 has been reported in control of *Salmonella*[115] and viruses[117,118]. Gal9 has been shown to play a role in control of Mtb in macrophages, although this has been ascribed to its extracellular signaling[128]. The preliminary data (FIG. 17) indicate that Gal8 is necessary for protection against Mtb in mice, and this will be completed as one of deliverables during the R61 phase. Importantly, we now find that Gal8 and Gal9 control mTOR and AMPK, respectively, in response to endomembrane (lysosome, phagosome) perturbations/damage, a novel link that will be fully delineated during the R61 phase. Thus, for the R33 phase, we propose to use induction of Galectin (Gal8 and Gal9) puncta as a proxy test for drugs that will inhibit mTOR, activate AMPK, induce TFEB and promote immunometabolic changes accompanied by induction of the lysosomal and autophagosomal systems and lipolysis. We have dubbed this as an AMPK-mTOR-TFEB-Lysosome/oxphos/autophagy (AMT-LOA) axis. AMT-LOA is a protective response to the intracellular Mtb, an insidious pathogen that causes some endomembrane damage but mostly minimizes it as an AMT-LOA evasion strategy. The approach is two-pronged (a) A repurposing campaign to identify drugs that can stimulate AMT-LOA. Galectins will be used as markers and regulators of AMT-LOA. (b) With the known drugs that can already be moved forward, we will establish a dose response of metformin and other biguanides as frontline drugs, and compare with promising hits from the limited pilot drug testing from R61 phase.
Experimental Plan and Methods:
(a) We will test compound libraries and utilize well-established drug discovery infrastructure at UNM Center for Molecular Discovery (UNMCMD, Dr. Sklar, director). UNMCMD is designed for drug testing and is equipped with various robotic systems and functionalities as well as computational and data mining capabilities (see Facilities and Resources). The centerpiece drug library to be utilized is the California Institute for Biomedical Research (CALIBR) now one of the three companies of the Scripps Research Institutes and a proposed partner in UNM's CTSC Drug Repurposing Network. The ReFRAME library (FIG. 10), contains resynthesized compounds developed by pharmaceutical companies with safety studies completed. The ReFRAME project was sponsored by Bill & Melinda Gates Foundation, with emphasis on applications for Global Health. Auranofin, identified by CALIBR as noted below, with reported activity in autophagy, has promise in TB.

Those hits that pass primary and secondary tests as defined in the R61 phase, will be subjected to a series of tertiary tests: (i) Dose response analysis as we have published for autophagy-inducing HC screens[22]. (ii) The Galectin puncta-based secondary tests will include endogenous ubuqitin puncta formation (FK2 antibody) HC assay, which almost invariably parallels Galectin dots formation during endomembrane damaged[45]. (iii) Those compounds showing dose response will be tested in primary murine macrophages (BMMs) and primary human peripheral blood monocyte-derived macrophages (MDMs) and dose responses in these specific cell types determined relative to comparator agents/drugs (LLOMe, GPN and metformin).

(b) We establish a dose response for metformin and other biguanides as drugs already identified (independent of drug library testing) and ready to move forward. Our preliminary studies show that a widely used drug, metformin, causes lysosomal damage. This is a previously unknown property of metformin and is a part of how metformin works pharmacologically in activating AMPK (FIG. 26). This enables us to move forward with known compounds that cause endomembrane-lysosomal damage.

Anticipated Results, Potential Problems, and Alternative Approaches (Experimental Goal I)

The deliverables are listed in Milestones. At the very minimum we will have metformin or another biguanide to test in animal studies. As with most repurposing campaigns, effective concentrations of drugs needed to achieve a non-primary indication may be much higher, but this is inherent to repurposing. We may consider using loss of LysoTracker Red (FIG. 26 C) as a screening tool for lysosomal damage, independently of Galectin based tests. Another marker that will be useful is Magic Red Cathepsin B activity (FIG. 26 B). We will also consider approaches complementary to but independent of lysosomal damage: (i) TFEB nuclear translocation (increase)[45]; (ii) LC3 puncta counts (increase)[99]; (iii) lipid droplets counts (decrease)[37]. All of these are HC-test compatible and have been implemented in our laboratory as published by us[37,45,99].

If a very promising positive hit compound from the ReFRAME library is not available in sufficient quantities, we will work with CALIBR or another commercial source to synthesize the compound (and subject it to authentication by mass spectrometry). As a back-up to ReFRAME library of compounds we will consider the following ones available at UNMCMD: The Prestwick Chemical Library (1,280 small molecules, 100% approved drugs; fit for repurposing in clinical trials); The Microsource SPECTRUM Collection (2,560 compounds providing a range of biological activities and structural diversity); Tocriscreen Collection (1,120 biologically active compounds, considered as a starting point for pathway identification in cell-based phenotypic targets); Selleckchem L1700 (2,100 bioactive compounds including inhibitors, natural products, chemotherapeutic agents that are cell permeable); Johns Hopkins Collection (1500 FDA/foreign approved drugs). Collectively, these libraries represent the majority of the FDA-approved drugs and those drugs that have been in human trials in Europe and Japan, apart from additional natural products and bioactive molecules. We will prioritize and limit our search to collections with strongest potential for repurposing, as we have done for a recent autophagy screen[99] using the Prestwick Chemical Library, the Microsource Spectrum 2000 library, and the Johns Hopkins Library. Of note, although we did test these back-up libraries for autophagy, we did not screen them for Galectins and immunometabolic effects.

Experimental Goal II: Validate Drugs in Macrophages and Mouse Models

Experiments:

i) Validate Drugs for Effects on mTOR, AMPK, TFEB, Lipid Droplets, Mitochondrial Respiration and Autophagy.

*Background and purpose: The main purpose of our tests is to identify compounds that will induce protective immunometabolic responses (i.e. the AMT-LOA axis) in macrophages predicted to play a beneficial role in Mtb control: inhibition of mTOR, activation of AMPK, increased lipolysis/diminishing sources of neutral lipids for Mtb, and autophagy as anti-Mtb defense.

*Experimental plan and methods: Along with Galectin and ubiquitin assays, autophagy induction[99], TFEB nuclear translocation, and lipid droplet lipolysis will be determined by HC. We will test mTOR and AMPK activities with top 10 candidates using biochemical assays and physiological outputs from EGI and II, R61 phas: mTOR activity (pS6K, PULK1-Ser757; see FIG. 21, AMPK (pACC, pULK1-Ser777, see FIG. 21), TFEB nuclear translocation[45], autophagy (LC3 puncta, LC3-II flux±bafilomycin A1), and mitochondrial respiration, using Seahorse; mitochondrial oxygen consumption rate (OCR; FIG. 22), a key metric of mitochondrial function, and extracellular acidification rate (ECAR) for glycolytic activity. Lipid droplets will be quantified using two parameters: number of lipid droplets/cell (measure of neutral lipid stores), and total area of lipid droplets/cell to control for larger lipid droplet formation (lipid droplet size is controlled by phospholipid/neutral lipid ratios and other factors) as we have previously reported[37].

ii) Test Candidate Drugs in Macrophages for Control of Mtb

*Background and purpose: One of the two key properties we are expecting from repurposing drug candidates is to promote killing/inhibit survival of Mtb in cultured macrophages, the other independent element being reduction of inflammation and tissue damage. We will include a priori in these studies (in addition to new drugs) a series of biguanide drugs akin to metformin (bufromin, phenformin, proguanil, etc.; selections and concentrations to be guided by Drs. Ellner and Timmins), which contain additional hydrophobic groups and may have higher anti-Mtb activity in macrophages (where there may be import issues with metformin).

*Experimental plan and methods: We will use our standard methods of Mtb killing in macrophages[45,143,146-156] and compare to metformin as well as to starvation/EBSS and rapamycin (autophagy induction)[143,156]. We will use THP-1 and primary MDMs. If a drug causes Mtb killing in macrophages, we will test its activity dependence on Gal8 (mTOR) or Gal9 (AMPK) using primary BMMs from Gal8 and Gal9 KO mice relative to BMMs from wild type littermates, and for mTOR directly by comparing BMMs from Raptor$^{F1/F1}$ LysM-Cre mice and Raptor (Cre-negative) littermates. Biguanides (metformin, bufromin, phenformin, proguanil, etc.) will be included in these tests with the intent to find out whether any of the non-metformin biguanides shows higher anti-Mtb potency in macrophages. If they do, they will be subjected to assays as described above in Aim 1, EG2, experiment i. Given the results for metformin, It is expected that other biguanides will be more active than metformin in treating tuberculosis.

iii) Test Candidate Drugs for Control of Mtb Loads in C57BL/6J Mice.

*Background and purpose: A desirable element, but not necessarily critical for the purpose of this entire project, would be that a drug candidate promotes control of Mtb in mouse models of Mtb infection.

*Experimental plan and methods: We use 200 cfu GlasCol aerosol infection of C57BL6J mice in our UNM HSC ABSL3 facility. We test candidate drugs positive in macrophage killing assays and compare to metformin and other active biguanides. We give metformin in drinking water (daily doses calculated at 375-500 mg/kg/day); more hydrophobic compounds are formulated with transgenic paste feed as we have done with ambroxol (from our autophagy-based screen[99] FIG. 27), or use gavage or injections as a last resort. We will test new drugs and any active biguanides individually or in combination with standard testing doses of rifampin (Rif) for potential synergism (see FIG. 27 for synergism between ambroxol and Rif). Ambroxol was a drug (an active metabolite of the prodrug bromhexine) found in our screens for autophagy[99].

iv) Test Drugs for Control of Inflammation in C3HeB/FeJ Mouse Model of TB

*Background and purpose: A highly desirable property from an immunometabolic drug candidate is to prevent excessive inflammation and tissue damage during Mtb infection.

*Experimental plan and methods: We will advance top 2-5 drugs (regardless of anti-Mtb activity in ex vivo assays above)+ and one biguanide (metformin or a biguanide more active in macrophages) to tests in the C3HeB/FeJ mouse model of necrotizing responses[46,107-111]. We use the classical inhibitor of mTOR, rapamycin, as a comparator drug (see the data showing reduced inflammation, FIG. 20). Depending on the drug properties, it will be formulated and administrated accordingly in consultations with Dr. Timmins. We describe here how we administer rapamycin, as an example. To avoid gavages we use the established approach developed by the Strong group in murine aging studies with rapamycin[157]. Rapamycin is co-formulated with a Eudragit polymer (eRAPA) so it is stable and bioavailable orally at the doses ppm in mouse chow. In our studies thus far, when mice are on 42 ppm eRAPA dose, blood levels (mouse red blood cells) of rapamycin measured by mass spectrometry are at 205 ng/ml±35 ng/ml (n=8 animals, mean±SD). We will test effects of drugs alone or in combination with a standard Mtb chemotherapeutic agent (e.g. Rif for assessment of use in drug susceptible TB, and one for the drugs from Nix-TB, for assessment of use in MDR TB) and validate PK when possible.

v) Test Candidate Drugs for Effects on Immunometabolic Regulation in PBMCs from Mtb and HIV Infected Patients

*Background and purpose: The immunometabolic state of macrophages and other cells is expected to be altered in chronically infected patients. We therefore propose a complementary series of experiments in which cells are obtained from individuals with one or both infections (Mtb, HIV, or Mtb+HIV) to determine whether top drugs will function in the setting of changes and reversibility of cellular dysfunction.

*Experimental plan and methods: The human subjects for ex vivo studies will be recruited in Kampala Uganda. Uganda is designated by WHO as a high TB prevalence and high HIV prevalence country. The TB Research Laboratory designated by the World Health Organization as one of two supra-national mycobacterial reference laboratories in Sub-Saharan Africa. The study groups are HIV infected, ART naïve, CD4≥200; HIV infected, ART naïve, CD4<200; TB patients that are HIV infected, ART naïve, CD4≥200; TB cases that are HIV infected, ART naïve, CD4<200; TB cases that are HIV-uninfected; controls, no TB, no HIV (recruited from attendants that accompany patients to clinic). 10 subjects of both sexes will be recruited for each group (statistical power for medium to large size effects of 0.6-0.8 is based on data to date with HC assays using MDMs from healthy donors). Each subject will undergo venipuncture of 20 ml of blood; PBMC will be collected and cryopreserved. Blood will be obtained at 4-month intervals for 2 years during which the subjects will undergo standard treatment for TB and for HIV infection. Serial studies will assess immune reconstitution (CD4 count) and virologic suppression. Cryopreserved cells will be shipped to New Mexico for testing candidate drugs for responsiveness of immunometabolic readouts described in above sections.

In addition, top candidate drugs are tested for effects on immunometabolic regulators and Mtb control in macrophages (MDMs) from healthy donors infected with Mtb alone or co-infected ex vivo (in the laboratory) with both Mtb and HIV, to ascertain their potency despite Mtb evasion or antagonism by Mtb or HIV.

**Anticipated Results, Potential Problems, and Alternative Approaches (Experimental Goal II):

The deliverables are listed in Milestones. We anticipate that we will identify repurposing-fit drugs that will give comparable or better effects to metformin (for reducing bacterial loads in CS7BL/6J mice) and rapamycin (for reducing inflammation and lung pathology in C3HeB/FeJ), and will compare the efficacy/potential relative to metformin. A major challenge will be formulation, allometric dosing, pharmacokinetic, and pharmacodynamic adjustments of a repurposing drug for testing in murine models. However, we have been able to address this successfully for Ambroxol repurposing as an inducer of autophagy and tested it in mouse models. We have not previously tested Ambroxol for lysosomal damage activity, and will include it along with new hits and biguanides in the in vitro validation assays in this goal (EG II).

The experiments will deliver detailed signaling circuitry and define molecular targets in the Galectin 8-mTOR and Galectin 9-AMPK systems leading to immunometabolic programming and activation of the AMPK-mTOR-TFEB-Lysosome/oxphos/autophagy (AMT-LOA) axis in response to endomembrane damage.

The experiments will deliver mouse survival and lung CFU data with Galectin 8KO, Galectin 9KO, $Raptor^{F1/F1}$, and $TFEB^{F1/F1}$ mice (C57BL/6J background) infected in GlasCol aerosol 200 cfu, initial lung deposition of Mtb Erdman.

The experiments will deliver data on effects of at least one known drug targeting the AMT-LOA axis in Mtb infected C3HeB/FeJ mice on inflammatory pathology, as a proof of principle.

The experiments will deliver a robust test for drugs perturbing/damaging endomembranes.

The experiments will deliver ≥10 drugs perturbing or damaging endomembranes that stimulate Galectin responses.

The experiments deliver through secondary assays (activation of AMT-LOA axis in macrophages) 5 drugs (based on: AMT-LOA readouts, known toxicity and side effects, known pharmacokinetic and expected pharmacodynamics and clinical properties) from milestone #5, plus the drugs predicted a priori to affect AMT-LOA axis drugs (rapamycin, metformin and their analogs)

The experiments deliver protection data (cfu, survival) in C57BL/6J mice and protection against inflammation and pathology in C3HeB/FeJ mice of 5 top candidate repurposing-ready small molecules.

The experiments deliver data on drugs from milestone 7 for AMT-*LOA* activation in cells from HIV-Mtb co-infected patients. Deliver re-ranked 5 drugs by efficacy in above milestones, by clinical relevance and clinical trial potential.

Top drug(s) are moved into a Phase I/II clinical trial.

REFERENCES (FIRST SET)

Aits, S., Kricker, J., Liu, B., Ellegaard, A. M., Hamalisto, S., Tvingsholm, S., Corcelle-Termeau, E., Hogh, S., Farkas, T., Holm Jonassen, A., et al. (2015). Sensitive detection of lysosomal membrane permeabilization by lysosomal galectin puncta assay. Autophagy 11, 1408-1424.

Alemu, E. A., Lamark, T., Torgersen, K. M., Birgisdottir, A. B., Larsen, K. B., Jain, A., Olsvik, H., Overvatn, A., Kirkin, V., and Johansen, T. (2012). ATG8 family proteins act as scaffolds for assembly of the ULK complex:

sequence requirements for LC3-interacting region (LIR) motifs. The Journal of biological chemistry 287, 39275-39290.

Antonioli, M., Albiero, F., Nazio, F., Vescovo, T., Perdomo, A. B., Corazzari, M., Marsella, C., Piselli, P., Gretzmeier, C., Dengjel, J., et al. (2014). AMBRA1 interplay with cullin E3 ubiquitin ligases regulates autophagy dynamics. Dev Cell 37, 734-746.

Arthur, C. M., Baruffi, M. D., Cummings, R. D., and Stowell, S. R. (2015). Evolving mechanistic insights into galectin functions. Methods Mol Biol 1207, 1-35.

Axe, E. L., Walker, S. A., Manifava, M., Chandra, P., Roderick, H. L., Habermann, A., Griffiths, G., and Ktistakis, N. T. (2008). Autophagosome formation from membrane compartments enriched in phosphatidylinositol 3-phosphate and dynamically connected to the endoplasmic reticulum. J Cell Biol 182, 685-701.

Bar-Peled, L., and Sabatini, D. M. (2014). Regulation of mTORC1 by amino acids. Trends Cell Biol 24, 400-406.

Baskaran, S., Carlson, L. A., Stjepanovic, G., Young, L. N., Kim do, J., Grob, P., Stanley, R. E., Nogales, E., and Hurley, J. H. (2014). Architecture and dynamics of the autophagic phosphatidylinositol 3-kinase complex. eLife 3.

Beatty, W. L., Rhoades, E. R., Hsu, D. K., Liu, F. T., and Russell, D. G. (2002). Association of a macrophage galactoside-binding protein with *Mycobacterium*-containing phagosomes. Cell Microbiol 4, 167-176.

Bell, J. L., Malyukova, A., Holien, J. K., Koach, J., Parker, M. W., Kavallaris, M., Marshall, G. M., and Cheung, B. B. (2012). TRIM16 acts as an E3 ubiquitin ligase and can heterodimerize with other TRIM family members. PloS one 7, e37470.

Birgisdottir, A. B., Lamark, T., and Johansen, T. (2013). The LIR motif—crucial for selective autophagy. Journal of cell science/26, 3237-3247.

Blidner, A. G., Mendez-Huergo, S. P., Cagnoni, A. J., and Rabinovich, G. A. (2015). Re-wiring regulatory cell networks in immunity by galectin-glycan interactions. FEBS Lett 589, 3407-3418.

Bodemann, B. O., Orvedahl, A., Cheng, T., Ram, R. R., Ou, Y. H., Formstecher, E., Maiti, M., Hazelett, C. C., Wauson, E. M., Balakireva, M., et al. (2011). RalB and the Exocyst Mediate the Cellular Starvation Response by Direct Activation of Autophagosome Assembly. Cell 144, 253-267.

Castillo, E. F., Dekonenko, A., Arko-Mensah, J., Mandell, M. A., Dupont, N., Jiang, S., Delgado-Vargas, M., Timmins, G. S., Bhattacharya, D., Yang, H., et al. (2012). Autophagy protects against active tuberculosis by suppressing bacterial burden and inflammation. Proceedings of the National Academy of Sciences of the United States of America 109, E3168-3176.

Chan, E. Y., Kir, S., and Tooze, S. A. (2007). siRNA screening of the kinome identifies ULK1 as a multidomain modulator of autophagy. The Journal of biological chemistry 282, 25464-25474.

Chauhan, S., Mandell, M. A., and Deretic, V. (2015). IRGM Governs the Core Autophagy Machinery to Conduct Antimicrobial Defense. Mol Cell 58, 507-521.

Chen, D., Gao, F., Li, B., Wang, H., Xu, Y., Zhu, C., and Wang, G. (2010). Parkin mono-ubiquitinates Bcl-2 and regulates autophagy. The Journal of biological chemistry 285, 38214-38223.

Chen, X., Khambu, B., Zhang, H., Gao, W., Li, M., Chen, X., Yoshimori, T., and Yin, X. M. (2014). Autophagy induced by calcium phosphate precipitates targets damaged endosomes. The Journal of biological chemistry 289, 11162-11174.

Cheung, B. B., Koach, J., Tan, O., Kim, P., Bell, J. L., D'Andreti, C., Sutton, S., Malyukova, A., Sekyere, E., Norris, M., et al. (2012). The retinoid signalling molecule, TRIM16, is repressed during squamous cell carcinoma skin carcinogenesis in vivo and reduces skin cancer cell migration in vitro. J Pathol 226, 451-462.

Cunningham, C. N., Baughman, J. M., Phu, L., Tea, J. S., Yu, C., Coons, M., Kirkpatrick, D. S., Bingol, B., and Corn, J. E. (2015). USP30 and parkin homeostatically regulate atypical ubiquitin chains on mitochondria. Nat Cell Biol 17, 160-169.

de Waard, A., Hickman, S., and Kornfeld, S. (1976). Isolation and properties of beta-galactoside binding lectins of calf heart and lung. The Journal of biological chemistry 251, 7581-7587.

Deretic, V., Saitoh, T., and Akira, S. (2013). Autophagy in infection, inflammation, and immunity. Nature Reviews Immunology.

Diao, J., Liu, R., Rong, Y., Zhao, M., Zhang, J., Lai, Y., Zhou, Q., Wilz, L. M., Li, J., Vivona, S., et al. (2015). ATG14 promotes membrane tethering and fusion of autophagosomes to endolysosomes. Nature 520, 563-566.

Dooley, H. C., Razi, M., Polson, H. E., Girardin, S. E., Wilson, M. L., and Tooze, S. A. (2014). WIPI2 Links LC3 Conjugation with PI3P, Autophagosome Formation, and Pathogen Clearance by Recruiting Atg12-5-16L1. Mol Cell 55, 238-252.

Egan, D. F., Shackelford, D. B., Mihaylova, M. M., Gelino, S., Kohnz, R. A., Mair, W., Vasquez, D. S., Joshi, A., Gwinn, D. M., Taylor, R., et al. (2011). Phosphorylation of ULK1 (hATG1) by AMP-activated protein kinase connects energy sensing to mitophagy. Science 331, 456-461.

Fujita, N., Itoh, T., Omori, H., Fukuda, M., Noda, T., and Yoshimori, T. (2008). The Atg16L complex specifies the site of LC3 lipidation for membrane biogenesis in autophagy. Mol Biol Cell 19, 2092-2100.

Fujita, N., Morita, E., Itoh, T., Tanaka, A., Nakaoka, M., Osada, Y., Umemoto, T., Saitoh, T., Nakatogawa, H., Kobayashi, S., et al. (2013). Recruitment of the autophagic machinery to endosomes during infection is mediated by ubiquitin. J Cell Biol 203, 115-128.

Gammoh, N., Florey, O)., Overholtzer, M., and Jiang, X. (2013). Interaction between FIP200 and ATG16L1 distinguishes ULK1 complex-dependent and—independent autophagy. Nat Struct Mol Biol 20, 144-149.

Gutierrez, M. G., Master, S. S., Singh, S. B., Taylor, G. A., Colombo, M. I., and Deretic, V. (2004). Autophagy is a defense mechanism inhibiting BCG and *Mycobacterium tuberculosis* survival in infected macrophages. Cell 119, 753-766. Hatakeyama, S. (2011). TRIM proteins and cancer. Nat Rev Cancer 11, 792-804. Huett, A., Heath, R. J., Begun, J., Sassi, S. O., Baxt, L. A., Vyas, J. M., Goldberg, M. B., and Xavier, R. J. (2012). The LRR and RING Domain Protein LRSAM1 Is an E3 Ligase Crucial for Ubiquitin-Dependent Autophagy of Intracellular *Salmonella Typhimurium*. Cell host & microbe 12, 778-790.

Hung, Y. H., Chen, L. M., Yang, J. Y., and Yang, W. Y. (2013). Spatiotemporally controlled induction of autophagy-mediated lysosome turnover. Nature communications 4, 2111.

Imam, S., Talley, S., Nelson, R. S., Dharan, A., O'Connor, C., Hope, T. J., and Campbell, E. M. (2016). TRIM5alpha degradation via autophagy is not required for retroviral restriction. J Virol.

Itakura, E., Kishi-Itakura, C., and Mizushima, N. (2012). The hairpin-type tail-anchored SNARE syntaxin 17 targets to autophagosomes for fusion with endosomes/lysosomes. Cell/57, 1256-1269.

Joachim, J., Jefferies, H. B., Razi, M., Frith, D., Snijders, A. P., Chakravarty, P., Judith, D., and Tooze, S. A. (2015). Activation of ULK Kinase and Autophagy by GABARAP Trafficking from the Centrosome Is Regulated by WAC and GM130. Mol Cell 60, 899-913.

Kabeya, Y., Mizushima, N., Ueno, T., Yamamoto, A., Kirisako, T., Noda, T., Kominami, E., Ohsumi, Y., and Yoshimori, T. (2000). LC3, a mammalian homologue of yeast ApgSp, is localized in autophagosome membranes after processing. Embo J 19, 5720-5728.

Kabeya, Y., Mizushima, N., Yamamoto, A., Oshitani-Okamoto, S., Ohsumi, Y., and Yoshimori, T. (2004). LC3, GABARAP and GATE16 localize to autophagosomal membrane depending on form-II formation. J Cell Sci 117, 2805-2812.

Kane, L. A., Lazarou, M., Fogel, A. I., Li, Y., Yamano, K., Sarraf, S. A., Banerjee, S., and Youle, R. J. (2014). PINK1 phosphorylates ubiquitin to activate Parkin E3 ubiquitin ligase activity. J Cell Biol 205, 143-153.

Kawai, T., and Akira, S. (2011). Regulation of innate immune signalling pathways by the tripartite motif (TRIM) family proteins. EMBO molecular medicine 3, 513-527.

Khaminets, A., Behl, C., and Dikic, 1. (2016). Ubiquitin-Dependent And Independent Signals In Selective Autophagy. Trends Cell Biol 26, 6-16.

Kim, J., Kim, Y. C., Fang, C., Russell, R. C., Kim, J. H., Fan, W., Liu, R., Zhong, Q., and Guan, K. L. (2013a). Differential regulation of distinct Vps34 complexes by AMPK in nutrient stress and autophagy. Cell 152, 290-303.

Kim, J., Kundu, M., Viollet, B., and Guan, K. L. (2011). AMPK and mTOR regulate autophagy through direct phosphorylation of Ulk1. Nat Cell Biol 13, 132-141.

Kim, P. Y., Rahmanto, A. S., Tan, O., Norris, M. D., Haber, M., Marshall, G. M., and Cheung, B. B. (20136). TRIM16 overexpression induces apoptosis through activation of caspase-2 in cancer cells. Apoptosis 18, 639-651.

Kimura, T., Jain, A., Choi, S. W., Mandell, M. A., Schroder, K., Johansen, T., and Deretic, V. (2015). TRIM-mediated precision autophagy targets cytoplasmic regulators of innate immunity. J Cell Biol 2/0, 973-989.

Kimura, T., Mandell, M., and Deretic, V. (2016), Precision Autophagy directed by Receptor-Regulators. Journal of Cell Science In press.

Klionsky, D. J., Eskelinen, E. L., and Deretic, V. (2014), Autophagosomes, phagosomes, autolysosomes, phagolysosomes, autophagolysosomes . . . wait, I'm confused. Autophagy 10, 549-551.

Kondapalli, C., Kazlauskaite, A., Zhang, N., Woodroof, H. I., Campbell, D. G., Gourlay, R., Burchell, L., Walden, H., Macartney, T. J., Deak, M., et al. (2012). PINK1 is activated by mitochondrial membrane potential depolarization and stimulates Parkin E3 ligase activity by phosphorylating Serine 65. Open Biol 2, 120080.

Koyano, F., Okatsu, K., Kosako, H., Tamura, Y., Go, E., Kimura, M., Kimura, Y., Tsuchiya, H., Yoshihara, H., Hirokawa, T., et al. (2014). Ubiquitin is phosphorylated by PINK1 to activate parkin. Nature 510, 162-166.

Kuang, E., Okumura, C. Y., Sheffy-Levin, S., Varsano, T., Shu, V. C., Qi, J., Niesman, I. R., Yang, H. J., Lopez-Otin, C., Yang, W. Y., et al. (2012). Regulation of ATG4B stability by RNF5 limits basal levels of autophagy and influences susceptibility to bacterial infection. PLOS Genet 8, e1003007.

Lazarou, M., Sliter, D. A., Kane, L. A., Sarraf, S. A., Wang, C., Burman, J. L., Sideris, D. P., Fogel, A. I., and Youle, R. J. (2015). The ubiquitin kinase PINK1 recruits autophagy receptors to induce mitophagy. Nature 524, 309-314.

Li, Q., Yan, J., Mao, A. P., Li, C., Ran, Y., Shu, H. B., and Wang, Y. Y. (2011). Tripartite motif 8 (TRIM8) modulates TNFalpha- and IL-Ibeta-triggered NF-kappaB activation by targeting TAK1 for K63-linked polyubiquitination. Proc Natl Acad Sci USA 108, 19341-19346.

Liang, X. H., Jackson, S., Seaman, M., Brown, K., Kempkes, B., Hibshoosh, H., and Levine, B. (1999). Induction of autophagy and inhibition of tumorigenesis by beclin 1. Nature 402, 672-676.

Liu, C. C., Lin, Y. C., Chen, Y. H., Chen, C. M., Pang, L. Y., Chen, H. A., Wu, P. R., Lin, M. Y., Jiang, S. T., Tsai, T. F., et al. (2016). Cul3-KLHL20 Ubiquitin Ligase Governs the Turnover of ULK1 and VPS34 Complexes to Control Autophagy Termination. Mol Cell 61, 84-97.

Maejima, 1., Takahashi, A., Omori, H., Kimura, T., Takabatake, Y., Saitoh, T., Yamamoto, A., Hamasaki, M., Noda, T., Isaka, Y., et al. (2013). Autophagy sequesters damaged lysosomes to control lysosomal biogenesis and kidney injury. EMBO J 32, 2336-2347.

Mandell, M. A., Jain, A., Arko-Mensah, J., Chauhan, S., Kimura, T., Dinkins, C., Silvestri, G., Munch, J., Kirchhoff, F., Simonsen, A., et al. (2014). TRIM proteins regulate autophagy and can target autophagic substrates by direct recognition. Dev Cell 30, 394-409.

Manzanillo, P. S., Ayres, J. S., Watson, R. O., Collins, A. C., Souza, G., Rae, C. S., Schneider, D. S., Nakamura, K., Shiloh, M. U., and Cox, J. S. (2013). The ubiquitin ligase parkin mediates resistance to intracellular pathogens. Nature 501, 512-516.

Manzanillo, P. S., Shiloh, M. U., Portnoy, D. A., and Cox, J. S. (2012). *Mycobacterium Tuberculosis* Activates the DNA-Dependent Cytosolic Surveillance Pathway within Macrophages. Cell host & microbe 11, 469-480.

Marshall, G. M., Bell, J. L., Koach, J., Tan, O., Kim, P., Malyukova, A., Thomas, W., Sekyere, E. O., Liu, T., Cunningham, A. M., et al. (2010). TRIM16 acts as a tumour suppressor by inhibitory effects on cytoplasmic vimentin and nuclear E2F1 in neuroblastoma cells. Oncogene 29, 6172-6183.

Martina, J. A., Chen, Y., Gucek, M., and Puertollano, R. (2012). MTORC1 functions as a transcriptional regulator of autophagy by preventing nuclear transport of TFEB. Autophagy 8, 903-914.

Medina, D. L., Di Paola, S., Peluso, 1., Armani, A., De Stefani, D., Venditti, R., Montefusco, S., Scotto-Rosato, A., Prezioso, C., Forrester, A., et al. (2015). Lysosomal calcium signalling regulates autophagy through calcineurin and TFEB. Nat Cell Biol 17, 288-299.

Mizushima, N., Yoshimori, T., and Ohsumi, Y. (2011). The role of atg proteins in autophagosome formation. Annual review of cell and developmental biology 27, 107-132.

Nabi, I. R., Shankar, J., and Dennis, J. W. (2015). The galectin lattice at a glance. J Cell Sci 128, 2213-2219.

Napolitano, G., and Ballabio, A. (2016). TFEB at a glance. J Cell Sci.

Nazio, F., Strappazzon, F., Antonioli, M., Bielli, P., Cianfanelli, V., Bordi, M., Gretzmeier, C., Dengjel, J., Piacentini, M., Fimia, G. M., et al. (2013). mTOR inhibits autophagy by controlling ULK1 ubiquitylation, self-association and function through AMBRA1 and TRAF6. Nature cell biology 15, 406-416.

Nezich, C. L., Wang, C., Fogel, A. L., and Youle, R. J. (2015). MIT/TFE transcription factors are activated during mitophagy downstream of Parkin and Atg5. J Cell Biol 210, 435-450.

Nishimura, T., Kaizuka, T., Cadwell, K., Sahani, M. H., Saitoh, T., Akira, S., Virgin, H. W., and Mizushima, N. (2013). FIP200 regulates targeting of Atg16L1 to the isolation membrane. EMBO Rep 14, 284-291.

Orvedahl, A., Sumpter, R., Jr., Xiao, G., Ng, A., Zou, Z., Tang, Y., Narimatsu, M., Gilpin, C., Sun, Q., Roth, M., et al. (2011). Image-based genome-wide siRNA screen identifies selective autophagy factors. Nature 480, 113-117.

Ostenfeld, M. S., Hoyer-Hansen, M., Bastholm, L., Fehrenbacher, N., Olsen, O. D., Groth-Pedersen, L., Puustinen, P., Kirkegaard-Sorensen, T., Nylandsted, J., Farkas, T., et al. (2008). Anti-cancer agent siramesine is a lysosomotropic detergent that induces cytoprotective autophagosome accumulation. Autophagy 4, 487-499.

Perera, R. M., Stoykova, S., Nicolay, B. N., Ross, K. N., Fitamant, J., Boukhali, M., Lengrand, J., Deshpande, V., Selig, M. K., Ferrone, C. R., et al. (2015). Transcriptional control of autophagy-lysosome function drives pancreatic cancer metabolism. Nature 524, 361-365.

Petersen, N. H., Olsen, O. D., Groth-Pedersen, L., Ellegaard, A. M., Bilgin, M., Redmer, S., Ostenfeld, M. S., Ulanet, D., Dovmark, T. H., Lonborg, A., et al. (2013). Transformation-associated changes in sphingolipid metabolism sensitize cells to lysosomal cell death induced by inhibitors of acid sphingomyelinase. Cancer Cell 24, 379-393.

Peterson, T. R., Laplante, M., Thoreen, C. C., Sancak, Y., Kang, S. A., Kuehl, W. M., Gray, N. S., and Sabatini, D. M. (2009). DEPTOR is an mTOR inhibitor frequently overexpressed in multiple myeloma cells and required for their survival. Cell 137, 873-886.

Pineda, C. T., Ramanathan, S., Fon Tacer, K., Weon, J. L., Potts, M. B., On, Y. H., White, M. A., and Potts, P. R. (2015). Degradation of AMPK by a Cancer-Specific Ubiquitin Ligase. Cell 160, 715-728.

Platta, H. W., Abrahamsen, H., Thoresen, S. B., and Stenmark, H. (2012). Nedd4-dependent lysine-11-linked polyubiquitination of the tumour suppressor Beclin 1. Biochem J 441, 399-406.

Ponpuak, M., Davis, A. S., Roberts, E. A., Delgado, M. A., Dinkins, C., Zhao, Z., Virgin, H. W.t., Kyei, G. B., Johansen, T., Vergne, I., et al. (2010). Delivery of cytosolic components by autophagic adaptor protein p62 endows autophagosomes with unique antimicrobial properties. Immunity 32, 329-341.

Ran, F. A., Hsu, P. D., Wright, J., Agarwala, V., Scott, D. A., and Zhang, F. (2013). Genome engineering using the CRISPR-Cas9 system. Nat Protoc &, 2281-2308. Randow, F., and Youle, R. J. (2014). Self and nonself: how autophagy targets mitochondria and bacteria. Cell Host Microbe 15, 403-411.

Reymond, A., Meroni, G., Fantozzi, A., Merla, G., Cairo, S., Luzi, L., Riganelli, D., Zanaria, E., Messali, S., Cainarca, S., et al. (2001). The tripartite motif family identifies cell compartments. EMBO J 20, 2140-2151.

Roczniak-Ferguson, A., Petit, C. S., Frochlich, F., Qian, S., Ky, J., Angarola, B., Walther, T. C., and Ferguson, S. M. (2012). The transcription factor TFEB links mTORC1 signaling to transcriptional control of lysosome homeostasis. Sci Signal 5, ra42.

Rogov, V., Dotsch, V., Johansen, T., and Kirkin, V. (2014). Interactions between autophagy receptors and ubiquitin-like proteins form the molecular basis for selective autophagy. Mol Cell 53, 167-178.

Rostislavleva, K., Soler, N., Ohashi, Y., Zhang, L., Pardon, E., Burke, J. E., Masson, G. R., Johnson, C., Steyaert, J., Ktistakis, N. T., et al. (2015). Structure and flexibility of the endosomal Vps34 complex reveals the basis of its function on membranes. Science 350, aac 7365.

Rubinsztein, D. C., Bento, C. F., and Deretic, V. (2015). Therapeutic targeting of autophagy in neurodegenerative and infectious diseases. J Exp Med 212, 979-990.

Russell, R. C., Tian, Y., Yuan, H., Park, H. W., Chang, Y. Y., Kim, J., Kim, H., Neufeld, T. P., Dillin, A., and Guan, K. L. (2013). ULK1 induces autophagy by phosphorylating Beclin-1 and activating VPS34 lipid kinase. Nat Cell Biol 15, 741-750.

Settembre, C., Di Malta, C., Polito, V. A., Garcia Arencibia, M., Vetrini, F., Erdin, S., Erdin, S. U., Huynh, T., Medina, D., Colella, P., et al. (2011). TFEB links autophagy to lysosomal biogenesis. Science 332, 1429-1433.

Settembre, C., Zoncu, R., Medina, D. L., Vetrini, F., Erdin, S., Huynh, T., Ferron, M., Karsenty, G., Vellard, M. C., Facchinetti, V., et al. (2012). A lysosome-to-nucleus signalling mechanism senses and regulates the lysosome via mTOR and TFEB. The EMBO journal 37, 1095-1108.

Shi, C. S., and Kehrl, J. H. (2010). TRAF6 and A20 regulate lysine 63-linked ubiquitination of Beclin-1 to control TLR4-induced autophagy. Sci Signal 3, ra42. Sica, V., Galluzzi, L., Bravo-San Pedro, J. M., Izzo, V., Maiuri, M. C., and Kroemer, G. (2015). Organelle-Specific Initiation of Autophagy. Mol Cell 59, 522-539.

Sun, Q., Fan, W., Chen, K., Ding, X., Chen, S., and Zhong, Q. (2008). Identification of Barkor as a mammalian autophagy-specific factor for Beclin 1 and class III phosphatidylinositol 3-kinase. Proc Natl Acad Sci USA 105, 19211-19216.

Sutton, S. K., Koach, J., Tan, O., Liu, B., Carter, D. R., Wilmott, J. S., Yosufi, B., Haydu, L. E., Mann, G. J., Thompson, J. F., et al. (2014). TRIM16 inhibits proliferation and migration through regulation of interferon beta 1 in melanoma cells. Oncotarget 5, 10127-10139.

Thiele, D. L., and Lipsky, P. E. (1990). Mechanism of L-leucyl-L-leucine methyl ester-mediated killing of cytotoxic lymphocytes: dependence on a lysosomal thiol protease, dipeptidyl peptidase 1, that is enriched in these cells. Proc Natl Acad Sci USA 87, 83-87.

Thurston, T. L., Wandel, M. P., von Muhlinen, N., Foeglein, A., and Randow, F. (2012). Galectin 8 targets damaged vesicles for autophagy to defend cells against bacterial invasion. Nature 482, 414-418.

von Muhlinen, N., Thurston, T., Ryzhakov, G., Bloor, S., and Randow, F. (2010). NDP52, a novel autophagy receptor for ubiquitin-decorated cytosolic bacteria. Autophagy 6, 288-289.

Wang, S. F., Tsao, C. H., Lin, Y. T., Hsu, D. K., Chiang, M. L., Lo, C. H., Chien, F. C., Chen, P., Arthur Chen, Y. M., Chen, H. Y., et al. (2014), Galectin-3 promotes HIV-1 budding via association with Alix and Gag p6. Glycobiology 24, 1022-1035.

Watson, R. O., Manzanillo, P. S., and Cox, J. S. (2012). Extracellular *M. tuberculosis* DNA Targets Bacteria for Autophagy by Activating the Host DNA-Sensing Pathway. Cell 150, 803-815.

Wauer, T., Simicek, M., Schubert, A., and Komander, D. (2015). Mechanism of phospho-ubiquitin-induced PARKIN activation. Nature 524, 370-374.

Wei, Y., An, Z., Zou, Z., Sumpter, R., Su, M., Zang, X., Sinha, S., Gaestel, M., and Levine, B. (2015). The stress-responsive kinases MAPKAPK2/MAPKAPK3 activate starvation-induced autophagy through Beclin 1 phosphorylation. eLife 4. Weidberg, H., Shvets, E., Shpilka, T., Shimron, F., Shinder, V., and Elazar, Z. (2010). LC3 and GATE-16/GABARAP subfamilies are both essential yet act differently in autophagosome biogenesis. The EMBO journal 29, 1792-1802.

Wild, P., Farhan, H., McEwan, D. G., Wagner, S., Rogov, V. V., Brady, N. R., Richter, B., Korac, J., Waidmann, O., Choudhary, C., et al. (2011). Phosphorylation of the autophagy receptor optineurin restricts *Salmonella* growth. Science 333, 228-233.

Xia, P., Wang, S., Du, Y., Zhao, Z, Shi, L., Sun, L., Huang, G., Ye, B., Li, C., Dai, Z, et al. (2013). WASH inhibits autophagy through suppression of Beclin 1 ubiquitination. EMBO J 32, 2685-2696.

Xia, P., Wang, S., Huang, G., Du, Y., Zhu, P., Li, M., and Fan, Z. (2014). RNF2 is recruited by WASH to ubiquitinate AMBRA1 leading to downregulation of autophagy. Cell Res 24, 943-958.

Xu, C., Feng, K., Zhao, X., Huang, S., Cheng, Y., Qian, L., Wang, Y., San, H., Jin, M., Chuang, T. H., et al. (2014). Regulation of autophagy by E3 ubiquitin ligase RNF216 through BECN1 ubiquitination. Autophagy 10, 2239-2250.

Zhang, T., Dong, K., Liang, W., Xu, D., Xia, H., Geng, J., Najafov, A., Lin, M., Li, Y., Han, X., et al. (2015). G-protein-coupled receptors regulate autophagy by ZBTB16-mediated ubiquitination and proteasomal degradation of Atg14L. eLife 4, e06734.

Zhao. Y., Xiong, X., and Sun, Y. (2011). DEPTOR, an mTOR inhibitor, is a physiological substrate of SCF (betaTICP) E3 ubiquitin ligase and regulates survival and autophagy. Mol Cell 44, 304-316.

REFERENCES (SUPPLEMENTARY EXPERIMENTAL PROCEDURES)

Chauban, S., Mandell, M. A., and Deretic, V. (2015). IRGM Governs the Core Autophagy Machinery to Conduct Antimicrobial Defense. Mol Cell 58, 507-521.

Fujita, N., Morita, E., Itob. T., Tanaka, A., Nakaoka, M., Osada, Y., Umemoto, T., Saitoh, T., Nakatogawa, H., Kobayashi, S., et al. (2013). Recruitment of the autophagic machinery to endosomes during infection is mediated by ubiquitin. J Cell Biol 203, 115-128.

Mandell, M. A., Jain, A., Arko-Mensah, J., Chauhan, S., Kimura, T., Dinkins, C., Silvestri, G., Munch, J., Kirchhoff, F., Simonsen, A., et al. (2014). TRIM proteins regulate autophagy and can target autophagic substrates by direct recognition. Dev Cell 30, 394-409.

McAlpine, F., Williamson, L. E., Tooze, S. A., and Chan, E. Y. (2013). Regulation of nutrient-sensitive autophagy by uncoordinated 51-like kinases 1 and 2. Autophagy 9, 361-373.

Pankiv, S., Clausen, T. H., Lamark, T., Brech, A., Bruun, J. A., Outzen, H., Overvatn, A., Bjorkoy, G., and Johansen, T. (2007). p62/SQSTM1 binds directly to Atg8/LC3 to facilitate degradation of ubiquitinated protein aggregates by autophagy. The Journal of biological chemistry 282, 24131-24145.

Ponpuak, M., Delgado, M. A., Elmaoued, R. A., and Deretic, V. (2009). Monitoring autophagy during *Mycobacterium tuberculosis* infection. Methods Enzymol 452, 345-361.

REFERENCES (TUBERCULOSIS EXPERIMENTS)

1. WHO. Tuberculosis: Fact sheet No104 Reviewed Ferbuary 2013. web site: who.int/mediacentre/factsheets/fs104/en/index. html (2013).
2. Jasmer, R. M., Nahid, P. & Hopewell, P. C. Clinical practice. Latent tuberculosis infection. *The New England journal of medicine* 347, 1860-1866 (2002).
3. Horsburgh, C. R., Jr. & Rubin, E. J. Clinical practice. Latent tuberculosis infection in the United States. *The New England journal of medicine* 364, 1441-1448 (2011).
4. Kaufmann, S. H. & Dorhoi, A. Inflammation in tuberculosis: interactions, imbalances and interventions. *Current opinion in immunology* (2013).
5. Berry, M. P., Graham, C. M., McNab, F. W., Xu, Z., Bloch, S. A., Oni, T., Wilkinson, K. A., Banchereau, R., Skinner, J., Wilkinson, R. J., Quinn, C., Blankenship, D., Dhawan, R., Cush, J. J., Mejias, A., Ramilo, O., Kon, O. M., Pascual, V., Banchereau, J., Chaussabel, D. & O'Garra, A. An interferon-inducible neutrophil-driven blood transcriptional signature in human tuberculosis. *Nature* 466, 973-977 (2010).
6. Ottenhoff, T. H., Dass, R. H., Yang, N., Zhang, M. M., Wong, H. E., Sahiratmadja, E., Khor, C. C., Alisjahbana, B., van Crevel, R., Marzuki, S., Seielstad, M., van de Vosse, E. & Hibberd, M. L. Genome-wide expression profiling identifies type I interferon response pathways in active tuberculosis. *PloS one* 7, e45839 (2012).
7. Maertzdorf, J., Ota, M., Repsilber, D., Mollenkopf, H. J., Weiner, J., Hill, P. C. & Kaufmann, S. H. Functional correlations of pathogenesis-driven gene expression signatures in tuberculosis. *PloS one* 6, e26938 (2011).
8. Teles, R. M., Graeber, T. G., Krutzik, S. R., Montoya, D., Schenk, M., Lee, D. J., Komisopoulou, E., Kelly-Scumpia, K., Chun, R., Iyer, S. S., Samo, E. N., Rea, T. H., Hewison, M., Adams, J. S., Popper, S. J., Relman, D. A., Stenger, S., Bloom, B. R., Cheng, G. & Modlin, R. L. Type I interferon suppresses type II interferon-triggered human anti-mycobacterial responses. *Science* 339, 1448-1453 (2013).
9. Novikov, A., Cardone, M., Thompson, R., Shenderov, K., Kirschman, K. D., Mayer-Barber, K. D., Myers, T. G., Rabin, R. L., Trinchieri, G., Sher, A. & Feng, C. G. *Mycobacterium tuberculosis* triggers host type I IFN signaling to regulate IL-1beta production in human macrophages. *Journal of immunology* 187, 2540-2547 (2011).
10. Master, S. S., Rampini, S. K., Davis, A. S., Keller, C., Ehlers, S., Springer, B., Timmins, G. S., Sander, P. & Deretic, V. *Mycobacterium tuberculosis* prevents inflammasome activation. *Cell Host Microbe* 3, 224-232 (2008).
11. Mattila, J. T., Ojo, O. O., Kepka-Lenhart, D., Marino, S., Kim, J. H., Eum, S. Y., Via, L. E., Barry, C. E., 3rd, Klein, E., Kirschner, D. E., Morris, S. M., Jr., Lin, P. L. & Flynn, J. L. Microenvironments in Tuberculous Granulomas Are Delineated by Distinct Populations of Macrophage Subsets and Expression of Nitric Oxide Synthase and Arginase Isoforms. *Journal of immunology* (2013).
12. Kozakiewicz, L., Phuab, J., Flynn, J. & Chan, J. The Role of B Cells and Humoral Immunity in *Mycobacterium tuberculosis* Infection. *Advances in experimental medicine and biology* 783, 225-250 (2013).

13. Rafi, W., Ribeiro-Rodrigues, R., Ellner, J. J. & Salgame, P. 'Coinfection-helminthes and tuberculosis'. *Current opinion in HIV and AIDS* 7, 239-244 (2012).
14. Kaufmann, S. H. Tuberculosis vaccines—a new kid on the block. *Nature medicine* 17, 159-160 (2011).
15. Jagannath, C., Lindsey, D. R., Dhandayuthapani, S., Xu, Y., Hunter, R. L., Jr. & Eissa, N. T. Autophagy enhances the efficacy of BCG vaccine by increasing peptide presentation in mouse dendritic cells. *Nat Med* 15, 267-276 (2009).
16. Kaufmann, S. H. Tuberculosis vaccine development: strength lies in tenacity. *Trends in immunology* 33, 373-379 (2012).
17. Danelishvili, L., Everman, J. L., McNamara, M. J. & Bermudez, L. E. Inhibition of the Plasma-Membrane-Associated Serine Protease Cathepsin G by *Mycobacterium tuberculosis* Rv3364c Suppresses Caspase-1 and Pyroptosis in Macrophages. *Frontiers in microbiology* 2, 281 (2011).
18. Khader, S. A., Guglani, L., Rangel-Moreno, J., Gopal, R., Junecko, B. A., Fountain, J. J., Martino, C., Pearl, J. E., Tighe, M., Lin, Y. Y., Slight, S., Kolls, J. K., Reinhart, T. A., Randall, T. D. & Cooper, A. M. IL-23 is required for long-term control of *Mycobacterium tuberculosis* and B cell follicle formation in the infected lung. *Journal of immmology* 187, 5402-5407 (2011).
19. Cruz, A., Fraga, A. G., Fountain, J. J., Rangel-Moreno, J., Torrado, E., Saraiva, M., Pereira, D. R., Randall, T. D., Pedrosa, J., Cooper, A. M. & Castro, A. G. Pathological role of interleukin 17 in mice subjected to repeated BCG vaccination after infection with *Mycobacterium* tuberculosis. The Journal of experimental medicine 207, 1609-1616 (2010).
20. Khader, S. A., Bell, G. K., Pearl, J. E., Fountain, J. J., Rangel-Moreno, J., Cilley, G. E., Shen, F., Eaton, S. M., Gaffen, S. L., Swain, S. L., Locksley, R. M., Haynes, L., Randall, T. D. & Cooper, A. M. IL-23 and IL-17 in the establishment of protective pulmonary CD4+ T cell responses after vaccination and during *Mycobacterium tuberculosis* challenge. *Nat Immunol* 8, 369-377 (2007).
21. Ouimet, M., Koster, S., Sakowski, E., Ramkhelawon, B., van Solingen, C., Oldebeken, S., Karunakaran, D., Portal-Celhay, C., Sheedy, F. J., Ray, T. D., Cecchini, K., Zamore, P. D., Rayner, K. J., Marcel, Y. L., Philips, J. A. & Moore, K. J. *Mycobacterium tuberculosis* induces the miR-33 locus to reprogram autophagy and host lipid metabolism. *Nat Immunol* (2016).
22. Deretic, V. Autophagy in tuberculosis. *Cold Spring Harb Perspect Med* 4, a018481 (2014).
23. Sardiello, M., Palmieri, M., di Ronza, A., Medina, D. L., Valenza, M., Gennarino, V. A., Di Malta, C., Donaudy, F., Embrione, V., Polishchuk, R. S., Banfi, S., Parenti, G., Cattaneo, E. & Ballabio, A. A gene network regulating lysosomal biogenesis and function. *Science* 325, 473-477 (2009).
24. Settembre, C., Di Malta, C., Polito, V. A., Garcia Arencibia, M., Vetrini, F., Erdin, S., Erdin, S. U., Huynh, T., Medina, D., Colella, P., Sardiello, M., Rubinsztein, D. C. & Ballabio, A. TFEB links autophagy to lysosomal biogenesis. *Science* 332, 1429-1433 (2011).
25. Settembre, C., Fraldi, A., Medina, D. L. & Ballabio, A. Signals from the lysosome: a control centre for cellular clearance and energy metabolism. *Nat Rev Mol Cell Biol* 14, 283-296 (2013).
26. Napolitano, G. & Ballabio, A. TFEB at a glance. *J Cell Sci* 129, 2475-2481 (2016).
27. Singh, V., Jamwal, S., Jain, R., Verma, P., Gokhale, R. & Rao, K. V. *Mycobacterium tuberculosis*-driven targeted recalibration of macrophage lipid homeostasis promotes the foamy phenotype. *Cell host & microbe* 12, 669-681 (2012).
28. Appelberg, R., Moreira, D., Barreira-Silva, P., Borges, M., Silva, L., Dinis-Oliveira, R. J., Resende, M., Correia-Neves, M., Jordan, M. B., Ferreira, N. C., Abrunhosa, A. J. & Silvestre, R. The Warburg effect in mycobacterial granulomas is dependent on the recruitment and activation of macrophages by interferon-gamma. *Immunology* 145, 498-507 (2015).
29. Mahon, R. N. & Hafner, R. Immune Cell Regulatory Pathways Unexplored as Host-Directed Therapeutic Targets for *Mycobacterium tuberculosis*: An Opportunity to Apply Precision Medicine Innovations to Infectious Diseases. *Clin Infect Dis* 61Suppl 3, $200-216 (2015).
30. Shi, L., Eugenin, E. A. & Subbian, S. Immunometabolism in Tuberculosis. *Front Immunol* 7, 150 (2016).
31. Kim, Y. S., Lee, H. M., Kim, J. K., Yang, C. S., Kim, T. S., Jung, M., Jin, H. S., Kim, S., Jang, J., Oh, G. T., Kim, J. M. & Jo, E. K. PPAR-alpha Activation Mediates Innate Host Defense through Induction of TFEB and Lipid Catabolism *J Immunol* (2017).
32. Singh, R., Xiang, Y., Wang, Y., Baikati, K., Cuervo, A. M., Luu, Y. K., Tang, Y., Pessin, J. E., Schwartz, G. J. & Czaja, M. J. Autophagy regulates adipose mass and differentiation in mice. *J Clin Invest* 119, 3329-3339 (2009).
33. Singh, R., Kaushik, S., Wang, Y., Xiang, Y., Novak, 1., Komatsu, M., Tanaka, K., Cuervo, A. M. & Czaja, M. J. Autophagy regulates lipid metabolism. *Nature* 458, 1131-1135 (2009).
34. Settembre, C., De Cegli, R., Mansueto, G., Saha, P. K., Vetrini, F., Visvikis, O., Huynh, T., Carissimo, A., Palmer, D., Klisch, T. J., Wollenberg, A. C., Di Bernardo, D., Chan, L., Irazoqui, J. E. & Ballabio, A. TFEB controls cellular lipid metabolism through a starvation-induced autoregulatory loop. *Nat Cell Biol* 15, 647-658 (2013).
35. Settembre, C. & Ballabio, A. Lysosome: regulator of lipid degradation pathways. *Trends Cell Biol* (2014).
36. Napolitano, G. & Ballabio, A. TFEB at a glance. *Journal of Cell Science* In press (2016).
37. Dupont, N., Chauhan, S., Arko-Mensah, J., Castillo, E. F., Masedunskas, A., Weigert, R., Robenek, H., Proikas-Cezanne, T. & Deretic, V. Neutral lipid stores and lipase PNPLAS contribute to autophagosome biogenesis. *Current biology: CB* 24, 609-620 (2014).
38. Shpilka, T., Welter, E., Borovsky, N., Amar, N., Mari, M., Reggiori, F. & Elazar, Z. Lipid droplets and their component triglycerides and steryl esters regulate autophagosome biogenesis, *EMBO J* 34, 2117-2131 (2015).
39. Deretic, V. Autophagosomes and lipid droplets: no longer just chewing the fat. *EMBO J* 34, 2111-2113 (2015).
40. Settembre, C., Zoncu, R., Medina, D. L., Vetrini, F., Erdin, S., Huynh, T., Ferron, M., Karsenty, G., Vellard, M. C., Facchinetti, V., Sabatini, D. M. & Ballabio, A. A lysosome-to-nucleus signalling mechanism senses and regulates the lysosome via mTOR and TFEB. *The EMBO journal* 31, 1095-1108 (2012).
41. Medina, D. L., Di Paola, S., Peluso, I., Armani, A., De Stefani, D., Venditti, R., Montefusco, S., Scotto-Rosato, A., Prezioso, C., Forrester, A., Settembre, C., Wang, W., Gao, Q., Xu. H., Sandri, M., Rizzuto, R., De Matteis, M.

42. Roczniak-Ferguson, A., Petit, C. S., Froehlich, F., Qian, S., Ky, J., Angarola, B., Walther, T. C. & Ferguson, S. M. The transcription factor TFEB links mTORC1 signaling to transcriptional control of lysosome homeostasis. *Sci Signal* 5, ra42 (2012).
43. Martina, J. A., Chen, Y., Gucek, M. & Puertollano, R. MTORC1 functions as a transcriptional regulator of autophagy by preventing nuclear transport of TFEB. *Autophagy* 8, 903-914 (2012).
44. Martina, J. A. & Puertollano, R. Rag GTPases mediate amino acid-dependent recruitment of TFEB and MITF to lysosomes. *J Cell Biol* 200, 475-491 (2013).
45. Chauhan, S., Kumar, S., Jain, A., Ponpuak, M., Mudd, M. H., Kimura, T., Choi, S. W., Peters, R., Mandell, M., Bruun, J. A., Johansen, T. & Deretic, V. TRIMs and Galectins Globally Cooperate and TRIM16 and Galectin-3 Co-direct Autophagy in Endomembrane Damage Homeostasis. *Dev Cell* 39, 13-27 (2016).
46. Kramnik, I. & Beamer, G. Mouse models of human TB pathology: roles in the analysis of necrosis and the development of host-directed therapies. *Semin Immunopathol* 38, 221-237 (2016).
47. O'Neill, L. A., Kishton, R. J. & Rathmell, J. A guide to immunometabolism for immunologists. *Nat Rev Immunol* 16, 553-565 (2016).
48. Deretic, V., Saitoh, T. & Akira, S. Autophagy in infection, inflammation and immunity. *Nat Rev Immunol* 13, 722-737 (2013).
49. Mihaylova, M. M. & Shaw, R. J. The AMPK signalling pathway coordinates cell growth, autophagy and metabolism. *Nature cell biology* 13, 1016-1023 (2011).
50. Saxton, R. A. & Sabatini, D. M. mTOR Signaling in Growth, Metabolism, and Disease. *Cell* 168, 960-976 (2017).
51. WHO. Global tuberculosis report 2016. http://www.who.int/tb/publications/global_report/en/(2016).
52. Malherbe, S. T., Shenai, S., Ronacher, K., Loxton, A. G., Dolganov, G., Kriel, M., Van, T., Chen, R. Y., Warwick, J., Via. L. E., Song. T., Lee, M., Schoolnik, G., Tromp, G., Alland, D., Barry, C. E., 3rd, Winter, J., Walzl, G., Catalysis, T. B. B. C., Lucas, L., Spuy, G. V., Stanley, K., Theart, L., Smith, B., Burger, N., Beltran, C. G., Maasdorp, E., Ellmann, A., Choi, H., Joh, J., Dodd, L. E., Allwood, B., Kogelenberg, C., Vorster, M. & Griffith-Richards, S. Persisting positron emission tomography lesion activity and *Mycobacterium tuberculosis* mRNA after tuberculosis cure. *Nat Med* 22, 1094-1100 (2016).
53. Jung, J. W., Choi, J. C., Shin, J. W., Kim, J. Y., Choi, B. W. & Park, I. W. Pulmonary Impairment in Tuberculosis Survivors: The Korean National Health and Nutrition Examination Survey 2008-2012. *PloS one* 10, e0141230 (2015).
54. Ralph, A. P., Kenangalem, E., Waramori, G., Pontororing, G. J., Sandjaja, Tjitra, E., Maguire, G. P., Kelly, P. M. & Anstey, N. M. High morbidity during treatment and residual pulmonary disability in pulmonary tuberculosis: under-recognised phenomena. *PloS one* 8, e80302 (2013).
55. Willcox, P. A. & Ferguson, A. D. Chronic obstructive airways disease following treated pulmonary tuberculosis. *Respir Med* 83, 195-198 (1989).
56. Ravimohan, S., Tamuhla, N., Kung, S. J., Nfanyana, K., Steenhoff, A. P., Gross, R., Weissman, D. & Bisson, G. P. Matrix Metalloproteinases in Tuberculosis-Immune Reconstitution Inflammatory Syndrome and Impaired Lung Function Among Advanced HIV/TB Co-infected Patients Initiating Antiretroviral Therapy. *EBioMedicine* 3, 100-107 (2016).
57. Hawn, T. R., Shah, J. A. & Kalman, D. New tricks for old dogs: countering antibiotic resistance in tuberculosis with host-directed therapeutics. *Immunol Rev* 264, 344-362 (2015).
58. Bruns, H., Stegelmann, F., Fabri, M., Dohner, K., van Zandbergen, G., Wagner, M., Skinner, M., Modlin, R. L. & Stenger, S. Abelson tyrosine kinase controls phagosomal acidification required for killing of *Mycobacterium tuberculosis* in homan macrophages. *J Immunol* 189, 4069-4078 (2012).
59. Pariliar, S. P., Guler, R., Khutlang, R., Lang, D. M., Hurdayal, R., Mhlanga, M. M., Suzuki, H., Marais, A. D. & Brombacher, F. Statin therapy reduces *Mycobacterium tuberculosis* infection in human macrophages and in mice by enhancing autophagy and phagosome maturation. *The Journal of infectious diseases* (2013).
60. Wallis, R. S. & Hafner, R. Advancing host-directed therapy for tuberculosis. *Nat Rev Immunol* 15, 255-263 (2015).
61. VanderVen, B. C., Huang, L., Rohde, K. H. & Russell, D. G. The Minimal Unit of Infection: *Mycobacterium tuberculosis* in the Macrophage. *Microbiol Spectr* 4(2016).
62. Gaber, T., Strehl, C. & Buttgereit, F. Metabolic regulation of inflammation. *Nat Rev Rheumatol* 13, 267-279 (2017).
63. Ma, E. H., Poffenberger, M. C., Wong, A. H. & Jones, R. O. The role of AMPK in T cell metabolism and function. *Curr Opin Immunol* 46, 45-52 (2017).
64. Kim, J., Kundu, M., Viollet, B. & Guan, K. I. AMPK and mTOR regulate autophagy through direct phosphorylation of Ulk1. *Nat Cell Biol* 13, 132-141 (2011).
65. Egan, D. F., Shackelford, D. B., Mihaylova, M. M., Gelino, S., Kohnz, R. A., Mair, W., Vasquez, D. S., Joshi, A., Gwinn, D. M., Taylor, R., Asara, J. M., Fitzpatrick, J., Dillin, A., Viollet, B., Kundu, M., Hansen, M. & Shaw, R. J. Phosphorylation of ULK1 (hATG1) by AMP-activated protein kinase connects energy sensing to mitophagy. *Science* 331, 456-461 (2011)
66. Kim, J., Kim, Y. C., Fang, C., Russell, R. C., Kim, J. H., Fan, W., Liu, R., Zhong, Q. & Guan, K. L. Differential regulation of distinct Vps34 complexes by AMPK in nutrient stress and autophagy. *Cell* 152, 290-303 (2013).
67. Nazio, F., Strappazzon, F., Antonioli, M., Bielli, P., Cianfanelli, V., Bordi, M., Gretzmeier, C., Dengjel, J., Piacentini, M., Fimia, G. M. & Cecconi, F. mTOR inhibits autophagy by controlling ULK1 ubiquitylation, self-association and function through AMBRA1 and TRAF6. *Nature cell biology* 15, 406-416 (2013).
68. Kim, Y. M., Jung, C. H., Seo, M., Kim, E. K., Park, J. M., Bae, S. S. & Kim, D. H. mTORC1 phosphorylates UVRAG to negatively regulate autophagosome and endosome maturation. *Mol Cell* 57, 207-218 (2015).
69. Settembre, C. & Ballabio, A. Lysosome: regulator of lipid degradation pathways. *Trends Cell Biol* 24, 743-750 (2014).
70. Castillo, E. F., Dekonenko, A., Arko-Mensah, J., Mandell, M. A., Dupont, N., Jiang, S., Delgado-Vargas, M., Timmins, G. S., Bhattacharya, D., Yang, H., Hutt, J., Lyons, C. R., Dobos, K. M. & Deretic, V. Autophagy protects against active tuberculosis by suppressing bacterial burden and inflammation. *Proceedings of the National Academy of Sciences of the United States of America* 109, E3168-3176 (2012).

71. Manzanillo, P. S., Ayres, J. S., Watson, R. O., Collins, A. C., Souza, G., Rae, C. S., Schneider, D. S., Nakamura, K., Shiloh, M. U. & Cox, J. S. The ubiquitin ligase parkin mediates resistance to intracellular pathogens. *Nature* 501, 512-516 (2013).
72. Watson, R. O., Manzanillo, P. S. & Cox, J. S. Extracellular *M. tuberculosis* DNA Targets Bacteria for Autophagy by Activating the Host DNA-Sensing Pathway *Cell* 150, 803-815 (2012).
73. Kimmey, J. M., Huynh, J. P., Weiss, L. A., Park, S., Kambal, A., Debnath, J., Virgin, H. W. & Stallings, C. L. Unique role for ATG5 in neutrophil-mediated immunopathology during *M. tuberculosis* infection. *Nature* 528, 565-569 (2015).
74. Biswas, D., Qureshi, O. S., Lee, W. Y., Croudace, J. E., Mara, M. & Lammas, D. A. ATP-induced autophagy is associated with rapid killing of intracellular mycobacteria within human monocytes/macrophages. *BMC Immunol* 9, 35 (2008).
75. Xu, Y., Jagannath, C., Liu, X. D., Sharafkhaneh, A., Kolodziejska, K. E. & Eissa, N. T. Toll-like receptor 4 is a sensor for autophagy associated with innate immunity. *Immunity* 27, 135-144 (2007)
76. Kumar, D., Nath, L., Kamal, M. A., Varshney, A., Jain, A., Singh, S. & Rao, K. V. Genome-wide analysis of the host intracellular network that regulates survival of *Mycobacterium* tuberculosis. Cell 140, 731-743 (2010).
77. Fabri, M., Stenger, S., Shin, D. M., Yuk, J. M., Lin, P. T., Realegeno, S., Lee, H. M., Krutzik, S. R., Schenk, M., Sieling, P. A., Teles, R., Montoya, D., Iyer, S. S., Bruns, H., Lewinsohn, D. M., Hollis, B. W., Hewison, M., Adams, J. S., Steinmeyer, A., Zugel, U., Cheng, G., Jo, E. K., Bloom, B. R. & Modlin, R. L. Vitamin D is required for IFN-gamma-mediated antimicrobial activity of human macrophages. *Science translational medicine* 3, 104ra 102 (2011).
78. Sundaramurthy, V., Barsacchi, R., Samusik, N., Marsico, G., Gilleron, J., Kalaidzidis, I., Meyenhofer, F., Bickle, M., Kalaidzidis, Y. & Zerial, M. Integration of chemical and RNAi multiparametric profiles identifies triggers of intracellular mycobacterial killing. *Cell host & microbe* 13, 129-142 (2013).
79. Ghadimi, D., de Vrese, M., Heller, K. J. & Schrezenmeir, J. Lactic acid bacteria enhance autophagic ability of mononuclear phagocytes by increasing Th1 autophagy-promoting cytokine (IFN-gamma) and nitric oxide (NO) levels and reducing Th2 autophagy-restraining cytokines (IL-4 and IL-13) in response to *Mycobacterium tuberculosis* antigen, *Int Immunopharmacol* 10, 694-706 (2010).
80. Petruccioli, E., Romagnoli, A., Corazzari, M., Coccia, E. M., Butera, O., Delogu, G., Piacentini, M., Girardi, E., Fimia, G. M. & Goletti, D. Specific T cells restore the autophagic flux inhibited by *Mycobacterium tuberculosis* in human primary macrophages. *The Journal of infectious diseases* 205, 1425-1435 (2012).
81. Juarez, E., Carranza, C., Hernandez-Sanchez, F., Leon-Contreras, J. C., Hernandez-Pando, R., Escobedo, D., Torres, M. & Sada, E. NOD2 enhances the innate response of alveolar macrophages to *Mycobacterium tuberculosis* in humans. *European journal of immunology* 42, 880-889 (2012).
82. Kim, J. J., Lee, H. M., Shin, D. M., Kim, W., Yuk, J. M., Jin, H. S., Lee, S. H., Cha, G. H., Kim, J. M., Lee, Z. W., Shin, S. J., Yoo, H., Park, Y. K., Park, J. B., Chung, J., Yoshimori, T. & Jo, E. K. Host cell autophagy activated by antibiotics is required for their effective antimycobacterial drug action. *Cell host & microbe* 11, 457-468 (2012).
83. Floto, R. A., Sarkar, S., Perlstein, E. O., Kampmann, B., Schreiber, S. L. & Rubinsztein, D. C. Small molecule enhancers of rapamycin-induced TOR inhibition promote autophagy, reduce toxicity in Huntington's disease models and enhance killing of mycobacteria by macrophages. *Autophagy* 3, 620-622 (2007).
84. Lam, K. K., Zheng, X., Forestieri, R., Balgi, A. D., Nodwell, M., Vollett, S., Anderson, H. J., Andersen, R. J., Av-Gay, Y. & Roberge, M. Nitazoxanide Stimulates Autophagy and Inhibits mTORC1 Signaling and Intracellular Proliferation of *Mycobacterium* tuberculosis. PLOS pathogens 8, e1002691 (2012).
85. Estrella, J. L., Kan-Sutton, C., Gong, X., Rajagopalan, M., Lewis, D. E., Hunter, R. L., Eissa, N. T. & Jagannath, C. A Novel in vitro Human Macrophage Model to Study the Persistence of *Mycobacterium tuberculosis* Using Vitamin D(3) and Retinoic Acid Activated THP-1 Macrophages. *Frontiers in microbiology* 2, 67 (2011).
86. Wang, J., Yang, K., Zhou, L., Minhaowu, Wu, Y., Zhu, M., Lai, X., Chen, T., Feng, L., Li, M., Huang, C., Zhong, Q. & Huang, X. MicroRNA-155 promotes autophagy to eliminate intracellular mycobacteria by targeting Rheb. *PLoS Pathog* 9, e1003697 (2013).
87. Sakowski, E. T., Koster, S., Portal Celhay, C., Park, H. S., Shrestha, E., Hetzenecker, S. E., Maurer, K., Cadwell, K. & Philips, J. A. Ubiquilin 1 Promotes IFN-gamma-Induced Xenophagy of *Mycobacterium* tuberculosis. PLOS Pathog 11, e1005076 (2015).
88. Home, D. J., Graustein, A. D., Shah, J. A., Peterson, G., Savlov, M., Steele, S., Narita, M. & Hawn, T. R. Human ULK1 Variation and Susceptibility to *Mycobacterium tuberculosis* Infection. *J Infect Dis* 214, 1260-1267 (2016).
89. Collins, A. C., Cai, H., Li, T., Franco, L. H., Li, X. D., Nair, V. R., Scharn, C. R., Stamm, C. E., Levine, B., Chen, Z. J. & Shiloh, M. U. Cyclic GMP-AMP Synthase Is an Innate Immune DNA Sensor for *Mycobacterium* tuberculosis. Cell Host Microbe 17, 820-828 (2015).
90. Franco, L. H., Nair, V. R., Scharn, C. R., Xavier, R. J., Torrealba, J. R., Shiloh, M. U. & Levine, B. The Ubiquitin Ligase Smurf1 Functions in Selective Autophagy of *Mycobacterium tuberculosis* and Anti-tuberculous Host Defense. *Cell Host Microbe* 21, 59-72 (2017).
91. Zullo, A. J. & Lee, S. Mycobacterial induction of autophagy varies by species and occurs independently of mammalian target of rapamycin inhibition. *The Journal of biological chemistry* 287, 12668-12678 (2012).
92. Kim, K. H., An, D. R., Song, J., Yoon, J. Y., Kim, H. S., Yoon, H. J., Im, H. N., Kim, J., Kim do, J., Lee, S. J., Lee, H. M., Kim, H. J., Jo, E. K., Lee, J. Y. & Suh, S. W. *Mycobacterium tuberculosis* E is protein initiates suppression of host immune responses by acetylation of DUSP16/MKP-7. *Proceedings of the National Academy of Sciences of the United States of America* 109, 7729-7734 (2012).
93. Ganaie, A. A., Lella, R. K., Solanki, R. & Sharma, C. Thermostable hexameric form of Eis (Rv2416c) protein of *M. tuberculosis* plays an important role for enhanced intracellular survival within macrophages. *PloS one* 6, e27590 (2011).
94. Shin, D. M., Jeon, B. Y., Lee, H. M., Jin, H. S., Yuk, J. M., Song, C. H., Lee, S. H., Lee, Z. W., Cho, S. N., Kim, J. M., Friedman, R. L. & Jo, E. K. *Mycobacterium tuberculosis* eis regulates autophagy, inflammation, and 95. Shui, W., Petzold, C. J., Redding, A., Liu, J., Pitcher, A., Sheu, L., Hsieh, T. Y., Keasling, J. D. & Bertozzi, C. R. Organelle membrane proteomics reveals differential influence of mycobacterial lipoglycans on macrophage phagosome maturation and autophagosome accumulation. *J Protcome Res* 10, 339-348 (2011).
96. Romagnoli, A., Etna, M. P., Giacomini, E., Pardini, M., Remoli, M. E., Corazzari, M., Falasca, L., Goletti, D., Gafa, V., Simeone, R., Delogu, G., Piacentini, M., Brosch, R., Fimia, G. M. & Coccia, E. M. ESX-1 dependent impairment of autophagie flux by *Mycobacterium tuberculosis* in human dendritic cells. *Autophagy* 8, 1357-1370 (2012).
97. Zhang, L., Zhang, H., Zhao, Y., Mao, F., Wu, J., Bai, B., Xu, Z., Jiang, Y. & Shi, C. Effects of *Mycobacterium tuberculosis* ESAT-6/CFP-10 fusion protein on the autophagy function of mouse macrophages. *DNA and cell biology* 31, 171-179 (2012).
98. Ahluwalia, P. K., Pandey, R. K., Sehajpal, P. K. & Prajapati, V. K, Perturbed microRNA Expression by *Mycobacterium tuberculosis* Promotes Macrophage Polarization Leading to Pro-survival Foam Cell. *Front Immunol* 8, 107 (2017).
99. Chauhan, S., Ahmed, Z., Bradfute, S. B., Arko-Mensah, J., Mandell, M. A., Won Choi, S., Kimura, T., Blanchet, F., Waller, A., Madd, M. H., Jiang, S., Sklar, L., Timmins, G. S., Maphis, N., Bhaskar, K., Piguet, V. & Deretic, V. Pharmaceutical screen identifies novel target processes for activation of autophagy with a broad translational potential. *Nature communications* 6, 8620 (2015).
100. Kyei, G. B., Dinkins, C., Davis, A. S., Roberts, E., Singh, S. B., Dong, C., Wu, L., Kominami, E., Ueno, T., Yamamoto, A., Federico, M., Panganiban, A., Vergne, I. & Deretic, V. Autophagy pathway intersects with HIV-1 biosynthesis and regulates viral yields in macrophages. *J Cell Biol* 186, 255-268 (2009).
101. Dinkins, C., Arko-Mensah, J. & Deretic, V. Autophagy and HIV. *Semin Cell Dev Biol* 21, 712-718 (2010).
102. Blanchet, F. P., Moris, A., Nikolic, D. S., Lehmann, M., Cardinaud, S., Stalder, R., Garcia, E., Dinkins, C., Leuba, F., Wu, L., Schwartz, O., Deretic, V. & Piguet, V. Human immunodeficiency virus-1 inhibition of immunoamphisomes in dendritic cells impairs early innate and adaptive immune responses. *Immunity* 32, 654-669 (2010).
103. Mandell, M. A., Jain, A., Arko-Mensah, J., Chauhan, S., Kimura, T., Dinkins, C., Silvestri, G., Munch, J., Kirchhoff, F., Simonsen, A., Wei, Y., Levine, B., Johansen, T. & Deretic, V. TRIM proteins regulate autophagy and can target autophagic substrates by direct recognition. *Dev Cell* 30, 394-409 (2014).
104. Mandell, M. A., Kimura, T., Jain, A., Johansen, T. & Deretic, V. TRIM proteins regulate autophagy: TRIM5 is a selective autophagy receptor mediating HIV-1 restriction. *Autophagy* 10, 2387-2388 (2014).
105. Vergne, L, Chua, J., Singh, S. B. & Deretic, V. Cell biology of *Mycobacterium tuberculosis* phagosome. *Annu Rev Cell Dev Biol* 20, 367-394 (2004).
106. Russell, D. G., Cardona, P. J., Kim, M. J., Allain, S. & Altare, F. Foamy macrophages and the progression of the human tuberculosis granuloma. *Nat Immunol* 10, 943-948 (2009).
107. Kramnik, L, Dietrich, W. F., Demant, P. & Bloom, B. R. Genetic control of resistance to experimental infection with virulent *Mycobacterium* tuberculosis. Proc Natl Acad Sci U S A 97, 8560-8565 (2000).
108. Kamath, A. B., Alt, J., Debbabi, H. & Behar, S. M. Toll-like receptor 4-defective C3H/Hel mice are not more susceptible than other C3H substrains to infection with *Mycobacterium* tuberculosis. Infect Immun 71, 4112-4118 (2003).
109. Pan, H., Yan, B. S., Rojas, M., Shebzukhov, Y. V., Zhou, H., Kobzik, L., Higgins, D. E., Daly, M. J., Bloom, B. R. & Kramnik, I. Ipri gene mediates innate immunity to tuberculosis. *Nature* 434, 767-772 (2005).
110. Yan, B. S., Pichugin, A. V., Jobe, O., Helming, L., Eruslanov, E. B., Gutierrez-Pabello, J. A., Rojas, M., Shebzukhov, Y. V., Kobzik, L. & Kramnik, I. Progression of pulmonary tuberculosis and efficiency of *bacillus* Calmette-Guerin vaccination are genetically controlled via a common sstl-mediated mechanism of innate immunity. *J Immunol* 179, 6919-6932 (2007).
111. Pichagin, A. V., Yan, B. S., Sloutsky, A., Kobzik, L. & Kramnik, I. Dominant role of the sstl locus in pathogenesis of necrotizing lung granulomas during chronic tuberculosis infection and reactivation in genetically resistant hosts. *Am J Pathol* 174, 2190-2201 (2009).
112. Dupont, N., Lacas-Gervais, S., Bertout, J., Paz, I., Freche, B., Van Nhieu, G. T., van der Goot, F. C., Sansonetti, P. J. & Lafont, F. *Shigella* phagocytic vacuolar membrane remnants participate in the cellular response to pathogen invasion and are regulated by autophagy. *Cell Host Microbe* 6, 137-149 (2009).
113. Paz, I., Sachse, M., Dupont, N., Mounier, J., Cederfur, C., Enninga, J., Leffler, H., Poirier, F., Prevost, M. C., Lafont, F. & Sansonetti, P. Galectin-3, a marker for vacuole lysis by invasive pathogens. *Cell Microbiol* 12, 530-544 (2010).
114. Creasey, E. A. & Isberg. R. R. The protein SdhA maintains the integrity of the *Legionella*-containing vacuole. *Proc Natl Acad Sci USA* 109, 3481-3486 (2012).
115. Thurston, T. L., Wandel, M. P., von Muhlinen, N., Foeglein, A. & Randow, F. Galectin 8 targets damaged vesicles for autophagy to defend cells against bacterial invasion. *Nature* 482, 414-418 (2012).
116. Fujita, N., Morita, E., Itoh, T., Tanaka, A., Nakaoka, M., Osada, Y., Umemoto, T., Saitoh, T., Nakatogawa, H., Kobayashi, S., Haraguchi, T., Guan, J. L., Iwai, K., Tokunaga, F., Saito, K., Ishibashi, K., Akira, S., Fukuda, M., Noda, T. & Yoshimori, T. Recruitment of the autophagic machinery to endosomes during infection is mediated by ubiquitin. *J Cell Biol* 203, 115-128 (2013).
117. Montespan, C., Marvin, S. A., Austin, S., Burrage, A. M., Roger, B., Rayne, F., Faure, M., Campell, E. M., Schneider, C., Reimer, R., Grunewald, K., Wiethoff, C. M. & Wodrich, H. Multi-layered control of Galectin-8 mediated autophagy during adenovirus cell entry through a conserved PPxY motif in the viral capsid. *PLOS Pathog* 13, e 1006217 (2017).
118. Staring, J., von Castelmur, E., Blomen, V. A., van den Hengel, L. G., Brockmann, M., Baggen, J., Thibaut, H. J., Nieuwenhuis, J., Janssen, H., van Kuppeveld, F. J., Perrakis, A., Carette, J. E. & Brummelkamp, T. R. PLA2G16 represents a switch between entry and clearance of Picornaviridae. *Nature* 541, 412-416 (2017).
119. Feeley, E. M., Pilla-Moffett, D. M., Zwack, E. E., Piro, A. S., Finethy, R., Kolb, J. P., Martinez, J., Brodsky, I. E. & Coers, J. Galectin-3 directs antimicrobial guanylate binding proteins to vacuoles furnished with bacterial secretion systems. *Proc Natl Acad Sci USA* 114, E1698-E1706 (2017).
120. Castellano, B. M., Thelen, A. M., Moldavski, O., Feltes, M., van der Welle, R. E., Mydock-McGrane, L., 120. Jiang, X., van Eijkeren, R. J., Davis, O. B., Louie, S. M., Perera, R. M., Covey, D. F., Nomura, D. K., Ory, D. S. & Zoncu, R. Lysosomal cholesterol activates mTORC1 via an SLC38A9-Niemann-Pick C1 signaling complex. *Science* 355, 1306-1311 (2017).

121. Zoncu, R., Bar-Peled, L., Efeyan, A., Wang, S., Sancak, Y. & Sabatini, D. M. mTORC1 senses lysosomal amino acids through an inside-out mechanism that requires the vacuolar H(+)-ATPase. *Science* 334, 678-683 (2011).

122. Jung, J., Genau, H. M. & Behrends, C, Amino Acid-Dependent mTORC1 Regulation by the Lysosomal Membrane Protein SLC38A9. *Mol Cell Biol* 35, 2479-2494 (2015).

123. Wang. S., Tsun, Z. Y., Wolfson, R. L., Shen, K., Wyant, G. A., Plovanich, M. E., Yuan, E. D., Jones, T. D., Chantranupong, L., Comb, W., Wang, T., Bar-Peled, L., Zoncu, R., Straub, C., Kim, C., Park, J., Sabatini, B. L. & Sabatini, D. M. Metabolism. Lysosomal amino acid transporter SLC38A9 signals arginine sufficiency to mTORC1. *Science* 347, 188-194 (2015).

124. Rebsamen, M., Pochini, L., Stasyk, T., de Araujo, M. E., Galluccio, M., Kandasamy, R. K., Snijder, B., Fauster, A., Rudashevskaya, E. L., Bruckner, M., Scorzoni, S., Filipek, P. A., Huber, K. V., Bigenzahn, J. W., Heinz, L. X., Kraft, C., Bennett, K. L., Indiveri, C., Huber, L. A. & Superti-Furga, G. SLC38A9 is a component of the lysosomal amino acid sensing machinery that controls mTORC1. *Nature* 519, 477-481 (2015).

125, Via, L. E., Franti, R. A., McFalone, M., Pagan-Ramos, E., Deretic, D. & Deretic, V. Effects of cytokines on mycobacterial phagosome maturation. *J Cell Sci* 111, 897-905 (1998)

126. Stappenbeck, T. S. & Virgin, H. W. Accounting for reciprocal host-microbiome interactions in experimental science. *Nature* 534, 191-199 (2016).

127. Karsli-Uzunbas, G., Guo, J. Y., Price, S., Teng, X., Laddha, S. V., Khor, S., Kalaany, N. Y., Jacks. T., Chan, C. S., Rabinowitz, J. D. & White, E. Autophagy is required for glucose homeostasis and lung tumor maintenance. *Cancer Discov* 4, 914-927 (2014).

128. Jayaraman, P., Sada-Ovalle, 1., Beladi, S., Anderson, A. C., Dardalhon, V., Hotta, C., Kuchroo, V. K. & Behar, S. M. Tim3 binding to galectin-9 stimulates antimicrobial immunity. *J Exp Med* 207, 2343-2354 (2010).

129. Gwinn, D. M., Shackelford, D. B., Egan, D. F., Mihaylova, M. M., Mery, A., Vasquez, D. S., Turk, B. E. & Shaw, R. J. AMPK phosphorylation of raptor mediates a metabolic checkpoint. *Mol Cell* 30, 214-226 (2008).

130. Zhang, C. S., Jiang, B., Li. M., Zhu, M., Peng, Y., Zhang, Y. L., Wu, Y. Q., Li, T. Y., Liang, Y., Lu, Z., Lian, G., Liu, Q., Guo, H., Yin, Z., Ye, Z., Han, J., Wu, J. W., Yin, H., Lin, S. Y. & Lin, S. C. The lysosomal v-ATPase-Ragulator complex is a common activator for AMPK and mTORC1, acting as a switch between catabolismand anabolism. *Cell Metab* 20, 526-540 (2014).

131. Zhang, C. S., Li. M., Ma, T., Zong, Y., Cui, J., Feng, J. W., Wu, Y. Q., Lin, S. Y. & Lin, S. C. Metformin Activates AMPK through the Lysosomal Pathway. *Cell Metab* 24, 521-522 (2016).

132. Mick, D. U., Rodrigues, R. B., Leib, R. D., Adams, C. M., Chien, A. S., Gygi, S. P. & Nachury, M. V. Proteomics of Primary Cilia by Proximity Labeling, *Dev Cell* 35, 497-512 (2015).

133. Hung, V., Udeshi, N. D., Lam, S. S., Loh, K. H., Cox, K. J., Pedram, K., Carr, S. A. & Ting, A. Y. Spatially resolved proteomic mapping in living cells with the engineered peroxidase APEX2. *Nat Protoc* 11, 456-475 (2016).

134. Abe, Y., Sakairi, T., Beeson, C. & Kopp, J. B. TGF-beta1 stimulates mitochondrial oxidative phosphorylation and generation of reactive oxygen species in cultured mouse podocytes, mediated in part by the mTOR pathway. *Am J Physiol Renal Physiol* 305, F1477-1490 (2013).

135. Ye, L., Varamini, B., Lamming, D. W., Sabatini, D. M. & Baur, J. A. Rapamycin has a biphasic effect on insulin sensitivity in C2C12 myotubes due to sequential disruption of mTORC1 and mTORC2. *Front Gener* 3, 177 (2012).

136. Schieke, S. M., Phillips, D., McCoy, J. P., Jr., Aponte, A. M., Shen, R. F., Balaban, R. S. & Finkel, T. The mammalian target of rapamycin (mTOR) pathway regulates mitochondrial oxygen consumption and oxidative capacity. *The Journal of biological chemistry* 281, 27643-27652 (2006).

137. Singhal, A., Jie, L., Kumar, P., Hong, G. S., Leow, M. K., Paleja, B., Tsenova, L., Kurepina, N., Chen, J., Zolezzi, F., Kreiswirth, B., Poidinger, M., Chee, C., Kaplan, G., Wang, Y. T. & De Libero, G. Metformin as adjunct antituberculosis therapy. *Sci Transl Med* 6, 263ra159 (2014).

138. Settembre, C., De Cegli, R., Mansueto, G., Saba, P. K., Vetrini, F., Visvikis, O., Huynh, T., Carissimo, A., Palmer, D., Jurgen Klisch, T., Wollenberg, A. C., Di Bernardo, D., Chan, L., Irazoqui, J. E. & Ballabio, A. TFEB controls cellular lipid metabolism through a starvation-induced autoregulatory loop. *Nature cell biology* 15, 647-658 (2013).

139. D'Avila, H., Melo, R. C., Parreira, G. G., Werneck-Barroso, E., Castro-Faria-Neto, H. C. & Bozza, P. T. *Mycobacterium bovis bacillus* Calmette-Guerin induces TLR2-mediated formation of lipid bodies: intracellular domains for eicosanoid synthesis in vivo. *J Immunol* 176, 3087-3097 (2006).

140. Daniel, J., Maamar, H., Deb, C., Sirakova, T. D. & Kolattukudy, P. E. *Mycobacterium tuberculosis* uses host triacylglycerol to accumulate lipid droplets and acquires a dormancy-like phenotype in lipid-loaded macrophages. *PLoS pathogens* 7, e1002093 (2011).

141. Steingrimsson, E., Tessarollo, L., Reid, S. W., Jenkins, N. A. & Copeland, N. G. The bHLH-Zip transcription factor Tfeb is essential for placental vascularization. *Development* 125, 4607-4616 (1998).

142. Yang, L., Li, P., Fu, S., Calay, E. S. & Hotamisligil, G. S. Defective hepatic autophagy in obesity promotes ER stress and causes insulin resistance. *Cell Metab* 11, 467-478 (2010).

143. Gutierrez, M. G., Master, S. S., Singh, S. B., Taylor, G. A., Colombo, M. I. & Deretic, V. Autophagy is a defense mechanism inhibiting BCG and *Mycobacterium tuberculosis* survival in infected macrophages. *Cell* 119, 753-766 (2004).

144. Ponpuak, M., Davis, A. S., Roberts, E. A., Delgado, M. A., Dinkins, C., Zhao, Z., Virgin, H. W.t., Kyei, G. B., Johansen, T., Vergne, 1. & Deretic, V. Delivery of cytosolic components by autophagic adaptor protein p62 endows autophagosomes with unique antimicrobial properties. *Immunity* 32, 329-341 (2010).

145. Dupont, N., Jiang, S., Pilli, M., Ornatowski, W., Bhattacharya, D. & Deretic, V. Autophagy-based unconventional secretory pathway for extracellular delivery of IL-1beta. *EMBO J* 30, 4701-4711 (2011).

146. Pilli, M., Arko-Mensah, J., Ponpuak, M., Roberts, E., Master, S., Mandell, M. A., Dupont, N., Ornatowski, W., Jiang, S., Bradfute, S. B., Bruun, J. A., Hansen, T. E., Johansen, T. & Deretic, V. TBK-1 Promotes Autophagy-Mediated Antimicrobial Defense by Controlling Autophagosome Maturation. *Immunity* 37, 223-234 (2012).

147. Kashio, Y., Nakamura, K., Abedin, M. J., Seki, M., Nishi, N., Yoshida, N., Nakamura, T. & Hirashima, M. Galectin-9 induces apoptosis through the calcium-calpain-caspase-1 pathway. *J Immunol* 170, 3631-3636 (2003).

148. Steingrimsson, E., Tessarollo, L., Pathak, B., Hou, L., Amheiter, H., Copeland, N. G. & Jenkins, N. A. Mitf and Tfe3, two members of the Mitf-Tfe family of bHLH-Zip transcription factors, have important but functionally redundant roles in osteoclast development. *Proc Natl Acad Sci USA* 99, 4477-4482 (2002).

149. Kimura, T., Jia, J., Kumar, S., Choi, S. W., Gu, Y., Mudd, M., Dupont, N., Jiang, S., Peters, R., Farzam, F., Jain, A., Lidke, K. A., Adams, C. M., Johansen, T. & Deretic, V. Dedicated SNAREs and specialized TRIM cargo receptors mediate secretory autophagy. *EMBO J* 36, 42-60 (2017).

150. Mandell, M. A., Jain, A., Kumar, S., Castleman, M. J., Anwar, T., Eskelinen, E. L., Johansen, T., Prekeris, R. & Deretic, V. TRIM17 contributes to autophagy of midbodies while actively sparing other targets from degradation. *J Cell Sci* (2016).

151. Kimura, T., Jain, A., Choi, S. W., Mandell, M. A., Schroder, K., Johansen, T. & Deretic, V. TRIM-mediated precision autophagy targets cytoplasmic regulators of innate immunity. *J Cell Biol* 210, 973-989 (2015).

152. Thiele, D. L. & Lipsky, P. E. Mechanism of L-leucyl-L-leucine methyl ester-mediated killing of cytotoxic lymphocytes: dependence on a lysosomal thiol protease, dipeptidyl peptidase I, that is enriched in these cells. *Proc Natl Acad Sci USA* 87, 83-87 (1990).

153. Aits, S., Kricker, J., Liu, B., Ellegaard, A. M., Hamalisto, S., Tvingsholm, S., Corcelle-Termeau, E., Hogh, S., Farkas, T., Holm Jonassen, A., Gromova, L., Mortensen, M. & Jaattela, M. Sensitive detection of lysosomal membrane permeabilization by lysosomal galectin puncta assay. *Autophagy* 11, 1408-1424 (2015).

154. Garin, J., Diez, R., Kieffer, S., Dermine, J. F., Duclos, S., Gagnon, E., Sadoul, R., Rondeau, C. & Desjardins, M. The phagosome proteome: insight into phagosome functions. *J Cell Biol* 152, 165-180 (2001).

155. Zhang, J. H., Chung, T. D. & Oldenburg, K. R. A Simple Statistical Parameter for Use in Evaluation and Validation of High Throughput Screening Assays. *J Biomol Screen* 4, 67-73 (1999).

156. Ponpuak, M., Delgado, M. A., Elmaoued, R. A. & Deretic, V. Monitoring autophagy during *Mycobacterium tuberculosis* infection. *Methods Enzymol* 452, 345-361 (2009).

157. Wilkinson, J. E., Burmeister, L., Brooks, S. V., Chan, C. C., Friedline, S., Harrison, D. E., Hejtmancik, J. F., Nadon, N., Strong, R., Wood, L. K., Woodward, M. A. & Miller, R. A. Rapamycin slows aging in mice. *Aging Cell* 11, 675-682 (2012).

---

The invention claimed is:

1. A method of treating a *Mycobacterium tuberculosis* infection in a patient or subject in need comprising administering to said patient or subject an effective amount of TRIM 16 protein and at least one galectin selected from the group consisting of galectin 3, galectin 8 and galectin 9.

2. The method according to claim 1 wherein said galectin is galectin 3.

3. The method according to claim 1 wherein said galectin is galectin 8.

4. The method according to claim 1 wherein said galectin is galectin 9.

5. The method according to claim 1 wherein said galectin is a mixture of galectin 3 and galectin 8.

6. The method according to claim 1 wherein said galectin is a mixture of galectin 3 and galectin 9.

7. The method according to claim 1 wherein said galectin is a mixture of galectin 8 and galectin 9.

8. The method according to claim 1 wherein said galectin is a mixture of galectin 3, galectin 8 and galectin 9.

9. The method according to claim 1 wherein said TRIM 16 protein and said galectin(s) are administered to said patient or subject by parenteral administration.

10. The method according to claim 1 wherein said TRIM 16 protein and said galectin(s) are administered to said patient or subject by intravenous administration.

11. The method according to claim 1 wherein said TRIM 16 protein and said galectin(s) are administered to said patient or subject by intramuscular administration.

12. The method according to claim 1 wherein said TRIM 16 protein and said galectin(s) are administered to said patient or subject by topical administration.

13. The method according to claim 1 wherein said TRIM 16 protein and said galectin(s) are administered to said patient or subject by transdermal administration.

14. The method according to claim 1 wherein said TRIM 16 protein is administered to said patient or subject by parenteral, transdermal or topical administration and said galectin(s) are administered to said patient or subject by parenteral, transdermal or topical administration.

15. A method of treating tuberculosis in a patient or subject in need comprising administering to a patient or subject in need an effective amount of a composition comprising an effective amount of a TRIM 16 protein and at least one galectin selected from the group consisting of galectin 3, galectin 8 and galectin 9.

16. The method according to claim 15 wherein said galectin is galectin 3.

17. The method according to claim 15 wherein said galectin is galectin 8.

18. The method according to claim 15 wherein said galectin is galectin 9.

19. The method according to claim 15 wherein said composition is administered to said patient or subject by parenteral administration.

20. The method according to claim 15 wherein said composition is administered to said patient or subject by transdermal or topical administration.

* * * * *

SEQUENCE LISTING

```
<160> NUMBER OF SEQ ID NOS: 49

<210> SEQ ID NO 1
<211> LENGTH: 551
<212> TYPE: PRT
<213> ORGANISM: Homo sapiens

<400> SEQUENCE: 1

Met Ala Glu Asn Trp Lys Asn Cys Phe Glu Glu Leu Ile Cys Pro
1               5                   10                  15

Ile Cys Leu His Val Phe Val Glu Pro Val Gln Leu Pro Cys Lys His
                20                  25                  30

Asn Phe Cys Arg Gly Cys Ile Gly Glu Ala Trp Ala Lys Asp Ser Gly
            35                  40                  45

Leu Val Arg Cys Pro Glu Cys Asn Gln Ala Tyr Asn Gln Lys Pro Gly
        50                  55                  60

Leu Glu Lys Asn Leu Lys Leu Thr Asn Ile Val Glu Lys Phe Asn Ala
65                  70                  75                  80

Leu His Val Glu Lys Pro Pro Ala Ala Leu His Cys Val Phe Cys Arg
                85                  90                  95

Arg Gly Pro Pro Leu Pro Ala Gln Lys Val Cys Leu Arg Cys Glu Ala
                100                 105                 110

Pro Cys Cys Gln Ser His Val Gln Thr His Leu Gln Gln Pro Ser Thr
            115                 120                 125

Ala Arg Gly His Leu Leu Val Glu Ala Asp Asp Val Arg Ala Trp Ser
        130                 135                 140

Cys Pro Gln His Asn Ala Tyr Arg Leu Tyr His Cys Glu Ala Glu Gln
145                 150                 155                 160

Val Ala Val Cys Gln Tyr Cys Cys Tyr Tyr Ser Gly Ala His Gln Gly
```

```
                    165                 170                 175
His Ser Val Cys Asp Val Glu Ile Arg Arg Asn Glu Ile Arg Lys Met
                180                 185                 190

Leu Met Lys Gln Gln Asp Arg Leu Glu Glu Arg Glu Gln Asp Ile Glu
            195                 200                 205

Asp Gln Leu Tyr Lys Leu Glu Ser Asp Lys Arg Leu Val Glu Glu Lys
        210                 215                 220

Val Asn Gln Leu Lys Glu Val Arg Leu Gln Tyr Glu Lys Leu His
225                 230                 235                 240

Gln Leu Leu Asp Glu Asp Leu Arg Gln Thr Val Glu Val Leu Asp Lys
                245                 250                 255

Ala Gln Ala Lys Phe Cys Ser Glu Asn Ala Ala Gln Ala Leu His Leu
                260                 265                 270

Gly Glu Arg Met Gln Glu Ala Lys Lys Leu Leu Gly Ser Leu Gln Leu
            275                 280                 285

Leu Phe Asp Lys Thr Glu Asp Val Ser Phe Met Lys Asn Thr Lys Ser
        290                 295                 300

Val Lys Ile Leu Met Asp Arg Thr Gln Thr Cys Thr Ser Ser Ser Leu
305                 310                 315                 320

Ser Pro Thr Lys Ile Gly His Leu Asn Ser Lys Leu Phe Leu Asn Glu
                325                 330                 335

Val Ala Lys Lys Glu Lys Gln Leu Arg Lys Met Leu Glu Gly Pro Phe
                340                 345                 350

Ser Thr Pro Val Pro Phe Leu Gln Ser Val Pro Leu Tyr Pro Cys Gly
            355                 360                 365

Val Ser Ser Gly Ala Glu Lys Arg Lys His Ser Thr Ala Phe Pro
370                 375                 380

Glu Ala Ser Phe Leu Glu Thr Ser Ser Gly Pro Val Gly Gly Gln Tyr
385                 390                 395                 400

Gly Ala Ala Gly Thr Ala Ser Gly Glu Gly Gln Ser Gly Gln Pro Leu
                405                 410                 415

Gly Pro Cys Ser Ser Thr Gln His Leu Val Ala Leu Pro Gly Gly Ala
            420                 425                 430

Gln Pro Val His Ser Ser Pro Val Phe Pro Pro Ser Gln Tyr Pro Asn
        435                 440                 445

Gly Ser Ala Ala Gln Gln Pro Met Leu Pro Gln Tyr Gly Gly Arg Lys
    450                 455                 460

Ile Leu Val Cys Ser Val Asp Asn Cys Tyr Cys Ser Ser Val Ala Asn
465                 470                 475                 480

His Gly Gly His Gln Pro Tyr Pro Arg Ser Gly His Phe Pro Trp Thr
                485                 490                 495

Val Pro Ser Gln Glu Tyr Ser His Pro Leu Pro Pro Thr Pro Ser Val
            500                 505                 510

Pro Gln Ser Leu Pro Ser Leu Ala Val Arg Asp Trp Leu Asp Ala Ser
        515                 520                 525

Gln Gln Pro Gly His Gln Asp Phe Tyr Arg Val Tyr Gly Gln Pro Ser
    530                 535                 540

Thr Lys His Tyr Val Thr Ser
545                 550

<210> SEQ ID NO 2
<211> LENGTH: 395
<212> TYPE: PRT
<213> ORGANISM: Homo sapiens
```

```
<400> SEQUENCE: 2

Met Ala Ser Ala Ala Ser Val Thr Ser Leu Ala Asp Glu Val Asn Cys
1               5                   10                  15

Pro Ile Cys Gln Gly Thr Leu Arg Glu Pro Val Thr Ile Asp Cys Gly
            20                  25                  30

His Asn Phe Cys Arg Ala Cys Leu Thr Arg Tyr Cys Glu Ile Pro Gly
        35                  40                  45

Pro Asp Leu Glu Glu Ser Pro Thr Cys Pro Leu Cys Lys Glu Pro Phe
    50                  55                  60

Arg Pro Gly Ser Phe Arg Pro Asn Trp Gln Leu Ala Asn Val Val Glu
65                  70                  75                  80

Asn Ile Glu Arg Leu Gln Leu Val Ser Thr Leu Gly Leu Gly Glu Glu
                85                  90                  95

Asp Val Cys Gln Glu His Gly Glu Lys Ile Tyr Phe Phe Cys Glu Asp
            100                 105                 110

Asp Glu Met Gln Leu Cys Val Val Cys Arg Glu Ala Gly Glu His Ala
        115                 120                 125

Thr His Thr Met Arg Phe Leu Glu Asp Ala Ala Pro Tyr Arg Glu
    130                 135                 140

Gln Ile His Lys Cys Leu Lys Cys Leu Arg Lys Glu Arg Glu Glu Ile
145                 150                 155                 160

Gln Glu Ile Gln Ser Arg Glu Asn Lys Arg Met Gln Val Leu Leu Thr
                165                 170                 175

Gln Val Ser Thr Lys Arg Gln Gln Val Ile Ser Glu Phe Ala His Leu
            180                 185                 190

Arg Lys Phe Leu Glu Glu Gln Gln Ser Ile Leu Leu Ala Gln Leu Glu
        195                 200                 205

Ser Gln Asp Gly Asp Ile Leu Arg Gln Arg Asp Glu Phe Asp Leu Leu
    210                 215                 220

Val Ala Gly Glu Ile Cys Arg Phe Ser Ala Leu Ile Glu Glu Leu Glu
225                 230                 235                 240

Glu Lys Asn Glu Arg Pro Ala Arg Glu Leu Leu Thr Asp Ile Arg Ser
                245                 250                 255

Thr Leu Ile Arg Cys Glu Thr Arg Lys Cys Arg Lys Pro Val Ala Val
            260                 265                 270

Ser Pro Glu Leu Gly Gln Arg Ile Arg Asp Phe Pro Gln Gln Ala Leu
        275                 280                 285

Pro Leu Gln Arg Glu Met Lys Met Phe Leu Glu Lys Leu Cys Phe Glu
    290                 295                 300

Leu Asp Tyr Glu Pro Ala His Ile Ser Leu Asp Pro Gln Thr Ser His
305                 310                 315                 320

Pro Lys Leu Leu Leu Ser Glu Asp His Gln Arg Ala Gln Phe Ser Tyr
                325                 330                 335

Lys Trp Gln Asn Ser Pro Asp Asn Pro Gln Arg Phe Asp Arg Ala Thr
            340                 345                 350

Cys Val Leu Ala His Thr Gly Ile Thr Gly Gly Arg His Thr Trp Val
        355                 360                 365

Trp Met Ala Arg Val Pro Gly Asp Ser Gly Cys Cys Gln Phe Cys Ser
    370                 375                 380

Pro Pro Ser Val Leu Gly Thr Glu Val Ala Ala
385                 390                 395
```

```
<210> SEQ ID NO 3
<211> LENGTH: 564
<212> TYPE: PRT
<213> ORGANISM: Homo sapiens

<400> SEQUENCE: 3

Met Ala Glu Leu Asp Leu Met Ala Pro Gly Pro Leu Pro Arg Ala Thr
1               5                   10                  15

Ala Gln Pro Pro Ala Pro Leu Ser Pro Asp Ser Gly Ser Pro Ser Pro
            20                  25                  30

Asp Ser Gly Ser Ala Ser Pro Val Glu Glu Asp Val Gly Ser Ser
        35                  40                  45

Glu Lys Leu Gly Arg Glu Thr Glu Glu Gln Asp Ser Asp Ser Ala Glu
    50                  55                  60

Gln Gly Asp Pro Ala Gly Glu Gly Lys Glu Val Leu Cys Asp Phe Cys
65                  70                  75                  80

Leu Asp Asp Thr Arg Arg Val Lys Ala Val Lys Ser Cys Leu Thr Cys
                85                  90                  95

Met Val Asn Tyr Cys Glu Glu His Leu Gln Pro His Gln Val Asn Ile
            100                 105                 110

Lys Leu Gln Ser His Leu Leu Thr Glu Pro Val Lys Asp His Asn Trp
        115                 120                 125

Arg Tyr Cys Pro Ala His His Ser Pro Leu Ser Ala Phe Cys Cys Pro
    130                 135                 140

Asp Gln Gln Cys Ile Cys Gln Asp Cys Cys Gln Glu His Ser Gly His
145                 150                 155                 160

Thr Ile Val Ser Leu Asp Ala Ala Arg Arg Asp Lys Glu Ala Glu Leu
                165                 170                 175

Gln Cys Thr Gln Leu Asp Leu Glu Arg Lys Leu Lys Leu Asn Glu Asn
            180                 185                 190

Ala Ile Ser Arg Leu Gln Ala Asn Gln Lys Ser Val Leu Val Ser Val
        195                 200                 205

Ser Glu Val Lys Ala Val Ala Glu Met Gln Phe Gly Glu Leu Leu Ala
    210                 215                 220

Ala Val Arg Lys Ala Gln Ala Asn Val Met Leu Phe Leu Glu Glu Lys
225                 230                 235                 240

Glu Gln Ala Ala Leu Ser Gln Ala Asn Gly Ile Lys Ala His Leu Glu
                245                 250                 255

Tyr Arg Ser Ala Glu Met Glu Lys Ser Lys Gln Glu Leu Glu Arg Met
            260                 265                 270

Ala Ala Ile Ser Asn Thr Val Gln Phe Leu Glu Glu Tyr Cys Lys Phe
        275                 280                 285

Lys Asn Thr Glu Asp Ile Thr Phe Pro Ser Val Tyr Val Gly Leu Lys
    290                 295                 300

Asp Lys Leu Ser Gly Ile Arg Lys Val Ile Thr Glu Ser Thr Val His
305                 310                 315                 320

Leu Ile Gln Leu Leu Glu Asn Tyr Lys Lys Leu Gln Glu Phe Ser
                325                 330                 335

Lys Glu Glu Glu Tyr Asp Ile Arg Thr Gln Val Ser Ala Val Val Gln
            340                 345                 350

Arg Lys Tyr Trp Thr Ser Lys Pro Glu Pro Ser Thr Arg Glu Gln Phe
        355                 360                 365

Leu Gln Tyr Ala Tyr Asp Ile Thr Phe Asp Pro Asp Thr Ala His Lys
    370                 375                 380
```

```
Tyr Leu Arg Leu Gln Glu Glu Asn Arg Lys Val Thr Asn Thr Thr Pro
385                 390                 395                 400

Trp Glu His Pro Tyr Pro Asp Leu Pro Ser Arg Phe Leu His Trp Arg
            405                 410                 415

Gln Val Leu Ser Gln Gln Ser Leu Tyr Leu His Arg Tyr Tyr Phe Glu
        420                 425                 430

Val Glu Ile Phe Gly Ala Gly Thr Tyr Val Gly Leu Thr Cys Lys Gly
            435                 440                 445

Ile Asp Arg Lys Gly Glu Arg Asn Ser Cys Ile Ser Gly Asn Asn
450                 455                 460

Phe Ser Trp Ser Leu Gln Trp Asn Gly Lys Glu Phe Thr Ala Trp Tyr
465                 470                 475                 480

Ser Asp Met Glu Thr Pro Leu Lys Ala Gly Pro Phe Arg Arg Leu Gly
            485                 490                 495

Val Tyr Ile Asp Phe Pro Gly Gly Ile Leu Ser Phe Tyr Gly Val Glu
            500                 505                 510

Tyr Asp Thr Met Thr Leu Val His Lys Phe Ala Cys Lys Phe Ser Glu
            515                 520                 525

Pro Val Tyr Ala Ala Phe Trp Leu Ser Lys Lys Glu Asn Ala Ile Arg
530                 535                 540

Ile Val Asp Leu Gly Glu Glu Pro Glu Lys Pro Ala Pro Ser Leu Val
545                 550                 555                 560

Gly Thr Ala Pro

<210> SEQ ID NO 4
<211> LENGTH: 435
<212> TYPE: PRT
<213> ORGANISM: Homo sapiens

<400> SEQUENCE: 4

Met Glu Pro Ala Pro Ala Arg Ser Pro Arg Pro Gln Gln Asp Pro Ala
1               5                   10                  15

Arg Pro Gln Glu Pro Thr Met Pro Pro Glu Thr Pro Ser Glu Gly
            20                  25                  30

Arg Gln Pro Ser Pro Ser Pro Ser Pro Thr Glu Arg Ala Pro Ala Ser
            35                  40                  45

Glu Glu Glu Phe Gln Phe Leu Arg Cys Gln Gln Cys Gln Ala Glu Ala
        50                  55                  60

Lys Cys Pro Lys Leu Leu Pro Cys Leu His Thr Leu Cys Ser Gly Cys
65                  70                  75                  80

Leu Glu Ala Ser Gly Met Gln Cys Pro Ile Cys Gln Ala Pro Trp Pro
            85                  90                  95

Leu Gly Ala Asp Thr Pro Ala Leu Asp Asn Val Phe Phe Glu Ser Leu
            100                 105                 110

Gln Arg Arg Leu Ser Val Tyr Arg Gln Ile Val Asp Ala Gln Ala Val
        115                 120                 125

Cys Thr Arg Cys Lys Glu Ser Ala Asp Phe Trp Cys Phe Glu Cys Glu
            130                 135                 140

Gln Leu Leu Cys Ala Lys Cys Phe Glu Ala His Gln Trp Phe Leu Lys
145                 150                 155                 160

His Glu Ala Arg Pro Leu Ala Glu Leu Arg Asn Gln Ser Val Arg Glu
            165                 170                 175

Phe Leu Asp Gly Thr Arg Lys Thr Asn Asn Ile Phe Cys Ser Asn Pro
            180                 185                 190
```

-continued

```
Asn His Arg Thr Pro Thr Leu Thr Ser Ile Tyr Cys Arg Gly Cys Ser
        195                 200                 205

Lys Pro Leu Cys Cys Ser Cys Ala Leu Leu Asp Ser Ser His Ser Glu
210                 215                 220

Leu Lys Cys Asp Ile Ser Ala Glu Ile Gln Gln Arg Gln Glu Glu Leu
225                 230                 235                 240

Asp Ala Met Thr Gln Ala Leu Gln Glu Gln Asp Ser Ala Phe Gly Ala
                245                 250                 255

Val His Ala Gln Met His Ala Ala Val Gly Gln Leu Gly Arg Ala Arg
            260                 265                 270

Ala Glu Thr Glu Glu Leu Ile Arg Glu Arg Val Arg Gln Val Val Ala
        275                 280                 285

His Val Arg Ala Gln Glu Arg Glu Leu Leu Glu Ala Val Asp Ala Arg
    290                 295                 300

Tyr Gln Arg Asp Tyr Glu Glu Met Ala Ser Arg Leu Gly Arg Leu Asp
305                 310                 315                 320

Ala Val Leu Gln Arg Ile Arg Thr Gly Ser Ala Leu Val Gln Arg Met
                325                 330                 335

Lys Cys Tyr Ala Ser Asp Gln Glu Val Leu Asp Met His Gly Phe Leu
            340                 345                 350

Arg Gln Ala Leu Cys Arg Leu Arg Gln Glu Glu Pro Gln Ser Leu Gln
        355                 360                 365

Ala Ala Val Arg Thr Asp Gly Phe Asp Glu Phe Lys Val Arg Leu Gln
    370                 375                 380

Asp Leu Ser Ser Cys Ile Thr Gln Gly Lys Asp Ala Ala Val Ser Lys
385                 390                 395                 400

Lys Ala Ser Pro Glu Ala Ala Ser Thr Pro Arg Asp Pro Ile Asp Val
                405                 410                 415

Asp Leu Leu Pro Pro Ala His Ala Leu Thr Gly Pro Ala Gln Ser
            420                 425                 430

Ser Thr His
        435

<210> SEQ ID NO 5
<211> LENGTH: 452
<212> TYPE: PRT
<213> ORGANISM: Homo sapiens

<400> SEQUENCE: 5

Met Asn Ser Gly Ile Leu Gln Val Phe Gln Arg Ala Leu Thr Cys Pro
1               5                   10                  15

Ile Cys Met Asn Tyr Phe Leu Asp Pro Val Thr Ile Asp Cys Gly His
                20                  25                  30

Ser Phe Cys Arg Pro Cys Leu Tyr Leu Asn Trp Gln Asp Thr Ala Val
            35                  40                  45

Leu Ala Gln Cys Ser Glu Cys Lys Lys Thr Thr Arg Gln Arg Asn Leu
        50                  55                  60

Asn Thr Asp Ile Cys Leu Lys Asn Met Ala Phe Ile Ala Arg Lys Ala
65                  70                  75                  80

Ser Leu Arg Gln Phe Leu Ser Ser Glu Glu Gln Ile Cys Gly Met His
                85                  90                  95

Arg Glu Thr Lys Lys Met Phe Cys Glu Val Asp Lys Ser Leu Leu Cys
            100                 105                 110

Leu Pro Cys Ser Asn Ser Gln Glu His Arg Asn His Ile His Cys Pro
        115                 120                 125
```

Ile Glu Trp Ala Ala Glu Arg Arg Glu Glu Leu Leu Lys Lys Met
130                 135                 140

Gln Ser Leu Trp Glu Lys Ala Cys Glu Asn Leu Arg Asn Leu Asn Met
145                 150                 155                 160

Glu Thr Thr Arg Thr Arg Cys Trp Lys Asp Tyr Val Ser Leu Arg Ile
                165                 170                 175

Glu Ala Ile Arg Ala Glu Tyr Gln Lys Met Pro Ala Phe Leu His Glu
            180                 185                 190

Glu Gln His His Leu Glu Arg Leu Arg Lys Glu Gly Glu Asp Ile
        195                 200                 205

Phe Gln Gln Leu Asn Glu Ser Lys Ala Arg Met Glu His Ser Arg Glu
210                 215                 220

Leu Leu Arg Gly Met Tyr Glu Asp Leu Lys Gln Met Cys His Lys Ala
225                 230                 235                 240

Asp Val Glu Leu Leu Gln Ala Phe Gly Asp Ile Leu His Arg Tyr Glu
                245                 250                 255

Ser Leu Leu Leu Gln Val Ser Glu Pro Val Asn Pro Glu Leu Ser Ala
            260                 265                 270

Gly Pro Ile Thr Gly Leu Leu Asp Ser Leu Ser Gly Phe Arg Val Asp
        275                 280                 285

Phe Thr Leu Gln Pro Glu Arg Ala Asn Ser His Ile Phe Leu Cys Gly
290                 295                 300

Asp Leu Arg Ser Met Asn Val Gly Cys Asp Pro Gln Asp Asp Pro Asp
305                 310                 315                 320

Ile Thr Gly Lys Ser Glu Cys Phe Leu Val Trp Gly Ala Gln Ala Phe
                325                 330                 335

Thr Ser Gly Lys Tyr Tyr Trp Glu Val His Met Gly Asp Ser Trp Asn
            340                 345                 350

Trp Ala Phe Gly Val Cys Asn Asn Tyr Trp Lys Glu Lys Arg Gln Asn
        355                 360                 365

Asp Lys Ile Asp Gly Glu Gly Leu Phe Leu Leu Gly Cys Val Lys
370                 375                 380

Glu Asp Thr His Cys Ser Leu Phe Thr Thr Ser Pro Leu Val Val Gln
385                 390                 395                 400

Tyr Val Pro Arg Pro Thr Ser Thr Val Gly Leu Phe Leu Asp Cys Glu
                405                 410                 415

Gly Arg Thr Val Ser Phe Val Asp Val Asp Gln Ser Ser Leu Ile Tyr
            420                 425                 430

Thr Ile Pro Asn Cys Ser Phe Ser Pro Pro Leu Arg Pro Ile Phe Cys
        435                 440                 445

Cys Ser His Phe
    450

<210> SEQ ID NO 6
<211> LENGTH: 735
<212> TYPE: PRT
<213> ORGANISM: Homo sapiens

<400> SEQUENCE: 6

Met Gly Glu Ser Pro Ala Ser Val Val Leu Asn Ala Ser Gly Gly Leu
1               5                   10                  15

Phe Ser Leu Lys Met Glu Thr Leu Glu Ser Glu Leu Thr Cys Pro Ile
                20                  25                  30

Cys Leu Glu Leu Phe Glu Asp Pro Leu Leu Leu Pro Cys Ala His Ser

```
                35                  40                  45
Leu Cys Phe Ser Cys Ala His Arg Ile Leu Val Ser Ser Cys Ser Ser
 50                  55                  60

Gly Glu Ser Ile Glu Pro Ile Thr Ala Phe Gln Cys Pro Thr Cys Arg
 65                  70                  75                  80

Tyr Val Ile Ser Leu Asn His Arg Gly Leu Asp Gly Leu Lys Arg Asn
                     85                  90                  95

Val Thr Leu Gln Asn Ile Ile Asp Arg Phe Gln Lys Ala Ser Val Ser
                    100                 105                 110

Gly Pro Asn Ser Pro Ser Glu Ser Arg Arg Glu Arg Thr Tyr Arg Pro
                    115                 120                 125

Thr Thr Ala Met Ser Ser Glu Arg Ile Ala Cys Gln Phe Cys Glu Gln
130                 135                 140

Asp Pro Pro Arg Asp Ala Val Lys Thr Cys Ile Thr Cys Glu Val Ser
145                 150                 155                 160

Tyr Cys Asp Arg Cys Leu Arg Ala Thr His Pro Asn Lys Lys Pro Phe
                    165                 170                 175

Thr Ser His Arg Leu Val Glu Pro Val Pro Asp Thr His Leu Arg Gly
                    180                 185                 190

Ile Thr Cys Leu Asp His Glu Asn Glu Lys Val Asn Met Tyr Cys Val
                    195                 200                 205

Ser Asp Asp Gln Leu Ile Cys Ala Leu Cys Lys Leu Val Gly Arg His
210                 215                 220

Arg Asp His Gln Val Ala Ser Leu Asn Asp Arg Phe Glu Lys Leu Lys
225                 230                 235                 240

Gln Thr Leu Glu Met Asn Leu Thr Asn Leu Val Lys Arg Asn Ser Glu
                    245                 250                 255

Leu Glu Asn Gln Met Ala Lys Leu Ile Gln Ile Cys Gln Gln Val Glu
                    260                 265                 270

Val Asn Thr Ala Met His Glu Ala Lys Leu Met Glu Glu Cys Asp Glu
                    275                 280                 285

Leu Val Glu Ile Ile Gln Gln Arg Lys Gln Met Ile Ala Val Lys Ile
290                 295                 300

Lys Glu Thr Lys Val Met Lys Leu Arg Lys Leu Ala Gln Gln Val Ala
305                 310                 315                 320

Asn Cys Arg Gln Cys Leu Glu Arg Ser Thr Val Leu Ile Asn Gln Ala
                    325                 330                 335

Glu His Ile Leu Lys Glu Asn Asp Gln Ala Arg Phe Leu Gln Ser Ala
                    340                 345                 350

Lys Asn Ile Ala Glu Arg Val Ala Met Ala Thr Ala Ser Ser Gln Val
                    355                 360                 365

Leu Ile Pro Asp Ile Asn Phe Asn Asp Ala Phe Glu Asn Phe Ala Leu
                    370                 375                 380

Asp Phe Ser Arg Glu Lys Lys Leu Leu Glu Gly Leu Asp Tyr Leu Thr
385                 390                 395                 400

Ala Pro Asn Pro Pro Ser Ile Arg Glu Glu Leu Cys Thr Ala Ser His
                    405                 410                 415

Asp Thr Ile Thr Val His Trp Ile Ser Asp Asp Glu Phe Ser Ile Ser
                    420                 425                 430

Ser Tyr Glu Leu Gln Tyr Thr Ile Phe Thr Gly Gln Ala Asn Phe Ile
                    435                 440                 445

Ser Lys Ser Trp Cys Ser Trp Gly Leu Trp Pro Glu Ile Arg Lys Cys
                    450                 455                 460
```

```
Lys Glu Ala Val Ser Cys Ser Arg Leu Ala Gly Ala Pro Arg Gly Leu
465                 470                 475                 480

Tyr Asn Ser Val Asp Ser Trp Met Ile Val Pro Asn Ile Lys Gln Asn
                485                 490                 495

His Tyr Thr Val His Gly Leu Gln Ser Gly Thr Arg Tyr Ile Phe Ile
            500                 505                 510

Val Lys Ala Ile Asn Gln Ala Gly Ser Arg Asn Ser Glu Pro Thr Arg
            515                 520                 525

Leu Lys Thr Asn Ser Gln Pro Phe Lys Leu Asp Pro Lys Met Thr His
        530                 535                 540

Lys Lys Leu Lys Ile Ser Asn Asp Gly Leu Gln Met Glu Lys Asp Glu
545                 550                 555                 560

Ser Ser Leu Lys Lys Ser His Thr Pro Glu Arg Phe Ser Gly Thr Gly
                565                 570                 575

Cys Tyr Gly Ala Ala Gly Asn Ile Phe Ile Asp Ser Gly Cys His Tyr
            580                 585                 590

Trp Glu Val Val Met Gly Ser Ser Thr Trp Tyr Ala Ile Gly Ile Ala
        595                 600                 605

Tyr Lys Ser Ala Pro Lys Asn Glu Trp Ile Gly Lys Asn Ala Ser Ser
        610                 615                 620

Trp Val Phe Ser Arg Cys Asn Ser Asn Phe Val Val Arg His Asn Asn
625                 630                 635                 640

Lys Glu Met Leu Val Asp Val Pro Pro His Leu Lys Arg Leu Gly Val
                645                 650                 655

Leu Leu Asp Tyr Asp Asn Asn Met Leu Ser Phe Tyr Asp Pro Ala Asn
            660                 665                 670

Ser Leu His Leu His Thr Phe Asp Val Thr Phe Ile Leu Pro Val Cys
        675                 680                 685

Pro Thr Phe Thr Ile Trp Asn Lys Ser Leu Met Ile Leu Ser Gly Leu
        690                 695                 700

Pro Ala Pro Asp Phe Ile Asp Tyr Pro Glu Arg Gln Glu Cys Asn Cys
705                 710                 715                 720

Arg Pro Gln Glu Ser Pro Tyr Val Ser Gly Met Lys Thr Cys His
                725                 730                 735

<210> SEQ ID NO 7
<211> LENGTH: 781
<212> TYPE: PRT
<213> ORGANISM: Homo sapiens

<400> SEQUENCE: 7

Met Ala Lys Thr Pro Ser Asp His Leu Leu Ser Thr Leu Glu Glu Leu
1               5                   10                  15

Val Pro Tyr Asp Phe Glu Lys Phe Lys Phe Lys Leu Gln Asn Thr Ser
                20                  25                  30

Val Gln Lys Glu His Ser Arg Ile Pro Arg Ser Gln Ile Gln Arg Ala
            35                  40                  45

Arg Pro Val Lys Met Ala Thr Leu Leu Val Thr Tyr Tyr Gly Glu Glu
        50                  55                  60

Tyr Ala Val Gln Leu Thr Leu Gln Val Leu Arg Ala Ile Asn Gln Arg
65                  70                  75                  80

Leu Leu Ala Glu Glu Leu His Arg Ala Ala Ile Gln Glu Tyr Ser Thr
                85                  90                  95

Gln Glu Asn Gly Thr Asp Asp Ser Ala Ala Ser Ser Ser Leu Gly Glu
```

```
                100             105                 110
Asn Lys Pro Arg Ser Leu Lys Thr Pro Asp His Pro Glu Gly Asn Glu
            115                 120                 125

Gly Asn Gly Pro Arg Pro Tyr Gly Gly Ala Ala Ser Leu Arg Cys
            130                 135             140

Ser Gln Pro Glu Ala Gly Arg Gly Leu Ser Arg Lys Pro Leu Ser Lys
145                 150                 155                 160

Arg Arg Glu Lys Ala Ser Glu Gly Leu Asp Ala Gln Gly Lys Pro Arg
                165                 170                 175

Thr Arg Ser Pro Ala Leu Pro Gly Gly Arg Ser Pro Gly Pro Cys Arg
            180                 185                 190

Ala Leu Glu Gly Gly Gln Ala Glu Val Arg Leu Arg Arg Asn Ala Ser
            195                 200                 205

Ser Ala Gly Arg Leu Gln Gly Leu Ala Gly Gly Ala Pro Gly Gln Lys
            210                 215                 220

Glu Cys Arg Pro Phe Glu Val Tyr Leu Pro Ser Gly Lys Met Arg Pro
225                 230                 235                 240

Arg Ser Leu Glu Val Thr Ile Ser Thr Gly Glu Lys Ala Pro Ala Asn
                245                 250                 255

Pro Glu Ile Leu Leu Thr Leu Glu Glu Lys Thr Ala Ala Asn Leu Asp
            260                 265                 270

Ser Ala Thr Glu Pro Arg Ala Arg Pro Thr Pro Asp Gly Gly Ala Ser
            275                 280                 285

Ala Asp Leu Lys Glu Gly Pro Gly Asn Pro Glu His Ser Val Thr Gly
            290                 295                 300

Arg Pro Pro Asp Thr Ala Ala Ser Pro Arg Cys His Ala Gln Glu Gly
305                 310                 315                 320

Asp Pro Val Asp Gly Thr Cys Val Arg Asp Ser Cys Ser Phe Pro Glu
                325                 330                 335

Ala Val Ser Gly His Pro Gln Ala Ser Gly Ser Arg Ser Pro Gly Cys
            340                 345                 350

Pro Arg Cys Gln Asp Ser His Glu Arg Lys Ser Pro Gly Ser Leu Ser
            355                 360                 365

Pro Gln Pro Leu Pro Gln Cys Lys Arg His Leu Lys Gln Val Gln Leu
            370                 375                 380

Leu Phe Cys Glu Asp His Asp Glu Pro Ile Cys Leu Ile Cys Ser Leu
385                 390                 395                 400

Ser Gln Glu His Gln Gly His Arg Val Arg Pro Ile Glu Glu Val Ala
                405                 410                 415

Leu Glu His Lys Lys Lys Ile Gln Lys Gln Leu Glu His Leu Lys Lys
            420                 425                 430

Leu Arg Lys Ser Gly Glu Glu Gln Arg Ser Tyr Gly Glu Glu Lys Ala
            435                 440                 445

Val Ser Phe Leu Lys Gln Thr Glu Ala Leu Lys Gln Arg Val Gln Arg
            450                 455                 460

Lys Leu Glu Gln Val Tyr Tyr Phe Leu Glu Gln Gln Glu His Phe Phe
465                 470                 475                 480

Val Ala Ser Leu Glu Asp Val Gly Gln Met Val Gly Gln Ile Arg Lys
                485                 490                 495

Ala Tyr Asp Thr Arg Val Ser Gln Asp Ile Ala Leu Leu Asp Ala Leu
            500                 505                 510

Ile Gly Glu Leu Glu Ala Lys Glu Cys Gln Ser Glu Trp Glu Leu Leu
            515                 520                 525
```

-continued

```
Gln Asp Ile Gly Asp Ile Leu His Arg Ala Lys Thr Val Pro Val Pro
        530                 535                 540

Glu Lys Trp Thr Thr Pro Gln Glu Ile Lys Gln Lys Ile Gln Leu Leu
545                 550                 555                 560

His Gln Lys Ser Glu Phe Val Glu Lys Ser Thr Lys Tyr Phe Ser Glu
                565                 570                 575

Thr Leu Arg Ser Glu Met Glu Met Phe Asn Val Pro Glu Leu Ile Gly
            580                 585                 590

Ala Gln Ala His Ala Val Asn Val Ile Leu Asp Ala Glu Thr Ala Tyr
            595                 600                 605

Pro Asn Leu Ile Phe Ser Asp Leu Lys Ser Val Arg Leu Gly Asn
        610                 615                 620

Lys Trp Glu Arg Leu Pro Asp Gly Pro Gln Arg Phe Asp Ser Cys Ile
625                 630                 635                 640

Ile Val Leu Gly Ser Pro Ser Phe Leu Ser Gly Arg Arg Tyr Trp Glu
                645                 650                 655

Val Glu Val Gly Asp Lys Thr Ala Trp Ile Leu Gly Ala Cys Lys Thr
            660                 665                 670

Ser Ile Ser Arg Lys Gly Asn Met Thr Leu Ser Pro Glu Asn Gly Tyr
        675                 680                 685

Trp Val Val Ile Met Met Lys Glu Asn Glu Tyr Gln Ala Ser Ser Val
    690                 695                 700

Pro Pro Thr Arg Leu Leu Ile Lys Glu Pro Pro Lys Arg Val Gly Ile
705                 710                 715                 720

Phe Val Asp Tyr Arg Val Gly Ser Ile Ser Phe Tyr Asn Val Thr Ala
                725                 730                 735

Arg Ser His Ile Tyr Thr Phe Ala Ser Cys Ser Phe Ser Gly Pro Leu
            740                 745                 750

Gln Pro Ile Phe Ser Pro Gly Thr Arg Asp Gly Gly Lys Asn Thr Ala
        755                 760                 765

Pro Leu Thr Ile Cys Pro Val Gly Gly Gln Gly Pro Asp
770                 775                 780

<210> SEQ ID NO 8
<211> LENGTH: 475
<212> TYPE: PRT
<213> ORGANISM: Homo sapiens

<400> SEQUENCE: 8

Met Ala Ser Ala Ala Arg Leu Thr Met Met Trp Glu Glu Val Thr Cys
1               5                   10                  15

Pro Ile Cys Leu Asp Pro Phe Val Glu Pro Val Ser Ile Glu Cys Gly
            20                  25                  30

His Ser Phe Cys Gln Glu Cys Ile Ser Gln Val Gly Lys Gly Gly Gly
        35                  40                  45

Ser Val Cys Pro Val Cys Arg Gln Arg Phe Leu Leu Lys Asn Leu Arg
    50                  55                  60

Pro Asn Arg Gln Leu Ala Asn Met Val Asn Asn Leu Lys Glu Ile Ser
65                  70                  75                  80

Gln Glu Ala Arg Glu Gly Thr Gln Gly Glu Arg Cys Ala Val His Gly
                85                  90                  95

Glu Arg Leu His Leu Phe Cys Glu Lys Asp Gly Lys Ala Leu Cys Trp
            100                 105                 110

Val Cys Ala Gln Ser Arg Lys His Arg Asp His Ala Met Val Pro Leu
```

115                 120                 125
Glu Glu Ala Ala Gln Glu Tyr Gln Glu Lys Leu Gln Val Ala Leu Gly
            130                 135                 140

Glu Leu Arg Arg Lys Gln Leu Ala Glu Lys Leu Glu Val Glu Ile
145                 150                 155                 160

Ala Ile Lys Arg Ala Asp Trp Lys Lys Thr Val Glu Thr Gln Lys Ser
                165                 170                 175

Arg Ile His Ala Glu Phe Val Gln Gln Lys Asn Phe Leu Val Glu Glu
            180                 185                 190

Glu Gln Arg Gln Leu Gln Glu Leu Lys Asp Glu Arg Glu Gln Leu
        195                 200                 205

Arg Ile Leu Gly Glu Lys Glu Ala Lys Leu Ala Gln Ser Gln Ala
210                 215                 220

Leu Gln Glu Leu Ile Ser Glu Leu Asp Arg Arg Cys His Ser Ser Ala
225                 230                 235                 240

Leu Glu Leu Leu Gln Glu Val Ile Ile Val Leu Glu Arg Ser Glu Ser
                245                 250                 255

Trp Asn Leu Lys Asp Leu Asp Ile Thr Ser Pro Glu Leu Arg Ser Val
            260                 265                 270

Cys His Val Pro Gly Leu Lys Lys Met Leu Arg Thr Cys Ala Val His
            275                 280                 285

Ile Thr Leu Asp Pro Asp Thr Ala Asn Pro Trp Leu Ile Leu Ser Glu
290                 295                 300

Asp Arg Arg Gln Val Arg Leu Gly Asp Thr Gln Gln Ser Ile Pro Gly
305                 310                 315                 320

Asn Glu Glu Arg Phe Asp Ser Tyr Pro Met Val Leu Gly Ala Gln His
                325                 330                 335

Phe His Ser Gly Lys His Tyr Trp Glu Val Asp Val Thr Gly Lys Glu
            340                 345                 350

Ala Trp Asp Leu Gly Val Cys Arg Asp Ser Val Arg Arg Lys Gly His
        355                 360                 365

Phe Leu Leu Ser Ser Lys Ser Gly Phe Trp Thr Ile Trp Leu Trp Asn
370                 375                 380

Lys Gln Lys Tyr Glu Ala Gly Thr Tyr Pro Gln Thr Pro Leu His Leu
385                 390                 395                 400

Gln Val Pro Pro Cys Gln Val Gly Ile Phe Leu Asp Tyr Glu Ala Gly
                405                 410                 415

Met Val Ser Phe Tyr Asn Ile Thr Asp His Gly Ser Leu Ile Tyr Ser
            420                 425                 430

Phe Ser Glu Cys Ala Phe Thr Gly Pro Leu Arg Pro Phe Phe Ser Pro
        435                 440                 445

Gly Phe Asn Asp Gly Gly Lys Asn Thr Ala Pro Leu Thr Leu Cys Pro
450                 455                 460

Leu Asn Ile Gly Ser Gln Gly Ser Thr Asp Tyr
465                 470                 475

<210> SEQ ID NO 9
<211> LENGTH: 498
<212> TYPE: PRT
<213> ORGANISM: Homo sapiens

<400> SEQUENCE: 9

Met Asp Phe Ser Val Lys Val Asp Ile Glu Lys Glu Val Thr Cys Pro
1               5                   10                  15

```
Ile Cys Leu Glu Leu Leu Thr Glu Pro Leu Ser Leu Asp Cys Gly His
            20                  25                  30

Ser Phe Cys Gln Ala Cys Ile Thr Ala Lys Ile Lys Glu Ser Val Ile
            35                  40                  45

Ile Ser Arg Gly Glu Ser Ser Cys Pro Val Cys Gln Thr Arg Phe Gln
50                      55                  60

Pro Gly Asn Leu Arg Pro Asn Arg His Leu Ala Asn Ile Val Glu Arg
65                  70                  75                  80

Val Lys Glu Val Lys Met Ser Pro Gln Glu Gly Gln Lys Arg Asp Val
                85                  90                  95

Cys Glu His His Gly Lys Lys Leu Gln Ile Phe Cys Lys Glu Asp Gly
                100                 105                 110

Lys Val Ile Cys Trp Val Cys Glu Leu Ser Gln Glu His Gln Gly His
                115                 120                 125

Gln Thr Phe Arg Ile Asn Glu Val Val Lys Glu Cys Gln Glu Lys Leu
            130                 135                 140

Gln Val Ala Leu Gln Arg Leu Ile Lys Glu Asp Gln Glu Ala Glu Lys
145                 150                 155                 160

Leu Glu Asp Asp Ile Arg Gln Glu Arg Thr Ala Trp Lys Asn Tyr Ile
                165                 170                 175

Gln Ile Glu Arg Gln Lys Ile Leu Lys Gly Phe Asn Glu Met Arg Val
            180                 185                 190

Ile Leu Asp Asn Glu Glu Gln Arg Glu Leu Gln Lys Leu Glu Glu Gly
            195                 200                 205

Glu Val Asn Val Leu Asp Asn Leu Ala Ala Ala Thr Asp Gln Leu Val
210                 215                 220

Gln Gln Arg Gln Asp Ala Ser Thr Leu Ile Ser Asp Leu Gln Arg Arg
225                 230                 235                 240

Leu Arg Gly Ser Ser Val Glu Met Leu Gln Asp Val Ile Asp Val Met
                245                 250                 255

Lys Arg Ser Glu Ser Trp Thr Leu Lys Lys Pro Lys Ser Val Ser Lys
            260                 265                 270

Lys Leu Lys Ser Val Phe Arg Val Pro Asp Leu Ser Gly Met Leu Gln
            275                 280                 285

Val Leu Lys Glu Leu Thr Asp Val Gln Tyr Tyr Trp Val Asp Val Met
290                 295                 300

Leu Asn Pro Gly Ser Ala Thr Ser Asn Val Ala Ile Ser Val Asp Gln
305                 310                 315                 320

Arg Gln Val Lys Thr Val Arg Thr Cys Thr Phe Lys Asn Ser Asn Pro
                325                 330                 335

Cys Asp Phe Ser Ala Phe Gly Val Phe Gly Cys Gln Tyr Phe Ser Ser
                340                 345                 350

Gly Lys Tyr Tyr Trp Glu Val Asp Val Ser Gly Lys Ile Ala Trp Ile
            355                 360                 365

Leu Gly Val His Ser Lys Ile Ser Ser Leu Asn Lys Arg Lys Ser Ser
            370                 375                 380

Gly Phe Ala Phe Asp Pro Ser Val Asn Tyr Ser Lys Val Tyr Ser Arg
385                 390                 395                 400

Tyr Arg Pro Gln Tyr Gly Tyr Trp Val Ile Gly Leu Gln Asn Thr Cys
                405                 410                 415

Glu Tyr Asn Ala Phe Glu Asp Ser Ser Ser Asp Pro Lys Val Leu
            420                 425                 430

Thr Leu Phe Met Ala Val Pro Pro Cys Arg Ile Gly Val Phe Leu Asp
```

```
                435                 440                 445
Tyr Glu Ala Gly Ile Val Ser Phe Phe Asn Val Thr Asn His Gly Ala
    450                 455                 460
Leu Ile Tyr Lys Phe Ser Gly Cys Arg Phe Ser Arg Pro Ala Tyr Pro
465                 470                 475                 480
Tyr Phe Asn Pro Trp Asn Cys Leu Val Pro Met Thr Val Cys Pro Pro
                485                 490                 495
Ser Ser

<210> SEQ ID NO 10
<211> LENGTH: 755
<212> TYPE: PRT
<213> ORGANISM: Homo sapiens

<400> SEQUENCE: 10

Met Val Ser His Gly Ser Ser Pro Ser Leu Leu Glu Ala Leu Ser Ser
1               5                   10                  15
Asp Phe Leu Ala Cys Lys Ile Cys Leu Glu Gln Leu Arg Ala Pro Lys
                20                  25                  30
Thr Leu Pro Cys Leu His Thr Tyr Cys Gln Asp Cys Leu Ala Gln Leu
            35                  40                  45
Ala Asp Gly Gly Arg Val Arg Cys Pro Glu Cys Arg Glu Thr Val Pro
    50                  55                  60
Val Pro Pro Glu Gly Val Ala Ser Phe Lys Thr Asn Phe Phe Val Asn
65                  70                  75                  80
Gly Leu Leu Asp Leu Val Lys Ala Arg Ala Cys Gly Asp Leu Arg Ala
                85                  90                  95
Gly Lys Pro Ala Cys Ala Leu Cys Pro Leu Val Gly Gly Thr Ser Thr
                100                 105                 110
Gly Gly Pro Ala Thr Ala Arg Cys Leu Asp Cys Ala Asp Asp Leu Cys
            115                 120                 125
Gln Ala Cys Ala Asp Gly His Arg Cys Thr Arg Gln Thr His Thr His
    130                 135                 140
Arg Val Val Asp Leu Val Gly Tyr Arg Ala Gly Trp Tyr Asp Glu Glu
145                 150                 155                 160
Ala Arg Glu Arg Gln Ala Ala Gln Cys Pro Gln His Pro Gly Glu Ala
                165                 170                 175
Leu Arg Phe Leu Cys Gln Pro Cys Ser Gln Leu Leu Cys Arg Glu Cys
                180                 185                 190
Arg Leu Asp Pro His Leu Asp His Pro Cys Leu Pro Leu Ala Glu Ala
            195                 200                 205
Val Arg Ala Arg Arg Pro Gly Leu Glu Gly Leu Leu Ala Gly Val Asp
    210                 215                 220
Asn Asn Leu Val Glu Leu Glu Ala Ala Arg Arg Val Glu Lys Glu Ala
225                 230                 235                 240
Leu Ala Arg Leu Arg Glu Gln Ala Ala Arg Val Gly Thr Gln Val Glu
                245                 250                 255
Glu Ala Ala Glu Gly Val Leu Arg Ala Leu Leu Ala Gln Lys Gln Glu
                260                 265                 270
Val Leu Gly Gln Leu Arg Ala His Val Glu Ala Ala Glu Ala Ala
            275                 280                 285
Arg Glu Arg Leu Ala Glu Leu Glu Gly Arg Glu Gln Val Ala Arg Ala
    290                 295                 300
Ala Ala Ala Phe Ala Arg Arg Val Leu Ser Leu Gly Arg Glu Ala Glu
```

```
                305                 310                 315                 320
        Ile Leu Ser Leu Glu Gly Ala Ile Ala Gln Arg Leu Arg Gln Leu Gln
                        325                 330                 335

Gly Cys Pro Trp Ala Pro Gly Pro Ala Pro Cys Leu Leu Pro Gln Leu
                        340                 345                 350

Glu Leu His Pro Gly Leu Leu Asp Lys Asn Cys His Leu Leu Arg Leu
                        355                 360                 365

Ser Phe Glu Glu Gln Pro Gln Lys Asp Gly Lys Asp Gly Ala
        370                 375                 380

Gly Thr Gln Gly Gly Glu Glu Ser Gln Ser Arg Arg Glu Asp Glu Pro
        385                 390                 395                 400

Lys Thr Glu Arg Gln Gly Gly Val Gln Pro Gln Ala Gly Asp Gly Ala
                        405                 410                 415

Gln Thr Pro Lys Glu Glu Lys Ala Gln Thr Thr Arg Glu Glu Gly Ala
                        420                 425                 430

Gln Thr Leu Glu Glu Asp Arg Ala Gln Thr Pro His Glu Asp Gly Gly
                        435                 440                 445

Pro Gln Pro His Arg Gly Gly Arg Pro Asn Lys Lys Lys Phe Lys
                        450                 455                 460

Gly Arg Leu Lys Ser Ile Ser Arg Glu Pro Ser Pro Ala Leu Gly Pro
        465                 470                 475                 480

Asn Leu Asp Gly Ser Gly Leu Leu Pro Arg Pro Ile Phe Tyr Cys Ser
                        485                 490                 495

Phe Pro Thr Arg Met Pro Gly Asp Lys Arg Ser Pro Arg Ile Thr Gly
                        500                 505                 510

Leu Cys Pro Phe Gly Pro Arg Glu Ile Leu Val Ala Asp Glu Gln Asn
                        515                 520                 525

Arg Ala Leu Lys Arg Phe Ser Leu Asn Gly Asp Tyr Lys Gly Thr Val
                        530                 535                 540

Pro Val Pro Glu Gly Cys Ser Pro Cys Ser Val Ala Ala Leu Gln Ser
        545                 550                 555                 560

Ala Val Ala Phe Ser Ala Ser Ala Arg Leu Tyr Leu Ile Asn Pro Asn
                        565                 570                 575

Gly Glu Val Gln Trp Arg Arg Ala Leu Ser Leu Ser Gln Ala Ser His
                        580                 585                 590

Ala Val Ala Ala Leu Pro Ser Gly Asp Arg Val Ala Val Ser Val Ala
                        595                 600                 605

Gly His Val Glu Val Tyr Asn Met Glu Gly Ser Leu Ala Thr Arg Phe
        610                 615                 620

Ile Pro Gly Gly Lys Ala Ser Arg Gly Leu Arg Ala Leu Val Phe Leu
        625                 630                 635                 640

Thr Thr Ser Pro Gln Gly His Phe Val Gly Ser Asp Trp Gln Gln Asn
                        645                 650                 655

Ser Val Val Ile Cys Asp Gly Leu Gly Gln Val Val Gly Glu Tyr Lys
                        660                 665                 670

Gly Pro Gly Leu His Gly Cys Gln Pro Gly Ser Val Ser Val Asp Lys
                        675                 680                 685

Lys Gly Tyr Ile Phe Leu Thr Leu Arg Glu Val Asn Lys Val Val Ile
                        690                 695                 700

Leu Asp Pro Lys Gly Ser Leu Leu Gly Asp Phe Leu Thr Ala Tyr His
        705                 710                 715                 720

Gly Leu Glu Lys Pro Arg Val Thr Thr Met Val Asp Gly Arg Tyr Leu
                        725                 730                 735
```

```
Val Val Ser Leu Ser Asn Gly Thr Ile His Ile Phe Arg Val Arg Ser
            740                 745                 750

Pro Asp Ser
        755

<210> SEQ ID NO 11
<211> LENGTH: 517
<212> TYPE: PRT
<213> ORGANISM: Homo sapiens

<400> SEQUENCE: 11

Met Ala Ala Gln Leu Leu Glu Glu Lys Leu Thr Cys Ala Ile Cys Leu
1               5                   10                  15

Gly Leu Tyr Gln Asp Pro Val Thr Leu Pro Cys Gly His Asn Phe Cys
            20                  25                  30

Gly Ala Cys Ile Arg Asp Trp Trp Asp Arg Cys Gly Lys Ala Cys Pro
        35                  40                  45

Glu Cys Arg Glu Pro Phe Pro Asp Gly Ala Glu Leu Arg Arg Asn Val
    50                  55                  60

Ala Leu Ser Gly Val Leu Glu Val Val Arg Ala Gly Pro Ala Arg Asp
65                  70                  75                  80

Pro Gly Pro Asp Pro Gly Pro Asp Pro Ala Ala Arg Cys Pro
                85                  90                  95

Arg His Gly Arg Pro Leu Glu Leu Phe Cys Arg Thr Glu Gly Arg Cys
                100                 105                 110

Val Cys Ser Val Cys Thr Val Arg Glu Cys Arg Leu His Glu Arg Ala
            115                 120                 125

Leu Leu Asp Ala Glu Arg Leu Lys Arg Glu Ala Gln Leu Arg Ala Ser
        130                 135                 140

Leu Glu Val Thr Gln Gln Gln Ala Thr Gln Ala Glu Gly Gln Leu Leu
145                 150                 155                 160

Glu Leu Arg Lys Gln Ser Ser Gln Ile Gln Asn Ser Ala Cys Ile Leu
                165                 170                 175

Ala Ser Trp Val Ser Gly Lys Phe Ser Ser Leu Leu Gln Ala Leu Glu
            180                 185                 190

Ile Gln His Thr Thr Ala Leu Arg Ser Ile Glu Val Ala Lys Thr Gln
        195                 200                 205

Ala Leu Ala Gln Ala Arg Asp Glu Glu Gln Arg Leu Arg Val His Leu
    210                 215                 220

Glu Ala Val Ala Arg His Gly Cys Arg Ile Arg Glu Leu Leu Glu Gln
225                 230                 235                 240

Val Asp Glu Gln Thr Phe Leu Gln Glu Ser Gln Leu Leu Gln Pro Pro
                245                 250                 255

Gly Pro Leu Gly Pro Leu Thr Pro Leu Gln Trp Asp Glu Asp Gln Gln
            260                 265                 270

Leu Gly Asp Leu Lys Gln Leu Leu Ser Arg Leu Cys Gly Leu Leu Leu
        275                 280                 285

Glu Glu Gly Ser His Pro Gly Ala Pro Ala Lys Pro Val Asp Leu Ala
    290                 295                 300

Pro Val Glu Ala Pro Gly Pro Leu Ala Pro Val Pro Ser Thr Val Cys
305                 310                 315                 320

Pro Leu Arg Arg Lys Leu Trp Gln Asn Tyr Arg Asn Leu Thr Phe Asp
                325                 330                 335

Pro Val Ser Ala Asn Arg His Phe Tyr Leu Ser Arg Gln Asp Gln Gln
```

-continued

```
                340                 345                 350
Val Lys His Cys Arg Gln Ser Arg Gly Pro Gly Gly Pro Gly Ser Phe
            355                 360                 365

Glu Leu Trp Gln Val Gln Cys Ala Gln Ser Phe Gln Ala Gly His His
        370                 375                 380

Tyr Trp Glu Val Arg Ala Ser Asp His Ser Val Thr Leu Gly Val Ser
385                 390                 395                 400

Tyr Pro Gln Leu Pro Arg Cys Arg Leu Gly Pro His Thr Asp Asn Ile
                405                 410                 415

Gly Arg Gly Pro Cys Ser Trp Gly Leu Cys Val Gln Glu Asp Ser Leu
            420                 425                 430

Gln Ala Trp His Asn Gly Glu Ala Gln Arg Leu Pro Gly Val Ser Gly
        435                 440                 445

Arg Leu Leu Gly Met Asp Leu Asp Leu Ala Ser Gly Cys Leu Thr Phe
    450                 455                 460

Tyr Ser Leu Glu Pro Gln Thr Gln Pro Leu Tyr Thr Phe His Ala Leu
465                 470                 475                 480

Phe Asn Gln Pro Leu Thr Pro Val Phe Trp Leu Leu Glu Gly Arg Thr
                485                 490                 495

Leu Thr Leu Cys His Gln Pro Gly Ala Val Phe Pro Leu Gly Pro Gln
            500                 505                 510

Glu Glu Val Leu Ser
            515

<210> SEQ ID NO 12
<211> LENGTH: 250
<212> TYPE: PRT
<213> ORGANISM: Homo sapiens

<400> SEQUENCE: 12

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
                20                  25                  30

Ala Gly Gly Tyr Pro Gly Ala Ser Tyr Pro Gly Ala Tyr Pro Gly Gln
            35                  40                  45

Ala Pro Pro Gly Ala Tyr Pro Gly Gln Ala Pro Pro Gly Ala Tyr Pro
        50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190
```

```
Glu Ser Gly Lys Pro Phe Lys Ile Gln Val Leu Val Glu Pro Asp His
            195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

<210> SEQ ID NO 13
<211> LENGTH: 359
<212> TYPE: PRT
<213> ORGANISM: Homo sapiens

<400> SEQUENCE: 13

Met Met Leu Ser Leu Asn Asn Leu Gln Asn Ile Ile Tyr Asn Pro Val
1               5                   10                  15

Ile Pro Phe Val Gly Thr Ile Pro Asp Gln Leu Asp Pro Gly Thr Leu
            20                  25                  30

Ile Val Ile Arg Gly His Val Pro Ser Asp Ala Asp Arg Phe Gln Val
            35                  40                  45

Asp Leu Gln Asn Gly Ser Ser Met Lys Pro Arg Ala Asp Val Ala Phe
    50                  55                  60

His Phe Asn Pro Arg Phe Lys Arg Ala Gly Cys Ile Val Cys Asn Thr
65                  70                  75                  80

Leu Ile Asn Glu Lys Trp Gly Arg Glu Glu Ile Thr Tyr Asp Thr Pro
                85                  90                  95

Phe Lys Arg Glu Lys Ser Phe Glu Ile Val Ile Met Val Leu Lys Asp
                100                 105                 110

Lys Phe Gln Val Ala Val Asn Gly Lys His Thr Leu Leu Tyr Gly His
            115                 120                 125

Arg Ile Gly Pro Glu Lys Ile Asp Thr Leu Gly Ile Tyr Gly Lys Val
            130                 135                 140

Asn Ile His Ser Ile Gly Phe Ser Phe Ser Ser Asp Leu Gln Ser Thr
145                 150                 155                 160

Gln Ala Ser Ser Leu Glu Leu Thr Glu Ile Ser Arg Glu Asn Val Pro
                165                 170                 175

Lys Ser Gly Thr Pro Gln Leu Pro Ser Asn Arg Gly Gly Asp Ile Ser
            180                 185                 190

Lys Ile Ala Pro Arg Thr Val Tyr Thr Lys Ser Lys Asp Ser Thr Val
            195                 200                 205

Asn His Thr Leu Thr Cys Thr Lys Ile Pro Pro Met Asn Tyr Val Ser
    210                 215                 220

Lys Arg Leu Pro Phe Ala Ala Arg Leu Asn Thr Pro Met Gly Pro Gly
225                 230                 235                 240

Arg Thr Val Val Lys Gly Glu Val Asn Ala Asn Ala Lys Ser Phe
                245                 250                 255

Asn Val Asp Leu Leu Ala Gly Lys Ser Lys Asp Ile Ala Leu His Leu
            260                 265                 270

Asn Pro Arg Leu Asn Ile Lys Ala Phe Val Arg Asn Ser Phe Leu Gln
        275                 280                 285

Glu Ser Trp Gly Glu Glu Arg Asn Ile Thr Ser Phe Pro Phe Ser
    290                 295                 300

Pro Gly Met Tyr Phe Glu Met Ile Ile Tyr Cys Asp Val Arg Glu Phe
305                 310                 315                 320
```

-continued

Lys Val Ala Val Asn Gly Val His Ser Leu Glu Tyr Lys His Arg Phe
                325                 330                 335

Lys Glu Leu Ser Ser Ile Asp Thr Leu Glu Ile Asn Gly Asp Ile His
                340                 345                 350

Leu Leu Glu Val Arg Ser Trp
        355

<210> SEQ ID NO 14
<211> LENGTH: 355
<212> TYPE: PRT
<213> ORGANISM: Homo sapiens

<400> SEQUENCE: 14

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Phe Gln Ile Thr
                20                  25                  30

Val Asn Gly Ala Val Leu Ser Ser Gly Thr Arg Phe Ala Val Asp
                35                  40                  45

Phe Gln Thr Gly Phe Ser Gly Asn Asp Ile Ala Phe His Phe Asn Pro
        50                  55                  60

Arg Phe Glu Asp Gly Gly Tyr Val Val Cys Asn Thr Arg Gln Lys Gly
65                  70                  75                  80

Arg Trp Gly Pro Glu Glu Arg Lys Met His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ser Leu Phe Val Gln Tyr Phe His Arg Val Pro Phe
            115                 120                 125

His Arg Val Asp Thr Ile Ser Val Asn Gly Ser Val Gln Leu Ser Tyr
        130                 135                 140

Ile Ser Phe Gln Asn Pro Arg Thr Val Pro Val Gln Pro Ala Phe Ser
145                 150                 155                 160

Thr Val Pro Phe Ser Gln Pro Val Cys Phe Pro Pro Arg Pro Arg Gly
                165                 170                 175

Arg Arg Gln Lys Pro Pro Ser Val Arg Pro Ala Asn Pro Ala Pro Ile
            180                 185                 190

Thr Gln Thr Val Ile His Thr Val Gln Ser Ala Ser Gly Gln Met Phe
        195                 200                 205

Ser Thr Pro Ala Ile Pro Pro Met Met Tyr Pro His Pro Ala Tyr Pro
    210                 215                 220

Met Pro Phe Ile Thr Thr Ile Pro Gly Gly Leu Tyr Pro Ser Lys Ser
225                 230                 235                 240

Ile Ile Leu Ser Gly Thr Val Leu Pro Ser Ala Gln Arg Phe His Ile
                245                 250                 255

Asn Leu Cys Ser Gly Ser His Ile Ala Phe His Met Asn Pro Arg Phe
            260                 265                 270

Asp Glu Asn Ala Val Val Arg Asn Thr Gln Ile Asn Asn Ser Trp Gly
        275                 280                 285

Ser Glu Glu Arg Ser Leu Pro Arg Lys Met Pro Phe Val Arg Gly Gln
    290                 295                 300

Ser Phe Ser Val Trp Ile Leu Cys Glu Ala His Cys Leu Lys Val Ala
305                 310                 315                 320

Val Asp Gly Gln His Val Phe Glu Tyr Tyr His Arg Leu Arg Asn Leu

```
                        325                 330                 335
Pro Thr Ile Asn Lys Leu Glu Val Gly Gly Asp Ile Gln Leu Thr His
                340                 345                 350
Val Gln Thr
        355

<210> SEQ ID NO 15
<211> LENGTH: 336
<212> TYPE: PRT
<213> ORGANISM: Homo sapiens

<400> SEQUENCE: 15

Met Ser Gln Pro Ser Gly Gly Arg Ala Pro Gly Thr Arg Ile Tyr Ser
1               5                   10                  15

Trp Ser Cys Pro Thr Val Met Ser Pro Gly Glu Lys Leu Asp Pro Ile
                20                  25                  30

Pro Asp Ser Phe Ile Leu Gln Pro Val Phe His Pro Val Val Pro
            35                  40                  45

Tyr Val Thr Thr Ile Phe Gly Leu His Ala Gly Lys Met Val Met
        50                  55                  60

Leu Gln Gly Val Val Pro Leu Asp Ala His Arg Phe Gln Val Asp Phe
65                  70                  75                  80

Gln Cys Gly Cys Ser Leu Cys Pro Arg Pro Asp Ile Ala Phe His Phe
                85                  90                  95

Asn Pro Arg Phe His Thr Thr Lys Pro His Val Ile Cys Asn Thr Leu
            100                 105                 110

His Gly Gly Arg Trp Gln Arg Glu Ala Arg Trp Pro His Leu Ala Leu
            115                 120                 125

Arg Arg Gly Ser Ser Phe Leu Ile Leu Phe Leu Phe Gly Asn Glu Glu
130                 135                 140

Val Lys Val Ser Val Asn Gly Gln His Phe Leu His Phe Arg Tyr Arg
145                 150                 155                 160

Leu Pro Leu Ser His Val Asp Thr Leu Gly Ile Phe Gly Asp Ile Leu
                165                 170                 175

Val Glu Ala Val Gly Phe Leu Asn Ile Asn Pro Phe Val Glu Gly Ser
            180                 185                 190

Arg Glu Tyr Pro Ala Gly His Pro Phe Leu Leu Met Ser Pro Arg Leu
        195                 200                 205

Glu Val Pro Cys Ser His Ala Leu Pro Gln Gly Leu Ser Pro Gly Gln
210                 215                 220

Val Ile Ile Val Arg Gly Leu Val Leu Gln Glu Pro Lys His Phe Thr
225                 230                 235                 240

Val Ser Leu Arg Asp Gln Ala Ala His Ala Pro Val Thr Leu Arg Ala
                245                 250                 255

Ser Phe Ala Asp Arg Thr Leu Ala Trp Ile Ser Arg Trp Gly Gln Lys
            260                 265                 270

Lys Leu Ile Ser Ala Pro Phe Leu Phe Tyr Pro Gln Arg Phe Phe Glu
        275                 280                 285

Val Leu Leu Leu Phe Gln Glu Gly Gly Leu Lys Leu Ala Leu Asn Gly
    290                 295                 300

Gln Gly Leu Gly Ala Thr Ser Met Asn Gln Gln Ala Leu Glu Gln Leu
305                 310                 315                 320

Arg Glu Leu Arg Ile Ser Gly Ser Val Gln Leu Tyr Cys Val His Ser
                325                 330                 335
```

```
<210> SEQ ID NO 16
<211> LENGTH: 19
<212> TYPE: RNA
<213> ORGANISM: Homo sapiens

<400> SEQUENCE: 16
gcaagauucu cgucuguuc                                                  19

<210> SEQ ID NO 17
<211> LENGTH: 19
<212> TYPE: RNA
<213> ORGANISM: Homo sapiens

<400> SEQUENCE: 17
ggaaugaaau ccggaagau                                                  19

<210> SEQ ID NO 18
<211> LENGTH: 19
<212> TYPE: RNA
<213> ORGANISM: Homo Sapiens

<400> SEQUENCE: 18
ggacaacugu uacuguucu                                                  19

<210> SEQ ID NO 19
<211> LENGTH: 19
<212> TYPE: RNA
<213> ORGANISM: Homo sapiens

<400> SEQUENCE: 19
gaacaccaag ucugugaaa                                                  19

<210> SEQ ID NO 20
<211> LENGTH: 19
<212> TYPE: RNA
<213> ORGANISM: Homo sapiens

<400> SEQUENCE: 20
gagaggagau ucaagaaau                                                  19

<210> SEQ ID NO 21
<211> LENGTH: 19
<212> TYPE: RNA
<213> ORGANISM: Homo sapiens

<400> SEQUENCE: 21
cagaagcacu cuaauaaga                                                  19

<210> SEQ ID NO 22
<211> LENGTH: 19
<212> TYPE: RNA
<213> ORGANISM: Homo sapiens

<400> SEQUENCE: 22
gggaacaaau ccauaagug                                                  19

<210> SEQ ID NO 23
<211> LENGTH: 19
<212> TYPE: RNA
<213> ORGANISM: Homo sapiens

<400> SEQUENCE: 23
gcuuugaguu ggacuauga                                                  19
```

```
<210> SEQ ID NO 24
<211> LENGTH: 19
<212> TYPE: RNA
<213> ORGANISM: Homo sapiens

<400> SEQUENCE: 24
gaccacaacu ggcgauacu                                              19

<210> SEQ ID NO 25
<211> LENGTH: 19
<212> TYPE: RNA
<213> ORGANISM: Homo sapiens

<400> SEQUENCE: 25
gcagugaagu ccugucuaa                                              19

<210> SEQ ID NO 26
<211> LENGTH: 19
<212> TYPE: RNA
<213> ORGANISM: Homo sapiens

<400> SEQUENCE: 26
ggaacaggac agcgacucu                                              19

<210> SEQ ID NO 27
<211> LENGTH: 19
<212> TYPE: RNA
<213> ORGANISM: Homo sapiens

<400> SEQUENCE: 27
ccgcaucagg ugaacauca                                              19

<210> SEQ ID NO 28
<211> LENGTH: 19
<212> TYPE: RNA
<213> ORGANISM: Homo sapiens

<400> SEQUENCE: 28
gaggaguacu gcaaguuua                                              19

<210> SEQ ID NO 29
<211> LENGTH: 19
<212> TYPE: RNA
<213> ORGANISM: Homo sapiens

<400> SEQUENCE: 29
gcaaaggcau cgaccagaa                                              19

<210> SEQ ID NO 30
<211> LENGTH: 19
<212> TYPE: RNA
<213> ORGANISM: Homo sapiens

<400> SEQUENCE: 30
gcaaaguuau cacggaauc                                              19

<210> SEQ ID NO 31
<211> LENGTH: 19
<212> TYPE: RNA
<213> ORGANISM: Homo sapiens

<400> SEQUENCE: 31
```

```
aggauaaacu cucgggcau                                                19

<210> SEQ ID NO 32
<211> LENGTH: 19
<212> TYPE: RNA
<213> ORGANISM: Homo sapiens

<400> SEQUENCE: 32
ggggaaagau gcagcugua                                                19

<210> SEQ ID NO 33
<211> LENGTH: 19
<212> TYPE: RNA
<213> ORGANISM: Homo sapiens

<400> SEQUENCE: 33
gcaaagaguc ggccgacuu                                                19

<210> SEQ ID NO 34
<211> LENGTH: 19
<212> TYPE: RNA
<213> ORGANISM: Homo sapiens

<400> SEQUENCE: 34
gcgcuggugc agaggauga                                                19

<210> SEQ ID NO 35
<211> LENGTH: 19
<212> TYPE: RNA
<213> ORGANISM: Homo sapiens

<400> SEQUENCE: 35
ccgauggcuu cgacgaguu                                                19

<210> SEQ ID NO 36
<211> LENGTH: 19
<212> TYPE: RNA
<213> ORGANISM: Homo sapiens

<400> SEQUENCE: 36
ggaaggauua ugugaguuu                                                19

<210> SEQ ID NO 37
<211> LENGTH: 19
<212> TYPE: RNA
<213> ORGANISM: Homo sapiens

<400> SEQUENCE: 37
acuuggaaag gcugcgaaa                                                19

<210> SEQ ID NO 38
<211> LENGTH: 19
<212> TYPE: RNA
<213> ORGANISM: Homo sapiens

<400> SEQUENCE: 38
aagcagaugu ggagcuacu                                                19

<210> SEQ ID NO 39
<211> LENGTH: 19
<212> TYPE: RNA
<213> ORGANISM: Homo sapiens

<400> SEQUENCE: 39
```
ggacagccuc aguggauuc                                           19

<210> SEQ ID NO 40
<211> LENGTH: 25
<212> TYPE: DNA
<213> ORGANISM: Artificial Sequence
<220> FEATURE:
<223> OTHER INFORMATION: primer pair (forward)

<400> SEQUENCE: 40
caccatggcc caactgagga ttaag                                    25

<210> SEQ ID NO 41
<211> LENGTH: 30
<212> TYPE: DNA
<213> ORGANISM: Artificial Sequence
<220> FEATURE:
<223> OTHER INFORMATION: primer pair (reverse)

<400> SEQUENCE: 41
tcagcgtctc ccaaagatat tagtgataga                               30

<210> SEQ ID NO 42
<211> LENGTH: 28
<212> TYPE: DNA
<213> ORGANISM: Artificial Sequence
<220> FEATURE:
<223> OTHER INFORMATION: primer pair (forward)

<400> SEQUENCE: 42
caccatggca gacaattttt cgctccat                                 28

<210> SEQ ID NO 43
<211> LENGTH: 24
<212> TYPE: DNA
<213> ORGANISM: Artificial Sequence
<220> FEATURE:
<223> OTHER INFORMATION: primer pair (reverse)

<400> SEQUENCE: 43
ttatatcatg gtatatgaag cact                                     24

<210> SEQ ID NO 44
<211> LENGTH: 60
<212> TYPE: DNA
<213> ORGANISM: Homo sapiens

<400> SEQUENCE: 44
tctcttgtct gacttgggct gcacagatcc tgggccaagg gacagaagaa agacagccta    60

<210> SEQ ID NO 45
<211> LENGTH: 60
<212> TYPE: DNA
<213> ORGANISM: Homo sapiens

<400> SEQUENCE: 45
ggagcagagc ctcccagatg gctgagttgg atctaatggc tccagggcca ctgcccaggg    60

<210> SEQ ID NO 46
<211> LENGTH: 13
<212> TYPE: DNA
<213> ORGANISM: Homo sapiens
<220> FEATURE:
<221> NAME/KEY: misc_feature
<222> LOCATION: (11)..(13)

-continued

```
<223> OTHER INFORMATION: n is a, c, g, or t

<400> SEQUENCE: 46
ggagcagagc nnn                                                      13

<210> SEQ ID NO 47
<211> LENGTH: 60
<212> TYPE: DNA
<213> ORGANISM: Homo sapiens

<400> SEQUENCE: 47
ccactgctca gcccccagcc cctctcagcc cagactctgg gtcacccagc ccagattctg     60

<210> SEQ ID NO 48
<211> LENGTH: 16
<212> TYPE: PRT
<213> ORGANISM: Homo sapiens

<400> SEQUENCE: 48

Leu Gln Ser His Leu Leu Thr Glu Pro Val Lys Asp His Asn Trp Arg
1               5                   10                  15

<210> SEQ ID NO 49
<211> LENGTH: 16
<212> TYPE: PRT
<213> ORGANISM: Homo sapiens

<400> SEQUENCE: 49

Leu Gln Ala Asn Gln Lys Ser Val Leu Val Ser Val Ser Glu Val Lys
1               5                   10                  15
```